United States Patent
Xu et al.

(10) Patent No.: US 12,145,923 B2
(45) Date of Patent: Nov. 19, 2024

(54) TETRAHYDROISOQUINOLINE COMPOUND, PREPARATION METHOD THEREFOR, PHARMACEUTICAL COMPOSITION CONTAINING SAME, AND USE THEREOF

(71) Applicant: SHANGHAI INSTITUTE OF MATERIA MEDICA, CHINESE ACADEMY OF SCIENCES, Shanghai (CN)

(72) Inventors: Yechun Xu, Shanghai (CN); Hong Liu, Shanghai (CN); Wei Tang, Shanghai (CN); Xianglei Zhang, Shanghai (CN); Zhanni Gu, Shanghai (CN); Heng Li, Shanghai (CN); Xu Han, Shanghai (CN); Fenghua Zhu, Shanghai (CN); Chunlan Feng, Shanghai (CN); Guangyu Dong, Shanghai (CN); Tiantian Chen, Shanghai (CN); Wuyan Chen, Shanghai (CN); Hualiang Jiang, Shanghai (CN); Kaixian Chen, Shanghai (CN)

(73) Assignee: SHANGHAI INSTITUTE OF MATERIA MEDICA, CHINESE ACADEMY OF SCIENCES, Shanghai (CN)

(*) Notice: Subject to any disclaimer, the term of this patent is extended or adjusted under 35 U.S.C. 154(b) by 0 days.

(21) Appl. No.: 16/967,721

(22) PCT Filed: Feb. 3, 2019

(86) PCT No.: PCT/CN2019/074704
§ 371 (c)(1),
(2) Date: Aug. 5, 2020

(87) PCT Pub. No.: WO2019/154395
PCT Pub. Date: Aug. 15, 2019

(65) Prior Publication Data
US 2021/0040066 A1 Feb. 11, 2021

(30) Foreign Application Priority Data
Feb. 6, 2018 (CN) .......................... 201810118038.7

(51) Int. Cl.
| | |
|---|---|
| *C07D 401/14* | (2006.01) |
| *C07D 217/08* | (2006.01) |
| *C07D 401/06* | (2006.01) |
| *C07D 401/12* | (2006.01) |
| *C07D 403/04* | (2006.01) |
| *C07D 405/14* | (2006.01) |
| *C07D 409/06* | (2006.01) |
| *C07D 413/06* | (2006.01) |

(Continued)

(52) U.S. Cl.
CPC ......... *C07D 401/14* (2013.01); *C07D 217/08* (2013.01); *C07D 401/06* (2013.01); *C07D 401/12* (2013.01); *C07D 403/04* (2013.01); *C07D 405/14* (2013.01); *C07D 409/06* (2013.01); *C07D 413/06* (2013.01); *C07D 413/14* (2013.01); *C07D 417/14* (2013.01)

(58) Field of Classification Search
CPC .................................................... C07D 401/14
See application file for complete search history.

(56) References Cited

U.S. PATENT DOCUMENTS

| | | | |
|---|---|---|---|
| 3,326,923 A | 6/1967 | Shavel | |
| 3,452,023 A * | 6/1969 | Morrison | C07D 471/06 546/49 |
| 4,292,320 A | 9/1981 | Kishimoto et al. | |

(Continued)

FOREIGN PATENT DOCUMENTS

| | | |
|---|---|---|
| CN | 1441785 A | 9/2003 |
| CN | 105793250 A | 7/2016 |

(Continued)

OTHER PUBLICATIONS

Wermuth, Camille G. "Molecular Variation Based on Isosteric Replacements" in Chapter 13, The Practice of Medicinal Chemistry, Academic: 1996.*

(Continued)

*Primary Examiner* — David K O'Dell
(74) *Attorney, Agent, or Firm* — Panitch Schwarze Belisario & Nadel LLP

(57) ABSTRACT

Disclosed are a novel tetrahydroisoquinoline compound, a method for preparing intermediates thereof, a pharmaceutical composition thereof and the use thereof. The tetrahydroisoquinoline compound of the present invention has a good inhibitory effect on phosphodiesterase (PDE4), and can be used in the prevention, treatment or auxiliary treatment of multiple diseases associated with the activity or expression of phosphodiesterase, especially PDE4-associated immune and inflammatory diseases, such as psoriasis and arthritis.

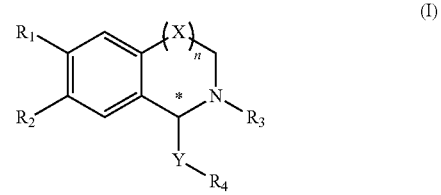

(I)

8 Claims, 1 Drawing Sheet

(51) Int. Cl.
   C07D 413/14      (2006.01)
   C07D 417/14      (2006.01)

(56)                References Cited

U.S. PATENT DOCUMENTS 6,908,931  B2 *  6/2005  Dubowchik ........... A61K 31/47
                                                        514/307
   2002/0022637 A1  2/2002  Li et al.
   2015/0158858 A1  6/2015  Amari et al.

FOREIGN PATENT DOCUMENTS

CN         106831577 A    6/2017
   WO           0164647 A1   9/2001
   WO         2004085403 A1  10/2004
   WO         2016100391 A1  6/2016

OTHER PUBLICATIONS

Nakamura "Imidazole derivatives as new potent and selective 20-HETE synthase inhibitors." Bioorganic & Medicinal Chemistry Letters 2004, 14, 333-336.*
Li "N-(Arylacetyl)-biphenylalanines as Potent VLA-4 Antagonists" Bioorganic & Medicinal Chemistry Letters 2002, 12, 2141-2144.*
Osante "Stereodivergent synthesis of hetero-fused isoquinolines by acyliminium and metallation methods." European Journal of Organic Chemistry 2001 (7), 1267-1277.*
Pai, Bantwal R. "Studies in protoberberine alkaloids. 14. Use of a mixture of phosphorus pentabromide and phosphorus pentoxide as a cyclizing reagent in protoberberine synthesis." Journal of Organic Chemistry, 1978, 43(10), 1992-4.*
Schneider "Natural and synthetic isoquinoline derivatives. 7. Synthesis of compounds with the homoproaporphine structure." Helvetica Chimica Acta, 53(5), 938-45 1970.*
The Van Nostrand Chemist's Dictionary 1953, entry for "aryl" p. 44. "ARYL".*
Xu "Synthesis of N-acylated/sulfonylated tetrahydroisoquinoline compounds." Zhongguo Yaoke Daxue Xuebao, 1993, 24(1), 1-6 (abstract only).*
STN chemical database Registry entry for RN 1381468-62-7 for [1-[2-(3,5-Dimethyl-4-isoxazolyl)ethyl]-3,4-dihydro-6,7-dimethoxy-2(1H)-isoquinolinyl]-2-thienylmethanone, Entered STN: Jul. 4, 2012 Chemical Library Supplier: ASINEX Ltd.*
Online "https://web.archive.org/web/20111229011706/http://www.asinex.com:80/building-blocks.html" dated Dec. 29, 2011.*
Humber, Leslie G. "Synthesis of 1H-benzo[d,e-1,7]naphthyridines, a novel heterocyclic ring system." Canadian Journal of Chemistry, 1971, 49(6), 857-62.*
Lin "In search of aromatic seven-membered rings" Journal of Molecular Structure: THEOCHEM 943 (2010) 23-31.*
Almerico et al., "In-silico screening of new potential Bcl-2/Bcl-xl inhibitors as apoptosis modulators," J. Mol. Model, vol. 15, pp. 349-355 (2009).
Boekelheide et al., "Additions and Corrections-Curariform Activity and Chemical Structure. VII. Some 1-Skatylisoquinoline Derivatives and a Novel Method for their Synthesis," Journal of the American Chemical Society, vol. 72, No. 12, p. 2134 (1950).
Borgulya et al., "Chemical and Pharmacological Studies on Derivatives of Benzo[de]quinoline. II," Helvetica Chimica Acta, vol. 60, No. 2, pp. 598-617 (1977)—Nr. 66 (with English Summary).
Chaudhary et al., "(±)-Nantenine analogs as antagonists at human 5-HT2A receptors: C1 and flexible congeners," Bioorganic & Medicinal Chemistry Letters, vol. 19, No. 9, pp. 2530-2532 (2009).
Cho et al., "Regioselectivity of Pictet-Spengler cyclization: synthesis of halotetrahydroisoquinolines," Tetrahedron Letters, vol. 42, pp. 6251-6253 (2001).
Copp et al., "Synthesis of 5,6,6a,7,7a, 12a-Hexahydro-4H-benzo[d,e] benzothieno-[2,3-g]quinolines and of 8-Phenyl-2,3,7,8,9,9a-hexahydro-1H-benzo[d,e]quinolines," J. Chem. Soc. Perkin Trans. 1, pp. 909-914 (1983).
Extended European Search Report issued Nov. 12, 2021 in EP Application No. 19750381.6.
Gupta et al., "Syntheses and Biological Activities of 1, 4-disubstituted Piperidines," Archiv der Pharmazie, vol. 317, No. 12, pp. 1010-1017 (1984).
Hromatka et al., "Piperazinsubstituierte Isochinolinderivate," Monatsheftefür Chemie, vol. 97, No. 1, pp. 19-32 (1966).
Ishiwata et al., "Syntheses of Ioquinoline Derivatives. VI. Syntheses of Alkyl Derivatives of Pyridine Nucleus (3)," Yakugaku Zasshi, vol. 71, No. 11, pp. 1261-1263 (1951) (with English Summary).
Knabe et al., "On the Mechanism of the 1,2-Dihydroisoquinoline-Rearrangement," Arch. Pharmaz., vol. 307, No. 9, pp. 727-731 (1973) (with English Abstract).
Liu et al., "Synthesis and Biological Activities of a Novel Class of Azole-containing Antifungal Agents," Bioorganic & Medicinal Chemistry Letters, vol. 6, No. 12, pp. 1335-1338 (1996).
Morrison et al., "Alternate Precursors in Biogenetic-Type Syntheses. III.1 A Ring D Indoline Analog of the Aporphine Alkaloids. Indole as the Alkylating Agent in the Friedel-Crafts Reaction," The Journal of Organic Chemistry, vol. 33, No. 4, pp. 1663-1664 (Apr. 1968).
Ngouansavanh et al., "IBX-Mediated Oxidative Ugi-Type Multicomponent Reactions: Application to the N and C1 Functionalization of Tetrahydroisoquinoline," Angewandte Chemie International Edition, vol. 46, No. 30, pp. 5775-5778 (2007).
Perego et al., "Copper-Catalyzed Hydroamination of Allenes: from Mechanistic Understanding to Methodology Development," ACS Catalysis, vol. 7, No. 7, pp. 1-19 (2017).
Rossetti et al., "Rapid access to reverse-turn peptidomimetics by a three-component Ugi reaction of 3,4-dihydroisoquinoline," Chemistry of Heterocyclic Compounds, vol. 53, No. 11, pp. 1214-1219 (2017).
Schneider et al., "Uber die Synthese von Verbindungen mit dem Skelett der Homoproaporphine. 7. Mitteilung über naturliche und synthetische Isochinolinderivate," Helvetica Chimica Acta, vol. 53, No. 5, pp. 939-945 (1970)—NR. 110 (with English Summary).
Vaccher et al., "A Novel Rearrangement Reaction. A Single-step Conversion of Tetrahydro-I-isoquinolinecarboxylic Acids into 1-isoquinolones," Journal of Heterocyclic Chemistry, vol. 21, No. 4, pp. 1201-1204 (1984).
Zhu et al., "An Ugi Reaction Incorporating a Redox-Neutral Amine C-H Functionalization Step," Organic Letters, vol. 18, No. 4, pp. 631-633 (2016).

* cited by examiner

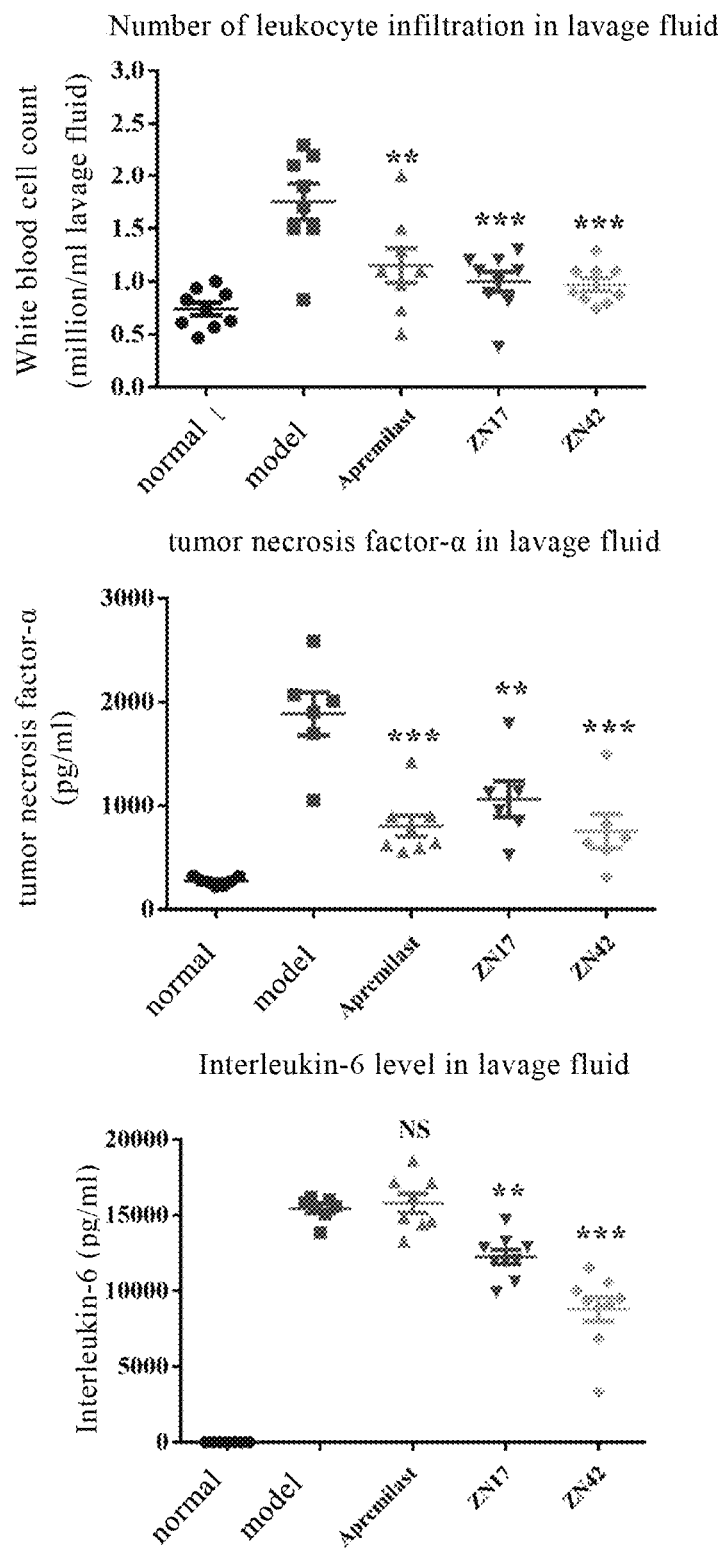

TETRAHYDROISOQUINOLINE COMPOUND, PREPARATION METHOD THEREFOR, PHARMACEUTICAL COMPOSITION CONTAINING SAME, AND USE THEREOF

FIELD OF THE INVENTION

The present invention relates to a novel tetrahydroisoquinoline compound, the preparation method thereof, a pharmaceutical composition comprising such compound and the use thereof, and belongs to the technical field of medicine. A novel tetrahydroisoquinoline compound represented by general formula (I), pharmaceutically acceptable salts, isomers, solvates, metabolites, metabolic precursors, pharmaceutical compositions containing them and their use in prevention and/or treatment or adjuvant treatment of PDE4-related diseases, such as psoriasis, psoriatic arthritis, allergic dermatitis, chronic obstructive pulmonary disease, asthma, allergic rhinitis, ankylosing spondylitis, systemic Lupus erythematosus, rheumatoid arthritis, inflammatory bowel disease, pulmonary fibrosis, multiple sclerosis, Alzheimers disease, Huntingtons disease, Parkinson's disease, ADHD, depression and schizophrenia, especially PDE4-related immune and inflammatory diseases, such as psoriasis and arthritis.

BACKGROUND OF THE INVENTION

Cyclic nucleotide phosphodiesterases (PDEs) selectively catalyze the hydrolysis of 3-phosphate linkages of the second messenger cyclic adenosine phosphate (cAMP) or cyclic guanosine phosphate (cGMP) in a cell to produce the product, 5-AMP or 5-GMP, thereby inactivating the cAMP or cGMP signal. The normal function of PDEs directly affects the intracellular concentration of cAMP and/or cGMP, which in turn affects the downstream signal transmission of such signaling pathways involved in such second messengers (Omori K, et al. Circ. Res. 2007, 100:309-327; Maurice D H, et al. Nat. Rev. Drug Discov. 2014, 13:290-314). It is known that there are many proteins downstream to cAMP that directly interact with cAMP, including PDEs, classic cAMP concentration-dependent protein kinases, exchange proteins directly activated by cAMP, cyclic nucleotide-gated ion channels, and binds to the DNA-binding protein directly bound by cAMP CRP/CAP and some proteins containing GAF domain. Correspondingly, in addition to PDEs, there are also other proteins that directly interact with cGMP, such as cGMP concentration-dependent protein kinases, cyclic nucleotide-gated ion channels, and some proteins that contain GAF domains. These signaling pathways are closely related to physiological processes, such as cell cycle control, cell differentiation, inflammation, cardiac function, smooth muscle relaxation and contraction, visual signaling, learning and memory and related pathological processes. Inhibiting the hydrolysis activity of PDEs will change the intracellular cAMP or cGMP concentration, thereby directly regulating cAMP or cGMP related signaling pathways and changing related functional symptoms. Therefore, PDEs are an important family of drug targets. PDEs inhibitors have been widely used in the research and treatment of pathological mechanisms of various diseases (Maurice D H, et al. Nat. Rev. Drug Discov. 2014, 13:290-314; Menniti F S, et al. Nat. Rev. Drug Discov. 2006, 5(8), 660-670).

PDEs are a multi-gene superfamily. So far, 21 PDE genes have been found in mammals, which are divided into 11 subfamilies, containing more than 100 different PDE isozymes (or subtypes) with different substrate specificities, enzyme kinetic characteristics, heterogeneous regulation characteristics, and different distribution in tissues and subcells, which participate in different signaling pathways and exhibit different sensitivity to inhibitors (Lugnier C, Pharmacol. Ther. 2006, 109:366-398; Francis S H, et al. Handb. Exp. Pharmacol. 2011, 204:47-84). For example, PDE4, 7 and 8 mainly hydrolyze cAMP; PDE5, 6 and 9 selectively act on cGMP; while PDE1, 2, 3, 10 and 11 can hydrolyze both cAMP and cGMP, although the affinity and hydrolysis activity of the different isozymes to the two substrates are different. Unlike the difference in selectivities for substrates, the structural characteristics of the members in PDEs family are similar, usually composed of a regulatory domain near the N-terminus and a catalytic domain near the C-terminus. The catalytic domain (about 270 amino acids) is responsible for the substrate hydrolysis reaction. Currently known PDEs inhibitors mainly act on the catalytic domain of PDEs, thereby achieving the function of inhibiting activities thereof.

PDE4 specifically hydrolyzes the second messenger molecule cAMP in the cell, inhibiting the activity of PDE4 will lead to the accumulation of cAMP, high concentration of cAMP will activate protein kinase A, and the activated protein kinase A will phosphorylate downstream transcription factors, thereby regulating a large number of cytokines transcription and expression (Houslay M D, et al. Biochem. J., 2003, 370:1-18). The PDE4 family includes four genes (PDE4A/B/C/D), which are alternatively spliced during the expression process to form more than 25 isozymes. PDE4 is widely distributed in the body, mainly expressed in immune-related cells, such as neutrophils, eosinophils and monocytes (Maurice D H, et al. Mol. Pharmacol., 2003, 64:533-546). PDE4 involves a wide variety of diseases, of which chronic obstructive pulmonary disease, asthma, psoriasis, allergic rhinitis, idiopathic pulmonary fibrosis and rheumatoid arthritis are related to the role of PDE4 in the inflammatory process. Diseases related to the nervous system include Alzheimer's disease, Parkinson's disease, depression, and schizophrenia (Menniti F S, et al. Nat. Rev. Drug Discov., 2006, 5:660-670; Burgin A B, et al. Nat. Biotechnol., 2010, 28:63-70; Garcia-Osta A, et al. ACS Chem. Neurosci., 2012, 3: 832-844.).

Psoriasis is an immune-mediated chronic recurrent skin inflammation characterized by keratinocyte proliferation and infiltration of a large number of white blood cells. The disease is stubborn and refractory, seriously affects the quality of life as well as physical and mental health of patients, and is one of the important diseases to be solved in the field of dermatology. The disease is one of the most common autoimmune diseases in the world, the incidence rate of which is 0.1%-3% of the whole population of the world. In addition, psoriasis is also closely related to other inflammatory diseases, such as psoriatic arthritis, inflammatory bowel disease and coronary artery disease. Although a series of drugs (including topical, oral and biological drugs) have been used for the symptomatic treatment of psoriasis, there is still a huge gap and urgent need for the discovery of new targets and new drugs. TNF-α is highly expressed in psoriasis, and blocking therapy against TNF-α exhibits significant clinical effects. Increasing the concentration of cAMP by inhibiting the hydrolysis activity of PDE4 can downregulate the expression of pro-inflammatory factors, such as TNF-α. Therefore, PDE4 inhibitor Apremilast was approved by the FDA in 2014 as oral medication for treating plaque psoriasis and psoriatic arthritis (Man H-W, et al. J. Med. Chem., 2009, 52:1522-1524). In addition, in December 2016, the FDA approved the local therapeutic medicine for eczema (allergic dermatitis) (Cricorborole) of Anacor Pharmaceuticals. Similar to psoriasis, allergic dermatitis is a common recurrent chronic inflammatory skin disease, and Crisaborole is a non-steroidal PDE4 inhibitor, which is the first new molecule approved by the FDA in the past 15 years to treat allergic dermatitis entity.

Therefore, since PDE4 involves many important diseases and some PDE4 inhibitors have been used in clinical treatment, designing and discovering new inhibitors targeting PDE4 is a hot spot in the field of new drug development.

SUMMARY OF THE INVENTION

The object of the present invention is to provide a new type of phosphodiesterase type 4 (PDE4) inhibitors, namely a new class of tetrahydroisoquinoline compounds, and intermediates, preparation methods, pharmaceutical compositions and applications thereof.

In the first aspect of the present invention, a tetrahydroisoquinoline compound represented by the general formula (I), or a pharmaceutically acceptable salt, enantiomer, diastereomer, or racemate thereof is provided:

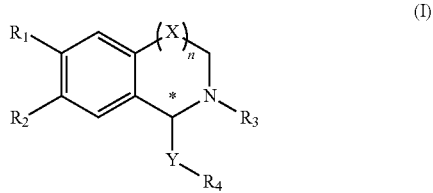

wherein,
the chiral carbon atom C* is independently of S type, R type, or a combination thereof:
n=1 or 2;
X is —$CH_2$— or —NH—;
Y is a linking group selected from a C1-C6 linear or branched alkylene, C2-C6 linear or branched alkenylene, —$CH_2O$—, —$CH_2NH_2$—, —$CH_2S$—, —CONH—, —NHCO—, —COO—, —OOC—,

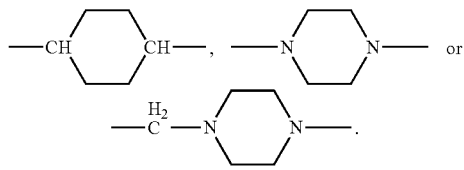

$R_1$ and $R_2$ are each independently selected from the group consisting of a hydrogen, deuterium, hydroxyl, halogen, substituted or unsubstituted C1-C6 linear or branched alkoxy, substituted or unsubstituted C2-C6 linear or branched alkenyloxy, substituted or unsubstituted C2-C6 linear or branched alkynyloxy, substituted or unsubstituted C3-C7 cycloalkoxy, substituted or unsubstituted C3-C7 cycloalkylmethoxy, benzyloxy, C1-C6 acyloxy, carboxy substituted C2-C8 linear alkoxy, N, N-dimethylamino substituted C2-C8 linear alkoxy, $COOR_5$ or $CONR_5R_6$; the substitutent is selected from deuterium or halogen; or $R_1$, $R_2$ together with the carbon atom to which they are attached to form a 5-7 membered carbocyclic or heterocyclic ring (including saturated ring, unsaturated ring or aromatic ring);

$R_3$ is selected from the following groups that are unsubstituted or substituted with 1-3 substituents: a —C(O)-(5 to 7-membered heteroaryl), —C(O)-(4 to 7-membered heterocyclic group), —C1-C4 acyl (preferably formyl-CHO), —C1-C4 alkyl, $R_7SO_2$—, $NH_2(CH_2)_mSO_2$—, $R_7SO_2(CH_2)_m$—, $R_7O(CH_2)_mCO$—, $R_7OCO(CH_2)_m$—, difluoromethyl, trifluoromethyl. C1-C4 sulfinyl, benzenesulfonyl, 5-7 membered heteroarylsulfonyl, phenyl, benzyl, 5-7 membered heteroaryl, 4-7 membered heterocyclic group; wherein each of the heterocyclic groups or heteroaryl groups contains 1 to 3 heteroatoms selected from oxygen, sulfur or nitrogen; and the substituents are each independently selected from a deuterium, halogen, C1-C6 linear or branched alkoxy, C1-C6 linear or branched alkylcarbonyloxy, C1-C6 linear or branched alkoxycarbonyl, cyano, hydroxyl, amino, hydroxymethyl group, trifluoromethyl group, trifluoromethoxy group, carboxyl group, hydroxime group, phosphorate, mercapto group, C1-C4 amide, C0-C4 sulfonyl group, amino C0-C4 sulfonyl group, C1-C4 alkyl-substituted sulfonyl phenyl, benzyl, 5-7 membered heteroaryl, 4-7 membered heterocyclic group, wherein each of the heterocyclic groups or heteroaryl groups contains 1 to 3 heteroatoms selected from oxygen, sulfur or nitrogen;

$R_5$, $R_6$ and $R_7$ are each independently selected from a hydrogen, substituted or unsubstituted C1-C4 linear or branched alkyl, substituted or unsubstituted C3-C8 cycloalkyl, substituted or unsubstituted C6-C10 aryl; wherein the substituent is selected from deuterium or halogen;

m is selected from 0, 1, 2, 3 or 4;

$R_4$ is a group, which is unsubstituted or substituted with 1-3 substituents and selected from a C3-C7 cycloalkyl, 5-12 membered heterocyclic group, C7-C12 aryl, 5-12 membered heteroaryl group (preferably benzo 5-7 membered heteroaryl); wherein each of said heterocyclic groups or heteroaryl comprises 1 to 3 heteroatoms selected from oxygen, sulfur or nitrogen; each of said substituents is independently selected from a deuterium, halogen, C1-C6 linear or branched alkyl, C2-C6 linear or branched alkenyl, C2-C6 linear or branched alkynyl, C1-C6 linear or branched alkoxy, C1-C6 linear or branched alkylcarbonyloxy, cyano, nitro, hydroxy, amino, hydroxymethyl, trifluoromethyl, trifluoromethoxy, difluoromethyl, difluoromethoxy, $COOR_5$, $CONR_5R_6$, C1-C6 carboxyl, mercapto, C1-C4 acyl, C1-C4 amide, sulfonyl, aminosulfonyl, C1-C4 alkyl substituted sulfonyl, C1-C4 alkyl substituted sulfonamide, N, N-dimethyl substituted C1-C6 alkoxy, carboxy substituted C1-C6 alkoxy, or two adjacent substituents together with the carbon atom to which they are attached to form a 5-7 membered carbocyclic or heterocyclic (including saturated ring, unsaturated ring or aromatic ring);

In another preferred example, in the general formula (I):
n=1;
$R_1$ and $R_2$ are each independently selected from the group consisting of a substituted or unsubstituted C1-C6 linear or branched alkoxy, substituted or unsubstituted C3-C7 cycloalkoxy, substituted or unsubstituted C3-C7 cycloalkylmethoxy, C1-C6 acyloxy, carboxy substituted C2-C8 linear alkoxy, N, N-dimethylamino substituted C2-C8 linear alkoxy, carboxy substituted C2-C8 linear alkoxy, N, N-dimethylamino substituted C2-C8 linear alkoxy, $COOR_5$ or $CONR_5R_6$; and the substituent is selected from deuterium or halogen (including fluorine, chlorine, bromine and iodine).

In another preferred example, $R_5$ and $R_6$ are each independently selected from a hydrogen, C1-C4 linear or branched alkyl.

In another preferred example, in the general formula (I):

X is —CH$_2$—;

Y is selected from the group consisting of —CH$_2$—, —CH$_2$—CH$_2$—, —CH=CH—,

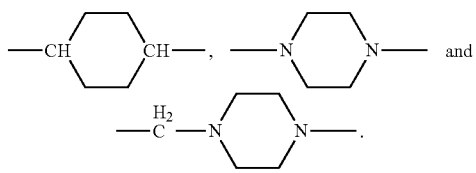 and

R$_4$ is a group which is unsubstituted or substituted with 1-3 substituents and selected from a 5-12 membered heterocyclic group, C6-C12 aryl, 5-12 membered heteroaryl group (preferably benzo 5-7 membered heteroaryl); preferably, the heterocyclic and heteroaryl portions in the group are selected from indole, benzodioxole, isoxazole, pyridine, pyrazole, dihydroimidazopyridine, imidazopyridine, benzothiophene, dihydrobenzodioxane, quinoxaline, pyrrole, benzofuran, indazole, benzimidazole, quinoline, 1,3-dioxoisoindole.

In another preferred example, in the general formula (I):

R$_3$ is a group which is unsubstituted or substituted with 1-3 substituents and selected from a C1-C4 acyl (preferably formyl), C1-C4 alkyl. R$_7$SO$_2$—, NH$_2$(CH$_2$)$_m$SO$_2$—, R$_7$SO$_2$(CH$_2$)$_m$—, R$_7$O(CH$_2$)$_m$CO—, difluoromethyl, trifluoromethyl, C1-C3 sulfinyl, benzenesulfonyl, 5-7 membered heteroarylsulfonyl, phenyl, benzyl, 5-7 membered heteroaryl, 4-7 membered heterocyclic group; wherein each of the heterocyclic groups or heteroaryl contains 1 to 3 heteroatoms selected from oxygen, sulfur or nitrogen; the substituents are each independently selected from a deuterium, halogen, C1-C6 linear or branched alkoxy, C1-C6 linear or branched alkylcarbonyloxy, C1-C6 linear or branched alkoxycarbonyl, cyano, hydroxy, amino, hydroxymethyl, trifluoromethyl, trifluoromethoxy, carboxy, hydroxyl oxime group, phosphate, thiol, C1-C4 amido, C1-C4 sulfonyl, amino C1-C4 sulfonyl, C1-C4 alkyl-substituted sulfonyl phenyl, benzyl, 5-7 membered heteroaryl, 4-7 membered heterocyclic group; and each heterocyclic group or heteroaryl comprises 1 to 3 heteroatoms selected from oxygen, sulfur or nitrogen:

R$_7$ is selected from a hydrogen, C1-C4 linear or branched alkyl;

m is selected from 0, 1, or 2.

In another preferred example, R$_1$ and R$_2$ are each independently C1-C6 linear or branched alkoxy, trifluoromethoxy, difluoromethoxy, COOR$_5$, CONR$_5$R$_6$.

In another preferred example, the R$_4$ is indolyl unsubstituted or substituted with 1-3 substituents; preferably, the indolyl is substituted with a substituent selected from the group consisting of halogen, C1-C4 alkyl, C1-C4 alkoxy, cyano, trifluoromethyl, trifluoromethoxy, difluoromethyl, difluoromethoxy, COOR$_5$, CONR$_5$R$_6$.

In another preferred example, in the general formula (I): The chiral carbon atom C* is of S type.

In the second aspect of the present invention, a preparation method for compound (I) of the first aspect of the present invention is provided, which comprises the following steps:

(1) In an inert solvent, in the presence of a condensing agent, reacting a compound of formula II and a compound of formula Ic to obtain a compound of formula Id; preferably, the condensing agent is EDCI (1-ethyl-(3-dimethyl aminopropyl) carbodiimide hydrochloride);

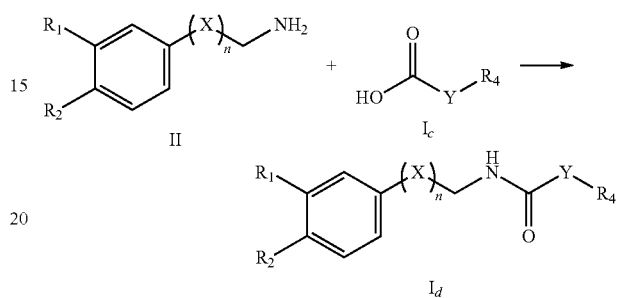

(2) subjecting a compound of formula Id to Bischler-Napieralski ring closure reaction in an inert solvent to obtain a compound of formula Ie; preferably, phosphorus oxychloride is used as a Lewis acid in the ring closure reaction;

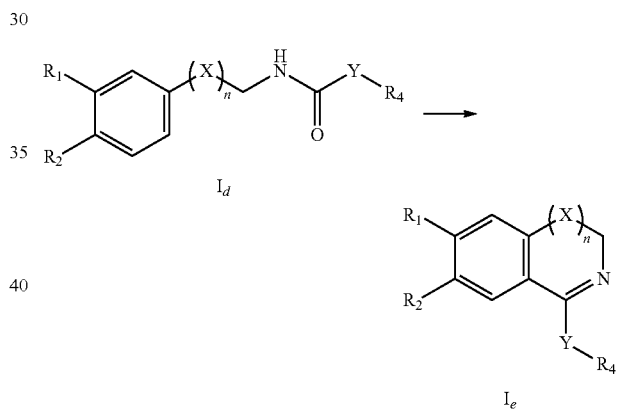

(3) In a inert solvent, subjecting a compound of formula Ie to a reduction reaction to obtain a compound of formula If; preferably, borohydride is used as a reducing agent or Noyori catalyst is used as an asymmetric reduction catalyst in the reduction reaction;

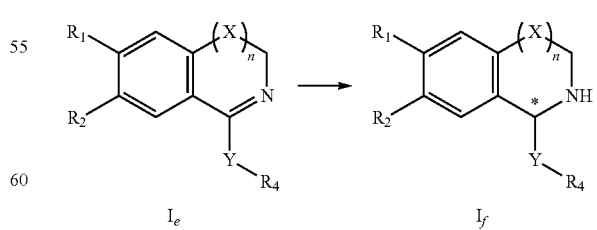

(4) In an inert solvent, subjecting a compound of formula If to a condensation reaction or an N-alkylation reaction or a Buchwald-Hartwig reaction to obtain a compound of formula (I);

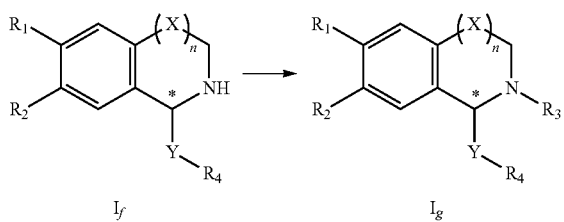

wherein the groups are defined as in the first aspect of the present invention.

In the third aspect of the present invention, a pharmaceutical composition is provided, comprising: a therapeutically effective amount of one or more compound (I) of the first aspect of the invention, or a pharmaceutically acceptable salt thereof.

In the fourth aspect of the present invention, a use of the general formula (I) as described in the first aspect of the present invention in preparing a pharmaceutical composition for preventing, treating or adjuvant treating diseases related to PDE4 activity or expression is provided; preferably, the disease is an immune or inflammatory disease related to PDE4 activity or expression.

In another preferred example, the disease related to PDE4 activity or expression is selected from the group consisting of psoriasis, psoriatic arthritis, allergic dermatitis, chronic obstructive pulmonary disease, asthma, allergic rhinitis, ankylosing spondylitis, systemic lupus erythematosus, rheumatoid arthritis, inflammatory bowel disease, pulmonary fibrosis, multiple sclerosis, Alzheimer's disease, Huntington's disease, Parkinson's disease, ADHD, depression and schizophrenia.

It should be understood that, in the present invention, each of the technical features specifically described above and below (such as those in the Examples) can be combined with each other, thereby constituting new or preferred technical solutions which need not be specified again herein.

DESCRIPTION OF THE DRAWINGS

FIG. 1 shows the therapeutic effects of the tested compounds ZN17 and ZN42 on a mouse model of dorsal gasbag acute inflammation.

EMBODIMENTS FOR CARRYING OUT THE INVENTION

After a long and intensive study, the inventors prepared a class of compounds of formula I capable of inhibiting phosphodiesterase (PDE4). Compared with the phosphodiesterase 4 (PDE4) inhibitory compounds in the prior art, the compounds exhibit higher inhibitory activities. The present invention is completed on this basis.

An object of the present invention is to provide a tetrahydroisoquinoline compound represented by the general formula (I), a pharmaceutically acceptable salt, an enantiomer, a diastereomer or a racemate thereof.

Another object of the present invention is to provide a method for preparing the compound represented by the general formula (I).

Still another object of the present invention is to provide a pharmaceutical composition containing a therapeutically effective amount of one or more compounds represented by the above general formula (I) or a pharmaceutically acceptable salt thereof.

Still another object of the present invention is to provide the above-mentioned compound represented by general formula (I) in use of the preparation of drugs for the treatment of autoimmune diseases, such as psoriasis, psoriatic arthritis, atopic dermatitis, etc.

The compounds of the present invention can be used to inhibit phosphodiesterase 4 (PDE4).

Terms

Unless specifically indicated, in the present invention, the term "substitute" means that one or more hydrogen groups from a group are substituted by substituents selected from group consisting of a C1-C10 alkyl, C3-C10 cycloalkyl, C1-C10 alkoxy, halogen, hydroxy, carboxy (—COOH), C1-C10 aldehyde group, C2-C10 acyl group, C2-C10 ester group, amino group, phenyl group; wherein the phenyl includes unsubstituted phenyl or phenyl substituted by 1-3 substituents, wherein the substituent is selected from the group consisting of a halogen, C1-C10 alkyl, cyano, OH, nitro group, C3-C7 cycloalkyl, C1-C10 alkoxy, amino.

Unless otherwise stated, in compounds of the present invention, each chiral carbon atom may optionally be in R configuration or S configuration, or the mixture of R configuration and S configuration.

As used herein, the term "C1-C6 alkyl" refers to linear or branched alkyl with 1 to 6 carbon atoms, such as methyl, ethyl, propyl, isopropyl, butyl, isobutyl, sec-butyl, tert-butyl, or similar groups.

The term "3-8 membered heterocyclic group" refers to a group formed by losing one hydrogen atom from a 3-8 membered saturated ring having 1-3 heteroatoms selected from the group: N, S, O; e.g., pyrrolidinyl, piperidinyl, piperazinyl, morpholinyl, or similar groups.

The term "6-10 membered aryl group" refers to a group formed by losing one hydrogen atom from a 6-10 membered aryl; for example, phenyl, naphthyl, or similar groups.

Term "5-10 membered heteroaryl group" refers to a group formed by losing one hydrogen atom from a 5-8 membered aryl having 1-3 heteroatoms selected from the group: N, S or O, wherein each heteroaryl ring system may be mono-cyclic or polycyclic; for example, pyrrolyl, pyridyl, thienyl, furyl, imidazolyl, pyrimidinyl, benzothienyl, indolyl, imidazopyridyl, quinolinyl, or similar groups.

The term "C1-C6 alkoxy" refers to a straight or branched chain alkyl group having 1 to 6 carbon atoms, such as methoxy, ethoxy, propoxy, isopropoxy, butoxy, iso-butoxy, sec-butoxy, and tert-butoxy, or similar groups.

The term "C2-C6 ester group" refers to a R—O—C (=O)— group having 2-6 carbon atoms, such as —COOCH$_3$, —COOC$_2$H$_5$, —COOC$_3$H$_7$, —COOC$_4$H$_9$, or similar groups.

The term "C2-C6 alkenyl" refers to a group formed by losing one or two hydrogen atom from an olefin having 2 to 6 carbon atoms. The olefin may be a mono-olefin, a di-olefin or a tri-olefin, such as —CH=CH$_2$, —C$_2$H$_4$=CH$_2$, —CH=C$_2$H$_4$, or similar groups.

The term "halogen" refers to F, C, Br and I.

Unless otherwise specified, the structural formula described herein are intended to include all isomeric forms (such as enantiomeric, diastereomeric, and geometric isomers (or conformational isomers)): for example, R, S configuration of asymmetrical centers, (Z), (E) isomers of double bonds, and (Z), (E) conformational isomer, etc. Therefore the single stereochemical isomers or enantiomers, diastereomers or geometric isomers (or conformers) of the compounds of the invention, or mixtures thereof all fall within the scope of the invention.

The term "tautomer" means that structural isomers having different energies can exceed the low energy barrier and thereby transform between each other. For example, proton tautomers (i.e., proton shifts) include interconversions by proton transfer, such as 1H-carbazole and 2H-carbazole, 1H-benzo[d]imidazole and 3H-benzo[d]imidazole. The valence tautomers include interconversion through some bonding electron recombination.

Herein, terms such as "C1-C6" means that the group may have 1 to 6 carbon atoms, for example, 1, 2, 3, 4, or 5 carbon atoms.

Unless otherwise specified, the compounds of the present application may include compounds formed from isotopes known in the art, such as hydrogen isotopes (deuterium, tritium, etc.) and carbon isotopes (C14). Generally, the abundance of the above-mentioned isotope is not greater than its abundance in the natural environment, but it can also be prepared by using reaction raw materials containing the isotope to obtain isotopical substituted compounds with an abundance higher than natural abundance, such as deuterated compounds, etc. In a preferred embodiment, the abundance of deuterium atoms in a deuterated compound is >99%.

Tetrahydroisoquinoline Compounds Represented by Formula (I)

The present invention provides a tetrahydroisoquinoline compound represented by the general formula (I), enantiomers, diastereomers, racemates and mixtures or pharmaceutically acceptable salts thereof,

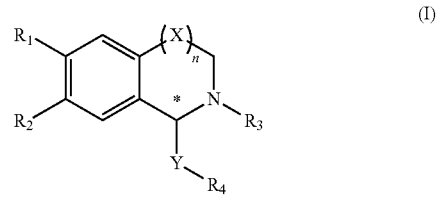

(I)

wherein the definition of each group is as described above.

In another preferred example, n, X, Y, $R_1$, $R_2$, $R_3$ and $R_4$ are each independently the corresponding group which corresponds to each specific compound in the example.

In particular, the tetrahydroisoquinoline compounds of the present invention are preferably selected from the compounds shown in table A below:

TABLE A

| No. | Name | Structure |
|---|---|---|
| A1 | 1-(2-(1H-indol-3-yl)ethyl)-6,7-dimethoxy-3,4-dihydroisoquinoline-2(1H)-formaldehyde | 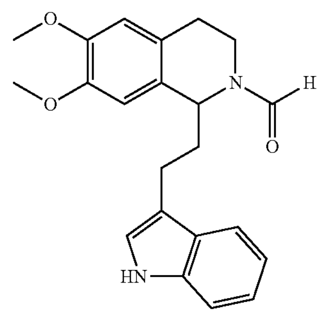 [SMILES: COc1cc2c(cc1OC)C(CCc1c[nH]c3ccccc13)N(C=O)CC2] |
| (S)-A1 | (S)-1-(2-(1H-indol-3-yl)ethyl)-6,7-dimethoxy-3,4-dihydroisoquinoline-2(1H)-formaldehyde | 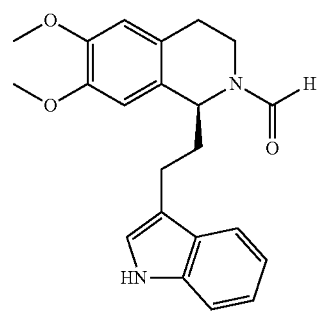 [SMILES: COc1cc2c(cc1OC)[C@H](CCc1c[nH]c3ccccc13)N(C=O)CC2] |
| (R)-A1 | (R)-1-(2-(1H-indol-3-yl)ethyl)-6,7-dimethoxy-3,4-dihydroisoquinoline-2(1H)-formaldehyde | 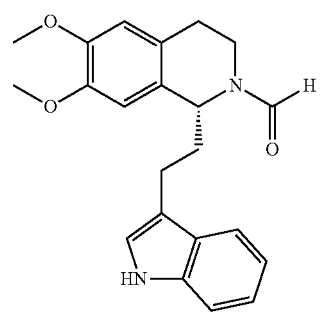 [SMILES: COc1cc2c(cc1OC)[C@@H](CCc1c[nH]c3ccccc13)N(C=O)CC2] |

TABLE A-continued

| No. | Name | Structure |
|---|---|---|
| A2 | 1-(2-(1H-indol-3-yl)ethyl)-7-(cyclopentyloxy)-6-metthoxy-3,4-dihydroisoquinoline-2(1H)-formaldehyde | 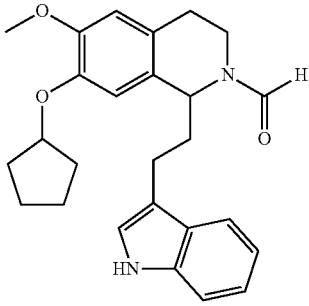 [SMILES: COc1cc2c(cc1OC1CCCC1)C(CCc1c[nH]c3ccccc13)N(C=O)CC2] |
| (S)-A2 | (S)-1-(2-(1H-indol-3-yl)ethyl)-7-(cyclopentyl-oxy)-6-methoxy-3,4-dihydroisoquinoline-2(1H)-formaldehyde | 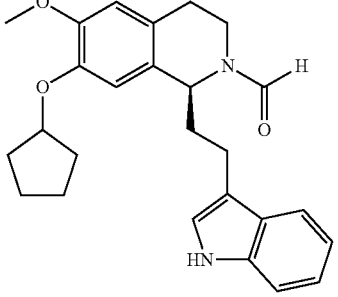 |
| (R)-A2 | (R)-1-(2-(1H-indol-3-yl)ethyl)-7-(cyclopentyl-oxy)-6-methoxy-3,4-dihydroisoquinoline-2(1H)-formaldehyde | 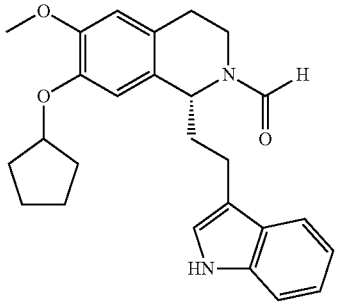 [SMILES: COc1cc2c(cc1OC1CCCC1)[C@@H](CCc1c[nH]c3ccccc13)N(C=O)CC2] |
| A3 | 1-(2-(1H-indol-3-yl)ethyl)-7-(cyclopropyl-methoxy)-6-methoxy-3,4-dihydroisoquinoline-2(1H)-formaldehyde | 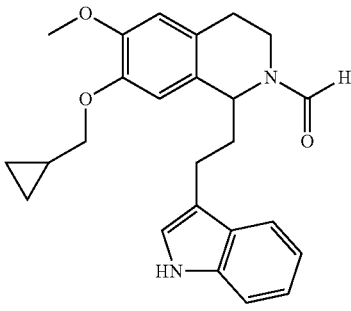 [SMILES: COc1cc2c(cc1OCC1CC1)C(CCc1c[nH]c3ccccc13)N(C=O)CC2] |
| (S)-A3 | (S)-1-(2-(1H-indol-3-yl)ethyl)-7-(cyclopropyl-methoxy)-6-methoxy-3,4-dihydroisoquinoline-2(1H)-formaldehyde | 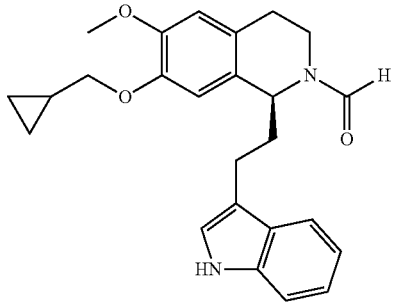 [SMILES: COc1cc2c(cc1OCC1CC1)[C@H](CCc1c[nH]c3ccccc13)N(C=O)CC2] |

TABLE A-continued

| No. | Name | Structure |
|---|---|---|
| (R)-A3 | (R)-1-(2-(1H-indol-3-yl)ethyl)-7-(cyclopropyl-methoxy)-6-methoxy-3,4-dihydroisoquinoline-2(1H)-formaldehyde | 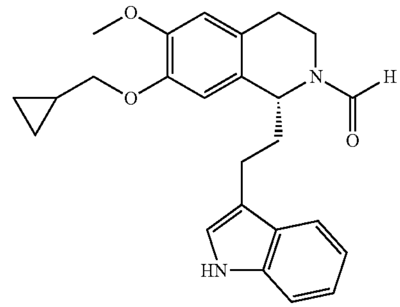 [SMILES: COc1cc2c(cc1OCC1CC1)[C@@H](CCc1c[nH]c3ccccc13)N(C=O)CC2] |
| A4 | 1-(2-(1H-indol-3-yl)ethyl)-7-ethoxy-6-methoxy-3,4-dihydroisoquinoline-2(1H)-formaldehyde | 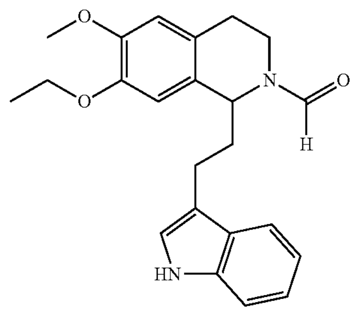 |
| (S)-A4 | (S)-1-(2-(1H-indol-3-yl)ethyl)-7-ethoxy-6-methoxy-3,4-dihydroisoquinoline-2(1H)-formaldehyde | 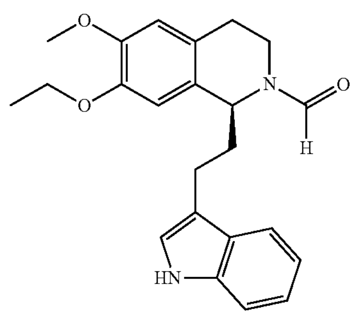 [SMILES: CCOc1cc2c(cc1OC)CCN(C=O)[C@H]2CCc1c[nH]c2ccccc12] |
| (R)-A4 | (R)-1-(2-(1H-indol-3-yl)ethyl)-7-ethoxy-6-methoxy-3,4-dihydroisoquinoline-2(1H)-formaldehyde | 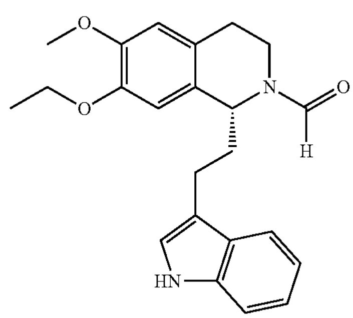 |
| A5 | 1-(2-(1H-indol-3-yl)ethyl)-7-(benzyloxy)-6-methoxy-3,4-dihydroisoquinoline-2(1H)-formaldehyde | 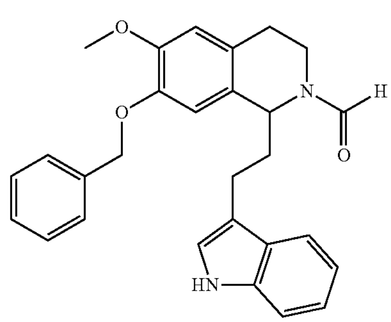 |

TABLE A-continued

| No. | Name |
|---|---|
| (S)-A5 | (S)-1-(2-(1H-indol-3-yl)ethyl)-7-(benzyloxy)-6-methoxy-3,4-dihydroisoquine-2(1H)-formaldehyde |
| (R)-A5 | (R)-1-(2-(1H-indol-3-yl)ethyl)-7-(benzyloxy)-6-methoxy-3,4-dihydroisoquine-2(1H)-formaldehyde |
| A6 | 1-(2-(1H-indol-3-yl)ethyl)-7-(2-(dimethylamino)ethoxy)-6-methoxy-3,4-dihydroisoquinoline-2(1H)-formaldehyde |
| (S)-A6 | (S)-1-(2-(1H-indol-3-yl)ethyl)-7-(2-(dimethylamino)ethoxy)-6-methoxy-3,4-dihydroisoquinoline-2(1H)-formaldehyde |
| (R)-A6 | (S)-1-(2-(1H-indol-3-yl)ethyl)-7-(2-(dimethylamino)ethoxy)-6-methoxy-3,4-dihydroisoquinoline-2(1H)-formaldehyde |

TABLE A-continued

| No. | Name | Structure |
|---|---|---|
| A7 | 3-((1-(2-(1H-indol-3-yl)ethyl)-2-formyl-6-methoxy-1,2,3,4-tetrahydroisoquinoline-7-yl)oxo)propionic acid | 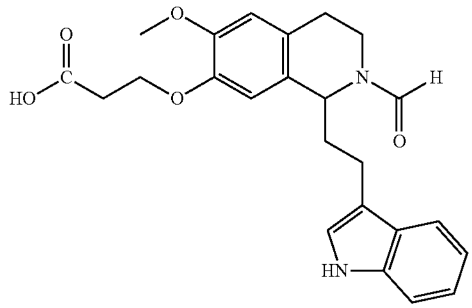 |
| (S)-A7 | (S)-3-((1-(2-(1H-idnol-3-yl)ethyl)-2-formyl-6-methoxy-1,2,3,4-tetrahydroisoquinolin-7-yl)oxo)propionic acid | 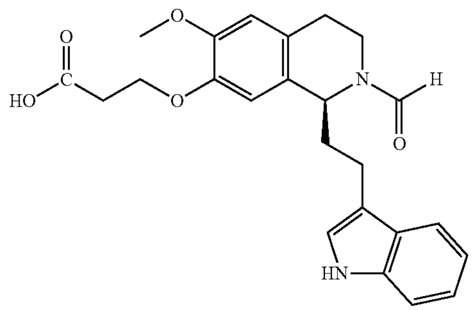 [SMILES: COc1cc2c(cc1OCCC(=O)O)[C@H](CCc1c[nH]c3ccccc13)N(C=O)CC2] |
| (R)-A7 | (R)-3-((1-(2-(1H-indol-3-yl)ethyl)-2-formyl-6-methoxy-1,2,3,4-tetrahydroisoquinolin-7-yl)oxo)propionic acid | 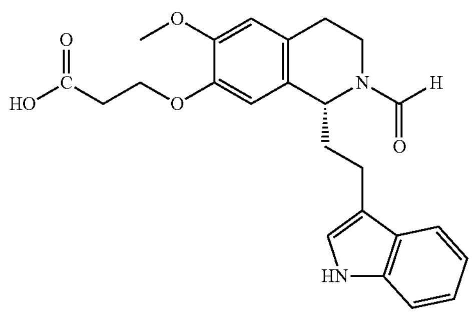 |
| A8 | 1-(2-(1H-indol-3-yl)ethyl)-7-ethoxy-6-(methoxy-$d_3$)-3,4-dihydroisoquinoline-2(1H)-formaldehyde | 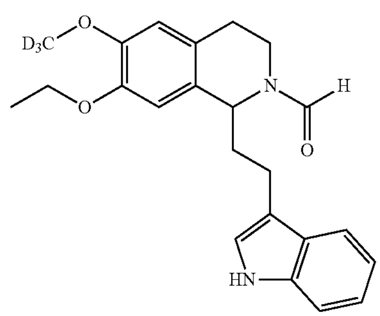 [SMILES: [2H]C([2H])([2H])Oc1cc2c(cc1OCC)C(CCc1c[nH]c3ccccc13)N(C=O)CC2] |
| (S)-A8 | (S)-1-(2-(1H-indol-3-yl)ethyl)-7-ethoxy-6-(methoxy-$d_3$)-3,4-dihydroisoquinoline-2(1H)-formaldehyde | 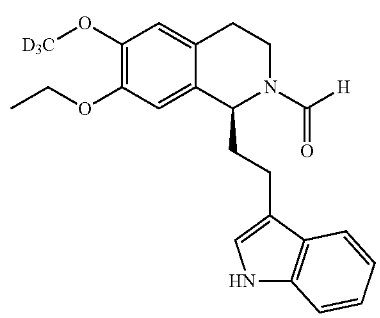 [SMILES: [2H]C([2H])([2H])Oc1cc2c(cc1OCC)[C@H](CCc1c[nH]c3ccccc13)N(C=O)CC2] |

TABLE A-continued

| No. | Name | Structure |
|---|---|---|
| (R)-A8 | (R)-1-(2-(1H-indol-3-yl)ethyl)-7-ethoxy-6-(methoxy-d$_3$)-3,4-dihydroisoquinoline-2(1H)-formaldehyde | 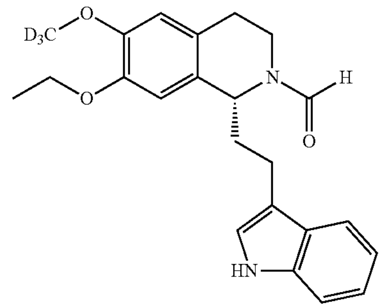 |
| B1 | (1-(2-(1H-indol-3-yl)ethyl)-6,7-dimethoxy-3,4-dihydroisoquinoline-2-(1H)-yl)(pyridin-4-yl)methanone | 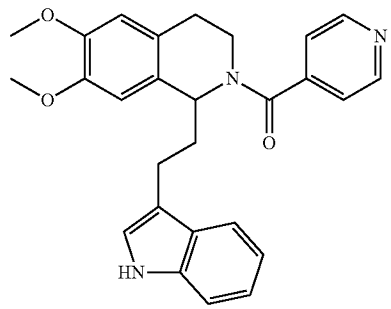 |
| (S)-B1 | (S)-(1-(2-(1H-idnol-3-yl)ethyl)-6,7-dimethoxy-3,4-dihydroisoquinoline-2(1H)-yl)(pyridin-4-yl)methanone | 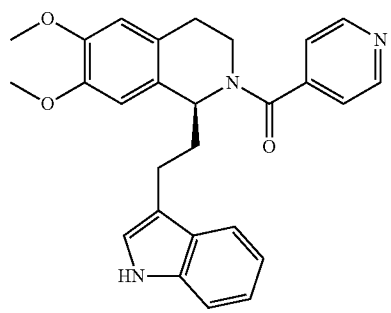 [SMILES: COc1cc2c(cc1OC)[C@H](CCc1c[nH]c3ccccc13)N(C(=O)c1ccncc1)CC2] |
| (R)-B1 | (R)-(1-(2-(1H-indol-3-yl)ethyl)-6,7-dimethoxy-3,4-dihydroisoquinoline-2(1H)-yl)(pyridin-4-yl)methanone | 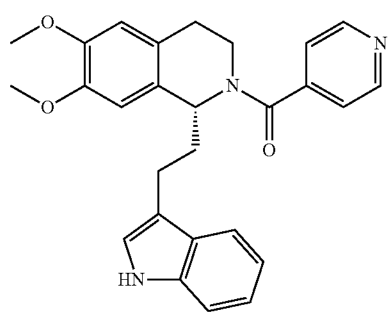 |
| B2 | 1-(2-(1H-indol-3-yl)ethyl)-6,7-dimethoxy-2-(2-methoxyethyl)-1,2,3,4-tetrahydroisoquinoline | 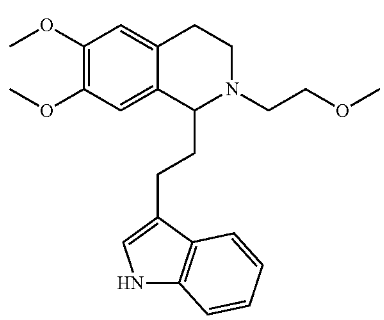 |

TABLE A-continued

| No. | Name |
|---|---|
| (S)-B2 | (S)-1-(2-(1H-indol-3-yl)ethyl)-6,7-dimethoxy-2-(2-(methoxyethyl)-1,2,3,4-tetrahydroisoquinoline |
| (R)-B2 | (R)-1-(2-(1H-indol-3-yl)ethyl)-6,7-dimethoxy-2-(2-methoxyethyl)-1,2,3,4-tetrahydroisoquinoline |
| B3 | (1-(2-(1H-indol-3-yl)ethyl)-6,7-dimethoxy-3,4-dihydroisoquinoline-2(1H)-yl)(tetrahydro-2H-pyran-4-yl)ketone |
| (S)-B3 | (S)-(1-(2-(1H-indol-3-yl)ethyl)-6,7-dimethoxy-3,4-dihydroisoquinoline-2(1H)-yl)(tetrahydro-2H-pyran-4-yl)methanone |
| (R)-B3 | (R)-(1-(2-(1H-indol-3-yl)ethyl)-6,7-dimethoxy-3,4-dihydroixoquinoline-2(1H)-yl)(tetrahydro-2H-pyran-4-yl)methanone |

TABLE A-continued

| No. | Name | Structure |
|---|---|---|
| B4 | 1-(1-(2-(1H-indol-3-yl)ethyl)-6,7-dimethoxy-3,4-dihydroisoquinoline-2(1H)-yl)-2-methoxyethane-1-one | 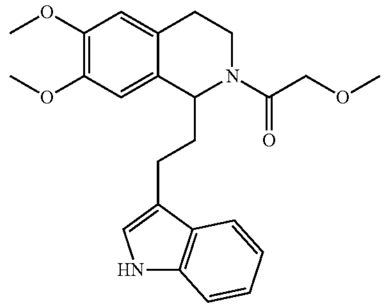 |
| (S)-B4 | (S)-1-(1-(2-(1H-indol-3-yl)ethyl)-6,7-dimethoxy-3,4-dihydroisoquinoline-2(1H)-yl)-2-methoxyethane-1-one | 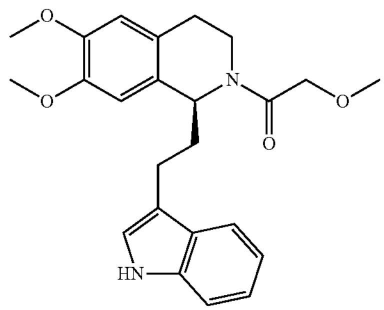 |
| (R)-B4 | (R)-1-(1-(2-(1H-indol-3-yl)ethyl)-6,7-dimethoxy-3,4-dihydroisoquinoline-2(1H)-yl)-2-methoxyethane-1-one | 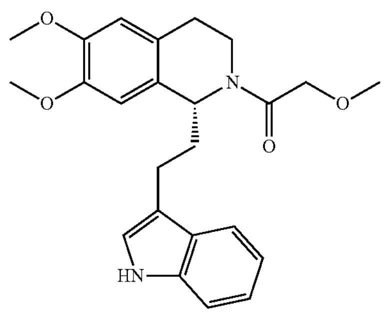 |
| B5 | methyl-2-(1-(2-(1H-indol-3-yl)ethyl)-6,7-dimethoxy-3,4-dihydroisoquinoline-2(1H)-yl) acetate | 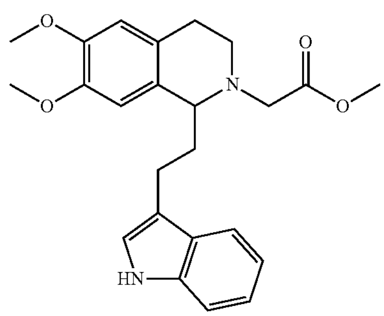 |
| (S)-B5 | (S)-methyl-2-(1-(2-(1H-indol-3-yl)ethyl)-6,7-dimethoxy-3,4-dihydroisoquinoine-2(1H)-yl) acetate | 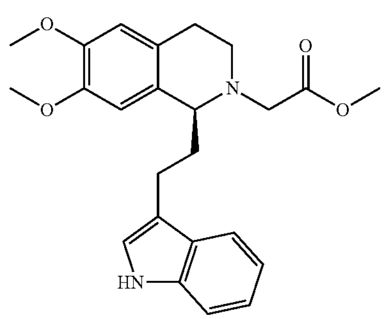 |

TABLE A-continued

| No. | Name | Structure |
|---|---|---|
| (R)-B5 | (R)-methyl-2-(1-(2-(1H-indol-3-yl)ethyl)-6,7-dimethoxy-3,4-dihydroisoquinoline-2(1H)-yl)acetate | 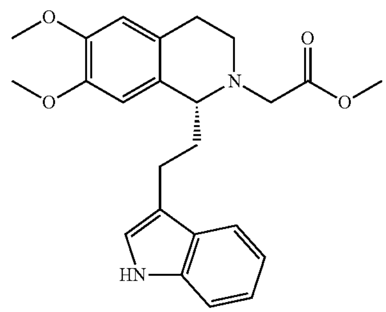 |
| B6 | 1-(2-(1H-indol-3-yl)ethyl)-6,7-dimethoxy-2-(2,2,2-trifluoroethyl)-1,2,3,4-tetrahydroisoquinoline | 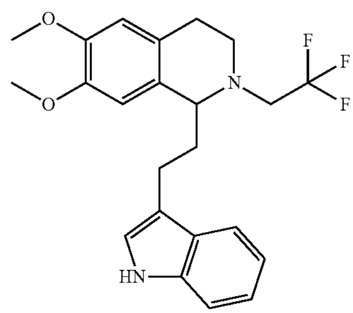 [SMILES: COc1cc2c(cc1OC)C(CCc1c[nH]c3ccccc13)N(CC(F)(F)F)CC2] |
| (S)-B6 | (S)-1-(2-(1H-indol-3-yl)ethyl)-6,7-dimethoxy-2-(2,2,2-trifluoroethyl)-1,2,3,4-tetrahydroisoquinoline | 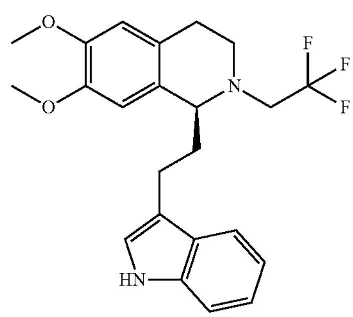 [SMILES: COc1cc2c(cc1OC)[C@H](CCc1c[nH]c3ccccc13)N(CC(F)(F)F)CC2] |
| (R)-B6 | (R)-1-(2-(1H-indol-3-yl)ethyl)-6,7-dimethoxy-2-(2,2,2-trifluoroethyl)-1,2,3,4-tetrahydroisoquinoline | 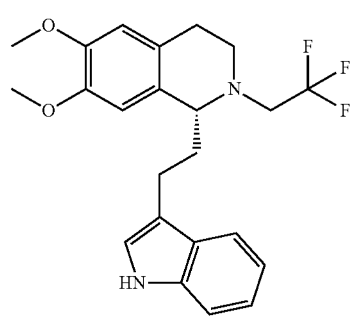 [SMILES: COc1cc2c(cc1OC)[C@@H](CCc1c[nH]c3ccccc13)N(CC(F)(F)F)CC2] |
| B7 | 1-(2-(1H-indol-3-yl)ethyl)-6,7-dimethoxy-2-((tetrahydro-2H-pyran-4-yl)methyl)-1,2,3,4-tetrahydroisoquinoline | 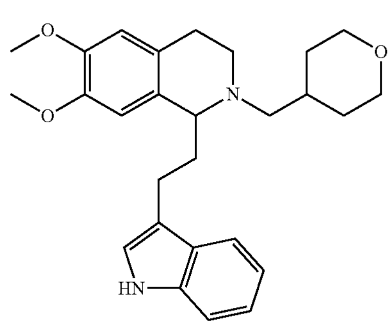 [SMILES: COc1cc2c(cc1OC)C(CCc1c[nH]c3ccccc13)N(CC1CCOCC1)CC2] |

TABLE A-continued

| No. | Name |
|---|---|
| (S)-B7 | (S)-1-(2-(1H-indol-3-yl)ethyl)-6,7-dimethoxy-2-((tetrahydro-2H-pyran-4-yl)methyl)-1,2,3,4-tetrahydroisoquinoline |
| (R)-B7 | (R)-1-(2-(1H-indol-3-yl)ethyl)-6,7-dimethoxy-2-((tetrahydro-2H-pyran-4-yl)methyl-1,2,3,4-tettrahydroisoquinoline |
| B8 | 1-(2-(1H-indol-3-yl)ethyl)-6,7-dimethoxy-2-(2-(methylsulfonyl)ethyl)-1,2,3,4-tetrahydroisoquinoline |
| (S)-B8 | (S)-1-(2-(1H-indol-3-yl)ethyl)-6,7-dimethoxy-2-(2-(methylsulfonyl)ethyl)-1,2,3,4-tetrahydroisoquinoline |
| (R)-B8 | (R) 1-(2-(1H-indol-3-yl)ethyl)-6,7-dimethoxy-2-(2-methylsulfonyl)ethyl-1,2,3,4-tetrahydroisoquinoline |

TABLE A-continued

| No. | Name | Structure |
|---|---|---|
| B9 | 1-(2-(1H-indol-3-yl)ethyl)-6,7-dimethoxy-3,4-dihydroisoquinolin-2(1H)-yl)-2-(methanesulfonyl)ethane-1-one | 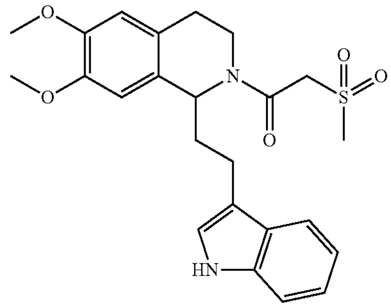 [SMILES: COc1cc2c(cc1OC)C(CCc1c[nH]c3ccccc13)N(C(=O)CS(C)(=O)=O)CC2] |
| (S)-B9 | (S)-1-(2-(1H-indol-3-yl)ethyl)-6,7-dimethoxy-3,4-dihydroisoquinoline-2(1H)-yl)-2-(methanesulfonyl)ethane-1-one | 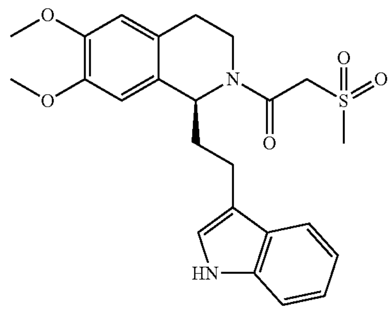 [SMILES: COc1cc2c(cc1OC)[C@H](CCc1c[nH]c3ccccc13)N(C(=O)CS(C)(=O)=O)CC2] |
| (R)-B9 | (R)-1-(2-(1H-indol-3-yl)ethyl)-6,7-dimethoxy-3,4-dihydroisoquinoline-2(1H)-yl)-2-(methanesulfonyl)ethane-1-one | 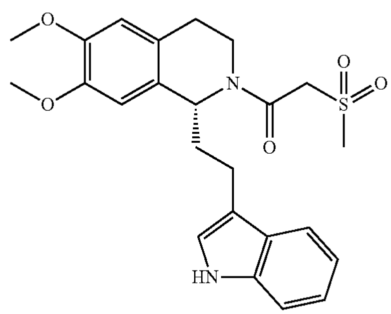 [SMILES: COc1cc2c(cc1OC)[C@@H](CCc1c[nH]c3ccccc13)N(C(=O)CS(C)(=O)=O)CC2] |
| B10 | 1-(1-(2-(1H-indol-3-yl)ethyl)-6,7-dimethoxy-3,4-diyhydroisoquinoline-2(1H)-yl)-2,2,2-trifluoroethane-1-one | 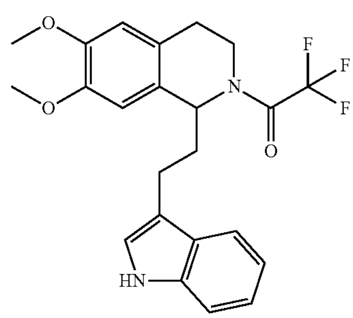 [SMILES: COc1cc2c(cc1OC)C(CCc1c[nH]c3ccccc13)N(C(=O)C(F)(F)F)CC2] |
| (S)-B10 | (S)-1-(1-(2-(1H-indol-3-yl)ethyl)-6,7-dimethoxy-3,4-dihydroisoquinoline-2(1H)-yl)-2,2,2-trifluoroethane-1-one | 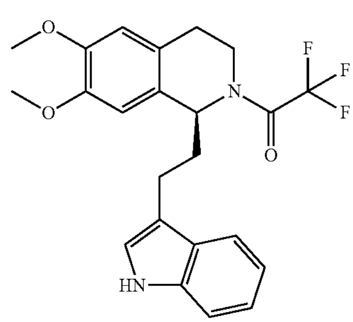 [SMILES: COc1cc2c(cc1OC)[C@H](CCc1c[nH]c3ccccc13)N(C(=O)C(F)(F)F)CC2] |

TABLE A-continued

| No. | Name |
|---|---|
| (R)-B10 | (R) 1-(1-(2-(1H-indol-3-yl)ethyl)-6,7-dimethoxy-3,4-dihydroisoquinoline-2(1H)-yl)-2,2,2-trifluoroethane-1-one |
| B11 | 1-(1-(2-(1H-indol-3-yl)ethyl)-6,7-dimethoxy-3,4-dihydroisoquinoline-2(1H)-yl)-2-methoxyethane-1-one |
| (S)-B11 | (S)-1-(1-(2-(1H-indol-3-yl)ethyl)-6,7-dimethoxy-3,4-dihydroisoquinoline-2(1H)-yl)-2-methoxyethane-1-one |
| (R)-B11 | (R)-1-(1-(2-(1H-indol-3-yl)ethyl)-6,7-dimethoxy-3,4-dihydroisoquinoline-2(1H)-yl)-2-methoxyethane-1-one |
| B12 | 1-(1-(2-(1H-indol-3-yl)ethyl)-7-ethoxy-6-methoxy-3,4-dihydroisoquinoline-2(1H)-yl)-2-methoxyethane-1-one |

TABLE A-continued

| No. | Name |
|---|---|
| (S)-B12 | (S)-1-(1-(2-(1H-indol-3-yl)ethyl)-7-ethoxy-6-methoxy-3,4-dihydroisoquinoline-2(1H)-yl)-2-methoxyethane-1-one |
| (R)-B12 | (R)-1-(1-(2-(1H-indol-3-yl)ethyl)-7-ethoxy-6-methoxy-3,4-dihydroisoquinoline-2(1H)-yl)-2-methoxyethane-1-one |
| B13 | 1-(2-(1H-indol-3-yl)ethyl)-6,7-dimethoxy-2-(methylsulfonyl)-1,2,3,4-tetrahydroisoquinoline |
| (S)-B13 | (S)-1-(2-(1H-indol-3-yl)ethyl)-6,7-dimethoxy-2-(methylsulfonyl)-1,2,3,4-tetrahydroisoquinoline |
| (R)-B13 | (R)-1-(2-(1H-indol-3-yl)ethyl)-6,7-dimethoxy-2-(methylsulfonyl)ethyl)-1,2,3,4-tetrahydroisoquinoline |

TABLE A-continued

| No. | Name |
|---|---|
| B14 | (1-(2-(1H-indol-3-yl)ethyl)-6,7-dimethoxy-3,4-dihydroisoquinoline-2(1H)-yl)(morpholino)ketone |
| (S)-B14 | (S)-(1-(2-(1H-indol-3-yl)ethyl)-6,7-dimethoxy-3,4-dihydroisoquinoline-2(1H)-yl)(morpholino)ketone |
| (R)-B14 | (R)-(1-(2-(1H-indol-3-yl)ethyl)-6,7-dimethoxy-3,4-dihydroisoquinoline-2(1H)-yl)(morpholino)ketone |
| B15 | methyl-1-(2-(1H-indol-3-yl)ethyl)-6,7-dimethoxy-3,4-dihydroisoquinoline-2(1H)-carboxylate |
| (S)-B15 | (S)-methyl-1-(2-(1H-indol-3-yl)ethyl)-6,7-dimethoxy-3,4-dihydroisoquinoline-2(1H)-carboxylate |

TABLE A-continued

| No. | Name | Structure |
|---|---|---|
| (R)-B15 | (R)-methyl-1-(2-(1H-indol-3-yl)ethyl)-6,7-dimethoxy-3,4-dihydroisoquinolline-2(1H)-carboxylate | 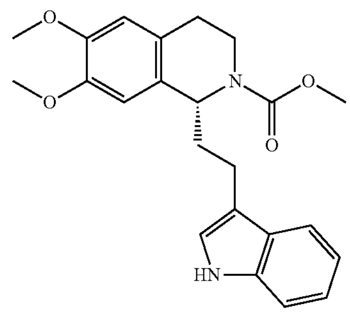 |
| B16 | 2-(1-(2-(1H-indol-3-yl)ethyl)-2-ethoxy-6-methoxy-3,4-dihydroisoquinoline-2(1H)-yl)acetamide | 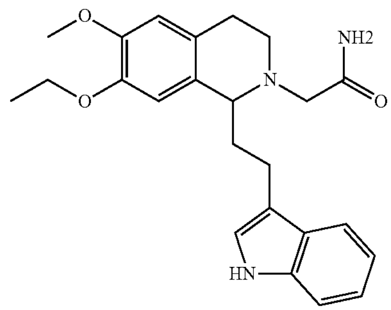 [SMILES: CCOc1cc2c(cc1OC)CCN(CC(N)=O)C2CCc1c[nH]c2ccccc12] |
| (S)-B16 | (S)-2-(1-(2-(1H-indol-3-yl)ethyl)-7-ethoxy-6-methoxy-3,4-dihydroisoquinoline-2(1H)-yl)acetamide | 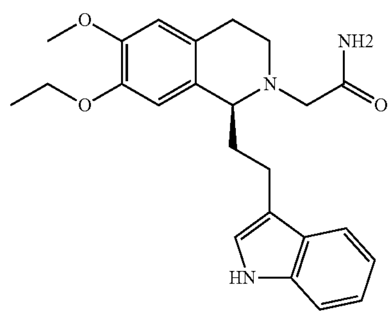 [SMILES: CCOc1cc2c(cc1OC)CCN(CC(N)=O)[C@H]2CCc1c[nH]c2ccccc12] |
| (R)-B16 | (R)-2-(1-(2-(1H-indol-3-yl)ethyl)-7-ethoxy-6-methoxy-3,4-dihydroisoquinoline-2(1H)-yl)acetamide | 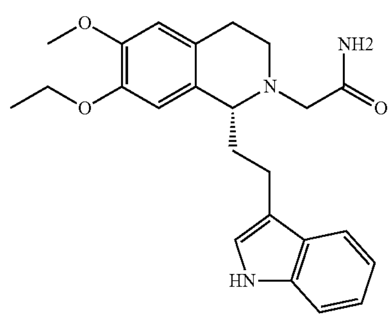 [SMILES: CCOc1cc2c(cc1OC)CCN(CC(N)=O)[C@@H]2CCc1c[nH]c2ccccc12] |
| C1 | 1-(2-(5-bromo-1H-indol-3-yl)ethyl)-7-(cyclopentyloxy)-6-methoxy-3,4-dihydroisoquinoline-2(1H)-formaldehyde | 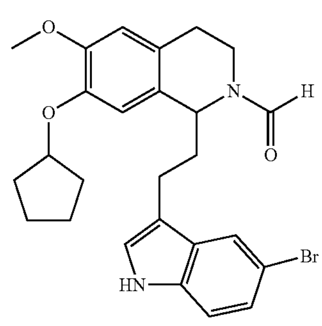 [SMILES: COc1cc2c(cc1OC1CCCC1)C(CCc1c[nH]c3ccc(Br)cc13)N(C=O)CC2] |

TABLE A-continued

| No. | Name | Structure |
|---|---|---|
| (S)-C1 | (S)-1-(2-(5-bromo-1H-indol-3-yl)ethyl)-7-(cyclopentyloxy)-6-methoxy-3,4-dihydroisoquinoline-2(1H)-formaldehyde | 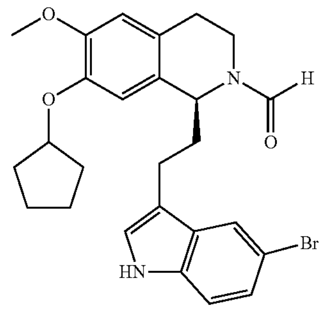 [SMILES: COc1cc2c(cc1OC1CCCC1)[C@H](CCc1c[nH]c3ccc(Br)cc13)N(C=O)CC2] |
| (R)-C1 | (R)-1-(2-(5-bromo-1H-indol-3-yl)ethyl)-7-(cyclopentyloxy)-6-methoxy-3,4-dihydroisoquinoline-2(1H)-formaldehyde | 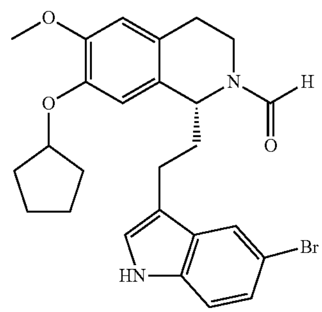 [SMILES: COc1cc2c(cc1OC1CCCC1)[C@@H](CCc1c[nH]c3ccc(Br)cc13)N(C=O)CC2] |
| C2 | 7-(cyclopentyloxy)-6-methoxy-1-(2-(5-methyl-1H-indol-3-yl)ethyl)-3,4-dihydroisoquinoline-2(1H)-formaldehyde | 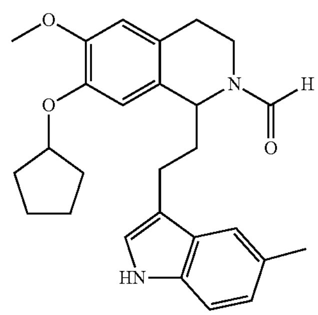 [SMILES: COc1cc2c(cc1OC1CCCC1)C(CCc1c[nH]c3ccc(C)cc13)N(C=O)CC2] |
| (S)-C2 | (S)-7-(cyclopentyloxy)-6-methoxy-1-(2-(5-methyl-1H-indol-3-yl)ethyl)-3,4-dihydroisoquinoline-2(1H)-formaldehyde | 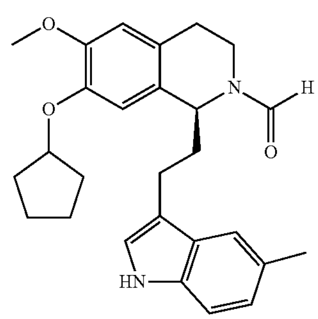 [SMILES: COc1cc2c(cc1OC1CCCC1)[C@H](CCc1c[nH]c3ccc(C)cc13)N(C=O)CC2] |
| (R)-C2 | (R)-7-(cyclopentyloxy)-6-methoxy-1-(2-(5-methyl-1H-indol-3-yl)ethyl)-3,4-dihydroisoquinoline-2(1H)-formaldehyde | 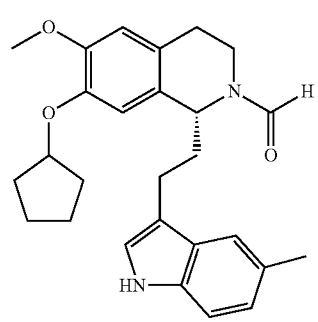 [SMILES: COc1cc2c(cc1OC1CCCC1)[C@@H](CCc1c[nH]c3ccc(C)cc13)N(C=O)CC2] |

TABLE A-continued

| No. | Name | Structure |
|---|---|---|
| C3 | 7-(cyclopentyloxy)-6-methoxy-1-(2-(6-methyl-1H-indol-3-yl)ethyl)-3,4-dihydroisoquinoline-2(1H)-formaldehyde | 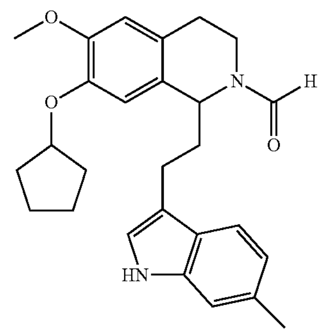 [SMILES: COc1cc2c(cc1OC1CCCC1)C(CCc1c[nH]c3cc(C)ccc13)N(C=O)CC2] |
| (S)-C3 | (S)-7-(cyclopentyloxy)-6-methoxy-1-(2-(6-methyl-1H-indol-3-yl)ethyl)-3,4-dihydroisoquinoline-2(1H)-formaldehyde | 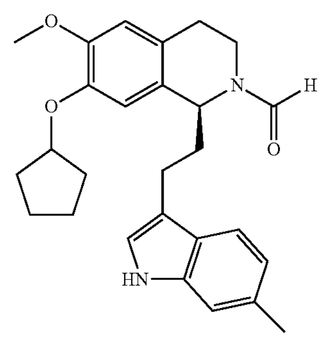 [SMILES: COc1cc2c(cc1OC1CCCC1)[C@H](CCc1c[nH]c3cc(C)ccc13)N(C=O)CC2] |
| (R)-C3 | (R)-7-(cyclopentyloxy)-6-methoxy-1-(2-(6-methyl-1H-indol-3-yl)ethyl)-3,4-dihydroisoquinoline-2(1H)-formaldehyde | 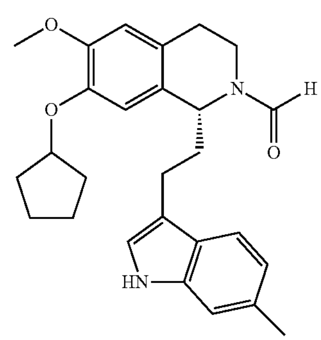 [SMILES: COc1cc2c(cc1OC1CCCC1)[C@@H](CCc1c[nH]c3cc(C)ccc13)N(C=O)CC2] |
| C4 | 7-(cyclopropylmethoxy)-6-methoxy-1-(2-(6-methyl-1H-indol-3-yl)ethyl)-3,4-dihydroisoquinoline-2(1H)-formaldehyde | 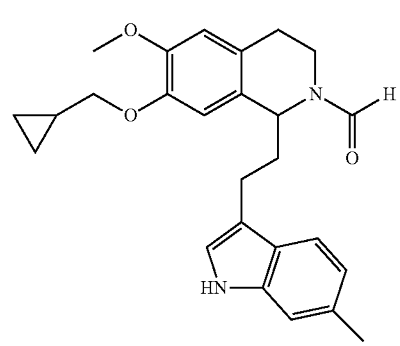 [SMILES: COc1cc2c(cc1OCC1CC1)C(CCc1c[nH]c3cc(C)ccc13)N(C=O)CC2] |

TABLE A-continued

| No. | Name | Structure |
|---|---|---|
| (S)-C4 | (S)-7-(cyclopropylmethoxy)-6-methoxy-1-(2-(6-methyl-1H-indol-3-yl)ethyl)-3,4-dihydroisoquinoline-2(1H)-formaldehyde | 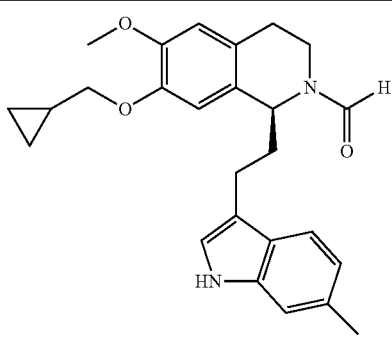 |
| (R)-C4 | (R)-7-(cyclopropylmethoxy)-6-methoxy-1-(2-(6-methyl-1H-indol-3-yl)ethyl)-3,4-dihydroisoquinoline-2(1H)-formaldehyde | 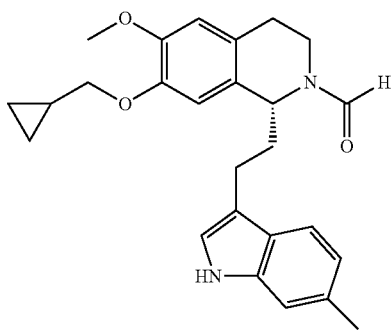 [SMILES: COc1cc2c(cc1OCC1CC1)[C@@H](CCc1c[nH]c3cc(C)ccc13)N(C=O)CC2] |
| C5 | 6,7-dimethoxy-1-(2-(6-methyl-1H-indol-3-yl)ethyl)-3,4-dihydroisoquinoline-2(1H)-formaldehyde | 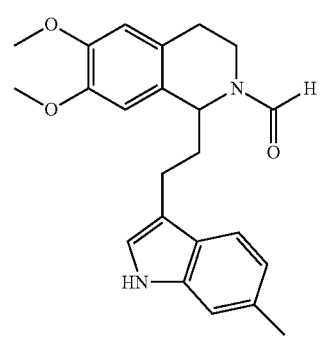 [SMILES: COc1cc2c(cc1OC)C(CCc1c[nH]c3cc(C)ccc13)N(C=O)CC2] |
| (S)-C5 | (S)-6,7-dimethoxy-1-(2-(6-methyl-1H-indol-3-yl)ethyl)-3,4-dihydroisoquinoline-2(1H)-formaldehyde | 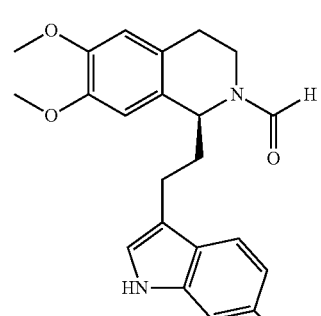 |

TABLE A-continued

| No. | Name |
|---|---|
| (R)-C5 | (R)-6,7-dimethoxy-1-(2-(6-methyl-1H-indol-3-yl)ethyl)-3,4-dihydroisoquinoline-2(1H)-formaldehyde |
| C6 | 1-(2-(6-fluoro-1H-indol-3-yl)ethyl)-6,7-dimethoxy-3,4-dihydroisoquinoline-2(1H)-formaldehyde |
| (S)-C6 | (S)-1-(2-(6-fluoro-1H-indol-3-yl)ethyl)-6,7-dimethoxy-3,4-dihydroisoquinoline-2(1H)-formaldehyde |
| (R)-C6 | (R)-1-(2-(6-fluoro-1H-indol-3-yl)ethyl)-6,7-dimethoxy-3,4-dihydroisoquinoline-2(1H)-formaldehyde |

TABLE A-continued

| No. | Name | Structure |
|---|---|---|
| C7 | 7-ethoxy-6-methoxy-1-(2-(6-methyl-1H-indol-3-yl)ethyl)-3,4-dihydroisoquinoline-2(1H)-formaldehyde | 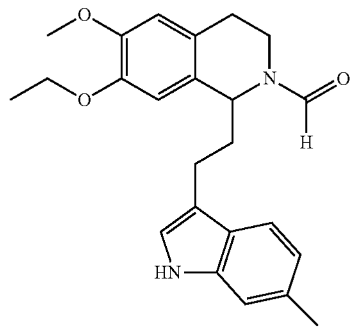 [SMILES: CCOc1cc2c(cc1OC)CCN(C=O)C2CCc1c[nH]c2cc(C)ccc12] |
| (S)-C7 | (S)-7-ethoxy-6-methoxy-1-(2-(6-methyl-1H-indol-3-yl)ethyl)-3,4-dihydroisoquinoline-2(1H)-formaldehyde | 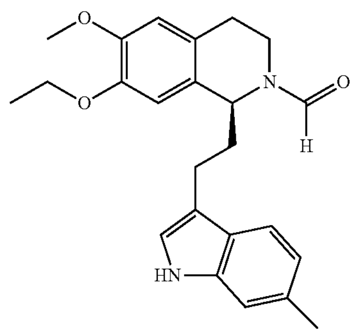 [SMILES: CCOc1cc2c(cc1OC)CCN(C=O)[C@H]2CCc1c[nH]c2cc(C)ccc12] |
| (R)-C7 | (R)-7-ethoxy-6-methoxy-1-(2-(6-methyl-1H-indol-3-yl)ethyl)-3,4-dihydroisoquinoline-2(1H)-formaldehyde | 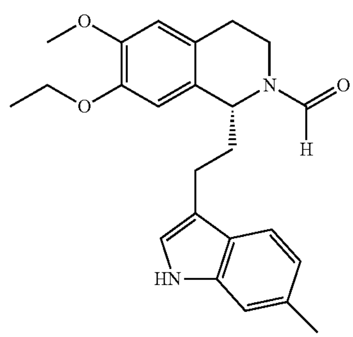 [SMILES: CCOc1cc2c(cc1OC)CCN(C=O)[C@@H]2CCc1c[nH]c2cc(C)ccc12] |
| C8 | 7-ethoxy-6-methoxy-1-(2-(5-methoxy-1H-indol-3-yl)ethyl)-3,4-dihydroisoquinoline-2(1H)-formaldehyde | 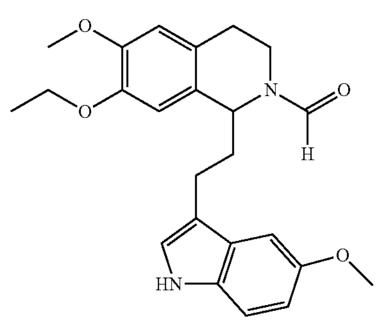 [SMILES: CCOc1cc2c(cc1OC)CCN(C=O)C2CCc1c[nH]c2ccc(OC)cc12] |

TABLE A-continued

| No. | Name | Structure |
|---|---|---|
| (S)-C8 | (S)-7-ethoxy-6-methoxy-1-(2-(5-methoxy-1H-indol-3-yl)ethyl)-3,4-dihydroisoquinoline-2(1H)-formaldehyde | 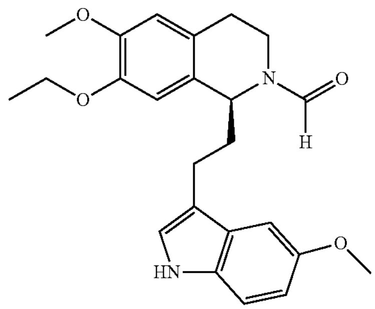 [SMILES: CCOc1cc2c(cc1OC)CCN(C=O)[C@H]2CCc1c[nH]c2ccc(OC)cc12] |
| (R)-C8 | (R)-7-ethoxy-6-methoxy-11-(2-(5-methoxy-1H-indol-3-yl)ethyl)-3,4-dihydroisoquinoline-2(1H)-formaldehyde | 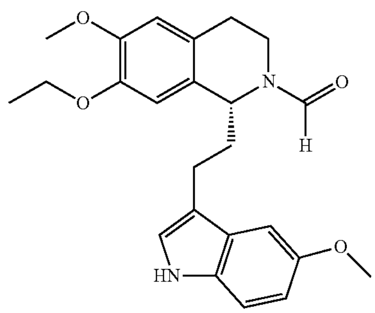 [SMILES: CCOc1cc2c(cc1OC)CCN(C=O)[C@@H]2CCc1c[nH]c2ccc(OC)cc12] |
| C9 | 1-((1H-indol-3-yl)methyl)-6,7-dimethoxy-3,4-dihydroisoquinoline-2(1H)-formaldehyde | 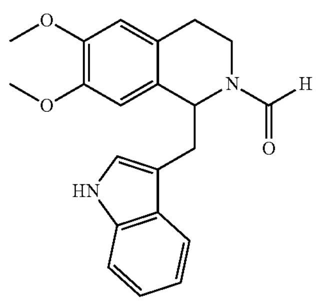 [SMILES: COc1cc2c(cc1OC)C(Cc1c[nH]c3ccccc13)N(C=O)CC2] |
| (S)-C9 | (S)-1-((1H-indol-3-yl)methyl)-6,7-dimethoxy-3,4-dihydroisoquinoline-2(1H)-formaldehyde | 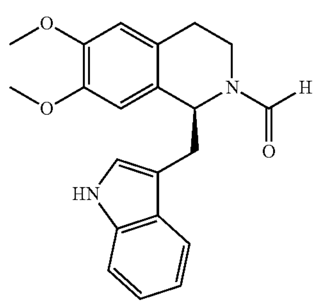 [SMILES: COc1cc2c(cc1OC)[C@H](Cc1c[nH]c3ccccc13)N(C=O)CC2] |
| (R)-C9 | (R)-1-((1H-indol-3-yl)methyl)-6,7-dimethoxy-3,4-dihydroisoquinoline-2(1H)-formaldehyde | 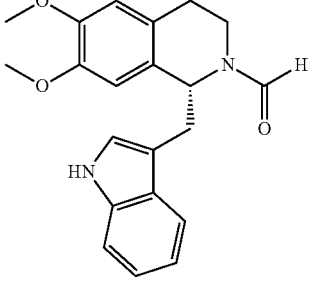 |

TABLE A-continued

| No. | Name | Structure |
|---|---|---|
| C10 | 1-((1H-indol-3-yl)methyl)-7-ethoxy-6-methoxy-3,4-dihydroisoquinoline-2(1H)-formaldehyde | 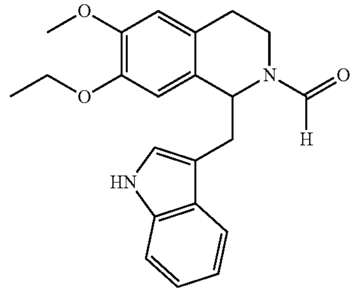 [SMILES: CCOc1cc2c(cc1OC)CCN(C=O)C2Cc1c[nH]c2ccccc12] |
| (S)-C10 | (S)-1-((1H-indol-3-yl)methyl)-7-ethoxy-6-methoxy-3,4-dihydroisoquinoline-2(1H)-formaldehyde | 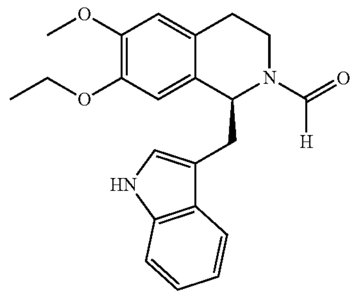 [SMILES: CCOc1cc2c(cc1OC)CCN(C=O)[C@H]2Cc1c[nH]c2ccccc12] |
| (R)-C10 | (R)-1-((1H-indol-3-yl)methyl)-7-ethoxy-6-methoxy-3,4-dihydroisoquinoline-2(1H)-formaldehyde | 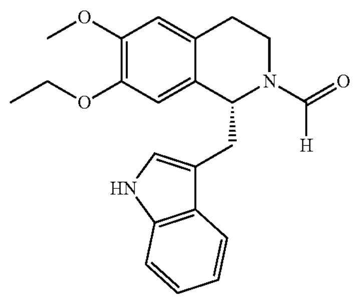 [SMILES: CCOc1cc2c(cc1OC)CCN(C=O)[C@@H]2Cc1c[nH]c2ccccc12] |
| C11 | 1-(1-((1H-indol-3-yl)methyl)-6,7-dimethoxy-3,4-dihydroisoquinoline-2(1H)-yl)-2-methoxyethane-1-one | 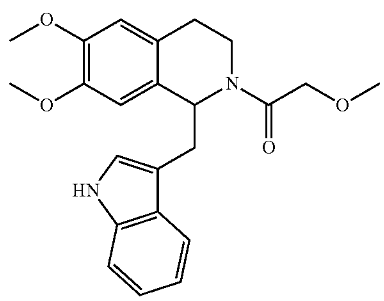 |
| (S)-C11 | (S)-1-(1-((1H-indol-3-yl)methyl)-6,7-dimethoxy-3,4-dihydroisoquinoline-2(1H)-yl)-2-methoxyethane-1-one | 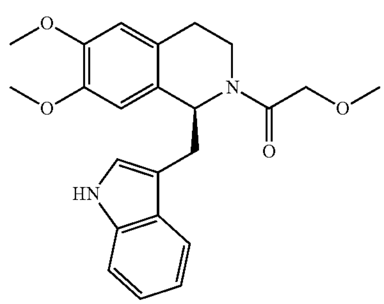 |

TABLE A-continued

| No. | Name | Structure |
|---|---|---|
| (R)-C11 | (R)-1-(1-((1H-indol-3-yl)methyl)-6,7-dimethoxy-3,4-dihydroisoquinoline-2(1H)-yl)-2-methoxyethane-1-one | 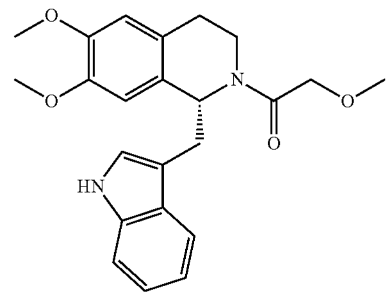 |
| C12 | 1-((1H-indol-3-yl)methyl)-6,7-dimethoxy-2-(2-(methylsulfonyl)ethyl)-1,2,3,4-tetrahydroisoquinoline | 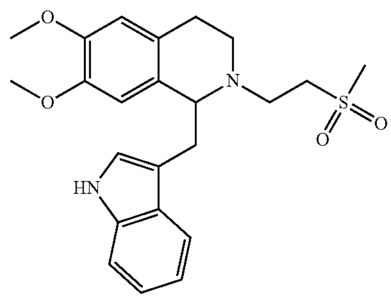 [SMILES: COc1cc2c(cc1OC)C(Cc1c[nH]c3ccccc13)N(CCS(C)(=O)=O)CC2] |
| (S)-C12 | (S)-1-((1H-indol-3-yl)methyl)-6,7-dimethoxy-2-(2-(methylsulfonyl)ethyl)-1,2,3,4-tetrahydroisoquinoline | 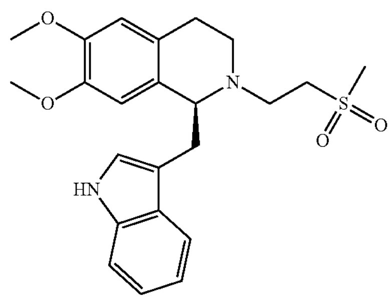 [SMILES: COc1cc2c(cc1OC)[C@H](Cc1c[nH]c3ccccc13)N(CCS(C)(=O)=O)CC2] |
| (R)-C12 | (R)-1-((1H-indol-3-yl)methyl)-6,7-dimethoxy-2-(2-(methylsulfonyl)ethyl)-1,2,3,4-tetrahydroisoquinoline | 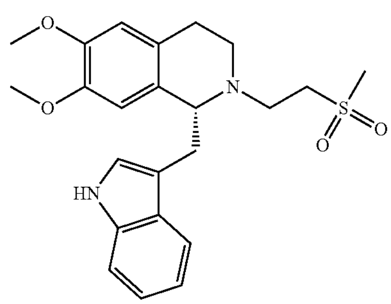 [SMILES: COc1cc2c(cc1OC)[C@@H](Cc1c[nH]c3ccccc13)N(CCS(C)(=O)=O)CC2] |
| C13 | 1-(1-((1H-indol-3-yl)methyl)-6,7-dimethoxy-3,4-dihydroisoquinoline-2(1H)-yl)-2-(methanesulfonyl)ethane-1-one | 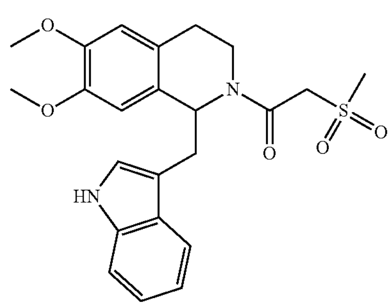 [SMILES: COc1cc2c(cc1OC)C(Cc1c[nH]c3ccccc13)N(C(=O)CS(C)(=O)=O)CC2] |

TABLE A-continued

| No. | Name | Structure |
|---|---|---|
| (S)-C13 | (S)-1-(1-((1H-indol-3-yl)methyl)-6,7-dimethoxy-3,4-dihydroisoquinoline-2(1H)-yl)-2-(methanesulfonyl)ethane-1-one | 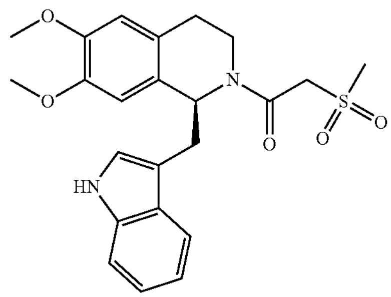 [SMILES: COc1cc2c(cc1OC)[C@H](Cc1c[nH]c3ccccc13)N(C(=O)CS(C)(=O)=O)CC2] |
| (R)-C13 | (R)-1-(1-((1H-indol-3-yl)methyl)-6,7-dimethoxy-3,4-dihydroisoquinoline-2(1H)-yl)-2-(methanesulfonyl)ethane-1-one | 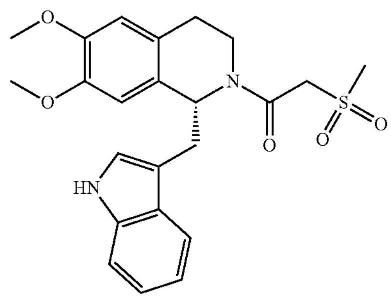 [SMILES: COc1cc2c(cc1OC)[C@@H](Cc1c[nH]c3ccccc13)N(C(=O)CS(C)(=O)=O)CC2] |
| C14 | 1-((1H-indol-3-yl)methyl)-7-ethoxy-6-methoxy-2-(2-(methylsulfonyl)ethyl)-1,2,3,4-tetrahydroisoquinoline | 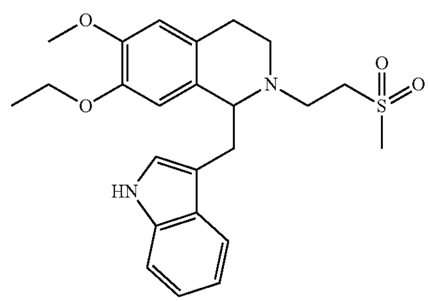 [SMILES: CCOc1cc2c(cc1OC)CCN(CCS(C)(=O)=O)C2Cc1c[nH]c2ccccc12] |
| (S)-C14 | (S)-1-((1H-indol-3-yl)methyl)-7-ethoxy-6-methoxy-2-(2-(methylsulfonyl)ethyl)-1,2,3,4-tetrahydroisoquinoline | 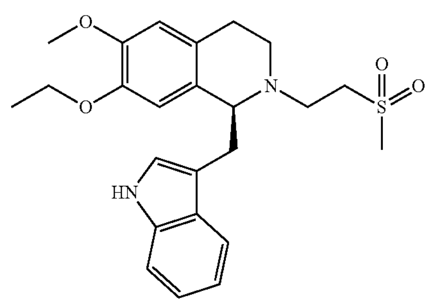 [SMILES: CCOc1cc2c(cc1OC)CCN(CCS(C)(=O)=O)[C@H]2Cc1c[nH]c2ccccc12] |
| (R)-C14 | (R)-1-((1H-indol-3-yl)methyl)-7-ethoxy-6-methoxy-2-(2-(methylsulfonyl)ethyl)-1,2,3,4-tetrahydroisoquinoline | 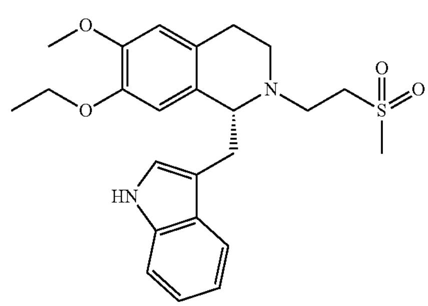 [SMILES: CCOc1cc2c(cc1OC)CCN(CCS(C)(=O)=O)[C@@H]2Cc1c[nH]c2ccccc12] |

TABLE A-continued

| No. | Name | Structure |
|---|---|---|
| C15 | 1-(1-((1H-indol-3-yl)methyl)-7-ethoxy-6-methoxy-3,4-dihydroisoquinoline-2(1H)-yl)-2-methanesulfonyl)ethane-1-one | 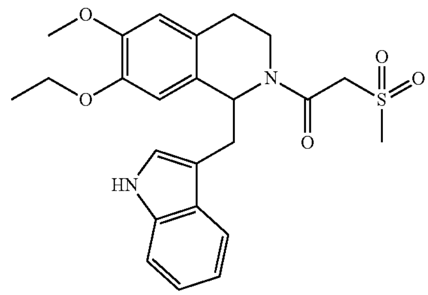 [SMILES: CCOc1cc2c(cc1OC)CCN(C(=O)CS(C)(=O)=O)C2Cc1c[nH]c2ccccc12] |
| (S)-C15 | (S)-1-(1-((1H-indol-3-yl)methyl)-7-ethoxy-6-methoxy-3,4-dihydroisoquinoline-2(1H)-yl)-2-(methanesulfonyl)ethane-1-one ZN 40 | 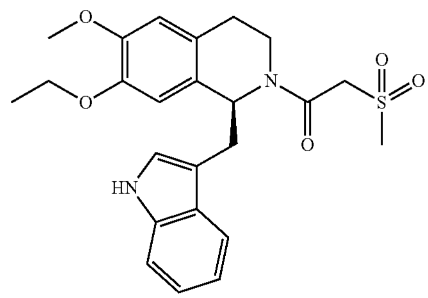 |
| (R)-C15 | (R)-1-(1-((1H-indol-3-yl)methyl)-7-ethoxy-6-methoxy-3,4-dihydroisoquinoline-2(1H)-yl)-2-(methanesulfonyl)ethane-1-one | 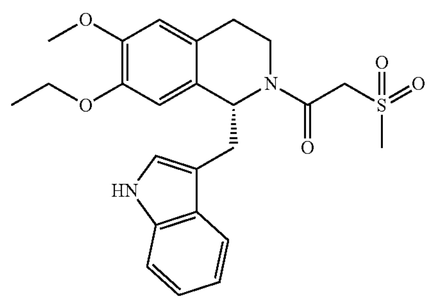 [SMILES: CCOc1cc2c(cc1OC)CCN(C(=O)CS(C)(=O)=O)[C@@H]2Cc1c[nH]c2ccccc12] |
| C16 | 1-(1-((1H-indol-3-yl)methyl)-7-ethoxy-6-methoxy-3,4-dihydroisoquinoline-2(1H)-yl)-2-methoxyethane-1-one | 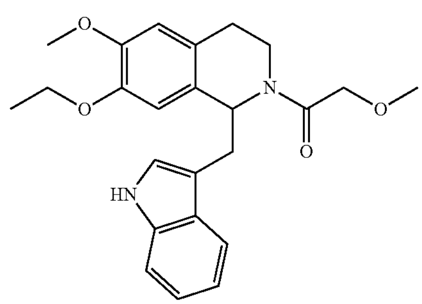 [SMILES: CCOc1cc2c(cc1OC)CCN(C(=O)COC)C2Cc1c[nH]c2ccccc12] |
| (S)-C16 | (S)-1-(1-((1H-indol-3-yl)methyl)-7-ethoxy-6-methoxy-3,4-dihydroisoquinoline-2(1H)-yl)-2-methoxyethane-1-one | 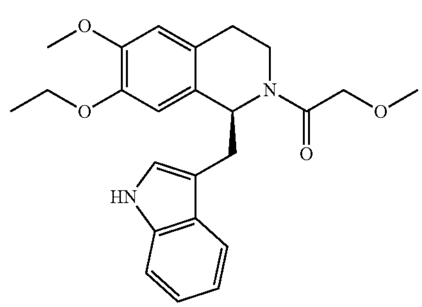 [SMILES: CCOc1cc2c(cc1OC)CCN(C(=O)COC)[C@H]2Cc1c[nH]c2ccccc12] |

TABLE A-continued

| No. | Name |
|---|---|
| (R)-C16 | (R)-1-(1-((1H-indol-3-yl)methyl)-7-ethoxy-6-methoxy-3,4-dihydroisoquinoline-2(1H)-yl)-2-methoxyethane-1-one |
| C17 | 7-ethoxy-6-methoxy-1-((5-methyl-1H-indol-3-yl)methyl)-3,4-dihydroisoquinoline-2(1H)-formaldehyde |
| (S)-C17 | (S)-7-ethoxy-6-methoxy-1-((5-methyl-1H-indol-3-yl)methyl)-3,4-dihydroisoquinoline-2(1H)-formaldehyde |
| (R)-C17 | (R)-7-ethoxy-6-methoxy-1-((5-methyl-1H-indol-3-yl)methyl)-3,4-dihydroisoquinoline-2(1H)-formaldehyde |
| C18 | 7-ethoxy-6-methoxy-1-((5-methoxy-1H-indol-3-yl)methyl)-3,4-dihydroisoquinoline-2(1H)-formaldehyde |

TABLE A-continued

| No. | Name | Structure |
|---|---|---|
| (S)-C18 | (S)-7-ethoxy-6-methoxy-1-((5-methoxy-1H-indol-3-yl)methyl)-3,4-dihydroisoquinoline-2(1H)-formaldehyde | 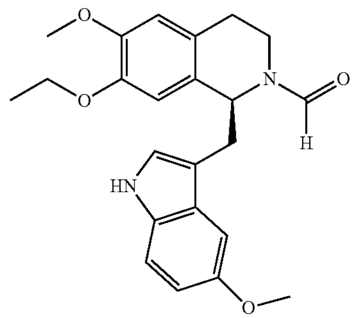 [SMILES: CCOc1cc2c(cc1OC)CCN(C=O)[C@H]2Cc1c[nH]c2ccc(OC)cc12] |
| (R)-C18 | (R)-7-ethoxy-6-methoxy-1-((5-methoxy-1H-indol-3-yl)methyl)-3,4-dihydroisoquinoline-2(1H)-formaldehyde | 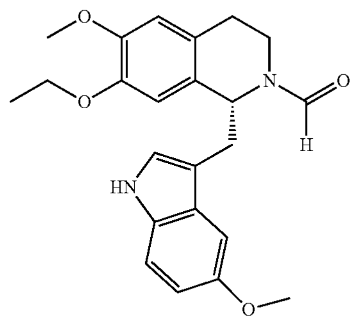 [SMILES: CCOc1cc2c(cc1OC)CCN(C=O)[C@@H]2Cc1c[nH]c2ccc(OC)cc12] |
| C19 | N-(3-(2-(7-ethoxy-2-formyl-6-methoxy-1,2,3,4-tetrahydroisoquinolin-1-yl)ethyl)-1H-indol-5-yl)acetamide | 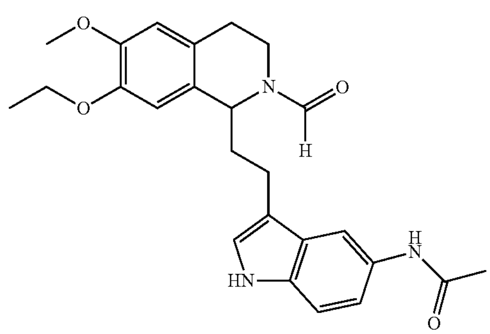 [SMILES: CCOc1cc2c(cc1OC)CCN(C=O)C2CCc1c[nH]c2ccc(NC(C)=O)cc12] |
| (S)-C19 | (S)-N-(3-(2-(7-ethoxy-2-formyl-6-methoxy-1,2,3,4-tetrahydroisoquinolin-1-yl)ethyl)-1H-indol-5-yl)acetamide | 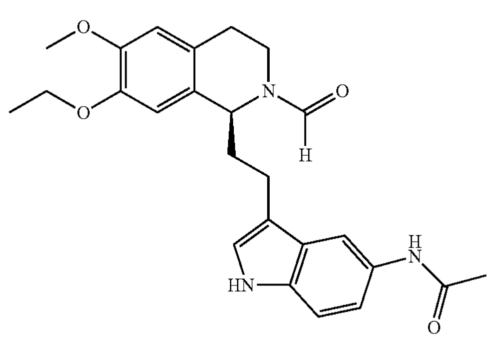 [SMILES: CCOc1cc2c(cc1OC)CCN(C=O)[C@H]2CCc1c[nH]c2ccc(NC(C)=O)cc12] |

TABLE A-continued

| No. | Name | Structure |
| --- | --- | --- |
| (R)-C19 | (R)-N-(3-(2-(7-ethoxy-2-formyl-6-methoxy-1,2,3,4-tetrahydroisoquinolin-1-yl)ethyl)-1H-indol-5-yl)acetamide | 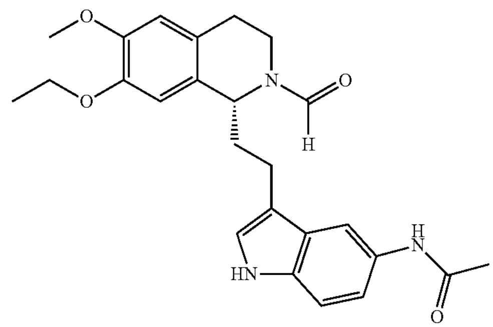 |
| C20 | (E)-7-ethoxy-6-methoxy-1-(2-(5-methoxy-1H-indol-3-yl)-3,4-dihydroisoquinolin-2(1H)-formaldehyde | 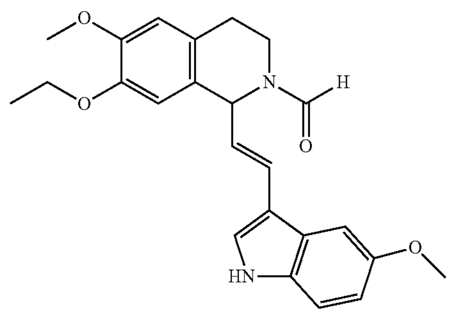 [SMILES: CCOc1cc2c(cc1OC)CCN(C=O)C2/C=C/c1c[nH]c2ccc(OC)cc12] |
| (S)-C20 | (S,E)-7-ethoxy-6-methoxy-1-(2-(5-methoxy-1H-indol-3-yl)vinyl)-3,4-dihydroisoquinolin-2(1H)-formaldehyde | 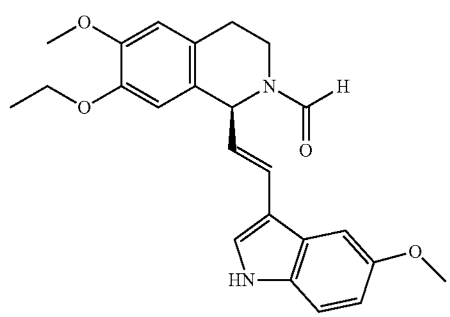 [SMILES: CCOc1cc2c(cc1OC)CCN(C=O)[C@H]2/C=C/c1c[nH]c2ccc(OC)cc12] |
| (R)-C20 | (R,E)-7-ethoxy-6-methoxy-1-(2-(5-methoxy-1H-indol-3-yl)vinyl)-3,4-dihydroisoquinoline-2(1H)-formaldehyde | 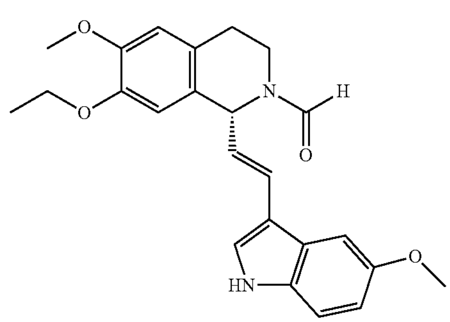 [SMILES: CCOc1cc2c(cc1OC)CCN(C=O)[C@@H]2/C=C/c1c[nH]c2ccc(OC)cc12] |

| No. | Name | Structure |
|-----|------|-----------|
| C21 | 7-ethoxy-6-methoxy-1-(4-(5-methoxy-1H-indol-3-yl)cyclohexyl)-3,4-dihydroisoquinoline-2(1H)-formaldehyde | 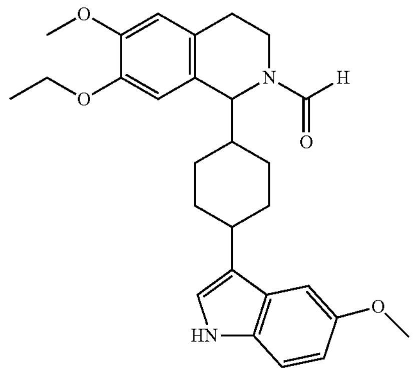 |
| (S)-C21 | (1S)-7-ethoxy-6-methoxy-1-(4-(5-methoxy-1H-indol-3-yl)cyclohexyl)-3,4-dihydroisoquinoline-2(1H)-formadehyde | 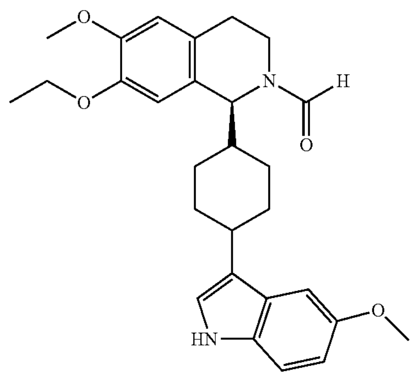 [SMILES: CCOc1cc2c(cc1OC)CCN(C=O)[C@H]2C1CCC(c2c[nH]c3ccc(OC)cc23)CC1] |
| (R)-C21 | (1R)-7-ethoxy-6-methoxy-1-(4-(5-methoxy-1H-indol-3-yl)cyclohexyl)-3,4-dihydroisoquinoline-2(1H)-formaldehyde | 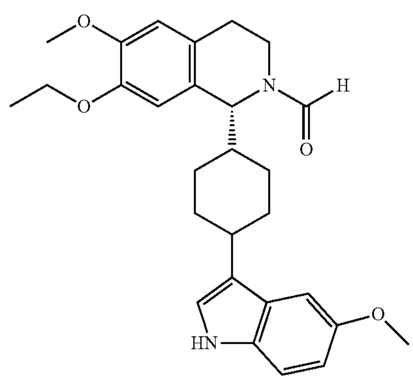 [SMILES: CCOc1cc2c(cc1OC)CCN(C=O)[C@@H]2C1CCC(c2c[nH]c3ccc(OC)cc23)CC1] |
| C22 | 1-(2-(1H-indazol-3-yl)ethyl)-7-ethoxy-6-methoxy-3,4-dihydroisoquinolin-2(1H)-formaldehyde | 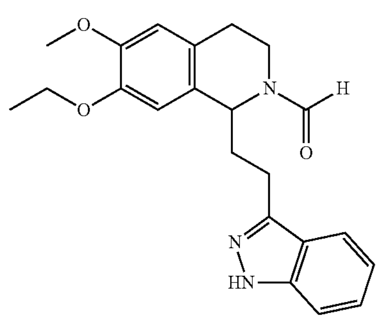 |

TABLE A-continued

| No. | Name | Structure |
| --- | --- | --- |
| (S)-C22 | (S)-1-(2-(1H-indazol-3-yl)ethyl)-7-ethoxy-6-methoxy-3,4-dihydroisoquinolin-2(1H)-formaldehyde | 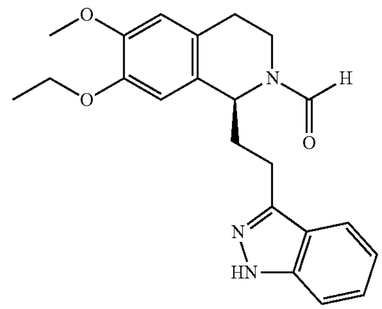 [SMILES: CCOc1cc2c(cc1OC)CCN(C=O)[C@H]2CCc1n[nH]c2ccccc12] |
| (R)-C22 | (R)-1-(2-(1H-indazol-3-yl)ethyl)-7-ethoxy-6-methoxy-3,4-dihydroisoquinolin-2(1H)-formaldehyde | 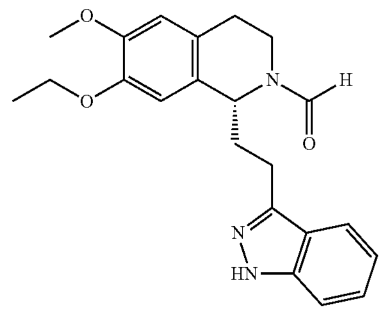 [SMILES: CCOc1cc2c(cc1OC)CCN(C=O)[C@@H]2CCc1n[nH]c2ccccc12] |
| C23 | 1-(2-(benzofuran-2-yl)ethyl)-7-ethoxy-6-methoxy-3,4-dihydroisoquinoline-2(1H)-formaldehyde | 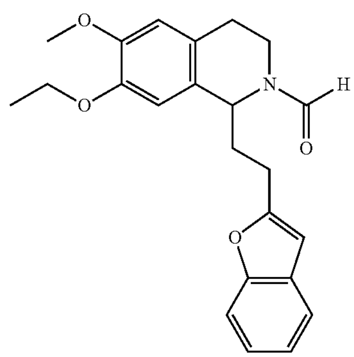 [SMILES: CCOc1cc2c(cc1OC)CCN(C=O)C2CCc1cc2ccccc2o1] |
| (S)-C23 | (S)-1-(2-(benzofuran-2-yl)ethyl)-7-ethoxy-6-methoxy-3,4-dihydroisoquinoline-2(1H)-formaldehyde | 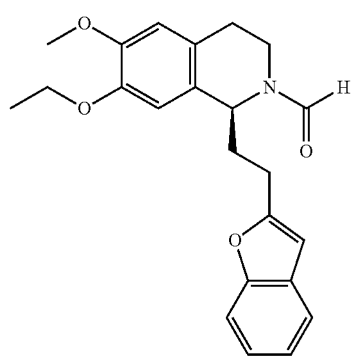 |

TABLE A-continued

| No. | Name |
|---|---|
| (R)-C23 | (R)-1-(2-(benzofuran-2-yl)ethyl)-7-ethoxy-6-methoxy-3,4-dihydroisoquinolin-2(1H)-formaldehyde |
| C24 | 1-(2-(benzo[b]thiophen-2-yl)ethyl)-7-ethoxy-6-methoxy-3,4-dihydroisoquinolin-2(1H)-formaldehyde |
| (S)-C24 | (S)-1-(2-(benzo[b]thiophen-2-yl)ethyl)-7-ethoxy-6-methoxy-3,4-dihydroisoquinoline-2(1H)-formaldehyde |
| (R)-C24 | (R)-1-(2-(benzo[b]thiophen-2-yl)ethyl)-7-ethoxy-6-methoxy-3,4-dihydroisoquinoline-2(1H)-formaldehyde |

TABLE A-continued

| No. | Name | Structure |
|---|---|---|
| C25 | 1-(2-(1H-indol-2-yl)ethyl)-7-ethoxy-6-methoxy-3,4-dihydroisoquinoline-2(1H)-formaldehyde | 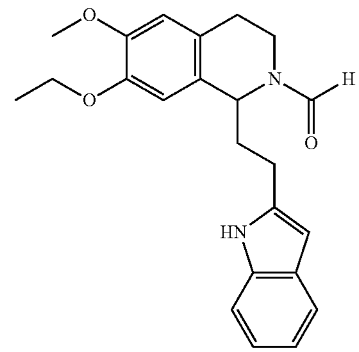 [SMILES: CCOc1cc2c(cc1OC)CCN(C=O)C2CCc1cc2ccccc2[nH]1] |
| (S)-C25 | (S)-1-(2-(1H-indol-2-yl)ethyl)-7-ethoxy-6-methoxy-3,4-dihydroisoquinoline-2(1H)-formaldehyde | 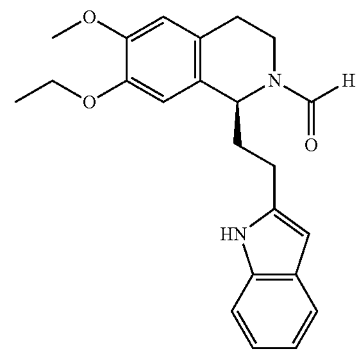 [SMILES: CCOc1cc2c(cc1OC)CCN(C=O)[C@H]2CCc1cc2ccccc2[nH]1] |
| (R)-C25 | (R)-1-(2-(1H-indol-2-yl)ethyl)-7-ethoxy-6-methoxy-3,4-dihydroisoquinoline-2(1H)-formaldehyde | 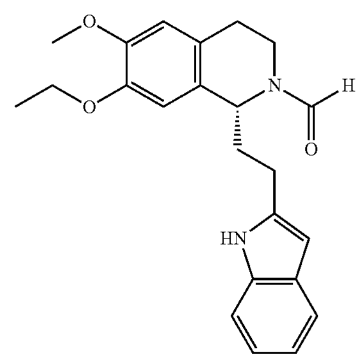 [SMILES: CCOc1cc2c(cc1OC)CCN(C=O)[C@@H]2CCc1cc2ccccc2[nH]1] |
| C26 | 1-(2-(1H-pyrrolo[2,3-b]pyridin-3-yl)ethyl)-7-ethoxy-6-methoxy-3,4-dihydroisoquinolin-2(1H)-formaldehyde | 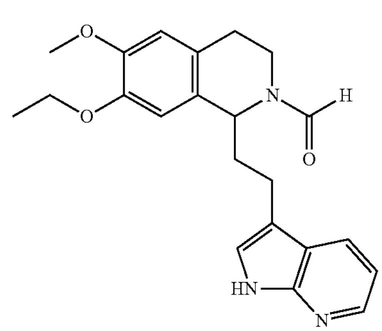 [SMILES: CCOc1cc2c(cc1OC)CCN(C=O)C2CCc1c[nH]c2ncccc12] |

TABLE A-continued

| No. | Name | Structure |
|---|---|---|
| (S)-C26 | (S)-1-(2-(1H-pyrrolo[2,3-b]pyridin-3-yl)ethyl)-7-ethoxy-6-methoxy-3,4-dihydroisoquinolin-2(1H)-formaldehyde | 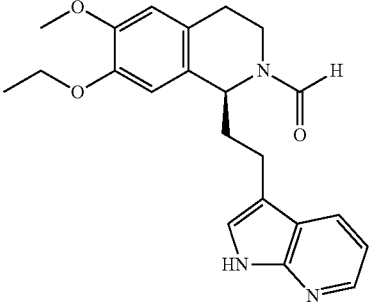 [SMILES: CCOc1cc2c(cc1OC)CCN(C=O)[C@H]2CCc1c[nH]c2ncccc12] |
| (R)-C26 | (R)-1-(2-(1H-pyrrolo[2,3-b]pyridin-3-yl)ethyl)-7-ethoxy-6-methoxy-3,4-dihydroisoquinoline-2(1H)-formaldehyde | 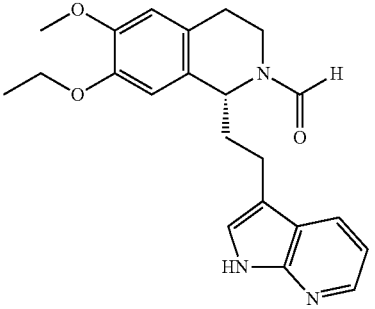 |
| C27 | 1-(2-cyclohexylethyl)-7-ethoxy-6-methoxy-3,4-dihydroisoquinoline-2(1H)-formaldehyde | 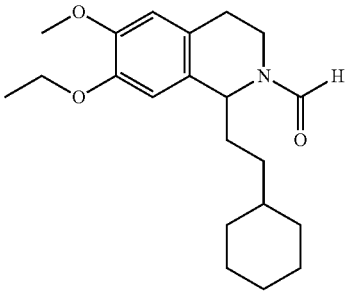 [SMILES: CCOc1cc2c(cc1OC)CCN(C=O)C2CCC1CCCCC1] |
| (S)-C27 | (S)-1-(2-cyclohexylethyl)-7-ethoxy-6-methoxy-3,4-dihydroisoquinoline-2(1H)-formaldehyde | 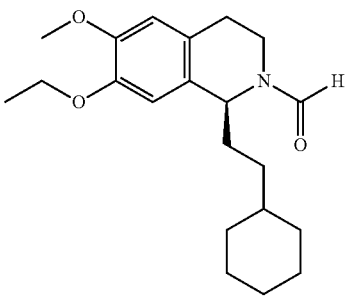 [SMILES: CCOc1cc2c(cc1OC)CCN(C=O)[C@H]2CCC1CCCCC1] |
| (R)-C27 | (R)-1-(2-cyclohexylethyl)-7-ethoxy-6-methoxy-3,4-dihydroisoquinoline-2(1H)-formaldehyde | 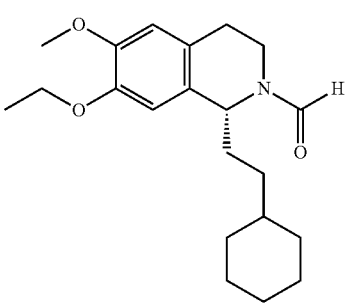 [SMILES: CCOc1cc2c(cc1OC)CCN(C=O)[C@@H]2CCC1CCCCC1] |

TABLE A-continued

| No. | Name | Structure |
|---|---|---|
| C28 | 7-ethoxy-6-methoxy-1-(2-morpholinoethyl)-3,4-dihydroisoquinoline-2(1H)-formaldehyde | 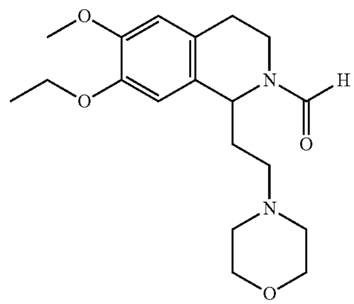 [SMILES: CCOc1cc2c(cc1OC)CCN(C=O)C2CCN1CCOCC1] |
| (S)-C28 | (S)-7-ethoxy-6-methoxy-1-(2-morpholinoethyl)-3,4-dihydroisoquinolin-2(1H)-formaldehyde | 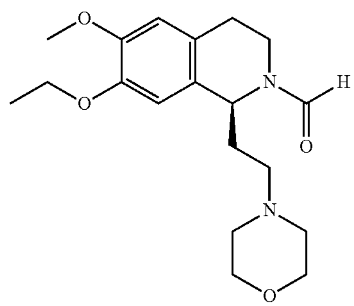 [SMILES: CCOc1cc2c(cc1OC)CCN(C=O)[C@H]2CCN1CCOCC1] |
| (R)-C28 | (R)-7-ethoxy-6-methoxy-1-(2-morpholinoethyl)-3,4-dihydroisoquinolin-2(1H)-formaldehyde | 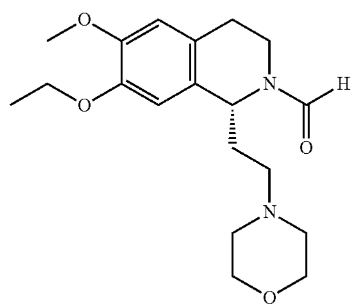 [SMILES: CCOc1cc2c(cc1OC)CCN(C=O)[C@@H]2CCN1CCOCC1] |
| C29 | 7-ethoxy-6-methoxy-1-(2-(pyridin-3-yl)ethyl-3,4-dihydroisoquinolin-2(1H)-formaldehyde | 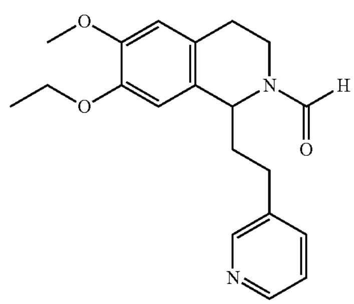 [SMILES: CCOc1cc2c(cc1OC)CCN(C=O)C2CCc1cccnc1] |
| (S)-C29 | (S)-7-ethoxy-6-methoxy-1-(2-(pyridin-3-yl)ethyl)-3,4-dihydroisoquinoline-2(1H)-formaldehyde | 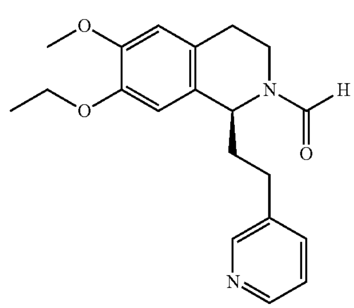 [SMILES: CCOc1cc2c(cc1OC)CCN(C=O)[C@H]2CCc1cccnc1] |

TABLE A-continued

| No. | Name | Structure |
|---|---|---|
| (R)-C29 | (R)-7-ethoxy-6-methoxy-1-(2-(pyridin-3-yl)ethyl)-3,4-dihydroisoquinolin-2(1H)-formaldehyde | 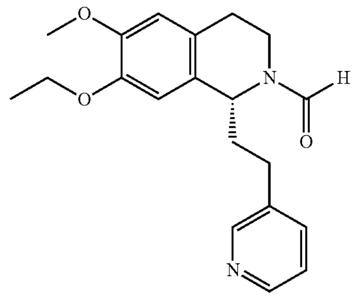 [SMILES: CCOc1cc2c(cc1OC)CCN(C=O)[C@@H]2CCc1cccnc1] |
| C30 | 7-ethoxy-6-methoxy-1-(((5-methoxy-1H-indol-3-yl)oxo)methyl)-3,4-dihydroisoquinoline-2(1H)-formaldehyde | 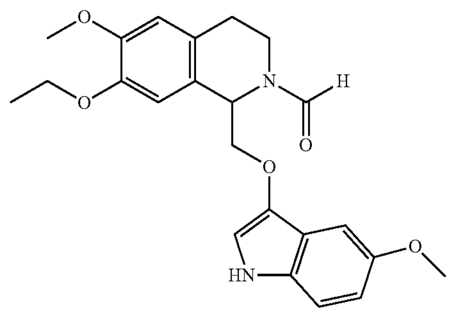 |
| (S)-C30 | (R)-7-ethoxy-6-methoxy-1-(((5-methoxy-1H-indol-3-yl)oxo)methyl)-3,4-dihydroisoquinoline-2(1H)-formaldehyde | 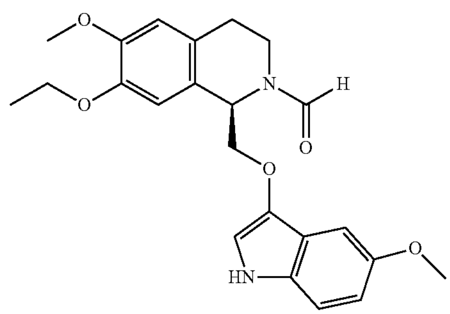 [SMILES: CCOc1cc2c(cc1OC)CCN(C=O)[C@H]2COc1c[nH]c2ccc(OC)cc12] |
| (R)-C30 | (S)-7-ethoxy-6-methoxy-1-(((5-methoxy-1H-indol-3-yl)oxo)methyl)-3,4-dihydroisoquinoline-2(1H)-formaldehyde | 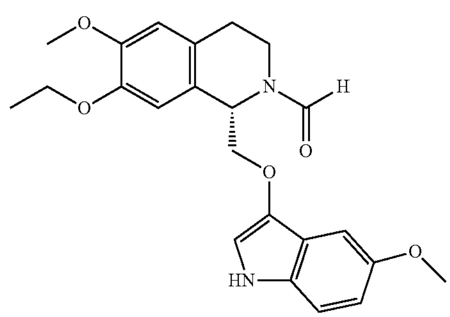 [SMILES: CCOc1cc2c(cc1OC)CCN(C=O)[C@@H]2COc1c[nH]c2ccc(OC)cc12] |
| C31 | 7-ethoxy-6-methoxy-1-(((5-methoxy-1H-indol-3-yl)thio)methyl)-3,4-dihydroisoquinoline-2(1H)-formaldehyde | 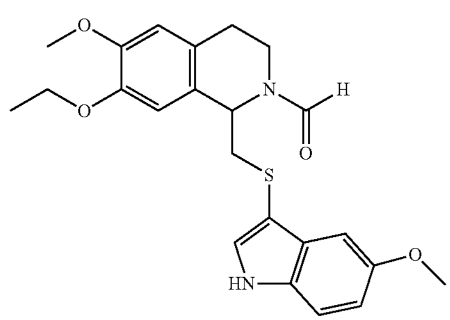 [SMILES: CCOc1cc2c(cc1OC)CCN(C=O)C2CSc1c[nH]c2ccc(OC)cc12] |

TABLE A-continued

| No. | Name | Structure |
|---|---|---|
| (S)-C31 | (R)-7-ethoxy-6-methoxy-1-(((5-methoxy-1H-indol-3-yl)thio)methyl)-3,4-dihydroisoquinoline-2(1H)-formadehyde | 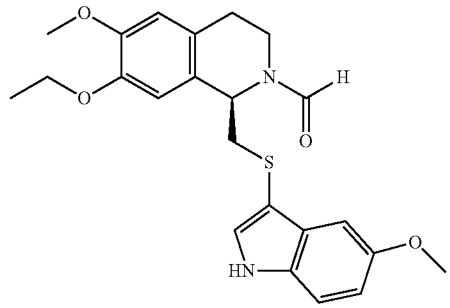 [SMILES: CCOc1cc2c(cc1OC)CCN(C=O)[C@H]2CSc1c[nH]c2ccc(OC)cc12] |
| (R)-C31 | (S)-7-ethoxy-6-methoxy-1-(((5-methoxy-1H-indol-3-yl)thio)methyl)-3,4-dihydroisoquinoline-2(1H)-formaldehyde | 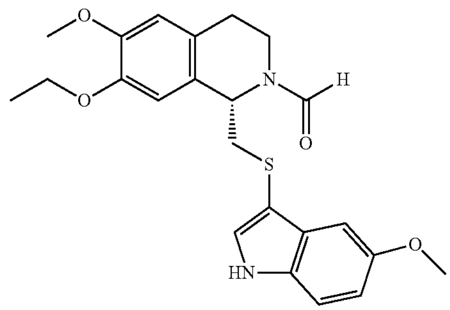 [SMILES: CCOc1cc2c(cc1OC)CCN(C=O)[C@@H]2CSc1c[nH]c2ccc(OC)cc12] |
| C32 | 7-ethoxy-6-methoxy-1-((4-(5-methoxy-1H-indol-3-yl)piperazin-1-yl)methyl)-3,4-dihydroisoquinoline-2(1H)-formaldehyde | 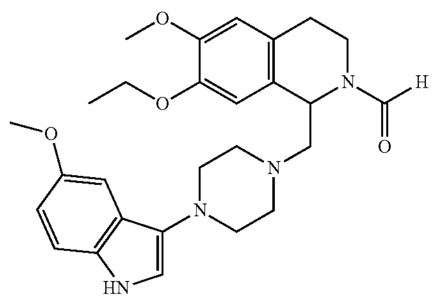 |
| (S)-C32 | (R)-7-ethoxy-6-methoxy-1-((4-(5-methoxy-1H-indol-3-yl)piperazin-1-yl)methyl)-3,4-dihydroisoquinoline-2(1H)-formaldehyde | 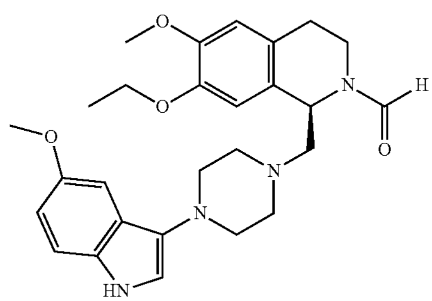 [SMILES: CCOc1cc2c(cc1OC)CCN(C=O)[C@H]2CN1CCN(c2c[nH]c3ccc(OC)cc23)CC1] |
| (R)-C32 | (S)-7-ethoxy-6-methoxy-1-((4-(5-methoxy-1H-indol-3-yl)piperazin-1-yl)methyl)-3,4-dihydroisoquinoline-2(1H)-formaldehyde | 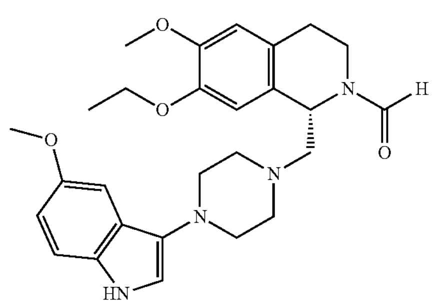 [SMILES: CCOc1cc2c(cc1OC)CCN(C=O)[C@@H]2CN1CCN(c2c[nH]c3ccc(OC)cc23)CC1] |

TABLE A-continued

| No. | Name | Structure |
|---|---|---|
| C33 | 7-ethoxy-1-(2-(5-hydroxy-1H-indol-3-yl)ethyl)-6-methoxy-3,4-dihydroisoquinoline-2(1H)-formaldehyde | 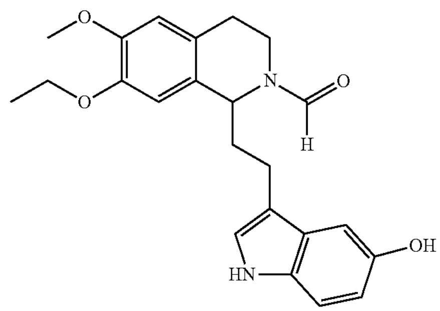 [SMILES: CCOc1cc2c(cc1OC)CCN(C=O)C2CCc1c[nH]c2ccc(O)cc12] |
| (S)-C33 | (S)-7-ethoxy-1-(2-(5-hydroxy-1H-indol-3-yl)ethyl)-6-methoxy-3,4-dihydroisoquinolline-2(1H)-formaldehyde | 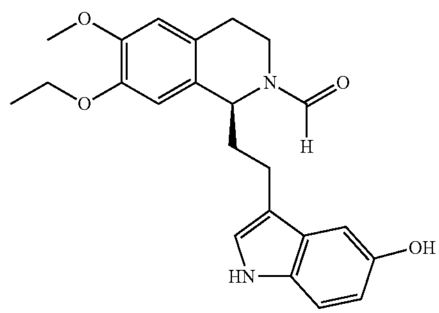 |
| (R)-C33 | (R)-7-ethoxy-1-(2-(5-hydroxy-1H-indol-3-yl)ethyl)-6-methoxy-3,4-dihydroisoquinoline-2(1H)-formaldehyde | 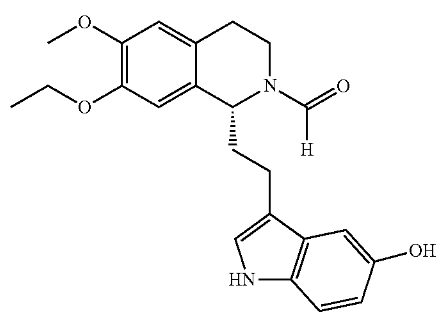 [SMILES: CCOc1cc2c(cc1OC)CCN(C=O)[C@@H]2CCc1c[nH]c2ccc(O)cc12] |
| C35 | 1-(((1H-indol-3-yl)amino)methyl)-7-ethoxy-6-methoxy-3,4-dihydroisoquinoline-2(1H)-formaldehyde | 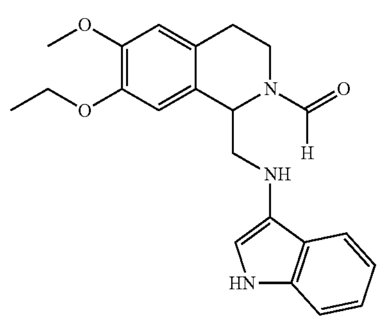 [SMILES: CCOc1cc2c(cc1OC)CCN(C=O)C2CNc1c[nH]c2ccccc12] |
| (S)-C35 | (S)-1-(((1H-indol-3-yl)amino)methyl)-7-ethoxy-6-methoxy-3,4-dihydroisoquinoline-2(1H)-formaldehyde | 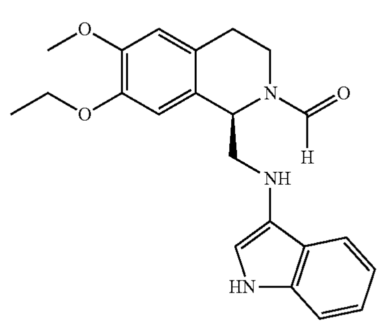 [SMILES: CCOc1cc2c(cc1OC)CCN(C=O)[C@H]2CNc1c[nH]c2ccccc12] |

TABLE A-continued

| No. | Name | Structure |
| --- | --- | --- |
| (R)-C35 | (R)-1-(((1H-indol-3-yl)amino)methyl)-7-ethoxy-6-methoxy-3,4-dihydroisoquinoline-2(1H)-formaldehyde | 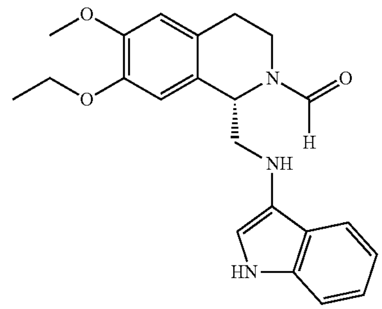 [SMILES: CCOc1cc2c(cc1OC)CCN(C=O)[C@@H]2CNc1c[nH]c2ccccc12] |
| C36 | 7-ethoxy-2-formyl-N-(1H-indol-3-yl)-6-methoxy-1,2,3,4-tetrahydroisoquinoline-1-formamide | 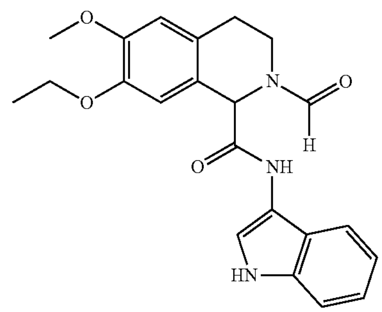 [SMILES: CCOc1cc2c(cc1OC)CCN(C=O)C2C(=O)Nc1c[nH]c2ccccc12] |
| (S)-C36 | (S)-7-ethoxy-2-formyl-N-(1H-indol-3-yl)-6-methoxy-1,2,3,4-tetrahydroisoquinoline-1-formamide | 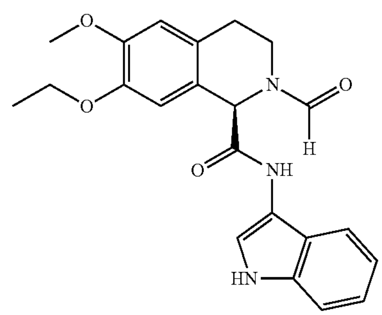 [SMILES: CCOc1cc2c(cc1OC)CCN(C=O)[C@H]2C(=O)Nc1c[nH]c2ccccc12] |
| (R)-C36 | (R)-7-ethoxy-2-formyl-N-(1H-indol-3-yl)-6-methoxy-1,2,3,4-tetrahydroisoquinoline-1-formaldehyde | 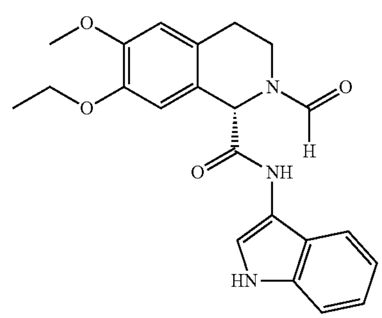 [SMILES: CCOc1cc2c(cc1OC)CCN(C=O)[C@@H]2C(=O)Nc1c[nH]c2ccccc12] |
| C37 | 1-(2-(1H-indol-3-yl)propyl)-6,7-dimethoxy-3,4-dihydroisoquinoline-2(1H)-formaldehyde | 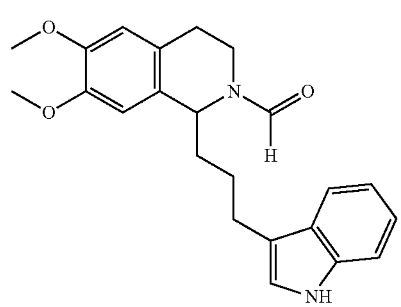 [SMILES: COc1cc2c(cc1OC)C(CCCc1c[nH]c3ccccc13)N(C=O)CC2] |

TABLE A-continued

| No. | Name | Structure |
| --- | --- | --- |
| (S)-C37 | (S)-1-(2-(1H-indol-3-yl)propyl)-6,7-dimethoxy-3,4-dihydroisoquinoline-2(1H)-formaldehyde | 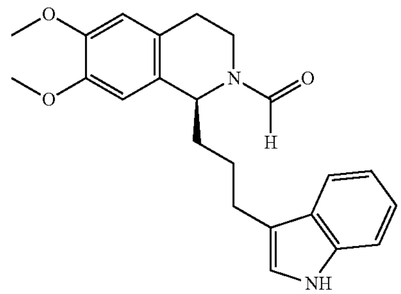 [SMILES: COc1cc2c(cc1OC)[C@H](CCCc1c[nH]c3ccccc13)N(C=O)CC2] |
| (R)-C37 | (R)-1-(2-(1H-indol-3-yl)propyl)-6,7-dimethoxy-3,4-dihydroisoquinoline-2(1H)-formaldehyde | 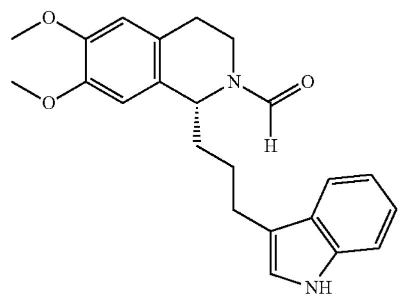 [SMILES: COc1cc2c(cc1OC)[C@@H](CCCc1c[nH]c3ccccc13)N(C=O)CC2] |
| C38 | 1-((1H-indol-3-yl)methyl)-6,7-dimethoxy-3,4-dihydroisoquinoline-2(1H)-ethyl-1-one | 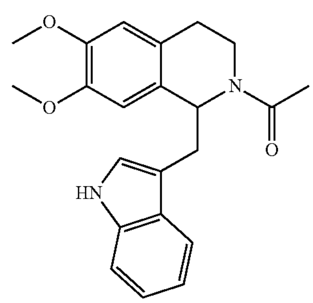 [SMILES: COc1cc2c(cc1OC)C(Cc1c[nH]c3ccccc13)N(C(C)=O)CC2] |
| (S)-C38 | (S)-1-((1H-indol-3-yl)methyl)-6,7-dimethoxy-3,4-dihydroisoquinoline-2(1H)-ethyl-1-one | 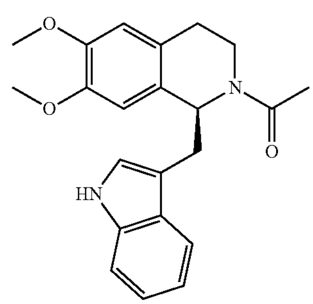 [SMILES: COc1cc2c(cc1OC)[C@H](Cc1c[nH]c3ccccc13)N(C(C)=O)CC2] |
| C39 | (1-((1H-indol-3-yl)methyl)-6,7-dimethoxy-3,4-dihydroisoquinolin-2(1H)-yl)(pyridin-4-yl)-methanone | 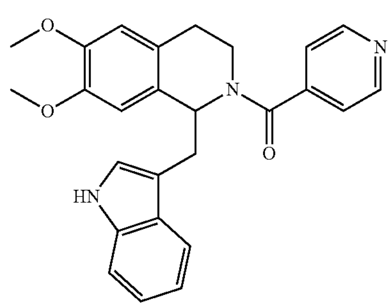 [SMILES: COc1cc2c(cc1OC)C(Cc1c[nH]c3ccccc13)N(C(=O)c1ccncc1)CC2] |

TABLE A-continued

| No. | Name |
|---|---|
| C40 | (1-((1H-indol-3-yl)methyl)-6,7-dimethoxy-3,4-dihydroisoquinolin-2(1H)-yl)(morpholine)-methanone |
| (S)-C40 | (S)-(1-((1H-indol-3-yl)methyl)-6,7-dimethoxy-3,4-dihydroisoquinoline-2(1H)-yl)(morpholine)-methanone |
| C41 | (1-((1H-indol-3-yl)methyl)-6,7-dimethoxy-3,4-dihydroisoquinolin-2(1H)-yl)(tetrahydro-2H-pyran-4-yl)-methanone |
| (S)-C41 | (S)-(1-((1H-indol-3-yl)methyl)-6,7-dimethoxy-3,4-dihydroisoquinoline-2(1H)-yl)(tetrahydro-2H-pyran-4-yl)-methanone |
| C42 | (1-((1H-indol-3-yl)methyl)-6,7-dimethoxy-3,4-dihydroisoquinolin-2(1H)-yl)(thiazole-2-yl)-methanone |

TABLE A-continued

| No. | Name | Structure |
|---|---|---|
| (S)-C42 | (S)-(1-((1H-indol-3-yl)methyl)-6,7-dimethoxy-3,4-dihydroisoquinoline-2(1H)-yl)(thiazol-2-yl)-methanone | 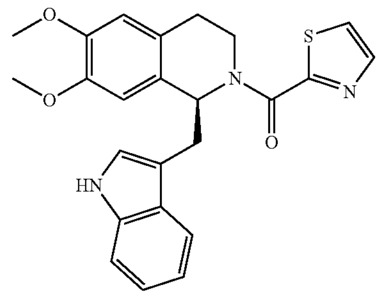 [SMILES: COc1cc2c(cc1OC)[C@H](Cc1c[nH]c3ccccc13)N(C(=O)c1nccs1)CC2] |
| C43 | methyl-2-(1-((1H-indol-3-yl)methyl)-6,7-dimethoxy-3,4-dihydroisoquinoline-2-(1H)-yl) acetate | 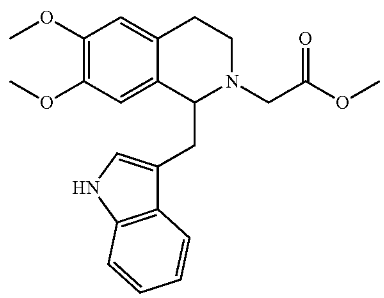 |
| C44 | 1-((6-chloro-1H-indol-3-yl)methyl)-6,7-dimethoxy-3,4-dihydroisoquinoline-2(1H)-formaldehyde | 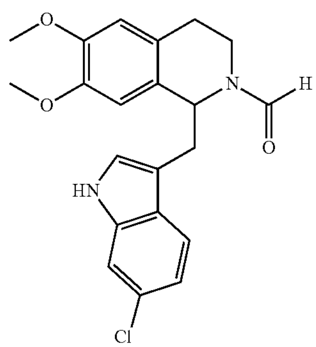 [SMILES: COc1cc2c(cc1OC)C(Cc1c[nH]c3cc(Cl)ccc13)N(C=O)CC2] |
| (S)-C44 | (S)-1-((6-chloro-1H-indol-3-yl)methyl)-6,7-dimethoxy-3,4-dihydroisoquinoline-2(1H)-formaldehyde | 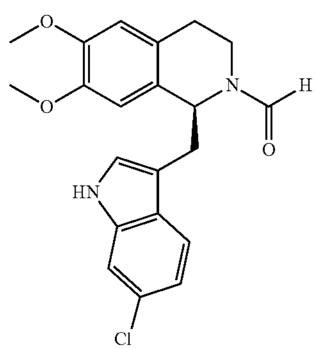 [SMILES: COc1cc2c(cc1OC)[C@H](Cc1c[nH]c3cc(Cl)ccc13)N(C=O)CC2] |
| C45 | 6,7-dimethoxy-1-((1-methyl-1H-indol-3-yl)methyl)-3,4-dihydroisoquinoline-2(1H)-formaldehyde | 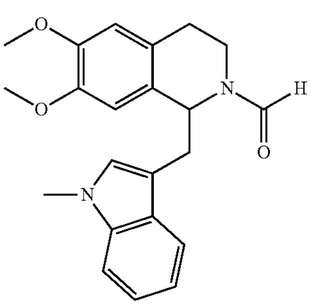 [SMILES: COc1cc2c(cc1OC)C(Cc1cn(C)c3ccccc13)N(C=O)CC2] |

TABLE A-continued

| No. | Name | Structure |
|---|---|---|
| C46 | 1-((1H-indol-3-yl)methyl)-7-benzyloxy-6-methoxy-3,4-dihydroisoquinoline-2(1H)-formaldehyde | 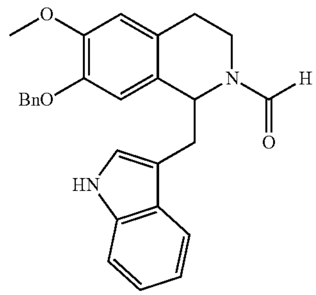 [SMILES: COc1cc2c(cc1OCc1ccccc1)C(Cc1c[nH]c3ccccc13)N(C=O)CC2] |
| (S)-C47 | (S)-7-ethoxy-6-methoxy-1-(2-(5-methoxy-1H-indol-3-yl)ethyl)-2-phenylsulfonyl-1,2,3,4-tetrahydroisoquinoline | 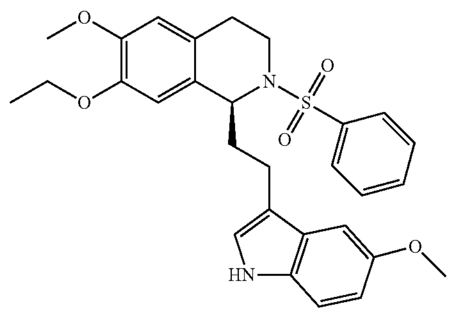 [SMILES: CCOc1cc2c(cc1OC)CCN(S(=O)(=O)c1ccccc1)[C@H]2CCc1c[nH]c2ccc(OC)cc12] |
| (S)-C48 | (S)-7-ethoxy-6-methoxy-1-(2-(5-methoxy-1H-indol-3-yl)ethyl)-2-cyclopropylsulfonyl-1,2,3,4-tetrahydroisoquinoline | 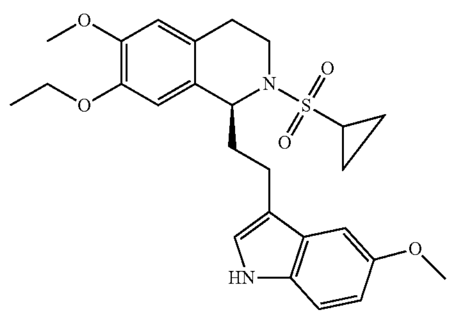 [SMILES: CCOc1cc2c(cc1OC)CCN(S(=O)(=O)C1CC1)[C@H]2CCc1c[nH]c2ccc(OC)cc12] |
| (S)-C49 | (S)-7-ethoxy-6-methoxy-1-(2-(5-methoxy-1H-indol-3-yl)ethyl)-2-cyclohexylsulfonyl-1,2,3,4-tetrahydroisoquinoline | 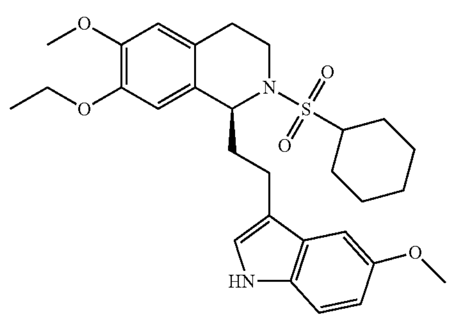 [SMILES: CCOc1cc2c(cc1OC)CCN(S(=O)(=O)C1CCCCC1)[C@H]2CCc1c[nH]c2ccc(OC)cc12] |
| (S)-C50 | (S)-7-ethoxy-6-methoxy-1-(2-(5-methoxy-1H-indol-3-yl)ethyl)-2-(3-fluorophenyl)sulfonyl-1,2,3,4-tetrahydroisoquinoline | 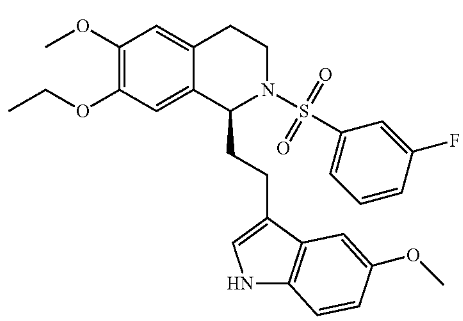 [SMILES: CCOc1cc2c(cc1OC)CCN(S(=O)(=O)c1cccc(F)c1)[C@H]2CCc1c[nH]c2ccc(OC)cc12] |

TABLE A-continued

| No. | Name | Structure |
|---|---|---|
| (S)-C51 | (S)-7-ethoxy-6-methoxy-1-(2-(5-methoxy-1H-indol-3-yl)ethyl)-2-(3,4-difluorophenyl)sulfonyl-1,2,3,4-tetrahydroisoquinoline | 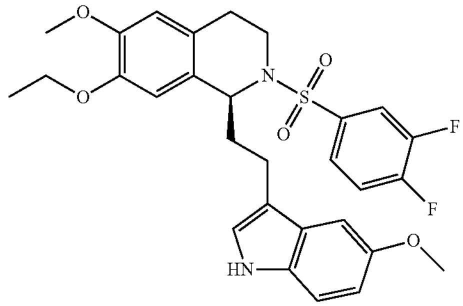 [SMILES: CCOc1cc2c(cc1OC)CCN(S(=O)(=O)c1ccc(F)c(F)c1)[C@H]2CCc1c[nH]c2ccc(OC)cc12] |
| (S)-C52 | (S)-7-ethoxy-6-methoxy-1-(2-(5-methoxy-1H-indol-3-yl)ethyl)-2-(2,4-difluorophenyl)sulfonyl-1,2,3,4-tetrahydroisoquinoline | 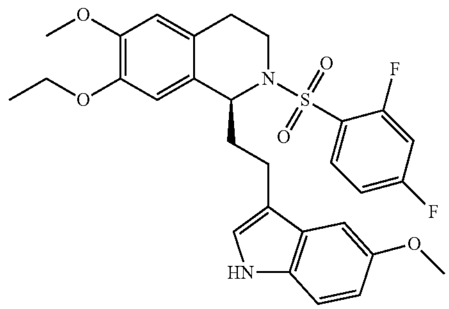 [SMILES: CCOc1cc2c(cc1OC)CCN(S(=O)(=O)c1ccc(F)cc1F)[C@H]2CCc1c[nH]c2ccc(OC)cc12] |
| (S)-C53 | (S)-7-ethoxy-6-methoxy-1-(2-(5-methoxy-1H-indol-3-yl)ethyl)-2-ethylsulfonyl-1,2,3,4-tetrahydroisoquinoline | 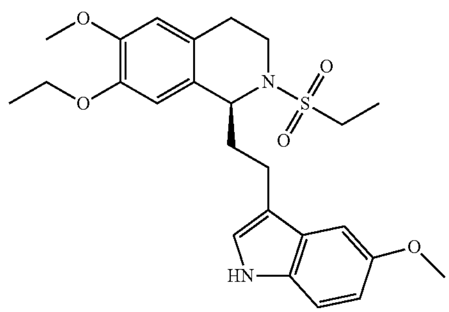 [SMILES: CCOc1cc2c(cc1OC)CCN(S(=O)(=O)CC)[C@H]2CCc1c[nH]c2ccc(OC)cc12] |
| (S)-C54 | (S)-7-ethoxy-1-(2-(5-methoxy-1H-indol-3-yl)ethyl)-6-methoxy-3,4-dihydroisoquinoline-2(1H)-trifluoroethane-1-one | 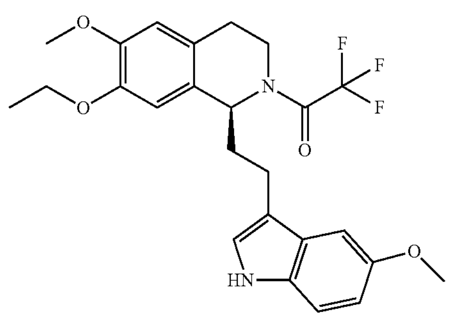 [SMILES: CCOc1cc2c(cc1OC)CCN(C(=O)C(F)(F)F)[C@H]2CCc1c[nH]c2ccc(OC)cc12] |
| (S)-C55 | (S)-7-ethoxy-6-methoxy-1-(2-(5-methoxy-1H-indol-3-yl)ethyl-2-(pyridin-3-yl)sulfonyl-1,2,3,4-tetrahydroisoquinoline | 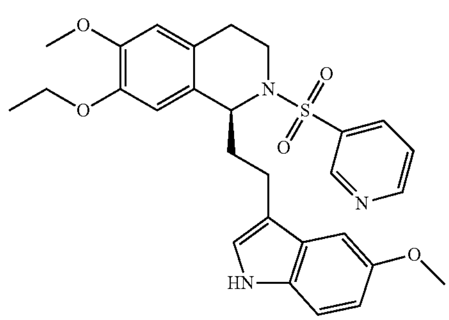 [SMILES: CCOc1cc2c(cc1OC)CCN(S(=O)(=O)c1cccnc1)[C@H]2CCc1c[nH]c2ccc(OC)cc12] |

TABLE A-continued

| No. | Name |
|---|---|
| (S)-C56 | (S)-7-ethoxy-6-methoxy-1-(2-(5-methoxy-1H-indol-3-yl)ethyl)-2-(3-fluoro-4-bromophenyl)sulfonyl-1,2,3,4-tetrahydroisoquinoline |
| (S)-C57 | (S)-7-ethoxy-6-methoxy-1-(2-(5-methoxy-1H-indol-3-yl)ethyl)-2-(2-fluorophenyl)sulfonyl-1,2,3,4-tetrahydroisoquinoline |
| (S)-C58 | (S)-7-ethoxy-6-methoxy-1-(2-(5-methoxy-1H-indol-3-yl)ethyl)-2-(4-fluorophenyl)sulfonyl-1,2,3,4-tetrahydroisoquinoline |
| (S)-C59 | (S)-7-ethoxy-1-(2-(5-methoxy-1H-indol-3-yl)ethyl)-6-methoxy-3,4-dihydroisoquinolin-2(1H)-2,2-difluoroethane-1-one |
| (S)-C60 | (S)-7-ethoxy-6-methoxy-1-(2-(5-methoxy-1H-indol-3-yl)ethyl)-2-(4-methoxyphenyl)sulfonyl-1,2,3,4-tetrahydroisoquinoline |

TABLE A-continued

| No. | Name | Structure |
|---|---|---|
| (S)-C61 | (S)-1-(2-(benzo[b]thiothiophen-3-yl)ethyl)-6,7-dimethoxy-3,4-dihydroisoquinoline-2(1H)-formaldehyde | 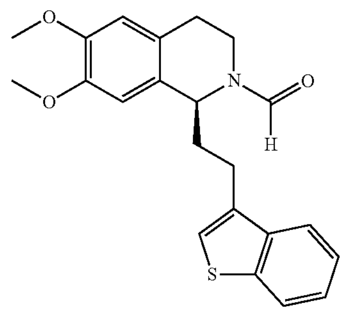 [SMILES: COc1cc2c(cc1OC)[C@H](CCc1csc3ccccc13)N(C=O)CC2] |
| (S)-C62 | (S)-7-ethoxy-1-(2-(5-methoxy-1H-indol-3-yl)ethyl)-6-methoxy-3,4-dihydroisoquinoline-2(1H)-ethoxyethane-1-one | 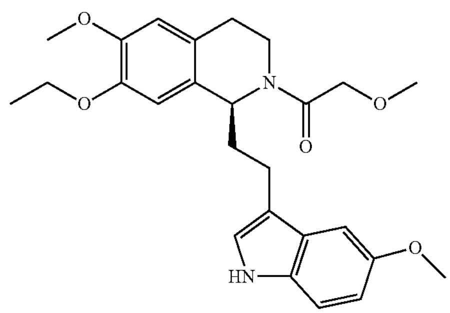 [SMILES: CCOc1cc2c(cc1OC)CCN(C(=O)COC)[C@H]2CCc1c[nH]c2ccc(OC)cc12] |
| (S)-C63 | (S)-7-trifluoromethoxy-1-(2-(5-methoxy-1H-indol-3-yl)ethyl)-6-methoxy-3,4-dihydroisoquinoline-2(1H)-formaldehyde | 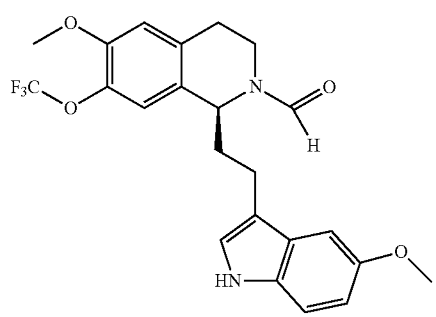 |
| (S)-C64 | (S)-7-difluoromethoxy-1-(2-(5-methoxy-1H-indol-3-yl)ethyl)-6-methoxy-3,4-dihydroisoquinoline-2(1H)-formaldehyde | 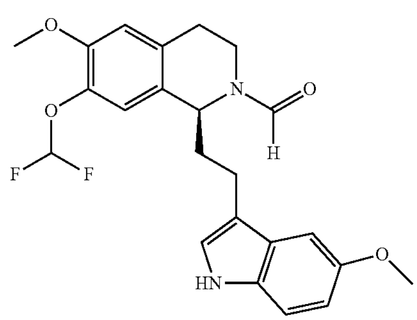 |
| (S)-C65 | (S)-7-ethoxy-6-methoxy-1-(2-(5-cyano-1H-indol-3-yl)ethyl)-3,4-dihydroisoquinoline-2(1H)-formaldehyde | 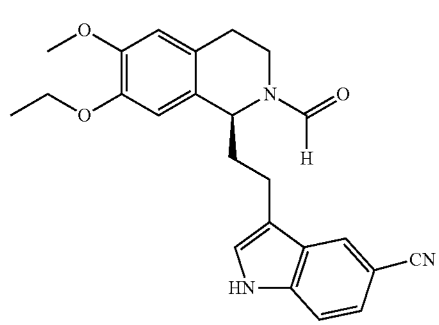 [SMILES: CCOc1cc2c(cc1OC)CCN(C=O)[C@H]2CCc1c[nH]c2ccc(C#N)cc12] |

TABLE A-continued

| No. | Name | Structure |
|---|---|---|
| (S)-C66 | methyl-(S)-2-formyl-6-methoxy-1-(2-(5-methoxy-1H-indol-3-yl)ethyl)-1,2,3,4-tetrahydroisoquinoline-7-carboxylate | 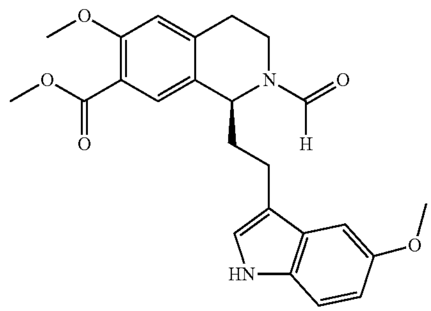 |
| (S)-C67 | methyl-(S)-2-formyl-7-methoxy-1-(2-(5-methoxy-1H-indol-3-yl)ethyl)-1,2,3,4-tetrahydroisoquinoline-6-carboxylate | 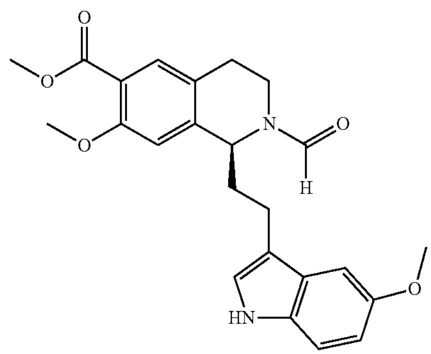 |
| (S)-C68 | (S)-2-formyl-6-methoxy-1-(2-(5-methoxy-1H-indol-3-yl)ethyl)-1,2,3,4-tetrahydroisoquinoline-7-carboxylic acid | 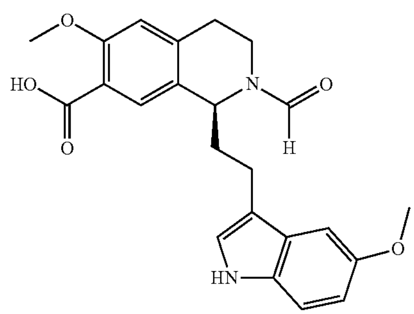 |
| (S)-C69 | (S)-2-formyl-6-methoxy-1-(2-(5-methoxy-1H-indol-3-yl)ethyl)-N-methyl-1,2,3,4-tetrahydroisoquinoline-7-carboxamide | 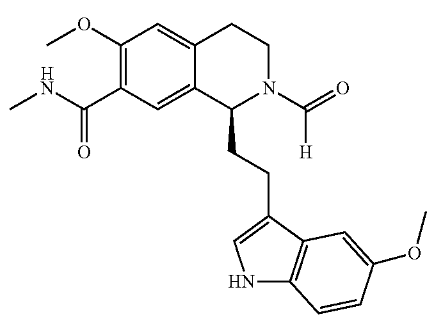 |
| (S)-C70 | (S)-2-formyl-6-methoxy-1-(2-(5-methoxy-1H-indol-3-yl)ethyl)-1,2,3,4-tetrahydroisoquinoline-7-carboxamide | 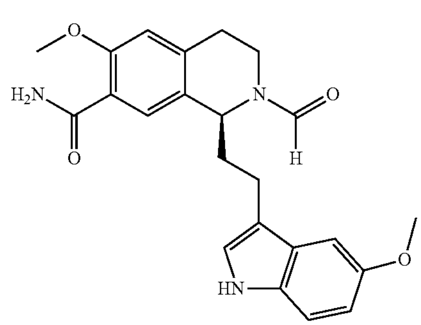 |

TABLE A-continued

| No. | Name | Structure |
|---|---|---|
| (S)-C71 | (S)-7-difluoromethyl-1-(2-(5-methoxy-1H-indol-3-yl)ethyl)-6-methoxy-3,4-dihydroisoquinoline-2(1H)-formaldehyde | 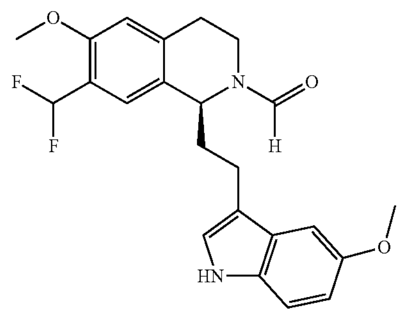 |
| (S)-C72 | (S)-2-difluoromethyl-7-ethoxy-6-methoxy-1-(2-(5-methoxy-1H-indol-3-yl)ethyl)-1,2,3,4-tetrahydroisoquinoline | 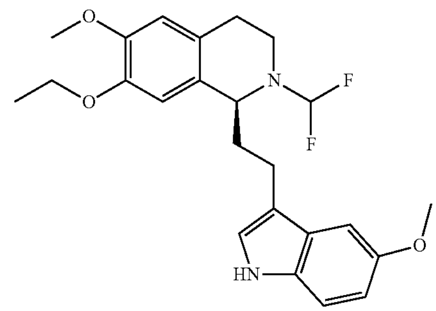 [SMILES: CCOc1cc2c(cc1OC)CCN(C(F)F)[C@H]2CCc1c[nH]c2ccc(OC)cc12] |
| (S)-C73 | (S)-7-ethoxy-6-methoxy-1-(2-(5-trifluoromethyl-1H-indol-3-yl)ethyl)-3,4-dihydroisoquinoline-2(1H)-formaldehyde | 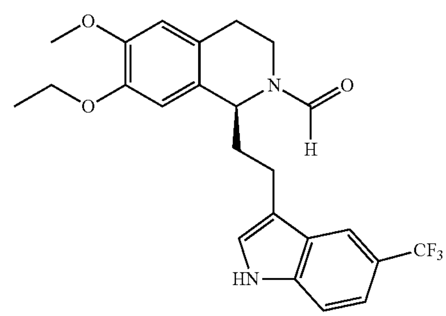 [SMILES: CCOc1cc2c(cc1OC)CCN(C=O)[C@H]2CCc1c[nH]c2ccc(C(F)(F)F)cc12] |
| (S)-C74 | (S)-7-ethoxy-6-methoxy-1-(2-(5-difluoromethyl-1H-indol-3-yl)ethyl)-3,4-dihydroisoquinoline-2(1H)-formaldehyde | 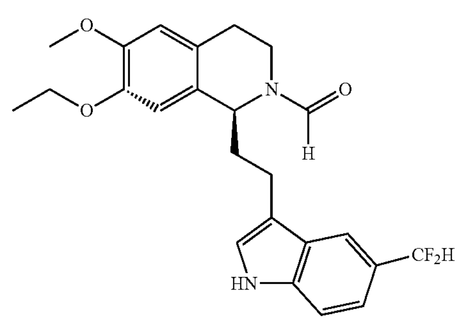 |
| (S)-C75 | methyl-(S)-3-(2-(7-ethoxy-2-formyl-6-methoxy-1,2,3,4-tetrahydroisoquinolin-1-yl)ethyl)-1H-indole-5-carboxylate | 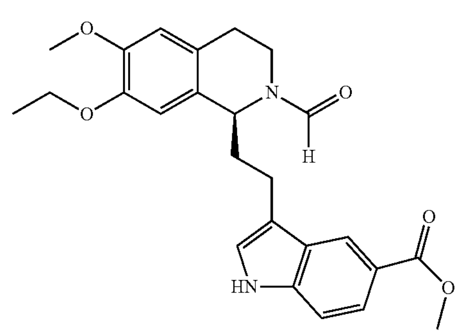 [SMILES: CCOc1cc2c(cc1OC)CCN(C=O)[C@H]2CCc1c[nH]c2ccc(C(=O)OC)cc12] |

TABLE A-continued

| No. | Name | Structure |
|---|---|---|
| (S)-C76 | (S)-7-ethoxy-6-methoxy-1-(2-(5-trifluoromethoxy-1H-indol-3-yl)ethyl)-3,4-dihydroisoquinoline-2(1H)-formaldehyde | 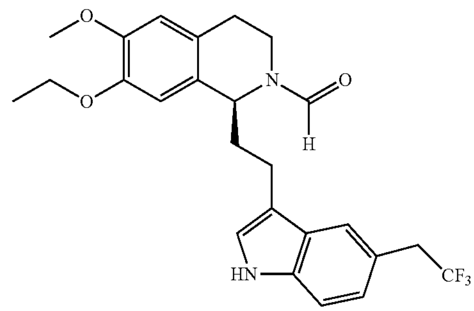 [SMILES: CCOc1cc2c(cc1OC)CCN(C=O)[C@H]2CCc1c[nH]c2ccc(CC(F)(F)F)cc12] |
| (S)-C77 | (S)-7-ethoxy-6-methoxy-1-(2-(5-difluoromethoxy-1H-indol-3-yl)ethyl)-3,4-dihydroisoquinoline-2(1H)-formaldehyde | 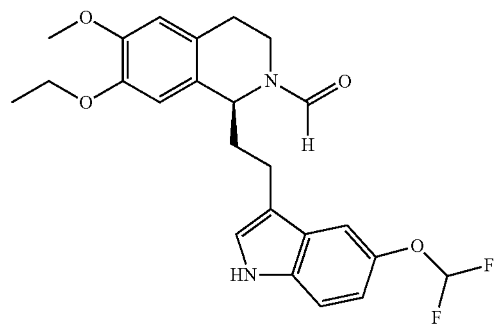 [SMILES: CCOc1cc2c(cc1OC)CCN(C=O)[C@H]2CCc1c[nH]c2ccc(OC(F)F)cc12] |
| (S)-C78 | (S)-7-ethoxy-6-methoxy-1-(2-(5-fluoro-1H-indol-3-yl)ethyl)-3,4-dihydroisoquinoline-2(1H)-formaldehyde | 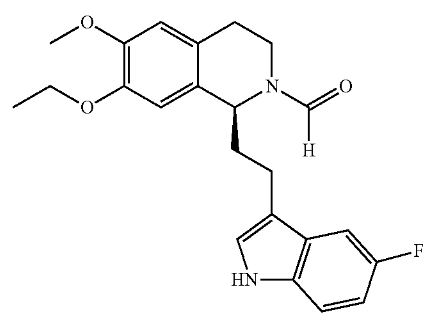 [SMILES: CCOc1cc2c(cc1OC)CCN(C=O)[C@H]2CCc1c[nH]c2ccc(F)cc12] |
| (S)-C79 | (S)-6-ethoxy-7-methoxy-1-(2-(5-methoxy-1H-indol-3-yl)ethyl)-3,4-dihydroisoquinoline-2(1H)-formaldehyde | 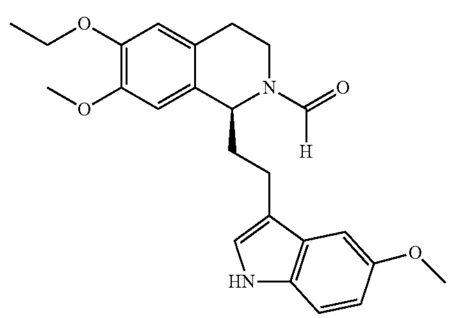 [SMILES: CCOc1cc2c(cc1OC)[C@H](CCc1c[nH]c3ccc(OC)cc13)N(C=O)CC2] |
| (S)-C80 | (S)-7-ethoxy-6-methoxy-1-(2-(5-methoxy-6-chloro-1H-indol-3-yl)ethyl)-3,4-dihydroisoquinoline-2(1H)-formaldehyde | 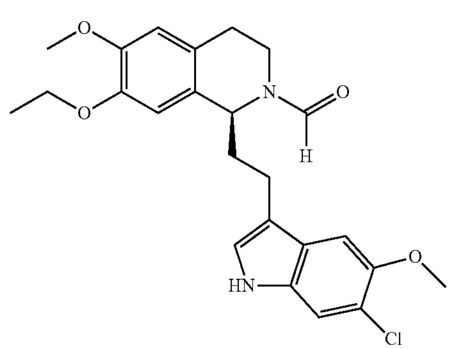 [SMILES: CCOc1cc2c(cc1OC)CCN(C=O)[C@H]2CCc1c[nH]c2cc(Cl)c(OC)cc12] |

TABLE A-continued

| No. | Name | Structure |
|---|---|---|
| (S)-C81 | (S)-7-ethoxy-6-methoxy-1-(2-(5-fluoro-6-chloro-1H-indol-3-yl)ethyl)-3,4-dihydroisoquinoline-2(1H)-formaldehyde | 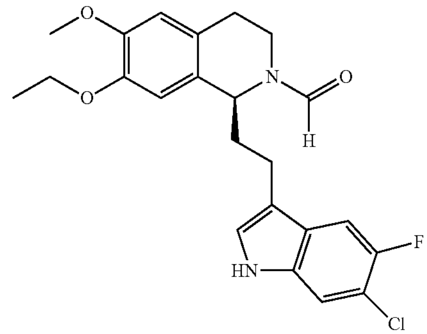 [SMILES: CCOc1cc2c(cc1OC)CCN(C=O)[C@H]2CCc1c[nH]c2cc(Cl)c(F)cc12] |
| (S)-C82 | (S)-7-ethoxy-1-(2-(5-fluoro-1H-indol-3-yl)ethyl)-6-methoxy-3,4-dihydroisoquinoline-2(1H)-ethoxyethane-1-one | 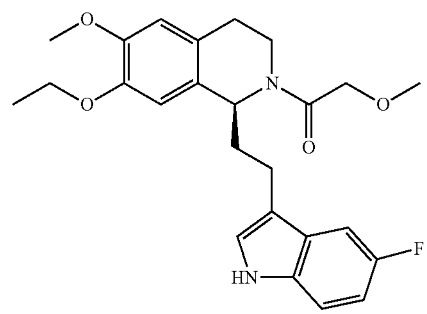 [SMILES: CCOc1cc2c(cc1OC)CCN(C(=O)COC)[C@H]2CCc1c[nH]c2ccc(F)cc12] |
| (S)-C83 | (S)-7-ethoxy-6-methoxy-1-(2-(5-methoxy-1H-indol-3-yl)ethyl)-2-(2-(methylsulfonyl)ethyl)-1,2,3,4-tetrahydroisoquinoline | 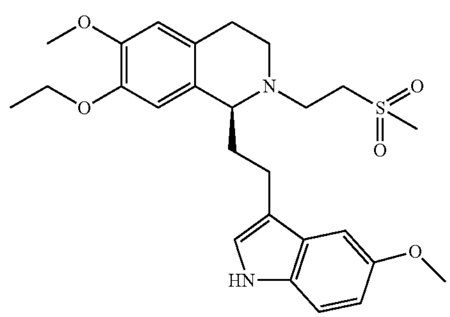 [SMILES: CCOc1cc2c(cc1OC)CCN(CCS(C)(=O)=O)[C@H]2CCc1c[nH]c2ccc(OC)cc12] |

The Preparation of Compound of Formula (I)

The present invention also provides a method for synthesizing a compound of general formula I. Specifically the compound of formula I is prepared b the following scheme:

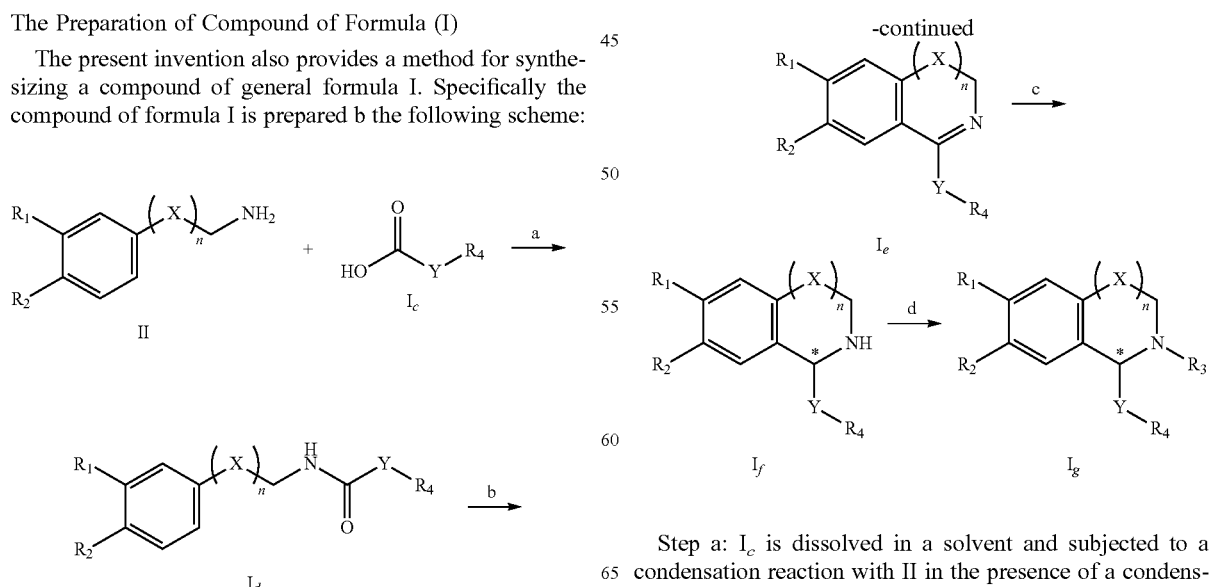

Step a: $I_c$ is dissolved in a solvent and subjected to a condensation reaction with II in the presence of a condensing agent to obtain compound Id; and the solvent is dichloromethane;

Step b: $I_d$ is dissolved in a solvent, and excess phosphorus oxychloride is added and stirred under reflux to obtain compound $I_e$, and the solvent is anhydrous acetonitrile;

Step c: $I_e$ is dissolved in a solvent and excess sodium borohydride is added and stirred until the reaction is completed. The solvent is dried in-vacuo to obtain compound $I_f$, wherein the solvent is methanol; or Noyori catalyst is added and stirred until the reaction is completed, wherein the solvent is a mixed solvent of water and dichloromethane.

Step d: $I_f$ is dissolved in a solvent and reacted with the corresponding raw materials to obtain compound $I_g$; and the solvent is ethyl formate or DMF or tetrahydrofuran;

X, Y, $R_1$, $R_2$, $R_3$, $R_4$ are defined as in the previous requirements.

Pharmaceutical Composition Containing the Compound of Formula (I)

The present invention also relates to a pharmaceutical composition comprising a therapeutically effective amount of a tetrahydroisoquinoline compound represented by formula (I), a pharmaceutically acceptable salt, a prodrug, hydrate and solvate thereof, and optionally one or more pharmaceutically acceptable carriers, which can be used to treat autoimmune-related diseases such as psoriasis. The pharmaceutical composition can be prepared in various forms depending on the route of administration.

One or more of the aldehyde compound represented by formula (I), the pharmaceutically acceptable salts, prodrugs, hydrates and solvates thereof according to the present invention, or a pharmaceutical composition containing a therapeutically effective amount of one selected from the group consisting of tetrahydroisoquinoline compounds represented by formula (I), the pharmaceutically acceptable salts, prodrugs, hydrates and solvates thereof, can be used as the phosphodiesterase 4 (PDE4) inhibitors to treat autoimmune-related diseases, such as psoriasis.

The preparation of the pharmaceutically acceptable salt of the compound of the present invention can be carried out through a direct salt formation reaction by using the free base of the compound with an inorganic or organic acid. The inorganic or organic acid may be selected from the group consisting of hydrochloric acid, sulfuric acid, phosphoric acid, nitric acid, hydrofluoric acid, hydrobromic acid, formic acid, acetic acid, picric acid, citric acid, maleic acid, methanesulfonic acid, trifluoromethanesulfonic acid, ethanesulfonic acid and p-toluenesulfonic acid, and the like.

Since the compound of the present invention has excellent inhibitory activity against phosphodiesterase 4 (PDE4), the compound of the present invention and its various crystal forms, pharmaceutically acceptable inorganic or organic salts, hydrates or solvates, and pharmaceutical compositions containing the compound of the present invention as the main active ingredient can be used to treat or alleviate diseases related to phosphodiesterase 4 (PDE4), for example, to treat diseases related to abnormal expression of phosphodiesterase 4 (PDE4). According to the prior art, the compounds of the present invention can be used to treat the following diseases: psoriasis, psoriatic arthritis, atopic dermatitis, chronic obstructive pulmonary disease, and the like.

The pharmaceutical composition of the invention comprises the compound of the present invention or the pharmaceutically acceptable salts thereof in a safe and effective dosage range and pharmaceutically acceptable excipients or carriers. Wherein the "safe and effective dosage" means that the amount of compound is sufficient to significantly ameliorate the condition without causing significant side effects. Generally, the pharmaceutical composition contains 1-2000 mg of the compound of the invention per dose, preferably, 5-200 mg of the compound of the invention per dose. Preferably, the "dose" is a capsule or tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on the administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or CaHPO4, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art, such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or a combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

The compounds according to the present invention as described above can be used clinically in mammals, including humans and animals, and can be administered through the oral, nasal, skin, lung, or gastrointestinal tract, and more preferably oral. The preferred daily dose is 0.01 to 200 mg/kg body weight, administrated at one time, or 0.01 to 100 mg/kg body weight, in divided doses. Regardless of the method of administration, the individual's optimal dose should be based on the specific treatment. Usually, it starts with a small dose, and gradually increase the dose until the most suitable dose is found. Of course, the particular dose should also depend on various factors, such as the route of administration, patient healthy status, which are well within the skills of an experienced physician.

Compared with the Prior Art, the Main Advantages of the Present Invention Includes:

The tetrahydroisoquinoline compounds of the present invention have a good inhibitory effect on type 4 phosphodiesterase (PDE4), thus can be used to prevent, treat or assist the treatment of diseases related to the activity of phosphodiesterase, such as psoriasis and psoriasis arthritis, allergic dermatitis, chronic obstructive pulmonary disease, asthma, allergic rhinitis, ankylosing spondylitis, systemic Lupus erythematosus, rheumatoid arthritis, inflammatory bowel disease, pulmonary fibrosis, multiple sclerosis, Alzheimers disease, Huntingtons disease, Parkinson's disease, ADHD, depression and schizophrenia, especially immune and inflammatory diseases related to PDE4, such as psoriasis and arthritis is involved.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

The invention will be further exemplified in the following examples. These examples are only for illustrating the present invention, but do not intend to limit the present invention in any way. Unless otherwise stated, all parameters and other descriptions in the examples are based on quality.

The analysis data of the sample is determined by the following instruments: NMR was measured by GEMINI-300, Bruker AMX-400 and INVOA-600 NMR instruments, and TMS (tetramethylsilane) was used as internal standard. Unit of chemical shift is ppm, and coupling constant unit was Hz; the mass spectrum was determined by Finnigan MAT-711, MAT-95 and LCQ-DECA mass spectrometers and IonSpec 4.7 Tesla mass spectrometers.

Silica gel 200-300 mesh was used for column chromatography (produced by Qingdao Ocean Chemical Plant); TLC silica gel plate was HSGF-254 thin layer chromatography prefabricated plate produced by Yantai Chemical Plant; petroleum ether boiling range was 60-90° C.; color development was by using ultraviolet lamp, Iodine cylinder. Unless otherwise stated, the conventional reagents and drugs used in the following examples were purchased from Sinopharm Group. The reagents and solvents used in the experiment are handled according to the specific conditions of the reaction.

Example A1: Synthesis of Compound A1

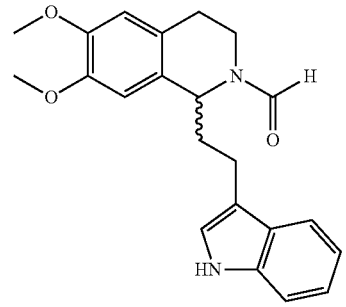 [SMILES: COc1cc2c(cc1OC)C(CCc1c[nH]c3ccccc13)N(C=O)CC2]

Synthetic Route:

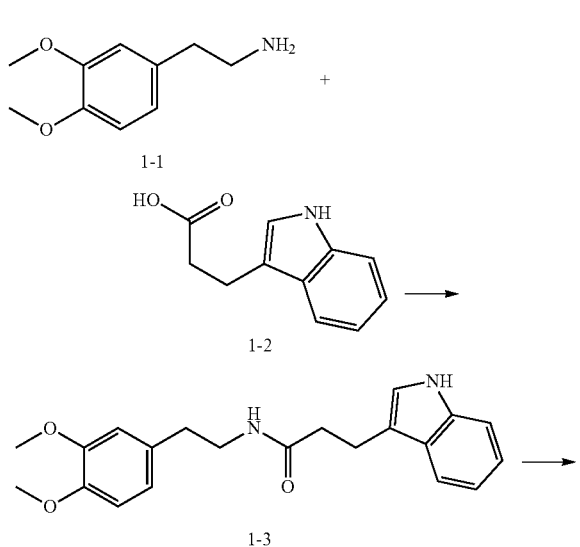

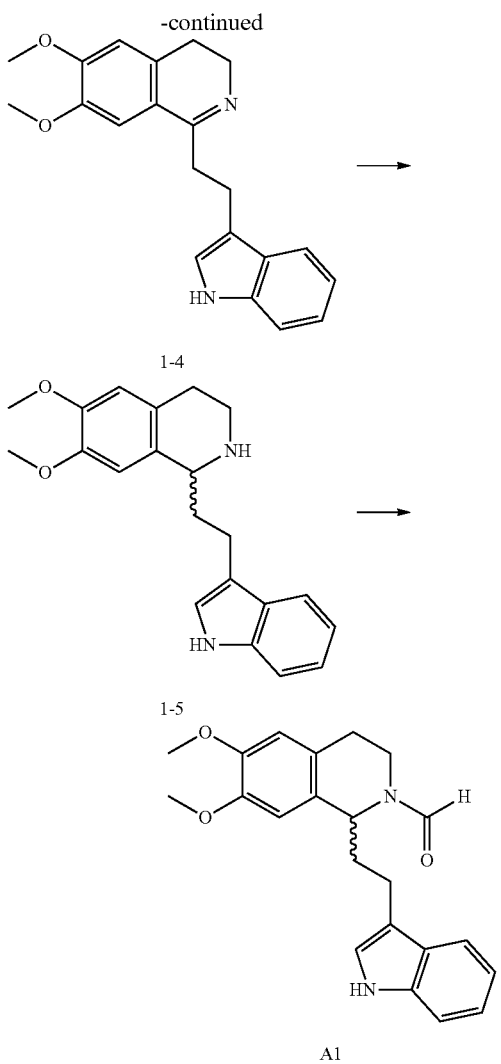

Synthesis of Compound 1-3:

1-2 was dissolved in dichloromethane, and EDCI, HOBT, TEA were added and stirred for 30 min. A solution of 1-1 in dichloromethane was added and stirred overnight, diluted with dichloromethane, then washed successively with saturated sodium bicarbonate, 1N diluted hydrochloric acid and saturated sodium chloride, dried over anhydrous sodium sulfate, and evaporated to dryness. The residue was purified through column chromatography with petroleum ether/ethyl acetate=1:1 to obtain a yellow-white solid 1.2 g, yield 92%. $^1$H NMR (400 MHz, CDCl$_3$) δ 7.75 (s, 1H), 7.57 (dd, J=7.5.1.4 Hz, 1H), 7.33 (dd, J=7.5, 1.4 Hz, 1H), 7.23-7.15 (m, 2H), 6.98 (td, J=7.4, 1.5 Hz, 1H), 6.79 (d, J=7.5 Hz, 1H), 6.74 (d, J=1.4 Hz, 1H), 6.60 (dd, J=7.5, 1.4 Hz, 1H), 5.62 (s, 1H), 3.83 (s, 3H), 3.75 (s, 3H), 3.37 (t, J=7.7 Hz, 2H), 2.68 (t, J=8.1 Hz, 2H), 2.60 (t, J=7.7 Hz, 2H), 2.28 (t, J=8.1 Hz, 2H). ESI-MS m/z 353.2 [M+H]$^+$.

Synthesis of Compound 1-4:

1 g of the compound 1-3 was dissolved in 100 mL of anhydrous acetonitrile, phosphorus oxychloride was added, and the mixture was refluxed and stirred under argon atmosphere. The solution was evaporated to dryness under reduced pressure after the reaction was completed as shown by TLC. Ice-cooled saturated sodium bicarbonate was added to make the solution weakly alkaline, then extracted with dichloromethane, dried over anhydrous sodium sulfate, and evaporated to dryness to obtain an orange oil, which was used in the further reaction without purification.

Synthesis of Compound 1-5:

The compound 1-4 was dissolved in methanol, sodium borohydride was added in portions under ice bath, and stirred at room temperature for 4 hours. Then the reaction was quenched with saturated ammonium chloride solution, extracted with dichloromethane, washed with saturated sodium bicarbonate and saturated sodium chloride. The organic layer was dried over sodium sulfate, concentrated, and purified through column chromatography with dichloromethane/methanol=20:1 to obtain a yellow solid, yield of two steps was 70%. $^1$H NMR (400 MHz, CDCl3) δ 8.19 (brs, 1H), 7.53 (d, J=7.8 Hz, 1H), 7.32 (d, J=8.1 Hz, 1H), 7.20-7.03 (m, 3H), 6.51 (s, 1H), 6.23 (s, 1H), 4.41 (t, J=5.8 Hz, 1H), 3.81 (s, 3H), 3.58 (s, 3H), 3.54-3.43 (m, 1H), 3.31-3.18 (m, 1H), 3.08-2.78 (m, 4H), 2.39 (dd, J=13.7, 7.1 Hz, 2H). ESI-MS m/z 337.2 [M+H]$^+$.

Synthesis of Compound A1:

100 mg of 1-5 was dissolved in ethyl formate, a catalytic amount of triethylamine was added dropwise, stirred and refluxed overnight. After the reaction was completed as shown by TLC, the solvent was evaporated to dryness, and purified through column chromatography with petroleum ether/ethyl acetate=1:1 to obtain a white solid A1, yield 90%. $^1$H NMR (400 MHz, CDCl$_3$) δ 8.29 (s, 1H (min)), 8.21 (s, 1H (maj)), 8.13 (brs, 1H (maj)), 8.06 (brs, 1H (min)), 7.63 (d, J=8.0 Hz, 1H (maj)), 7.58 (d, J=7.9 Hz, 1H (min)), 7.39 (d, J=8.1 Hz, 1H (maj)), 7.36 (d, J=8.1 Hz, 1H (min)), 7.24-7.06 (m, 2H (maj, min) 1H (min)), 7.03 (s, 1H (maj)), 6.57 (s, 1H (maj)), 6.55 (s, 1H (min)), 6.41 (s, 1H (min)), 6.39 (s, 1H (maj)), 5.47 (dd, J=7.6, 6.3 Hz, 1H (min)), 4.55 (dd, J=13.4, 5.2 Hz, 1H (maj)), 4.44 (dd, J=9.5, 4.1 Hz, 1H (maj)), 3.84 (s, 3H (maj)), 3.83 (s, 3H (min)), 3.78-3.70 (m, 1H (min) 3H (maj)), 3.68 (s, 3H (min)), 3.62 (ddd, J=13.4, 12.0, 4.4 Hz, 1H (min)), 3.13 (ddd, J=13.4, 12.0, 4.4 Hz, 1H (maj)), 3.02-2.63 (m, 4H), 2.36-2.17 (m, 2H). ESI-MS m/z 365.2 [M+H]$^+$ Example (S)-A1: Synthesis of Compound (S)-A1

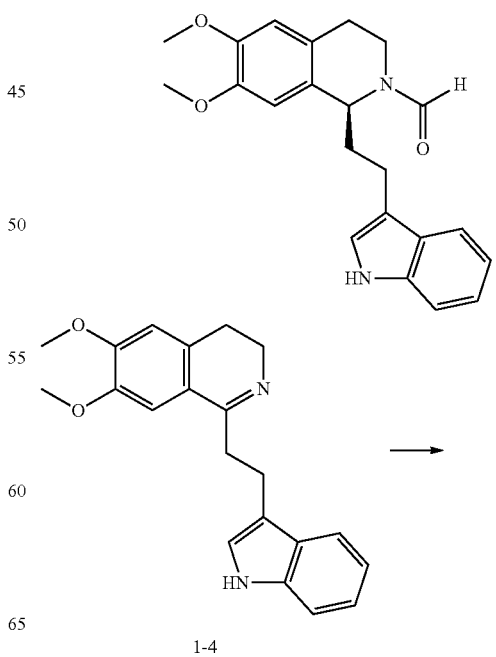

-continued

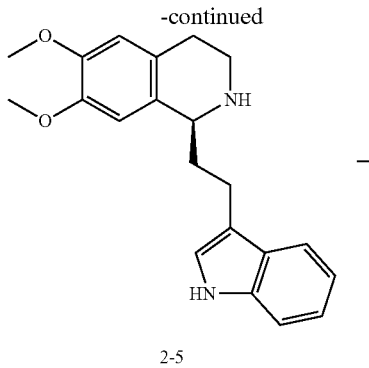

2-5

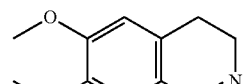

(S)-A1

1-4 was dissolved in a small amount of dichloromethane, deionized water, (R,R)-Noyori catalyst, silver hexafluoroantimonate, lanthanum trifluoromethanesulfonate, TBAB and sodium formate were added, and stirred at 40° C. under argon atmospheres overnight, extracted with dichloromethane, washed with water, and organic layer was filtered through celite, concentrated, purified through column chromatography with dichloromethane/methanol=40:1 to obtain 2-5. The compound (S)-A1 was obtained according to the synthesis method of compound A1. The compound (S)-A1 can also be obtained from A1 through chiral chromatography column. $^1$H NMR (400 MHz, CDCl$_3$) δ 8.29 (s, 1H (min)), 8.21 (s, 1H (maj)), 8.13 (brs, 1H (maj)), 8.06 (brs, 1H (min)), 7.63 (d, J=8.0 Hz, 1H (maj)), 7.58 (d, J=7.9 Hz, 1H (min)), 7.39 (d, J=8.1 Hz, 1H (maj)), 7.36 (d, J=8.1 Hz, 1H (min)), 7.24-7.06 (m, 2H (maj, min) 1H (min)), 7.03 (s, 1H (maj)), 6.57 (s, 1H (maj)), 6.55 (s, 1H (min)), 6.41 (s, 1H (min)), 6.39 (s, 1H (maj)), 5.47 (dd, J=7.6, 6.3 Hz, 1H (min)), 4.55 (dd, J=13.4, 5.2 Hz, 1H (maj)), 4.44 (dd, J=9.5, 4.1 Hz, 1H (maj)), 3.84 (s, 3H (maj)), 3.83 (s, 3H (min)), 3.78-3.70 (m, 1H (min) 3H (maj)), 3.68 (s, 3H (min)), 3.62 (ddd, J=13.4, 12.0, 4.4 Hz, 1H (min)), 3.13 (ddd, J=13.4, 12.0, 4.4 Hz, 1H (maj)), 3.02-2.63 (m, 4H), 2.36-2.17 (m, 2H).
ESI-MS m/z 365.2 [M+H]$^+$.

Example (R)-A1: Synthesis of Compound (R)-A1

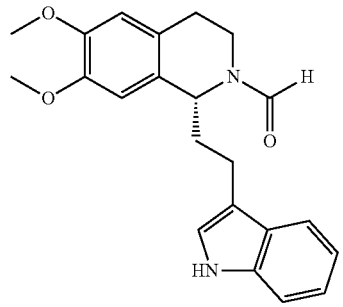

1-4

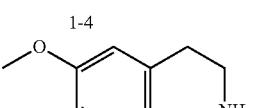

3-5

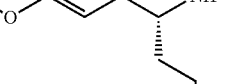

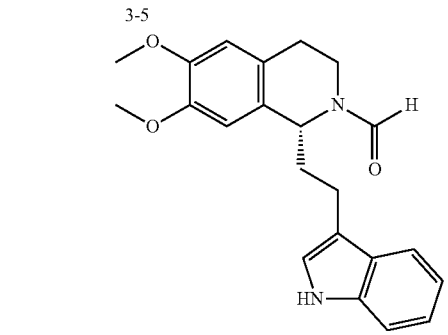

(R)-A1

The compound (R)-A1 was obtained according to the synthesis method of compound (S)-A1 by replacing the (R,R)-Noyori catalyst in Example (S)-A1 with (S,S)-Noyori catalyst. The compound (R)-A1 can also be obtained from A1 through chiral chromatography column. $^1$H NMR (400 MHz, CDCl$_3$) δ 8.29 (s, 1H (min)), 8.21 (s, 1H (maj)), 8.13 (brs, 1H (maj)), 8.06 (brs, 1H (min)), 7.63 (d, J=8.0 Hz, 1H (maj)), 7.58 (d, J=7.9 Hz, 1H (min)), 7.39 (d, J=8.1 Hz, 1H (maj)), 7.36 (d, J=8.1 Hz, 1H (min)), 7.24-7.06 (m, 2H (maj, min) 1H (min)), 7.03 (s, 1H (maj)), 6.57 (s, 1H (maj)), 6.55 (s, 1H (min)), 6.41 (s, 1H (min)), 6.39 (s, 1H (maj)), 5.47

(dd, J=7.6, 6.3 Hz, 1H (min)), 4.55 (dd, J=13.4, 5.2 Hz, 1H (maj)), 4.44 (dd, J=9.5, 4.1 Hz, 1H (maj)), 3.84 (s, 3H (maj)), 3.83 (s, 3H (min)), 3.78-3.70 (m, 1H (min) 3H (maj)), 3.68 (s, 3H (min)), 3.62 (ddd, J=13.4, 12.0, 4.4 Hz, 1H (min)), 3.13 (ddd, J=13.4, 12.0, 4.4 Hz, 1H (maj)), 3.02-2.63 (m, 4H), 2.36-2.17 (m, 2H). $^1$H NMR ESI-MS m/z 365.2 [M+H]$^+$.

Example A2: Synthesis of Compound A2

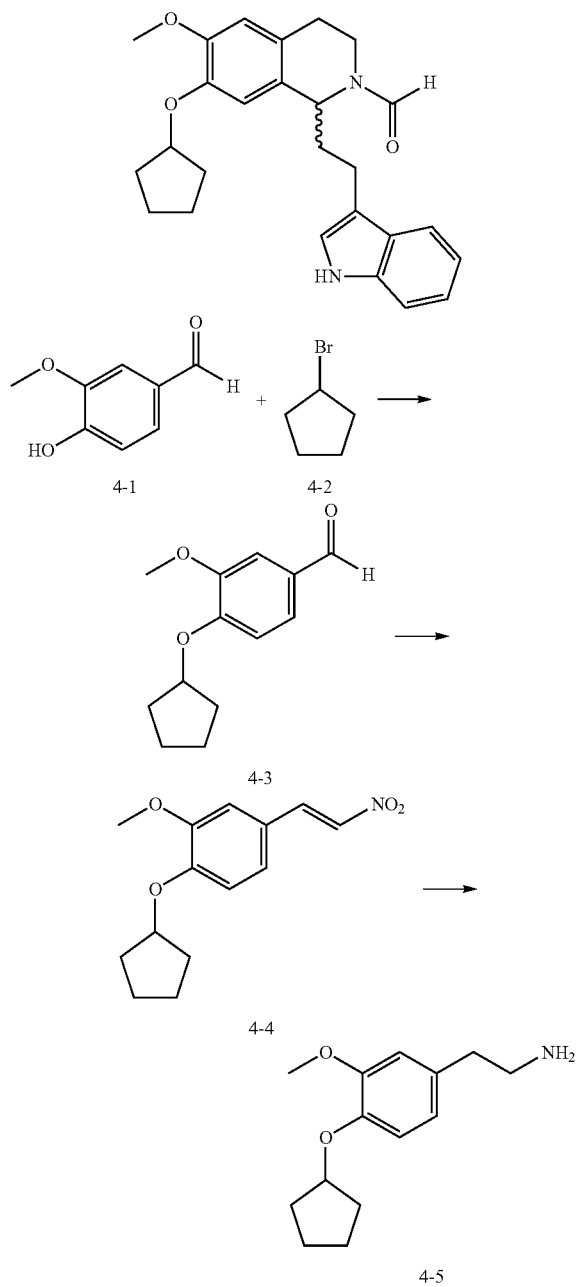

Synthesis of Compound 4-3:

4-1 was dissolved in acetone, potassium carbonate was added, and 4-2 was added dropwise and stirred under reflux overnight. The reaction solution was filtered, evaporated to dryness, diluted with dichloromethane, stirred with water for 10 min, and stood to separate the layers. The organic layer was evaporated to dryness to obtain a yellow solid 4-3, which was directly dropped into next step without purification.

Synthesis of Compound 4-4:

4-3 was dissolved in nitromethane, ammonium acetate was added and refluxed for 2 h, and the solvent was evaporated to dryness. The residue was added to ice water and stirred for 2 h, stood and filtered to obtain a yellow solid, yield 90%. $^1$H NMR (400 MHz, CDCl$_3$) δ 7.96 (s, 2H), 7.42 (dd, J=7.5, 1.4 Hz, 1H), 7.23 (d, J=1.4 Hz, 1H), 6.93 (d, J=7.5 Hz, 1H), 4.58 (dd, J=7.8 Hz, 1H), 3.85 (s, 3H), 2.12-2.00 (m, 2H), 1.84-1.66 (m, 2H), 1.67-1.54 (m, 1H). ESI-MS m/z 264.1 [M+H]+

Synthesis of Compound 4-5:

Lithium aluminum hydride was added to argon-protected tetrahydrofuran in batches under ice bath. A 4-4 tetrahydrofuran solution was added dropwise with stirring. After the addition was completed, the solution was refluxed for 2 h. Water was slowly added under ice bath to quench the reaction, then filtered. The filter cake was washed with ethyl acetate, and evaporated to provide a yellowish transparent oil. The product was directly used in the next step without purification.

The compound A2 was obtained according to the synthesis of the compound A1, while 1-1 in example A1 was replaced with compound 4-5. $^1$H NMR (400 MHz, CDCl$_3$) δ 8.28 (s, 1H (min)), 8.20 (s, 1H (maj)), 8.14 (brs, 1H (maj)), 8.07 (brs, 1H (min)), 7.63 (d, J=7.9 Hz, 1H (maj)), 7.58 (d, J=7.9 Hz, 1H (min)), 7.39 (d, J=8.1 Hz, 1H (maj)), 7.36 (d, J=8.1 Hz, 1H (min)), 7.24-7.16 (m, 2H (maj)), 7.15 (s, 1H (maj)), 7.13-7.06 (m, 2H (min)), 7.02 (s, 1H (min)), 6.56 (s, 1H (maj)), 6.54 (s, 1H (min)), 6.41 (s, 1H (min)), 6.39 (s, 1H (maj)), 5.45 (dd, J=8.6, 5.0 Hz, 1H (min)), 4.57 (m, 1H), 4.52 (m, 1H (maj)), 4.41 (dd, J=9.5, 4.4 Hz, 1H (maj)), 3.80 (s, 3H (maj)), 3.79 (s, 3H (min)), 3.72 (dd, J=13.4, 5.3 Hz, 1H (min)), 3.62 (ddd, J=13.6, 12.0, 4.5 Hz, 1H (min)), 3.12 (ddd, J=13.0, 12.0, 4.7 Hz, 1H (maj)), 3.01-2.61 (m, 4H), 2.32-2.17 (m, 2H), 1.92-1.66 (m, 6H), 1.64-1.48 (m, 2H). ESI-MS m/z 419.2 [M+H]$^+$.

Example (S)-A2: Synthesis of Compound (S)-A2

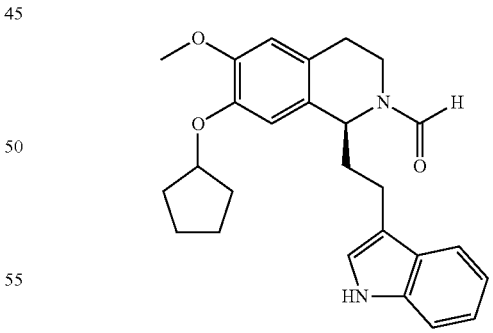

The compound (S)-A2 was obtained according to the synthesis of the compound (S)-A1, while 1-1 in example A1 was replaced with compound 4-5. $^1$H NMR (400 MHz, CDCl$_3$) δ 8.28 (s, 1H (min)), 8.20 (s, 1H (maj)), 8.14 (brs, 1H (maj)), 8.07 (brs, 1H (min)), 7.63 (d, J=7.9 Hz, 1H (maj)), 7.58 (d, J=7.9 Hz, 1H (min)), 7.39 (d, J=8.1 Hz, 1H (maj)), 7.36 (d, J=8.1 Hz, 1H (min)), 7.24-7.16 (m, 2H (maj)), 7.15 (s, 1H (maj)), 7.13-7.06 (m, 2H (min)), 7.02 (s, 1H (min)), 6.56 (s, 1H (maj)), 6.54 (s, 1H (min)), 6.41 (s, 1H (min)), 6.39 (s, 1H (maj)), 5.45 (dd, J=8.6, 5.0 Hz, 1H (min)), 4.57 (m, 1H), 4.52 (m, 1H (maj)), 4.41 (dd, J=9.5, 4.4 Hz, 1H (maj)), 3.80 (s, 3H (maj)), 3.79 (s, 3H (min)). 3.72 (dd. J=13.4, 5.3 Hz, 1H (min)), 3.62 (ddd, J=13.6, 12.0, 4.5 Hz, 1H (min)), 3.12 (ddd, J=13.0, 12.0, 4.7 Hz, 1H (maj)), 3.01-2.61 (m, 4H), 2.32-2.17 (m, 2H), 1.92-1.66 (m, 6H), 1.64-1.48 (m, 2H). ESI-MS m/z 419.2 [M+H]⁺.

Example (R)-A2: Synthesis of Compound (R)-A2

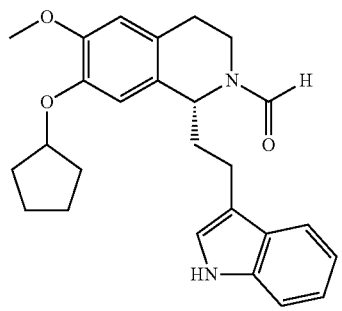 [SMILES: COc1cc2c(cc1OC1CCCC1)[C@@H](CCc1c[nH]c3ccccc13)N(C=O)CC2]

The compound (R)-A2 was obtained according to the synthesis of the compound (R)-A1, while 1-1 in example A1 was replaced with compound 4-5. ¹H NMR (400 MHz, CDCl₃) δ 8.28 (s, 1H (min)), 8.20 (s, 1H (maj)), 8.14 (brs, 1H (maj)), 8.07 (brs, 1H (min)), 7.63 (d, J=7.9 Hz, 1H (maj)), 7.58 (d, J=7.9 Hz, 1H (min)), 7.39 (d, J=8.1 Hz, 1H (maj)), 7.36 (d, J=8.1 Hz, 1H (min)), 7.24-7.16 (m, 2H (maj)), 7.15 (s, 1H (maj)), 7.13-7.06 (m, 2H (min)), 7.02 (s, 1H (min)), 6.56 (s, 1H (maj)), 6.54 (s, 1H (min)), 6.41 (s, 1H (min)), 6.39 (s, 1H (maj)), 5.45 (dd, J=8.6, 5.0 Hz, 1H (min)), 4.57 (m, 1H), 4.52 (m, 1H (maj)), 4.41 (dd, J=9.5, 4.4 Hz, 1H (maj)), 3.80 (s, 3H (maj)), 3.79 (s, 3H (min)), 3.72 (dd, J=13.4, 5.3 Hz, 1H (min)), 3.62 (ddd, J=13.6, 12.0, 4.5 Hz, 1H (min)). 3.12 (ddd, J=13.0, 12.0, 4.7 Hz, 1H (maj)), 3.01-2.61 (m, 4H), 2.32-2.17 (m, 2H), 1.92-1.66 (m, 6H), 1.64-1.48 (m, 2H).
ESI-MS m/z 419.2 [M+H]⁺.

Example A3: Synthesis of Compound A3

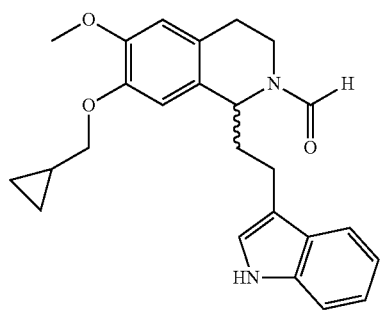

6-1

The compound A3 was obtained according to the synthesis of the compound A2, while 4-2 in example A2 was replaced with compound 6-1. H¹ NMR (400 MHz, CDCl₃) δ 8.28 (s, 1H (min)), 8.21 (brs, 1H (maj)), 8.20 (s, 1H (maj)), 8.12 (brs, 1H (min)), 7.62 (d, J=7.9 Hz, 1H (maj)), 7.56 (d, J=7.9 Hz, 1H (min)), 7.38 (d, J=8.1 Hz, 1H (maj)), 7.36 (d, J=8.1 Hz, 1H (min)), 7.24-7.16 (m, 2H (maj)), 7.13 (s, 1H (maj)), 7.12-7.05 (m, 2H (min)), 7.02 (s, 1H (min)), 6.57 (s, 1H (maj)), 6.55 (s, 1H (min)). 6.42 (s, 1H (min)), 6.40 (s, 1H (maj)), 5.44 (dd, J=8.6, 5.0 Hz, 1H (min)), 4.54 (dd, J=13.2, 5.0 Hz, 1H (maj)), 4.40 (dd, J=9.3, 4.3 Hz, 1H (maj)), 3.83 (s, 3H), 3.77-3.56 (m, 2H (min), 2H (maj, min)), 3.12 (ddd, J=12.4, 4.7, 4.7 Hz, 1H (maj)), 3.00-2.62 (m, 4H), 2.32-2.15 (m, 2H), 1.36-1.17 (m, 1H), 0.68-0.51 (m, 2H), 0.29 (m, 2H). ESI-MS m/z 405.2 [M+H]⁺.

Example (S)-A3: Synthesis of Compound (S)-A3

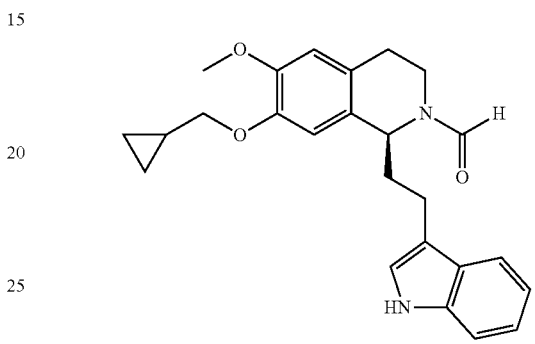

The compound (S)-A3 was obtained according to the synthesis of the compound (S)-A2, while 4-2 in example A2 was replaced with compound 6-1. H¹ NMR (400 MHz, CDCl₃) δ 8.28 (s, 1H (min)), 8.21 (brs. 1H (maj)), 8.20 (s, 1H (maj)), 8.12 (brs, 1H (min)), 7.62 (d, J=7.9 Hz, 1H (maj)), 7.56 (d, J=7.9 Hz, 1H (min)), 7.38 (d, J=8.1 Hz, 1H (maj)), 7.36 (d, J=8.1 Hz, 1H (min)), 7.24-7.16 (m, 2H (maj)), 7.13 (s, 1H (maj)), 7.12-7.05 (m, 2H (min)), 7.02 (s, 1H (min)), 6.57 (s, 1H (maj)), 6.55 (s, 1H (min)), 6.42 (s, 1H (min)), 6.40 (s, 1H (maj)), 5.44 (dd, J=8.6, 5.0 Hz, 1H (min)), 4.54 (dd, J=13.2, 5.0 Hz, 1H (maj)), 4.40 (dd, J=9.3, 4.3 Hz, 1H (maj)), 3.83 (s, 3H), 3.77-3.56 (m, 2H (min), 2H (maj, min)), 3.12 (ddd, J=12.4, 4.7, 4.7 Hz, 1H (maj)), 3.00-2.62 (m, 4H), 2.32-2.15 (m, 2H), 1.36-1.17 (m, 1H), 0.68-0.51 (m, 2H), 0.29 (m, 2H). ESI-MS m/z 405.2 [M+H]⁺.

Example (R)-A3: Synthesis of Compound (R)-A3

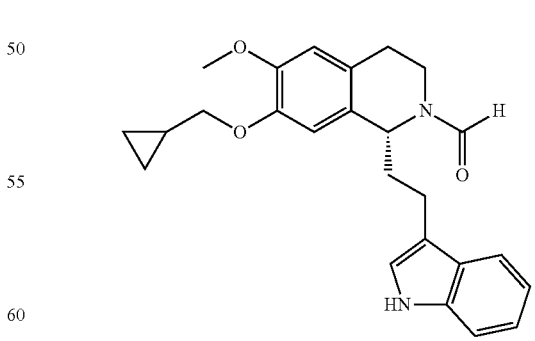

The compound (R)-A3 was obtained according to the synthesis of the compound (R)-A2, while 4-2 in example A2 was replaced with compound 6-1. ¹H NMR (400 MHz, CDCl₃) δ 8.28 (s, 1H (min)), 8.21 (brs, 1H (maj)), 8.20 (s, 1H (maj)), 8.12 (brs, 1H (min)), 7.62 (d, J=7.9 Hz, 1H (maj)), 7.56 (d, J=7.9 Hz, 1H (min)), 7.38 (d, J=8.1 Hz, 1H (maj)), 7.36 (d, J=8.1 Hz, 1H (min)), 7.24-7.16 (m, 2H (maj)), 7.13 (s, 1H (maj)), 7.12-7.05 (m, 2H (min)), 7.02 (s, 1H (min)), 6.57 (s, 1H (maj)), 6.55 (s, 1H (min)), 6.42 (s, 1H (min)), 6.40 (s, 1H (maj)), 5.44 (dd, J=8.6, 5.0 Hz, 1H (min)), 4.54 (dd, J=13.2, 5.0 Hz, 1H (maj)), 4.40 (dd, J=9.3, 4.3 Hz, 1H (maj)), 3.83 (s, 3H), 3.77-3.56 (m, 2H (min), 2H (maj, min)), 3.12 (ddd, J=12.4, 4.7, 4.7 Hz, 1H (maj)), 3.00-2.62 (m, 4H), 2.32-2.15 (m, 2H), 1.36-1.17 (m, 1H), 0.68-0.51 (m, 2H), 0.29 (m, 2H). ESI-MS m/z 405.2 [M+H]$^+$.

Example A4: Synthesis of Compound A4

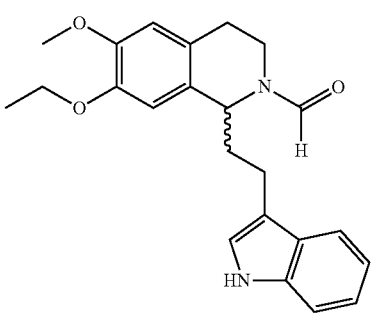

ZN 26

The compound A4 was obtained according to the synthesis of the compound A2, while 4-2 in example A2 was replaced with bromoethane. $^1$H NMR (400 MHz, CDCl$_3$) δ 8.28 (s, 1H (min)), 8.20 (s, 1H (maj)), 8.13 (brs, 1H (maj)), 8.06 (brs, 1H (min)), 7.62 (d, J=7.8 Hz, 1H (maj)), 7.57 (d, J=7.9 Hz, 1H (min)), 7.39 (d, J=8.1 Hz, 1H (maj)), 7.36 (d, J=8.1 Hz, 1H (min)), 7.24-7.00 (m, 3H), 6.57 (s, 1H (maj)), 6.54 (s, 1H (min)), 6.41 (s, 1H (min)), 6.40 (s, 1H (maj)), 5.45 (dd, J=8.2, 5.1 Hz, 1H (min)). 4.54 (dd. J=13.0, 4.4 Hz, 1H (maj)), 4.42 (dd, J=9.2, 4.7 Hz, 1H (maj)), 4.01-3.83 (m, 2H), 3.83 (s, 3H (maj)), 3.82 (s, 3H (min)), 3.73 (dd, J=13.3, 5.3 Hz, 1H (min)), 3.62 (ddd, J=13.4, 11.8, 4.6 Hz, 1H (min)), 3.12 (ddd, J=13.0, 11.7, 4.7 Hz, 1H (maj)). 2.99-2.63 (m, 4H), 2.31-2.17 (m, 2H), 1.40 (t, J=7.0 Hz, 3H (maj)), 1.36 (t, J=7.0 Hz, 3H (min)). ESI-MS m/z 379.2 [M+H]$^+$.

Example (S)-A4: Synthesis of Compound (S)-A4

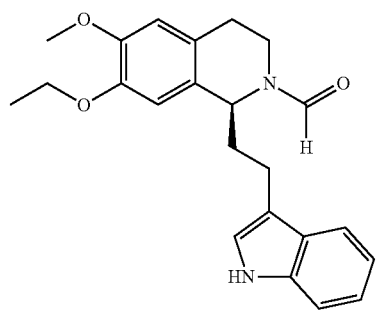 [SMILES: CCOc1cc2c(cc1OC)CCN(C=O)[C@H]2CCc1c[nH]c2ccccc12]

The compound (S)-A4 was obtained according to the synthesis of the compound (S)-A2, while 4-2 in example A2 was replaced with bromoethane. $^1$H NMR (400 MHz, CDCl$_3$) δ 8.28 (s, 1H (min)), 8.20 (s, 1H (maj)), 8.13 (brs, 1H (maj)), 8.06 (brs, 1H (min)), 7.62 (d, J=7.8 Hz, 1H (maj)), 7.57 (d, J=7.9 Hz, 1H (min)), 7.39 (d, J=8.1 Hz, 1H (maj)), 7.36 (d, J=8.1 Hz, 1H (min)), 7.24-7.00 (m, 3H), 6.57 (s, 1H (maj)), 6.54 (s, 1H (min)), 6.41 (s, 1H (min)), 6.40 (s, 1H (maj)), 5.45 (dd, J=8.2, 5.1 Hz, 1H (min)), 4.54 (dd, J=13.0, 4.4 Hz, 1H (maj)), 4.42 (dd, J=9.2, 4.7 Hz, 1H (maj)), 4.01-3.83 (m, 2H), 3.83 (s, 3H (maj)), 3.82 (s, 3H (min)), 3.73 (dd, J=13.3, 5.3 Hz, 1H (min)), 3.62 (ddd, J=13.4, 11.8, 4.6 Hz, 1H (min)), 3.12 (ddd, J=13.0, 11.7, 4.7 Hz, 1H (maj)), 2.99-2.63 (m, 4H), 2.31-2.17 (m, 2H), 1.40 (t, J=7.0 Hz, 3H (maj)), 1.36 (t, J=7.0 Hz, 3H (min)). ESI-MS m/z 379.2 [M+H]$^+$.

Example (R)-A4: Synthesis of Compound (R)-A4

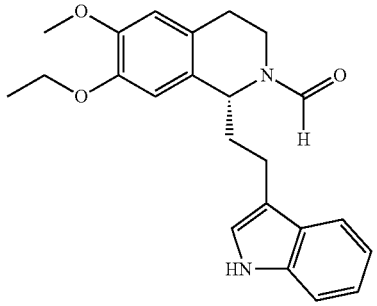 [SMILES: CCOc1cc2c(cc1OC)CCN(C=O)[C@@H]2CCc1c[nH]c2ccccc12]

The compound (R)-A4 was obtained according to the synthesis of the compound (R)-A2, while 4-2 in example A2 was replaced with bromoethane. $^1$H NMR (400 MHz, CDCl$_3$) δ 8.28 (s, 1H (min)). 8.20 (s, 1H (maj)). 8.13 (brs, 1H (maj)), 8.06 (brs, 1H (min)), 7.62 (d, J=7.8 Hz, 1H (maj)), 7.57 (d, J=7.9 Hz, 1H (min)), 7.39 (d, J=8.1 Hz, 1H (maj)), 7.36 (d, J=8.1 Hz, 1H (min)), 7.24-7.00 (m, 3H), 6.57 (s, 1H (maj)), 6.54 (s, 1H (min)), 6.41 (s, 1H (min)), 6.40 (s, 1H (maj)), 5.45 (dd, J=8.2, 5.1 Hz, 1H (min)), 4.54 (dd, J=13.0, 4.4 Hz, 1H (maj)), 4.42 (dd, J=9.2, 4.7 Hz, 1H (maj)), 4.01-3.83 (m, 2H), 3.83 (s, 3H (maj)), 3.82 (s, 3H (min)), 3.73 (dd, J=13.3, 5.3 Hz, 1H (min)), 3.62 (ddd, J=13.4, 11.8, 4.6 Hz, 1H (min)), 3.12 (ddd, J=13.0, 11.7, 4.7 Hz, 1H (maj)), 2.99-2.63 (m, 4H), 2.31-2.17 (m, 2H), 1.40 (t, J=7.0 Hz, 3H (maj)), 1.36 (t, J=7.0 Hz, 3H (min)). ESI-MS m/z 379.2 [M+H]+.

Example A5: Synthesis of Compound A5

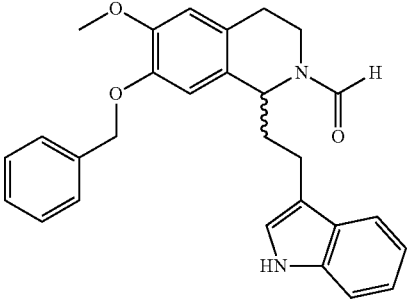 [SMILES: COc1cc2c(cc1OCc1ccccc1)C(CCc1c[nH]c3ccccc13)N(C=O)CC2]

The compound A5 was obtained according to the synthesis of the compound A2, while 4-2 in example A2 was replaced with benzyl bromide. $^1$H NMR (400 MHz, CDCl$_3$)

δ 8.27 (s, 1H (min)), 8.15 (s, 1H (maj)), 8.11 (brs. 1H (maj)), 8.05 (brs, 1H (min)), 7.59 (d, J=8.0 Hz, 1H (maj)), 7.56 (d, J=7.9 Hz, 1H (min)), 7.44-7.27 (m, 6H), 7.24-7.11 (m, 2H), 7.09 (s, 1H (min)), 6.95 (s, 1H (maj)), 6.59 (s, 1H (maj)), 6.57 (s, 1H (min)), 6.45 (s, 1H (min)), 6.41 (s, 1H (maj)), 5.38 (dd, J=9.2, 4.3 Hz, 1H (min)), 5.06-4.88 (m, 2H), 4.52 (dd, J=13.1, 4.9 Hz, 1H (maj)), 4.34 (dd, J=8.4, 5.6 Hz, 1H (maj)), 3.85 (s, 3H (maj)), 3.84 (s, 3H (min)), 3.71 (dd, J=13.4, 5.2 Hz, 1H (min)), 3.64-3.55 (m, 1H (min)), 3.15-3.03 (m, 1H (maj)), 2.80 (m, 4H), 2.13 (m, 2H). ESI-MS m/z 441.2 [M+H]$^+$.

Example (S)-A5: Synthesis of Compound (S)-A5

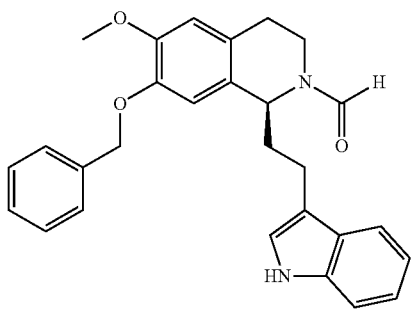 [SMILES: COc1cc2c(cc1OCc1ccccc1)[C@H](CCc1c[nH]c3ccccc13)N(C=O)CC2]

The compound (S)-A5 was obtained according to the synthesis of the compound (S)-A2, while 4-2 in example A2 was replaced with benzyl bromide. $^1$H NMR (400 MHz, CDCl$_3$) δ 8.27 (s, 1H (min)), 8.15 (s, 1H (maj)), 8.11 (brs, 1H (maj)), 8.05 (brs, 1H (min)), 7.59 (d, J=8.0 Hz, 1H (maj)), 7.56 (d, J=7.9 Hz, 1H (min)), 7.44-7.27 (m, 6H), 7.24-7.11 (m, 2H), 7.09 (s, 1H (min)), 6.95 (s, 1H (maj)), 6.59 (s, 1H (maj)), 6.57 (s, 1H (min)), 6.45 (s, 1H (min)), 6.41 (s, 1H (maj)), 5.38 (dd, J=9.2, 4.3 Hz, 1H (min)), 5.06-4.88 (m, 2H), 4.52 (dd, J=13.1, 4.9 Hz, 1H (maj)), 4.34 (dd, J=8.4, 5.6 Hz, 1H (maj)), 3.85 (s, 3H (maj)), 3.84 (s, 3H (min)), 3.71 (dd, J=13.4, 5.2 Hz, 1H (min)), 3.64-3.55 (m, 1H (min)), 3.15-3.03 (m, 1H (maj)). 2.80 (m, 4H), 2.13 (m, 2H). ESI-MS m/z 441.2 [M+H]$^+$.

Example (R)-A5: Synthesis of Compound (R)-A5

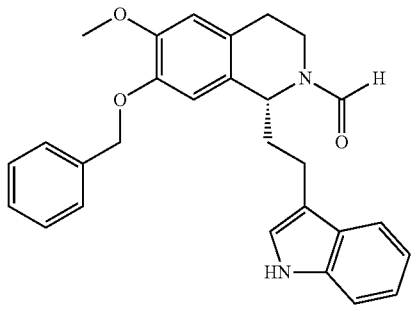 [SMILES: COc1cc2c(cc1OCc1ccccc1)[C@@H](CCc1c[nH]c3ccccc13)N(C=O)CC2]

The compound (R)-A5 was obtained according to the synthesis of the compound (R)-A2, while 4-2 in example A2 was replaced with benzyl bromide. $^1$H NMR (400 MHz, CDCl$_3$) δ 8.27 (s, 1H (min)), 8.15 (s, 1H (maj)), 8.11 (brs, 1H (maj)), 8.05 (brs, 1H (min)), 7.59 (d, J=8.0 Hz, 1H (maj)), 7.56 (d, J=7.9 Hz, 1H (min)), 7.44-7.27 (m, 6H), 7.24-7.11 (m, 2H), 7.09 (s, 1H (min)), 6.95 (s, 1H (maj)), 6.59 (s, 1H (maj)), 6.57 (s, 1H (min)), 6.45 (s, 1H (min)), 6.41 (s, 1H (maj)), 5.38 (dd, J=9.2, 4.3 Hz, 1H (min)), 5.06-4.88 (m, 2H), 4.52 (dd, J=13.1, 4.9 Hz, 1H (maj)), 4.34 (dd, J=8.4, 5.6 Hz, 1H (maj)), 3.85 (s, 3H (maj)), 3.84 (s, 3H (min)), 3.71 (dd, J=13.4, 5.2 Hz, 1H (min)), 3.64-3.55 (m, 1H (min)), 3.15-3.03 (m, 1H (maj)), 2.80 (m, 4H), 2.13 (m, 2H). ESI-MS m/z 441.2 [M+H]$^+$.

Example A6: Synthesis of Compound A6

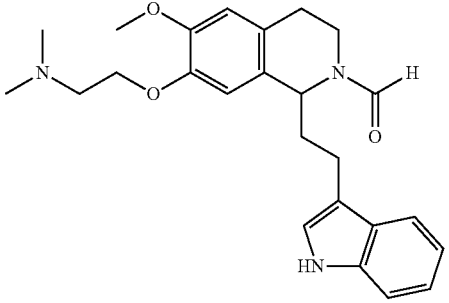 [SMILES: COc1cc2c(cc1OCCN(C)C)C(CCc1c[nH]c3ccccc13)N(C=O)CC2]

Compound A5 was subjected to palladium-carbon catalyzed hydrogenation to remove benzyl, and then reacted with (2-bromomethyl)dimethylamine in potassium carbonate/acetonitrile system to obtain A6.

Example (S)-A6: Synthesis of Compound A6

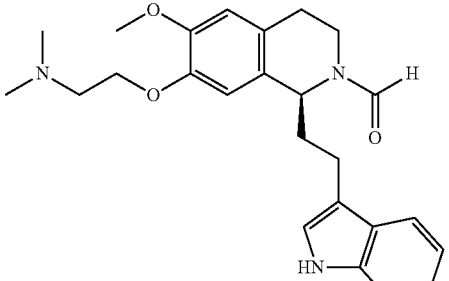

Compound (S)-A5 was subjected to palladium-carbon catalyzed hydrogenation to remove benzyl, and then reacted with (2-bromomethyl)dimethylamine in potassium carbonate/acetonitrile system to obtain (S)-A6

Example (R)-A6: Synthesis of Compound A6

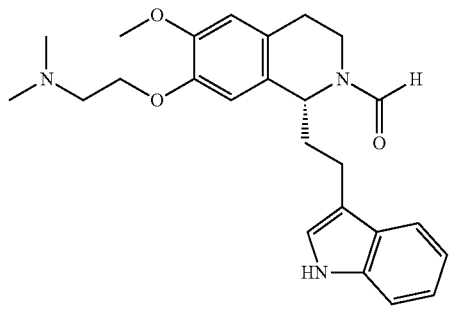 [SMILES: COc1cc2c(cc1OCCN(C)C)[C@@H](CCc1c[nH]c3ccccc13)N(C=O)CC2]

Compound (R)-A5 was subjected to palladium-carbon catalyzed hydrogenation to remove benzyl, and then reacted with (2-bromomethyl)dimethylamine in potassium carbonate/acetonitrile system to obtain (R)-A6

Example A7: Synthesis of Compound A7

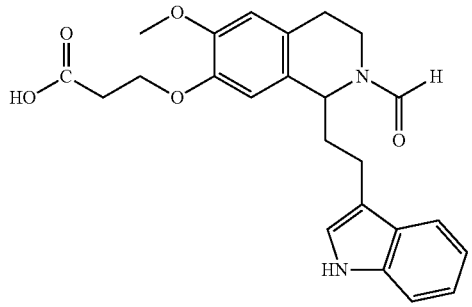 [SMILES: COc1cc2c(cc1OCCC(=O)O)C(CCc1c[nH]c3ccccc13)N(C=O)CC2]

Compound A5 was subjected to palladium-carbon catalyzed hydrogenation to remove benzyl, and then reacted with 3-bromopropionic acid in potassium carbonate/acetonitrile system to obtain A7.

Example (S)-A7: Synthesis of Compound A7

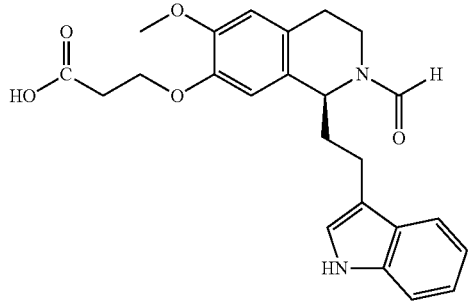 [SMILES: COc1cc2c(cc1OCCC(=O)O)[C@H](CCc1c[nH]c3ccccc13)N(C=O)CC2]

Compound (S)-A5 was subjected to palladium-carbon catalyzed hydrogenation to remove benzyl, and then reacted with 3-bromopropionic acid in potassium carbonate/acetonitrile system to obtain (S)-A7.

Example (R)-A7: Synthesis of Compound A7

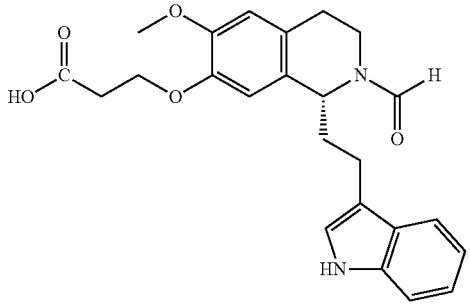

Compound (R)-A5 was subjected to palladium-carbon catalyzed hydrogenation to remove benzyl, and then reacted with 3-bromopropionic acid in potassium carbonate/acetonitrile system to obtain (R)-A7.

Example B1: Synthesis of Compound B1

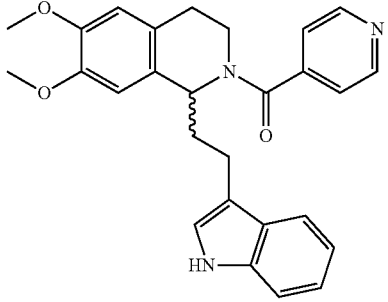

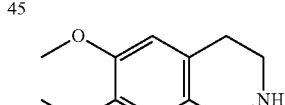

1-5

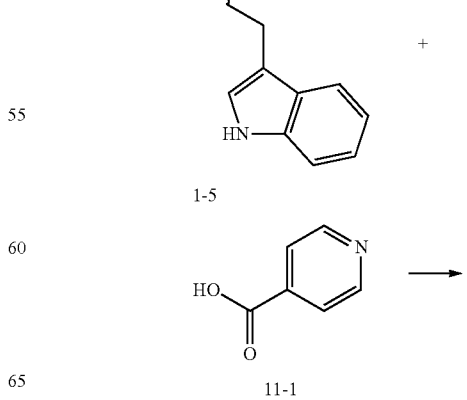

11-1

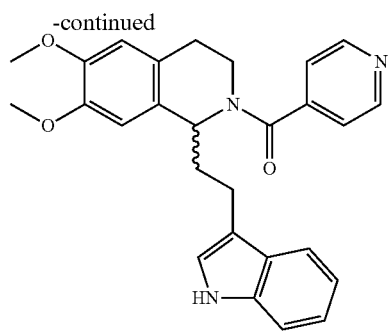

11

11-1 was dissolved in dichloromethane, and EDCI, HOBT, TEA were added and stirred for 30 min. A solution of 1-5 in dichloromethane was added slowly and stirred overnight, diluted with dichloromethane, then washed successively with saturated sodium bicarbonate, 1N diluted hydrochloric acid, and saturated sodium chloride, dried over anhydrous sodium sulfate, and evaporated to dryness. The residue was purified through column chromatography with petroleum ether/ethyl acetate=1:1 to obtain a white solid B1 50 mg, yield %. $^1$H NMR (400 MHz, CDCl$_3$) δ 8.72 (d, J=5.7 Hz, 2H (maj)), 8.56 (d, J=4.5 Hz, 2H (min)), 8.14 (brs, 1H (maj)), 8.06 (brs, 1H (min)), 7.61 (d, J=7.8 Hz, 1H (maj)), 7.49 (d, J=7.9 Hz, 1H (min)), 7.40-7.32 (m, 1H), 7.31-7.08 (m, 4H (min, maj) 1H (maj)), 6.65 (s, 1H (min)), 6.60 (s, 1H (min)), 6.56 (s, 1H (maj)), 6.48 (s, 1H (maj)), 6.23 (s, 1H (min)), 5.83 (dd, J=9.5, 4.4 Hz, 1H (maj)), 4.82 (dd, J=13.2, 5.1 Hz, 1H (min)), 4.64 (dd, J=8.3, 5.5 Hz, 1H (min)), 3.87 (s, 3H (min)), 3.84 (s, 3H (maj)), 3.75-3.62 (m, 3H (min, maj) 1H (maj)), 3.57 (ddd, J=13.7, 11.6, 4.2 Hz, 1H (maj)), 3.39 (ddd, J=13.2, 11.4, 5.0 Hz, 1H (min)), 3.16-2.74 (m, 3H), 2.71-2.57 (m, 1H), 2.47-2.36 (m, 1H (maj)), 2.35-2.23 (m, 1H), 2.20-2.10 (m, 1H (min)). ESI-MS m/z 442.2 [M+H]$^+$.

Example (S)-B1: Synthesis of Compound (S)-B1

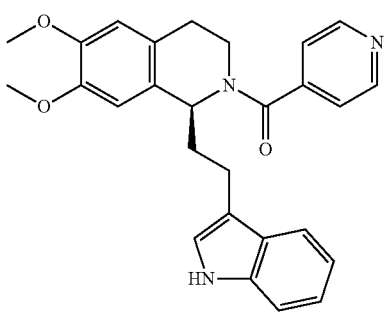 [SMILES: COc1cc2c(cc1OC)[C@H](CCc1c[nH]c3ccccc13)N(C(=O)c1ccncc1)CC2]

1-5 in Example B1 was replaced with 2-5 to obtain compound (S)-B1 as a white solid 50 mg, yield 60%. $^1$H NMR (400 MHz, CDCl$_3$) δ 8.72 (d, J=5.7 Hz, 2H (maj)), 8.56 (d, J=4.5 Hz, 2H (min)), 8.14 (brs. 1H (maj)), 8.06 (brs, 1H (min)), 7.61 (d, J=7.8 Hz, 1H (maj)), 7.49 (d, J=7.9 Hz, 1H (min)), 7.40-7.32 (m, 1H), 7.31-7.08 (m, 4H (min, maj) 1H (maj)), 6.65 (s, 1H (min)), 6.60 (s, 1H (min)), 6.56 (s, 1H (maj)), 6.48 (s, 1H (maj)), 6.23 (s, 1H (min)), 5.83 (dd, J=9.5, 4.4 Hz, 1H (maj)), 4.82 (dd, J=13.2, 5.1 Hz, 1H (min)), 4.64 (dd, J=8.3, 5.5 Hz, 1H (min)), 3.87 (s, 3H (min)), 3.84 (s, 3H (maj)), 3.75-3.62 (m, 3H (min, maj) 1H (maj)), 3.57 (ddd, J=13.7, 11.6, 4.2 Hz, 1H (maj)), 3.39 (ddd, J=13.2, 11.4, 5.0 Hz, 1H (min)), 3.16-2.74 (m, 3H), 2.71-2.57 (m, 1H), 2.47-2.36 (m, 1H (maj)). 2.35-2.23 (m, 1H), 2.20-2.10 (m, 1H (min)). ESI-MS m/z 442.2 [M+H]$^+$.

Example (R)-B1: Synthesis of Compound (R)-B1

1-5 in Example B1 was replaced with 3-5 to obtain compound (R)-B1 as a white solid 50 mg, yield 60%. $^1$H NMR (400 MHz, CDCl$_3$) δ 8.72 (d, J=5.7 Hz, 2H (maj)), 8.56 (d, J=4.5 Hz, 2H (min)), 8.14 (brs, 1H (maj)), 8.06 (brs, 1H (min)), 7.61 (d, J=7.8 Hz, 1H (maj)), 7.49 (d, J=7.9 Hz, 1H (min)), 7.40-7.32 (m, 1H), 7.31-7.08 (m, 4H (min, maj) 1H (maj)), 6.65 (s, 1H (min)), 6.60 (s, 1H (min)), 6.56 (s, 1H (maj)), 6.48 (s, 1H (maj)), 6.23 (s, 1H (min)). 5.83 (dd, J=9.5, 4.4 Hz, 1H (maj)), 4.82 (dd, J=13.2, 5.1 Hz, 1H (min)), 4.64 (dd, J=8.3, 5.5 Hz, 1H (min)), 3.87 (s, 3H (min)), 3.84 (s, 3H (maj)), 3.75-3.62 (m, 3H (min, maj) 1H (maj)), 3.57 (ddd, J=13.7, 11.6, 4.2 Hz, 1H (maj)), 3.39 (ddd, J=13.2, 11.4, 5.0 Hz, 1H (min)), 3.16-2.74 (m, 3H), 2.71-2.57 (m, 1H), 2.47-2.36 (m, 1H (maj)), 2.35-2.23 (m, 1H), 2.20-2.10 (m, 1H (min)). ESI-MS m/z 442.2 [M+H]$^+$.

Example B2: Synthesis of Compound B2

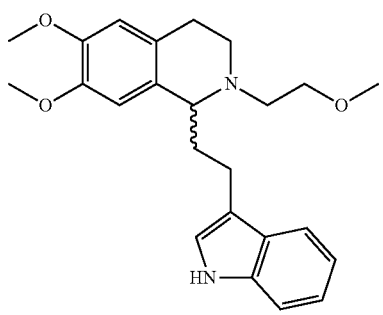

ZN 19

-continued

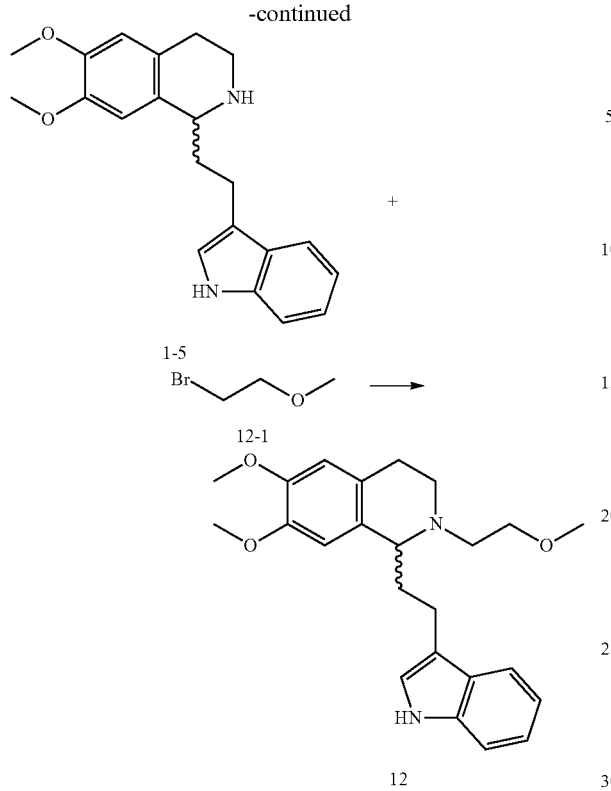

Compound 1-5 was dissolved in acetonitrile, and potassium carbonate and 12-1 were added and refluxed overnight. The mixture was evaporated to dryness, purified through column chromatography with petroleum ether/ethyl acetate=1:1 to obtain a white solid compound B2 50 mg, yield %. $^1$H NMR (400 MHz, CDCl$_3$) δ 8.06 (brs, 1H), 7.61 (d, J=7.9 Hz, 1H), 7.36 (d, J=8.1 Hz, 1H), 7.21-7.15 (m, 1H), 7.13-7.05 (m, 2H), 6.56 (s, 1H), 6.37 (s, 1H), 3.84 (s, 4H), 3.75 (s, 3H), 3.67 (s, 3H), 3.65-3.54 (m, 2H), 3.36 (s, 3H), 3.11-3.00 (m, 1H), 2.96 (t, J=7.5 Hz, 2H), 2.92-2.77 (m, 3H), 2.57 (d, J=16.0 Hz, 1H), 2.31 (m, 1H), 2.15-2.01 (m, 1H). ESI-MS m/z 395.2 [M+H]$^+$.

Example (S)-B2: Synthesis of Compound (S)-B2

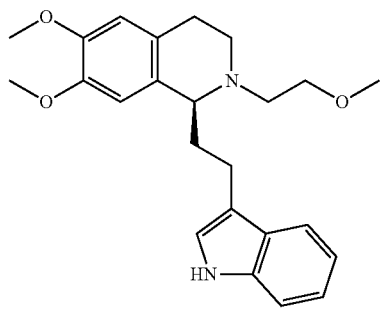

1-5 in example B1 was replaced with 2-5 to obtain compound (S)-B2. $^1$H NMR (400 MHz, CDCl$_3$) δ 8.06 (brs, 1H), 7.61 (d, J=7.9 Hz, 1H), 7.36 (d, J=8.1 Hz, 1H), 7.21-7.15 (m, 1H), 7.13-7.05 (m, 2H), 6.56 (s, 1H), 6.37 (s, 1H), 3.84 (s, 4H), 3.75 (s, 3H), 3.67 (s, 3H), 3.65-3.54 (m, 2H), 3.36 (s, 3H), 3.11-3.00 (m, 1H), 2.96 (t, J=7.5 Hz, 2H), 2.92-2.77 (m, 3H), 2.57 (d, J=16.0 Hz, 1H), 2.31 (m, 1H), 2.15-2.01 (m, 1H). ESI-MS m/z 395.2 [M+H]$^+$.

Example (R)-B2: Synthesis of Compound (R)-B2

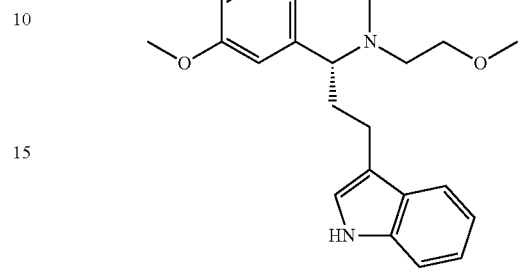

1-5 in example B1 was replaced with 3-5 to obtain compound (R)-B2. $^1$H NMR (400 MHz, CDCl$_3$) δ 8.06 (brs, 1H), 7.61 (d, J=7.9 Hz, 1H), 7.36 (d, J=8.1 Hz, 1H), 7.21-7.15 (m, 1H), 7.13-7.05 (m, 2H), 6.56 (s, 1H), 6.37 (s, 1H), 3.84 (s, 4H), 3.75 (s, 3H), 3.67 (s, 3H), 3.65-3.54 (m, 2H), 3.36 (s, 3H), 3.11-3.00 (m, 1H), 2.96 (t, J=7.5 Hz, 2H), 2.92-2.77 (m, 3H), 2.57 (d, J=16.0 Hz, 1H), 2.31 (m, 1H), 2.15-2.01 (m, 1H). ESI-MS m/z 395.2 [M+H]$^+$.

Example B3: Synthesis of Compound B3

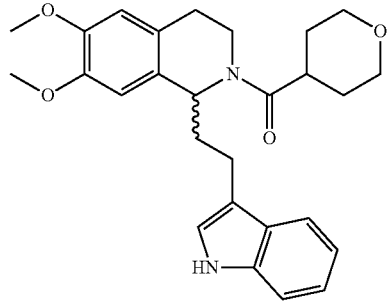

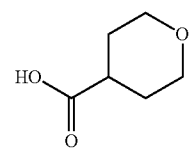

The compound B3 was obtained according to the synthesis of the compound B1, while 11-1 in example B1 was replaced with compound 13-1. $^1$H NMR (500 MHz, CDCl$_3$) δ 9.54 (t, J=2.4 Hz, 1H), 7.64-7.58 (m, 1H), 7.38-7.31 (m, 1H), 7.17 (ddd, J=8.1, 7.4, 1.0 Hz, 1H), 7.14-7.07 (m, 2H), 6.73 (d, J=1.1 Hz, 1H), 6.62 (t, J=1.0 Hz, 1H), 4.91 (td, J=6.1, 0.9 Hz, 1H), 3.90-3.81 (m, 7H), 3.78 (ddd, J=11.5, 7.3, 5.0 Hz, 2H), 3.60 (ddd, J=12.1, 6.5, 4.1 Hz, 1H), 3.40 (ddd, J=11.7, 7.4, 5.1 Hz, 2H), 3.08 (dddd, J=14.7, 6.4, 4.1, 0.9 Hz, 1H), 2.94 (dt, J=14.7, 7.3 Hz, 1H), 2.88-2.74 (m, 2H), 2.52 (dtd, J=12.6, 7.3, 6.0 Hz, 1H), 2.44 (p, J=6.5 Hz, 1H), 2.25 (dtd, J=12.6, 7.3, 6.1 Hz, 1H), 1.93-1.82 (m, 2H), 1.68 (dddd, J=13.2, 7.3, 6.5, 5.0 Hz, 2H). ESI-MS m/z 449.2 [M+H]$^+$.

Example (S)-B3: Synthesis of Compound (S)-B3

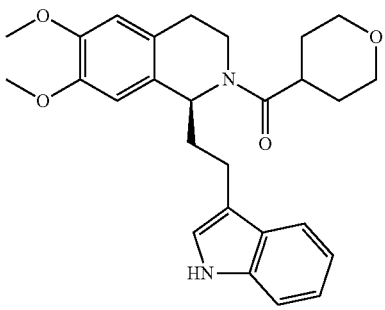 [SMILES: COc1cc2c(cc1OC)[C@H](CCc1c[nH]c3ccccc13)N(C(=O)C1CCOCC1)CC2]

The compound (S)-B3 was obtained according to the synthesis of the compound (S)-B1, while 11-1 in example B1 was replaced with compound 13-1. ESI-MS m/z 449.2 [M+H]⁺.

Example (R)-B3: Synthesis of Compound (R)-B3

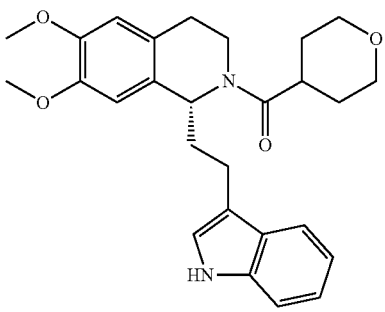 [SMILES: COc1cc2c(cc1OC)[C@@H](CCc1c[nH]c3ccccc13)N(C(=O)C1CCOCC1)CC2]

The compound (R)-B3 was obtained according to the synthesis of the compound (R)-B1, while 11-1 in example B1 was replaced with compound 13-1. ESI-MS m/z 449.2 [M+H]⁺.

Example B4: Synthesis of Compound B4

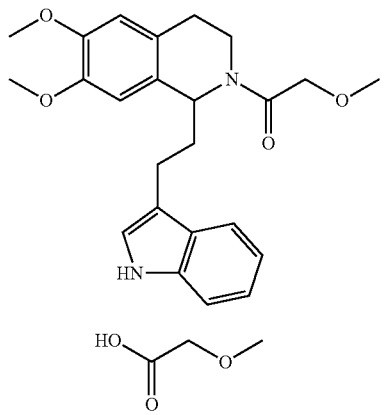

14-1

The compound B4 was obtained according to the synthesis of the compound B1, while 11-1 in example B1 was replaced with compound 14-1. $^1$H NMR (400 MHz, CDCl$_3$) δ 8.19 (brs, 1H (min)), 8.15 (brs, 1H (maj)), 7.61-7.54 (m, 1H), 7.39-7.33 (m, 1H), 7.24-7.00 (m, 3H), 6.60 (s, 1H (min)), 6.57 (s, 1H (maj)), 6.53 (s, 1H (min)), 6.40 (s, 1H (maj)), 5.66 (dd, J=9.2, 4.8 Hz, 1H (maj)), 4.77 (dd, J=7.1, 7.1 Hz, 1H (min)), 4.66 (ddd, J=7.5, 6.3, 2.0 Hz, 1H (min)), 4.27-4.05 (m, 2H), 3.90-3.82 (m, 3H (min, maj) 1H (maj)), 3.81 (s, 3H (min)), 3.65 (s, 3H (maj)), 3.55 (ddd, J=13.7, 11.0, 4.6 Hz, 1H (maj)), 3.48 (s, 3H (maj)). 3.32 (s, 3H (min)), 3.21 (ddd, J=13.3, 11.5, 4.9 Hz, 1H (min)), 2.97-2.64 (m, 4H), 2.35-2.10 (m, 2H). ESI-MS m/z 409.2 [M+H]⁺.

Example (S)-B4: Synthesis of Compound (S)-B4

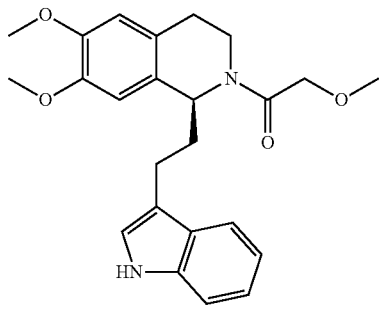

The compound (S)-B4 was obtained according to the synthesis of the compound (S)-B1, while 11-1 in example B1 was replaced with compound 14-1. ESI-MS m/z 409.2 [M+H]⁺.

Example (R)-B4: Synthesis of Compound (R)-B4

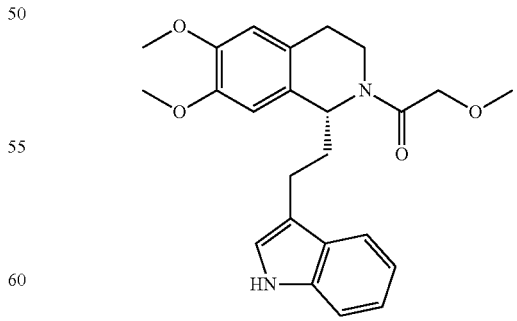

The compound (R)-B4 was obtained according to the synthesis of the compound (R)-B1, while 11-1 in example B1 was replaced with compound 14-1. ESI-MS m/z 409.2 [M+H]⁺.

Example B5: Synthesis of Compound B5

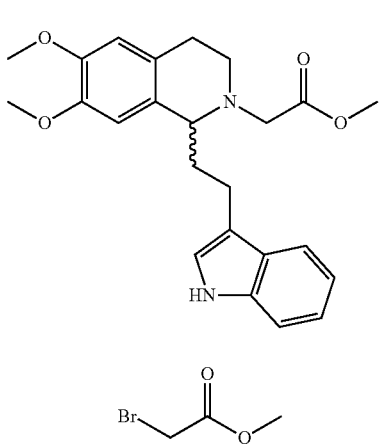
ZN 23

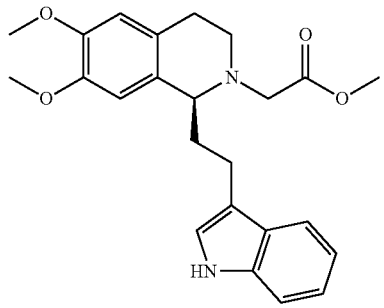
15-1

The compound B5 was obtained according to the synthesis of the compound B1, while 12-1 in example B2 was replaced with compound 15-1. $^1$H NMR (400 MHz, CDCl$_3$) δ 7.97 (brs, 1H), 7.60 (d, J=7.9 Hz, 1H), 7.35 (d, J=8.1 Hz, 1H), 7.17 (ddd, J=8.2, 7.2, 1.1 Hz, 11H), 7.09 (ddd, J=7.9, 7.1, 1.0 Hz, 1H), 7.04 (d, J=2.0 Hz, 1H), 6.56 (s, 1H), 6.37 (s, 1H), 3.84 (s, 3H), 3.78-3.70 (m, 4H), 3.68 (s, 3H), 3.48 (dd, J=39.3, 16.6 Hz, 2H), 3.34 (ddd, J=13.5, 9.8, 5.2 Hz, 1H), 3.04 (dt, J=9.7, 5.2 Hz, 1H), 3.00-2.87 (m, 2H), 2.82 (ddd, J=15.6, 9.7, 5.6 Hz, 1H), 2.60 (dt, J=16.5, 4.5 Hz, 1H), 2.27-2.15 (m, 1H), 2.14-2.03 (m, 1H). ESI-MS m/z 409.2 [M+H]$^+$.

Example (S)-B5: Synthesis of Compound (S)-B5

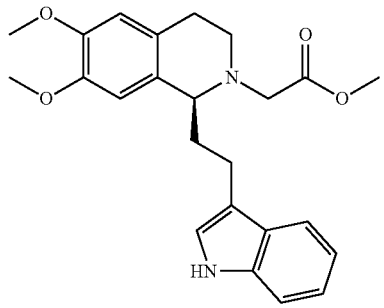

The compound (S)-B5 was obtained according to the synthesis of the compound (S)-B2, while 12-1 in example B2 was replaced with compound 15-1.

Example (R)-B5: Synthesis of Compound (R)-B5

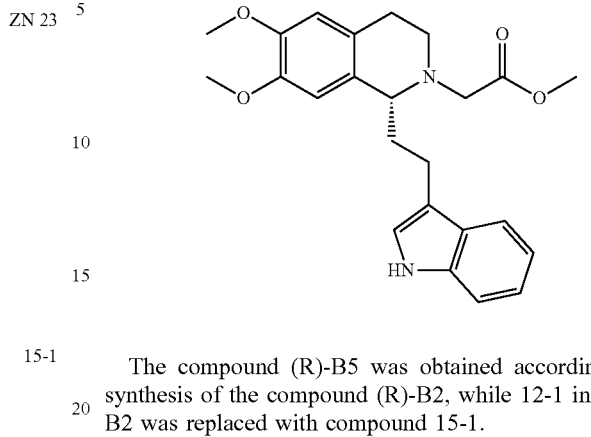

The compound (R)-B5 was obtained according to the synthesis of the compound (R)-B2, while 12-1 in example B2 was replaced with compound 15-1.

Example B6: Synthesis of Compound B6

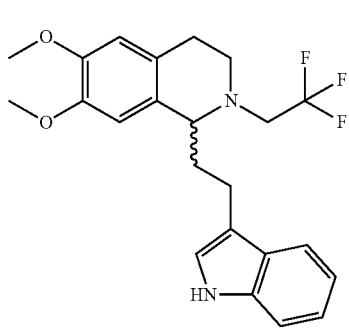
ZN 24

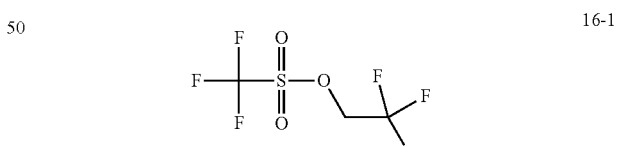
16-1

The compound B6 was obtained according to the synthesis of the compound B2, while 12-1 in example B2 was replaced with compound 16-1. $^1$H NMR (400 MHz, CDCl$_3$) δ 7.94 (brs, 1H), 7.61 (d, J=7.8 Hz, 1H), 7.36 (d, J=8.1 Hz, 1H), 7.21-7.14 (m, 1H), 7.13-7.06 (m, 1H), 7.02 (s, 1H), 6.56 (s, 1H), 6.37 (s, 1H), 3.84 (s, 3H), 3.72 (s, 3H), 3.67 (dd, J=8.4, 4.1 Hz, 1H), 3.43-3.31 (m, 1H), 3.24 (dq, J=15.4, 9.5 Hz, 1H), 3.11-2.81 (m, 5H), 2.52 (d, J=14.7 Hz, 1H), 2.16 (dt, J=13.9, 7.0 Hz, 1H), 2.10-1.98 (m, 1H). ESI-MS m/z 419.2 [M+H]$^+$.

Example (S)-B6: Synthesis of Compound (S)-B6

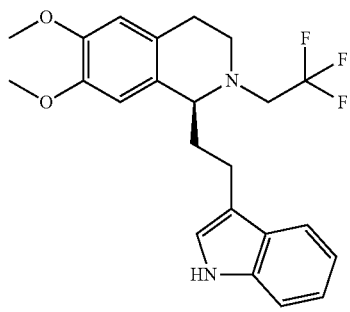 [SMILES: COc1cc2c(cc1OC)[C@H](CCc1c[nH]c3ccccc13)N(CC(F)(F)F)CC2]

The compound (S)-B6 was obtained according to the synthesis of the compound (S)-B2, while 12-1 in example B2 was replaced with compound 16-1. ESI-MS m/z 419.2 [M+H]$^+$.

Example (R)-B6: Synthesis of Compound (R)-B6

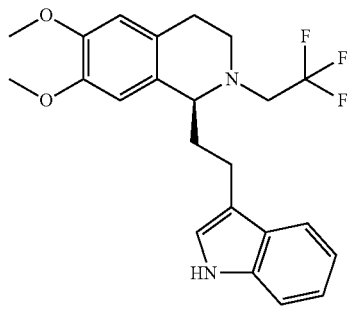 [SMILES: COc1cc2c(cc1OC)[C@H](CCc1c[nH]c3ccccc13)N(CC(F)(F)F)CC2]

The compound (R)-B6 was obtained according to the synthesis of the compound (R)-B2, while 12-1 in example B2 was replaced with compound 16-1. ESI-MS m/z 419.2 [M+H]$^+$.

Example B7: Synthesis of Compound B7

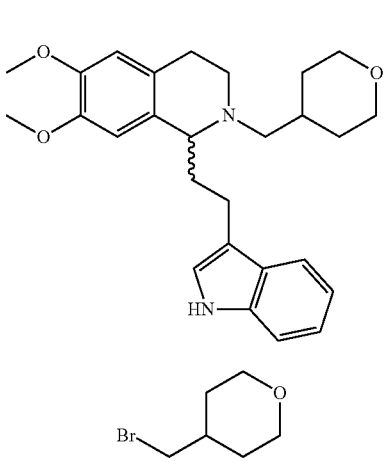

17-1

The compound B7 was obtained according to the synthesis of the compound B2, while 12-1 in example B2 was replaced with compound 17-1. $^1$H NMR (400 MHz, CDCl$_3$) δ 7.98 (brs, 1H), 7.59 (d, J=7.8 Hz, 1H), 7.36 (d, J=8.1 Hz, 1H), 7.18 (t, J=7.1 Hz, 1H), 7.11 (dd, J=11.0, 3.9 Hz, 1H), 6.99 (s, 1H), 6.56 (s, 1H), 6.46 (s, 1H), 3.98 (dd, J=11.4, 2.9 Hz, 1H), 3.84 (s, 3H), 3.76 (s, 3H), 3.63-3.47 (m, 1H), 3.38 (td, J=10.9, 3.3 Hz, 2H), 3.31-3.16 (m, 1H), 3.05-2.67 (m, 4H), 2.60-2.30 (m, 3H), 2.24-1.96 (m, 2H), 1.88-1.67 (m, 3H), 1.28 (m, 1H). ESI-MS m/z 435.3 [M+H]$^+$.

Example (S)-B7: Synthesis of Compound (S)-B7

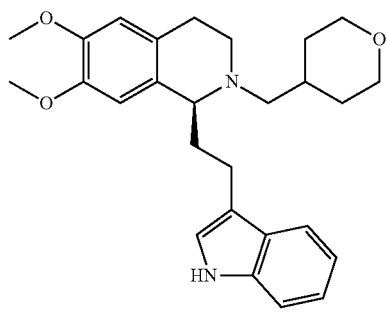 [SMILES: COc1cc2c(cc1OC)[C@H](CCc1c[nH]c3ccccc13)N(CC1CCOCC1)CC2]

The compound (S)-B7 was obtained according to the synthesis of the compound (S)-B2, while 12-1 in example B2 was replaced with compound 17-1. ESI-MS m/z 435.3 [M+H]$^+$.

Example (R)-B7: Synthesis of Compound (R)-B7

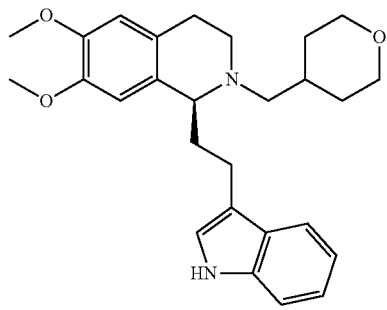 [SMILES: COc1cc2c(cc1OC)[C@H](CCc1c[nH]c3ccccc13)N(CC1CCOCC1)CC2]

The compound (R)-B7 was obtained according to the synthesis of the compound (R)-B2, while 12-1 in example B2 was replaced with compound 17-1. ESI-MS m/z 435.3 [M+H]$^+$.

Example B8: Synthesis of Compound B8

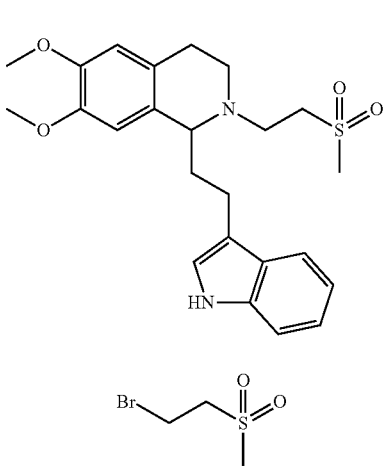

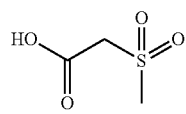

The compound B8 was obtained according to the synthesis of the compound B2, while 12-1 in example B2 was replaced with compound 18-1. $^1$H NMR (400 MHz, CDCl$_3$) δ 7.59 (d, J=7.9 Hz, 1H), 7.36 (d, J=8.2 Hz, 1H), 7.26 (t, J=7.6 Hz, 1H), 7.14 (m, 2H), 6.56 (s, 1H), 6.36 (s, 1H), 4.77-4.58 (m, 2H), 3.84 (s, 3H), 3.73 (s, 3H), 3.53 (t, J=6.4 Hz, 2H), 3.31-3.21 (m, 1H), 3.18-3.06 (m, 2H), 3.04-2.81 (m, 7H), 2.38-2.15 (m, 1H), 2.17-2.04 (m, 1H). ESI-MS m/z 443.2 [M+H]$^+$.

Example (31-8: Synthesis of Compound (S)-B8

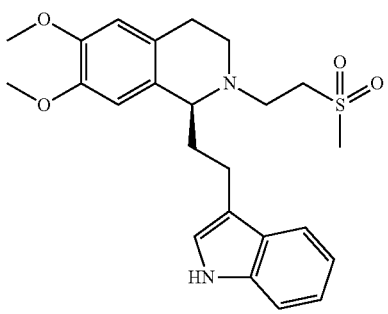 [SMILES: COc1cc2c(cc1OC)[C@H](CCc1c[nH]c3ccccc13)N(CCS(C)(=O)=O)CC2]

The compound (S)-B8 was obtained according to the synthesis of the compound (S)-B2, while 12-1 in example B2 was replaced with compound 18-1. ESI-MS m/z 443.2 [M+H]$^+$.

Example (R)-B8: Synthesis of Compound (R)-B8

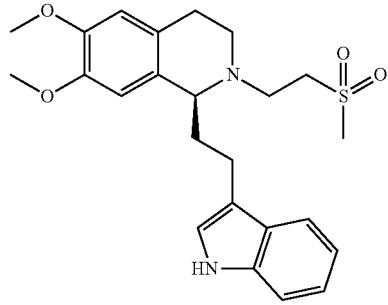 [SMILES: COc1cc2c(cc1OC)[C@H](CCc1c[nH]c3ccccc13)N(CCS(C)(=O)=O)CC2]

The compound (R)-B8 was obtained according to the synthesis of the compound (R)-B2, while 12-1 in example B2 was replaced with compound 18-1. ESI-MS m/z 443.2 [M+H]$^+$.

Example B9: Synthesis of Compound B9

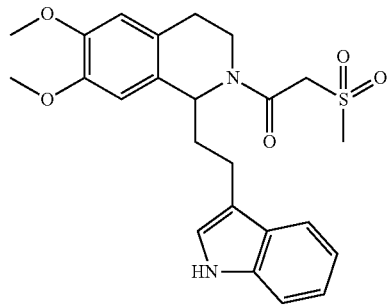

The compound B9 was obtained according to the synthesis of the compound B1, while 11-1 in example B1 was replaced with compound 19-1. $^1$H NMR (500 MHz, CDCl$_3$) δ 9.55 (t, J=2.4 Hz, 1H), 7.61 (dt, J=7.3, 0.9 Hz, 1H), 7.38-7.31 (m, 1H), 7.17 (ddd, J=8.1, 7.4, 1.0 Hz, 1H), 7.14-7.06 (m, 2H), 6.90 (d, J=0.9 Hz, 1H), 6.62 (t, J=1.0 Hz, 1H), 5.00 (td, J=6.0, 1.0 Hz, 1H), 4.38 (d, J=17.2 Hz, 1H), 4.04 (d, J=17.0 Hz, 1H), 3.91 (ddd, J=12.1, 6.3, 4.3 Hz, 1H), 3.83 (s, 6H), 3.75 (ddd, J=11.9, 6.2, 4.2 Hz, 1H), 2.98 (s, 3H), 3.03-2.87 (m, 3H), 2.81 (dt, J=14.9, 7.3 Hz, 1H), 2.39 (dtd, J=12.6, 7.3, 6.1 Hz, 1H), 2.26 (dtd, J=12.6, 7.3, 6.1 Hz, 1H). ESI-MS m/z 457.2 [M+H]$^+$ Example (S)-B9: Synthesis of Compound (S)-B9

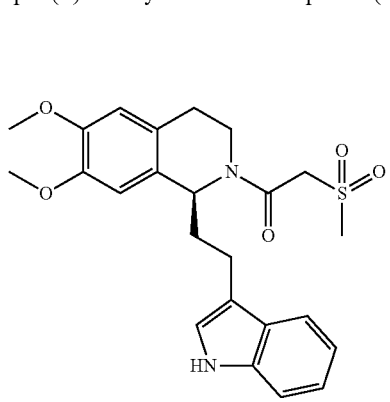

The compound (S)-B9 was obtained according to the synthesis of the compound (S)-B1, while 11-1 in example B was replaced with compound 19-1. ESI-MS m/z 457.2 [M+H]$^+$.

Example (R)-9 Synthesis of Compound (R)-B9

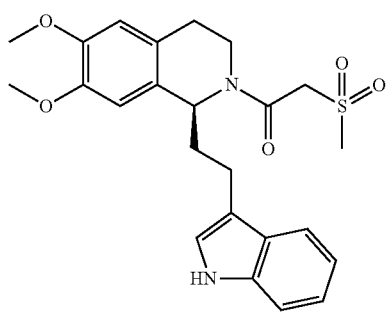 [SMILES: COc1cc2c(cc1OC)[C@H](CCc1c[nH]c3ccccc13)N(C(=O)CS(C)(=O)=O)CC2]

The compound (R)-B9 was obtained according to the synthesis of the compound (R)-B1, while 11-1 in example B was replaced with compound 19-1. ESI-MS m/z 457.2 [M+H]$^+$.

Example B10: Synthesis of Compound B10

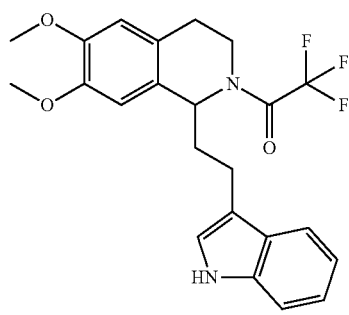 [SMILES: COc1cc2c(cc1OC)C(CCc1c[nH]c3ccccc13)N(C(=O)C(F)(F)F)CC2]

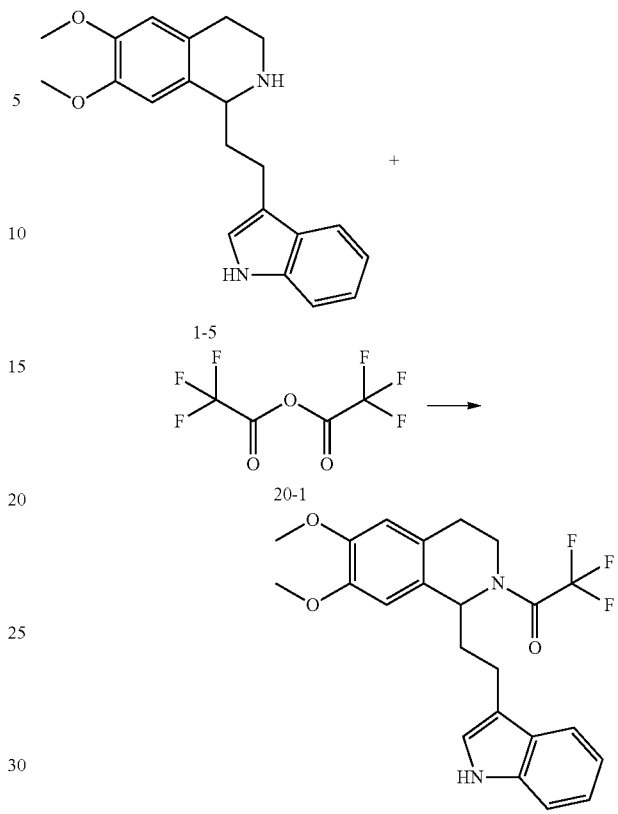

1-5 was dissolved in THF, and 20-1 was added and stirred at room temperature for 20 h, diluted with DCM, washed with saturated sodium bicarbonate and saturated sodium chloride, dried over anhydrous sodium sulfate and evaporated to dryness. The residue was purified through column chromatography with petroleum ether/ethyl acetate=1:1 to obtain 20 mg of yellow oily substance, yield 58%. $^1$H NMR (500 MHz, CDCl$_3$) δ 9.63 (t, J=2.4 Hz, 1H). 7.59 (ddd, J=7.3, 1.1, 0.6 Hz, 1H), 7.38-7.32 (m, 1H), 7.17 (td, J=7.7, 1.1 Hz, 1H), 7.15-7.07 (m, 2H), 6.83 (d, J=1.1 Hz, 1H), 6.61 (t, J=1.0 Hz, 1H), 4.96 (td, J=5.4, 1.0 Hz, 1H), 3.95 (ddd, J=11.9, 6.4, 4.0 Hz, 1H), 3.86-3.78 (m, 7H), 3.12-2.98 (m, 2H), 2.89-2.78 (m, 2H), 2.42-2.25 (m, 2H). ESI-MS m/z 433.2 [M+H]$^+$.

Example (S)-B10: Synthesis of Compound (S)-B10

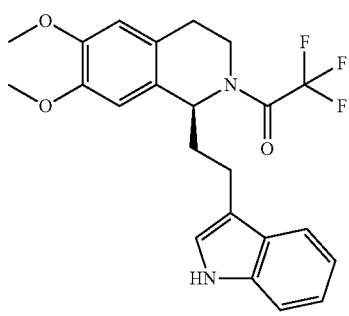 [SMILES: COc1cc2c(cc1OC)[C@H](CCc1c[nH]c3ccccc13)N(C(=O)C(F)(F)F)CC2]

Compound (S)-B10 was obtained by replacing 1-5 in Example B10 with 2-5. ESI-MS m/z 433.2.

Example (R)-B1: Synthesis of Compound (R)-B10

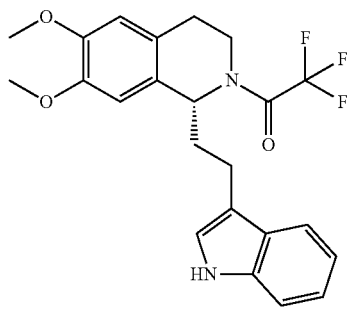 [SMILES: COc1cc2c(cc1OC)[C@@H](CCc1c[nH]c3ccccc13)N(C(=O)C(F)(F)F)CC2]

Compound (R)-B10 was obtained by replacing 1-5 in Example B10 with 3-5. ESI-MS m/z 433.2 [M+H]$^+$.

Example B11: Synthesis of Compound B11

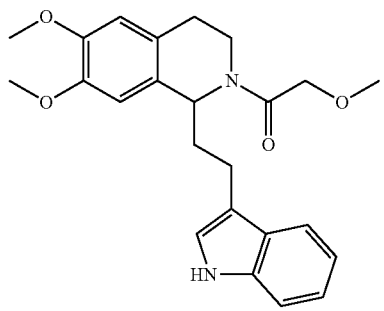

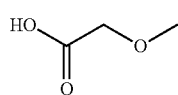

14-1

Compound B11 was synthesized according to the method of the compound B1, while 11-1 in example B1 was replaced with the compound 14-1. White solid 25 mg was obtained, yield 88%. $^1$H NMR (400 MHz, CDCl$_3$) δ 8.19 (brs, 1H (min)), 8.15 (brs, 1H (maj)), 7.61-7.54 (m, 1H), 7.39-7.33 (m, 1H), 7.24-7.00 (m, 3H), 6.60 (s, 1H (min)), 6.57 (s, 1H (maj)), 6.53 (s, 1H (min)). 6.40 (s, 1H (maj)), 5.66 (dd, J=9.2, 4.8 Hz, 1H (maj)), 4.77 (dd, J=7.1, 7.1 Hz, 1H (min)), 4.66 (ddd, J=7.5, 6.3, 2.0 Hz, 1H (min)), 4.27-4.05 (m, 2H), 3.90-3.82 (m, 3H (min, maj) 1H (maj)), 3.81 (s, 3H (min)), 3.65 (s, 3H (maj)), 3.55 (ddd, J=13.7, 11.0, 4.6 Hz, 1H (maj)), 3.48 (s, 3H (maj)), 3.32 (s, 3H (min)), 3.21 (ddd, J=13.3, 11.5, 4.9 Hz, 1H (min)), 2.97-2.64 (m, 4H), 2.35-2.10 (m, 2H). ESI-MS m/z 409.2 [M+H]$^+$.

Example (S)-B11: Synthesis of Compound (S)-B11

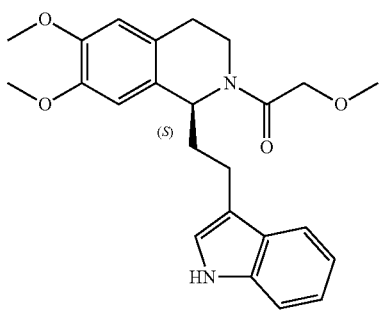

ZN 29

The compound (S)-B11 was obtained according to the synthesis of the compound (S)-B1, while 11-1 in example B1 was replaced with compound 14-1. ESI-MS m/z 409.2 [M+H]$^+$.

Example (R)-B11: Synthesis of Compound (R)-B11

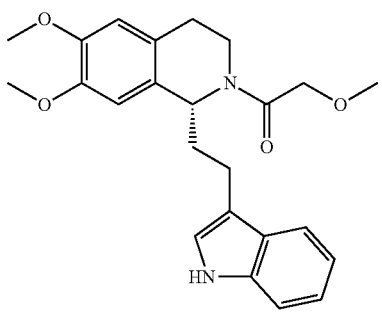

The compound (R)-B11 was obtained according to the synthesis of the compound (R)-B1, while 11-1 in example B1 was replaced with compound 14-1. ESI-MS m/z 409.2 [M+H]$^+$.

Example B12: Synthesis of Compound B12

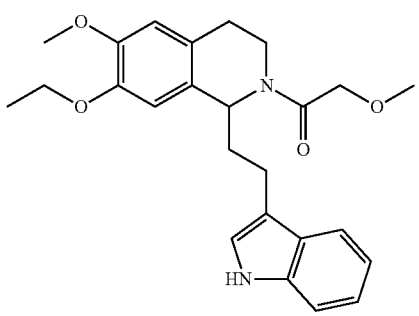 [SMILES: CCOc1cc2c(cc1OC)CCN(C(=O)COC)C2CCc1c[nH]c2ccccc12]

Compound B12 was synthesized according to the method of the compound B1, while 4-2 in example A2 was replaced with ethyl bromide, and 11-1 in example B1 was replaced with 14-1, yield 85%. $^1$H NMR (400 MHz, CDCl$_3$) δ 8.17 (brs, 1H (min)), 8.13 (brs, 1H (maj)), 7.62-7.52 (m, 1H), 7.41-7.32 (m, 1H), 7.23-6.98 (m, 3H), 6.60 (s, 1H (min)), 6.57 (s, 1H (maj)), 6.54 (s, 1H (min)), 6.40 (s, 1H (maj)), 5.64 (dd, J=9.1, 4.7 Hz, 1H (maj)), 4.76 (dd, J=7.6, 6.7 Hz, 1H (min)), 4.64 (ddd, J=8.2, 5.7, 1.9 Hz, 1H (min)), 4.20 (q, J=13.6 Hz, 2H (maj)), 4.06 (s, 2H (min)), 3.89-3.78 (m, 3H (min, maj) 1H (min) 1H (maj)), 3.55 (ddd, J=13.5, 10.8, 4.4 Hz, 1H (maj)), 3.48 (s, 3H (maj)), 3.31 (s, 3H (min)), 3.21 (ddd, J=12.6, 11.0, 4.2 Hz, 1H (min)), 3.03-2.61 (m, 4H), 2.38-2.20 (m, 2H (maj)), 2.18-2.08 (m, 2H (min)), 1.44 (t, J=7.0 Hz, 3H (min)), 1.35 (t, J=7.0 Hz, 3H (maj)). ESI-MS m/z 423.0 [M+H]$^+$.

Example (S)-B12: Synthesis of Compound (S)-B12

ZN 33

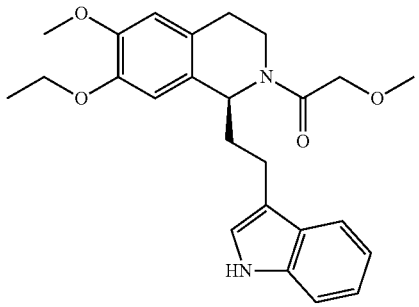

Compound (S)-B12 was synthesized according to the method of the compound (S)-B11, while 4-2 in example A2 was replaced with ethyl bromide, and 11-1 in example B1 was replaced with 14-1, yield 85%. ESI-MS m/z 423.0 [M+H]$^+$.

Example (R)-B12: Synthesis of Compound (R)-B12

ZN 33

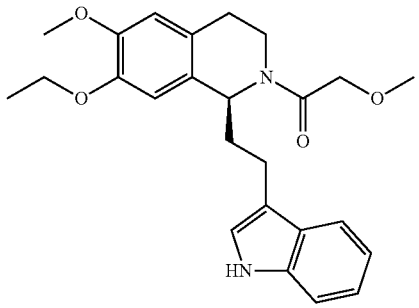

Compound (R)-B12 was synthesized according to the method of the compound (R)-B11, while 4-2 in example A2 was replaced with ethyl bromide, and 11-1 in example B1 was replaced with 14-1, yield 85%. ESI-MS m/z 423.0 [M+H]$^+$.

Example B13: Synthesis of Compound B13

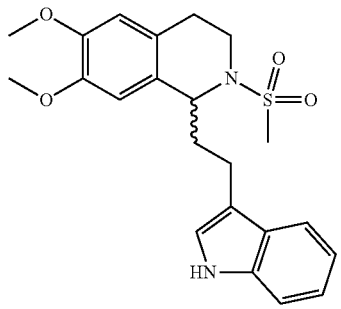

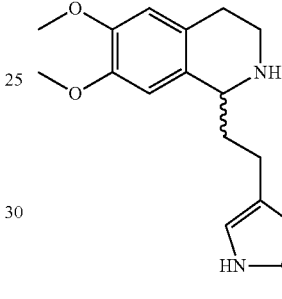 + 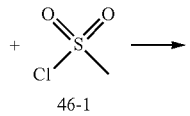 →

1-5     46-1

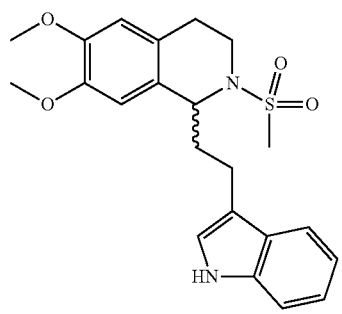

The intermediate 1-5 was dissolved in dichloromethane, and pyridine and 46-1 were added. The mixture was stirred at room temperature for 1 h, and the reaction was quenched by 0.1 N NaOH solution, extracted with dichloromethane, washed with 1 N diluted hydrochloric acid, and the organic layer was dried and evaporated to dryness, purified through column chromatography to obtain the compound B13. $^1$H NMR (400 MHz, CDCl$_3$) δ 7.69 (s, 1H), 7.55 (dd, J=14.9, 3.1 Hz, 1H), 7.32 (dd, J=15.0, 3.1 Hz, 1H), 7.23-7.12 (m, 2H), 7.02-6.91 (m, 2H), 6.87 (s, 1H), 4.49 (t, J=13.0 Hz, 1H), 3.74 (s, 6H), 3.42 (dt, J=24.7, 10.8 Hz, 1H), 3.14 (dt, J=24.7, 10.8 Hz, 1H), 2.94 (s, 3H), 2.86-2.66 (m, 4H), 2.12 (td, J=15.7, 13.1 Hz, 2H). ESI-MS m/z 415.2 [M+H]$^+$.

Example (S)-B13: Synthesis of Compound (S)-B13

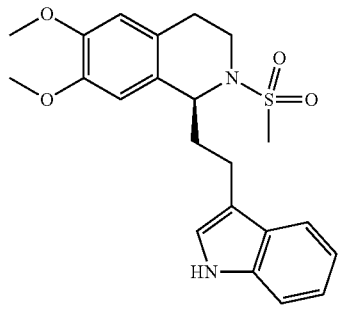 [SMILES: COc1cc2c(cc1OC)[C@H](CCc1c[nH]c3ccccc13)N(S(C)(=O)=O)CC2]

Compound (S)-B13 was obtained by replacing 1-5 in Example B13 by 2-5. ESI-MS m/z 415.2 [M+H]$^+$.

Example (R)-B13: Synthesis of Compound (R)-B13

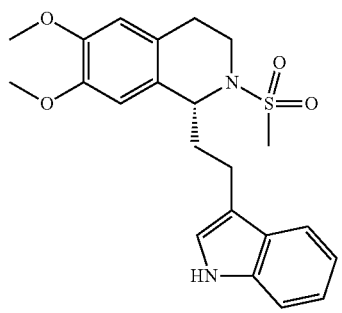 [SMILES: COc1cc2c(cc1OC)[C@@H](CCc1c[nH]c3ccccc13)N(S(C)(=O)=O)CC2]

Compound (R)-B13 was obtained by replacing 1-5 in Example B13 by 3-5. ESI-MS m/z 415.2 [M+H]$^+$.

Example B14: Synthesis of Compound B14

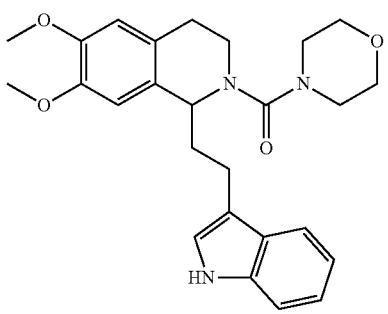

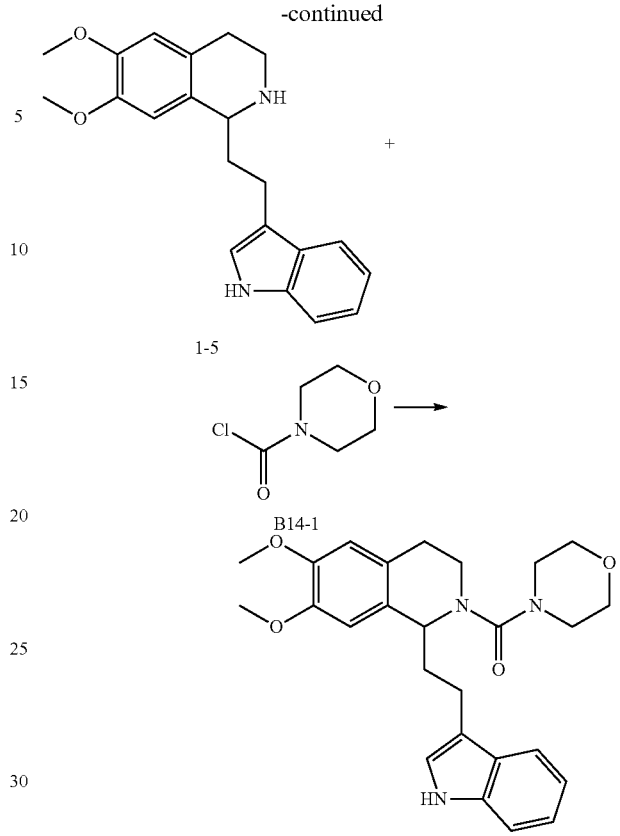

Intermediate 1-5 was dissolved in methylene chloride, and B14-1 and triethylamine were added. The mixture was stirred at room temperature for 2 h, and the reaction was quenched with saturated ammonium chloride solution, extracted with methylene chloride, washed with saturated brine. The organic layer was dried and evaporated to dryness, and purified through column chromatography to obtain the compound B14. $^1$H NMR (500 MHz, CDCl$_3$) δ 9.41 (t, J=2.4 Hz, 1H), 7.61 (ddt, J=7.3, 1.1, 0.6 Hz, 1H), 7.39-7.32 (m, 1H), 7.21-7.13 (m, 1H), 7.14-7.07 (m, 2H), 6.64 (t, J=1.0 Hz, 1H), 6.50 (d, J=1.1 Hz, 1H), 5.09 (td, J=5.4, 1.0 Hz, 1H), 4.03 (ddd, J=11.9, 6.2, 4.2 Hz, 1H), 3.83 (d, J=2.4 Hz, 6H), 3.64-3.53 (m, 5H), 3.17-3.08 (m, 4H), 3.04-2.87 (m, 3H), 2.79-2.69 (m, 1H), 2.50 (dtd, J=12.6, 7.3, 5.3 Hz, 1H), 2.28 (dtd, J=12.6, 7.3, 5.4 Hz, 1H). ESI-MS m/z 450.2[M+H]$^+$.

Example (S)-B14: Synthesis of Compound (S)-B14

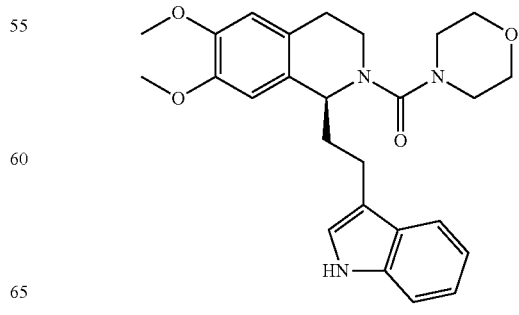

Compound (S)-B14 was obtained by replacing 1-5 in Example B14 by 2-5. ESI-MS m/z 450.2 [M+H]+.

Example (R)-B14: Synthesis of Compound (R)-B14

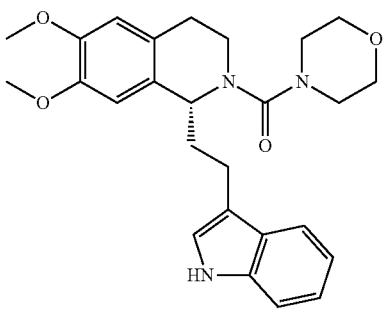 [SMILES: COc1cc2c(cc1OC)[C@@H](CCc1c[nH]c3ccccc13)N(C(=O)N1CCOCC1)CC2]

Compound (R)-B14 was obtained by replacing 1-5 in Example B14 by 3-5. ESI-MS m/z 450.2 [M+H]+.

Example B15: Synthesis of Compound B15

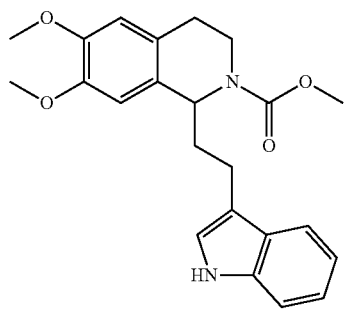

B14-1 in Example B14 was replaced by methyl chloroformate to give compound B15. $^1$H NMR (500 MHz, CDCl$_3$) δ 7.62-7.56 (m, 1H), 7.38-7.32 (m, 1H), 7.20-7.11 (m, 2H), 7.06 (td, J=7.5, 1.6 Hz, 1H), 6.84 (d, J=0.9 Hz, 1H), 6.73 (t, J=0.9 Hz, 1H), 5.04 (td, J=5.3, 1.0 Hz, 1H), 3.85-3.73 (m, 8H), 3.68 (s, 2H), 3.19 (qt, J=14.8, 7.3 Hz, 2H), 2.92 (ddd, J=6.2, 5.0, 1.1 Hz, 2H), 2.47 (dtd, J=12.7, 7.3, 5.3 Hz, 1H), 2.39 (dtd, J=12.7, 7.3, 5.4 Hz, 1H). ESI-MS m/z 395.2[M+H]+.

Example (S)-B15: Synthesis of Compound (S)-B15

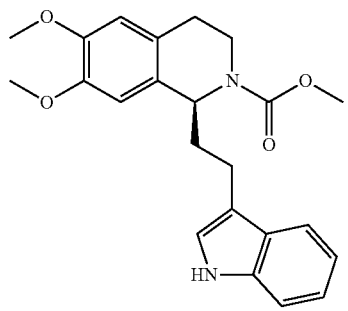

Compound (S)-B15 was obtained according to example B15, while 1-5 in example B14 was replaced by 2-5, and B14-1 in Example B15 was replaced by methyl chloroformate. ESI-MS m/z 395.2 [M+H]+.

Example R)-B15: Synthesis of Compound (R)-B15

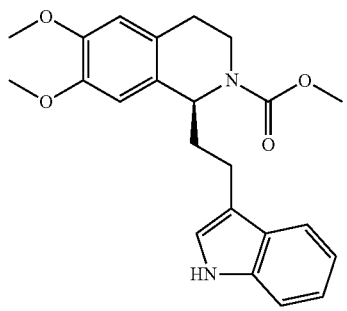

Compound (R)-B15 was obtained according to example B15, while 1-5 in example B14 was replaced by 3-5, and B14-1 in example B15 was replaced by methyl chloroformate. ESI-MS m/z 395.2 [M+H]+.

Example B16: Synthesis of Compound B16

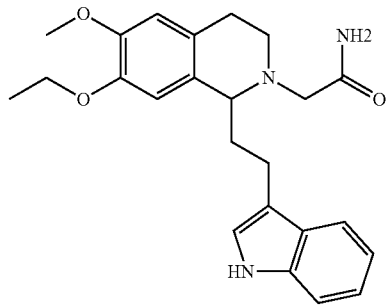

Compound B16 was obtained according to Example B2, while 4-2 in Example A2 was replaced by ethyl bromide, and 12-1 in Example B2 was replaced by 2-iodoacetamide.

Example (S)-B16: Synthesis of Compound (S)-B16

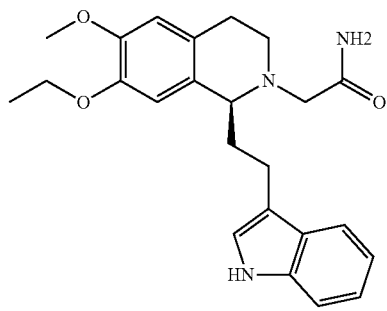

Compound B16 was obtained according to Example B2, while 4-2 in Example A2 was replaced by ethyl bromide, and 12-1 in Example B2 was replaced by 2-iodoacetamide.

Example (R)-B16: Synthesis of Compound (R)-B16

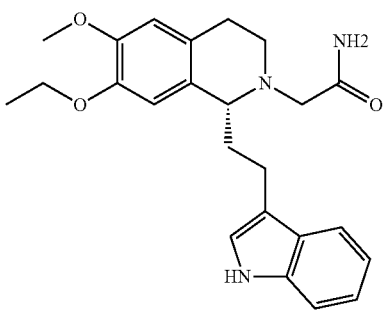

Compound B16 was obtained according to Example B2, while 4-2 in Example A2 was replaced by ethyl bromide, and 12-1 in Example B2 was replaced by 2-iodoacetamide.

Example C1: Synthesis of Compound C1

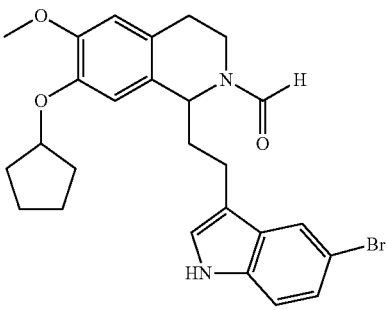

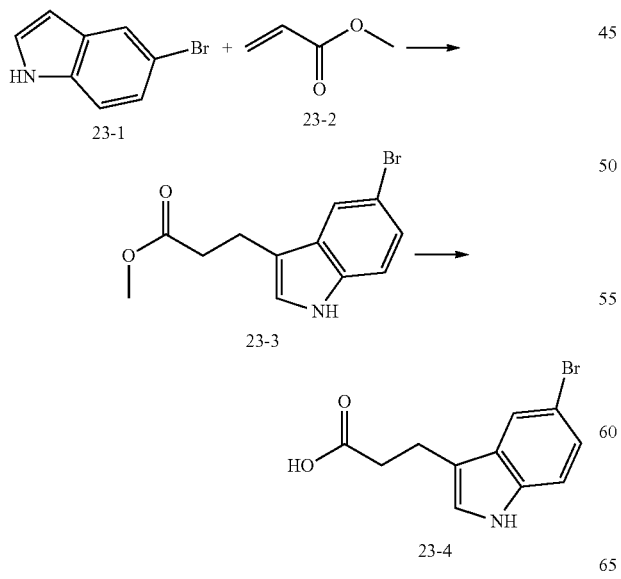

Synthesis of Compound 23-3:

23-2 was dissolved in methylene chloride, and zirconium tetrachloride was added. A solution of 23-1 in dichloromethane was slowly added dropwise, and stirred at room temperature for 1 h. The mixture was diluted with dichloromethane, washed with water, and the organic layer was evaporated to dryness for further use without purification.

Synthesis of Compound 23-4:

23-3 was dissolved in tetrahydrofuran/water=1:1 solvent, lithium hydroxide was added, and stirred at room temperature for 16 h. The mixture was extracted with ethyl acetate, the aqueous layer was collected and adjusted to acidic with 1N diluted hydrochloric acid, then extracted for three times with ethyl acetate. The organic layer was collected and dried with anhydrous sodium sulfate, and evaporated to give a brown solid 420 mg, yield of two steps was 68%. $^1$H NMR (500 MHz, Methanol-$d_4$) δ 10.04 (brs, 1H) 7.66 (d, J=1.9 Hz, 1H), 7.24 (d, J=8.6 Hz, 1H), 7.16 (dd, J=8.6, 1.9 Hz, 1H), 7.08 (s, 1H), 3.01 (t, J=7.4 Hz, 2H), 2.65 (t, J=7.5 Hz, 2H). ESI-MS m/z 268.0 [M+H]$^+$ The compound C1 was obtained according to the synthesis of the compound A1, while 1-1 in example A1 was replaced with compound 4-5, and 1-2 in example A1 was replaced with compound 23-4. $^1$H NMR (400 MHz, CDCl$_3$) δ 8.28 (s, 1H (min)), 8.19 (s, 2H (maj)), 8.13 (brs, 1H (min)), 7.77 (s, 1H (min)), 7.70 (s, 1H (maj)), 7.32-7.27 (m, 1H), 7.26-7.23 (m, 1H), 7.21 (s, 1H (min)), 7.04 (s, 1H (maj)), 6.56 (s, 1H (maj)), 6.54 (s, 1H (min)), 6.37 (s, 1H (maj)), 6.33 (s, 1H (min)), 5.40 (dd, J=9.0, 4.2 Hz, 1H (min)), 4.67-4.61 (m, 1H (min)), 4.58-4.54 (m, 1H (min)), 4.54-4.48 (m, 1H (maj)), 4.37 (dd, J=9.2, 4.4 Hz, 1H (maj)), 3.80 (s, 3H (maj)), 3.79 (s, 3H (min)), 3.73 (dd, J=13.3, 5.6 Hz, 1H (maj)). 3.61 (ddd, J=12.6, 12.6, 4.2 Hz, 1H (min)), 3.10 (ddd, J=12.6, 12.6, 4.8 Hz, 1H (maj)), 2.96-2.63 (m, 4H), 2.31-2.13 (m, 2H), 1.98-1.70 (m, 6H), 1.68-1.47 (m, 2H). ESI-MS m/z 497.1 [M+H]$^+$.

Example (S)-C1: Synthesis of Compound (S)-C1

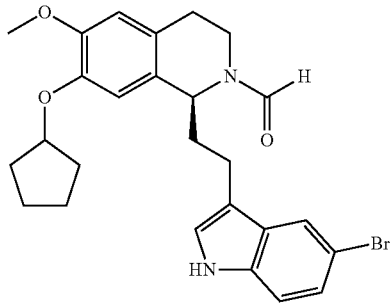 [SMILES: COc1cc2c(cc1OC1CCCC1)[C@H](CCc1c[nH]c3ccc(Br)cc13)N(C=O)CC2]

Compound (S)-C1 was obtained according to example (S)-A2 and example C1. ESI-MS m/z 497.1 [M+H]⁺.

Example (R)-C1: Synthesis of Compound (R)-C1

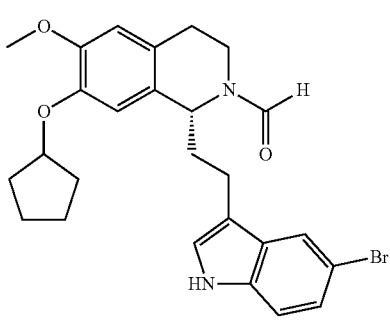 [SMILES: COc1cc2c(cc1OC1CCCC1)[C@@H](CCc1c[nH]c3ccc(Br)cc13)N(C=O)CC2]

Compound (R)-C1 was obtained according to example (R)-A2 and example C1. ESI-MS m/z 497.1 [M+H]⁺.

Example C2: Synthesis of Compound C2

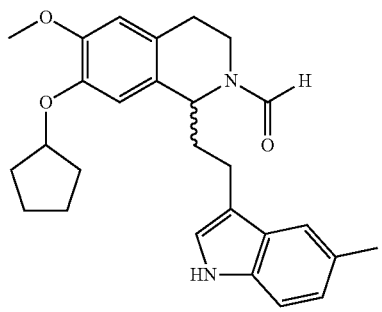

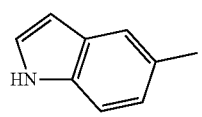

24-1

The compound C2 was obtained according to the synthesis of the compound C1, while 23-1 in example C1 was replaced with compound 24-1. ¹H NMR (400 MHz, CDCl₃) δ 8.28 (s, 1H (min)), 8.21 (s, 1H (maj)), 8.02 (brs, 1H (maj)), 7.95 (brs, 1H (min)), 7.41 (s, 1H (maj)), 7.35 (s, 1H (min)), 7.31-7.22 (m, 1H), 7.11 (s, 1H (min)), 7.07-6.99 (m, 1H), 6.99 (s, 1H (maj)), 6.56 (s, 1H (maj)), 6.54 (s, 1H (min)), 6.40 (s, 1H (min)), 6.38 (s, 1H (maj)), 5.45 (dd, J=8.1, 5.6 Hz, 1H (min)). 4.62-4.48 (m, 1H (maj, min), 1H (maj)), 4.42 (dd, J=9.9, 3.9 Hz, 1H (maj)), 3.80 (s, 3H), 3.73 (dd, J=13.2, 5.8 Hz, 1H (min)), 3.62 (ddd, J=13.3, 11.9, 4.4 Hz, 1H (min)), 3.12 (ddd, J=12.5, 12.5, 4.7 Hz, 1H (maj)), 2.98-2.63 (m, 4H), 2.46 (s, 3H (maj)), 2.44 (s, 3H (min)), 2.30-2.16 (m, 2H), 1.91-1.68 (m, 6H), 1.61-1.48 (m, 2H). ESI-MS m/z 433.2 [M+H]⁺.

Example (S)-C2: Synthesis of Compound (S)-C2

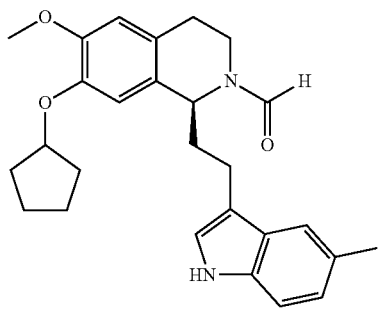

The compound (S)-C2 was obtained according to the synthesis of the compound (S)-C1, while 23-1 in example C1 was replaced with compound 24-1. ESI-MS m/z 433.2 [M+H]⁺.

Example (R)-C2: Synthesis of Compound (R)-C2

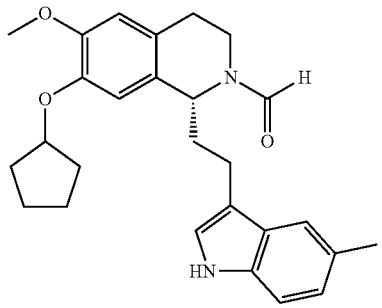

The compound (R)-C2 was obtained according to the synthesis of the compound (R)-C1, while 23-1 in example C1 was replaced with compound 24-1. ESI-MS m/z 433.2 [M+H]⁺.

Example C3: Synthesis of Compound C3

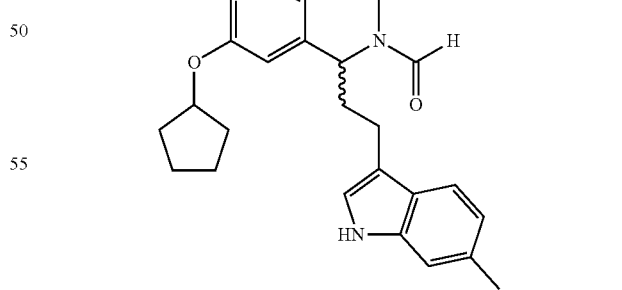

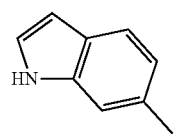

25-1

The compound C3 was obtained according to the synthesis of the compound C1, while 23-1 in example C1 was replaced with compound 25-1. ¹H NMR (400 MHz, CDCl₃) δ 8.27 (s, 1H (min)), 8.19 (s, 1H (maj)), 8.02 (brs. 1H (maj)), 7.94 (brs, 1H (min)), 7.51 (d, J=8.0 Hz, 1H (maj)), 7.45 (d, J=8.0 Hz, 1H (min)), 7.18 (s, 1H (maj)), 7.15 (s, 1H (min)), 7.06 (s, 1H (min)), 6.99-6.90 (m, 1H (maj, min) 1H (maj)) 6.56 (s, 1H (maj)), 6.53 (s, H (min)), 6.40 (s, 1H (min)). 6.38 (s, 1H (maj)), 5.44 (dd, J=8.4, 5.3 Hz, 1H (min)), 4.61-4.47 (m, 1H (maj, min) 1H (maj)), 4.40 (dd, J=9.4, 4.1 Hz, 1H (maj)), 3.80 (s, 3H (maj)), 3.79 (s, 3H (min)), 3.72 (dd, J=13.2, 6.4 Hz, 1H (min)), 3.62 (dd, J=18.3, 7.1 Hz, 1H (min)), 3.11 (ddd, J=12.4, 4.6, 4.6 Hz, 1H (maj)), 2.97-2.58 (m, 4H), 2.46 (s, 3H (maj)), 2.45 (s, 3H (min)), 2.32-2.13 (m, 2H), 1.92-1.64 (m, 6H), 1.65-1.45 (m, 2H). ESI-MS m/z 433.2 [M+H]⁺.

Example (S)-C3: Synthesis of Compound (S)-C3

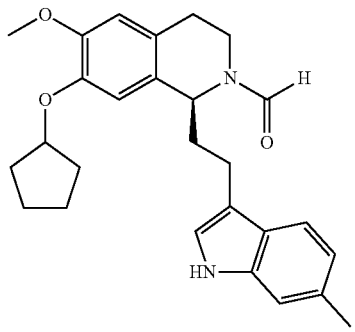

The compound (S)-C3 was obtained according to the synthesis of the compound (S)-C1, while 23-1 in example C1 was replaced with compound 25-1. ESI-MS m/z 433.2 [M+H]⁺.

Example (R)-C3: Synthesis of Compound (R)-C3

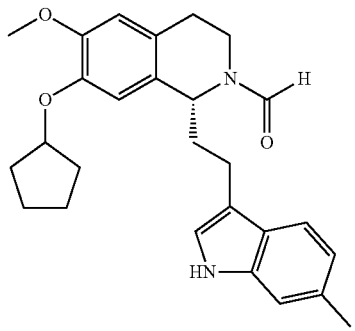

The compound (R)-C3 was obtained according to the synthesis of the compound (R)-C1, while 23-1 in example C1 was replaced with compound 25-1. ESI-MS m/z 433.2 [M+H]⁺.

Example C4: Synthesis of Compound C4

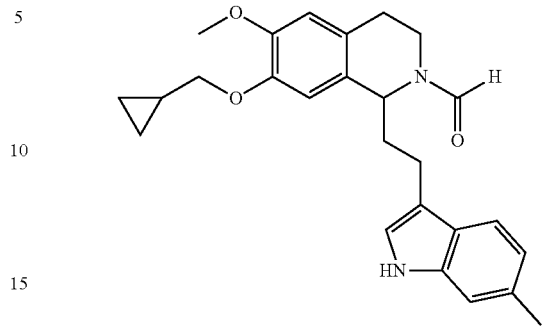

The compound C4 was obtained according to the synthesis of the compound A3, while 23-1 in example C1 was replaced with compound 25-1. ¹H NMR (400 MHz, CDCl₃) δ 8.27 (s, 1H (min)), 8.18 (s, 1H (maj)). 7.97 (brs, 1H (maj)), 7.90 (brs, 1H (min)). 7.50 (d, J=8.1 Hz, 1H (maj)), 7.44 (d, J=8.0 Hz, 1H (min)), 7.18 (s, 1H (maj)), 7.15 (s, 1H (min)), 7.05 (s, 1H (min)), 6.95 (m, 1H (min, maj) 1H (maj)), 6.57 (s, 1H (maj)), 6.55 (s, 1H (min)), 6.43 (s, 1H (min)), 6.40 (s, 1H (maj)), 5.44 (dd, J=8.5, 5.3 Hz, 1H (min)), 4.53 (dd, J=13.1, 5.7 Hz, 1H (min)), 4.39 (dd, J=9.6, 4.2 Hz, 1H (maj)), 3.83 (s, 3H), 3.77-3.55 (m, 2H (min), 2H (maj, min)), 3.11 (ddd, J=12.5, 12.5, 4.8 Hz, 1H (maj)), 2.98-2.60 (m, 4H), 2.47 (s, 3H (maj)), 2.45 (s, 3H (min)), 2.29-2.13 (m, 2H), 0.67-0.54 (m, 2H), 0.35-0.24 (m, 2H). ESI-MS m/z 419.2 [M+H]⁺.

Example (S)-C4: Synthesis of Compound (S)-C4

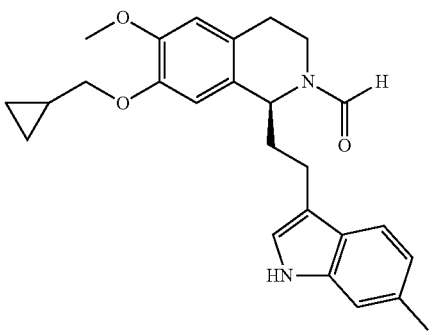 [SMILES: COc1cc2c(cc1OCC1CC1)[C@H](CCc1c[nH]c3cc(C)ccc13)N(C=O)CC2]

The compound (S)-C4 was obtained according to the synthesis of the compound (S)-A3, while 23-1 in example C was replaced with compound 25-1. ESI-MS m/z 419.2 [M+H]⁺.

Example (R)-C4: Synthesis of Compound (R)-C4

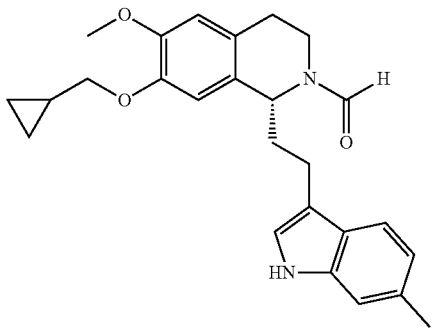 [SMILES: COc1cc2c(cc1OCC1CC1)[C@@H](CCc1c[nH]c3cc(C)ccc13)N(C=O)CC2]

The compound (R)-C4 was obtained according to the synthesis of the compound (R)-A3, while 23-1 in example C1 was replaced with compound 25-1. ESI-MS m/z 419.2 [M+H]$^+$.

Example C5: Synthesis of Compound C5

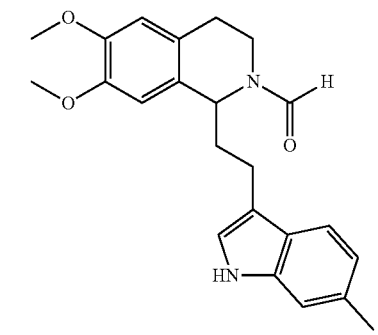

The compound C5 was obtained according to the synthesis of the compound A1, while 23-1 in example C1 was replaced with compound 25-1. $^1$H NMR (400 MHz, CDCl$_3$) δ 8.28 (s, 1H (min)), 8.19 (s, 1H (maj)), 7.97 (brs, 1H (maj)), 7.89 (brs, 1H (min)), 7.51 (d, J=8.0 Hz, 1H (maj)), 7.45 (d, J=8.1 Hz, 1H (min)), 7.18 (s, 1H (maj)), 7.15 (s, 1H (min)), 7.04 (s, 1H (min)), 7.00-6.89 (m, 1H (min, maj) 1H (maj)), 6.57 (s, 1H (maj)), 6.55 (s, 1H (min)), 6.43 (s, 1H (min)). 6.40 (s, 1H (maj)), 5.46 (dd, J=7.3, 6.3 Hz, 1H (min)), 4.54 (dd, J=13.2, 6.1 Hz, 1H (min)), 4.43 (dd, J=9.8, 3.8 Hz, 1H (maj)), 3.83 (s, 3H), 3.75 (s, 3H (maj)), 3.78-3.68 (m, 3H (min, maj) 1H (min)), 3.62 (ddd, J=12.2, 12.2, 4.2 Hz, 1H (maj)), 3.12 (ddd, J=12.2, 12.2, 4.5 Hz, 1H (min)), 2.98-2.63 (m, 4H), 2.46 (s, 3H (maj)), 2.45 (s, 3H (min)), 2.31-2.17 (m, 2H). ESI-MS m/z 379.2 [M+H]$^+$.

Example (S)-C5: Synthesis of Compound (S)-C5

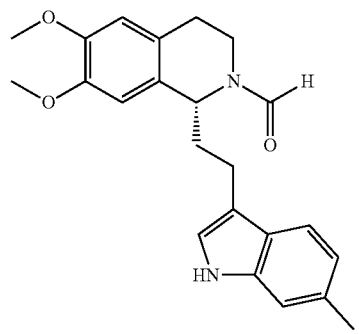

The compound (S)-C5 was obtained according to the synthesis of the compound (S)-A1, while 23-1 in example C1 was replaced with compound 25-1. ESI-MS m/z 379.2 [M+H]$^+$.

Example (R)-C5: Synthesis of Compound (R)-C5

The compound (R)-C5 was obtained according to the synthesis of the compound (R)-A1, while 23-1 in example C1 was replaced with compound 25-1. ESI-MS m/z 379.2 [M+H]$^+$.

Example C6: Synthesis of Compound C6

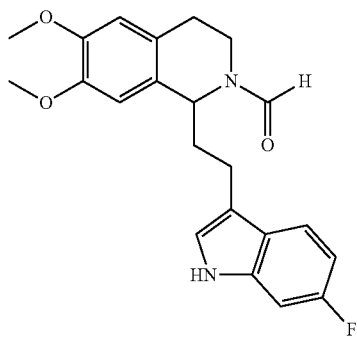

-continued 29-1

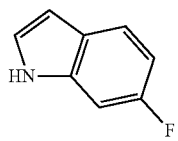

The compound C6 was obtained according to the synthesis of the compound A1, while 23-1 in example C1 was replaced with compound 29-1. $^1$H NMR (400 MHz, CDCl$_3$) δ 8.29 (s, 1H (min)), 8.20 (s, 1H (maj)), 8.19 (brs, 1H (maj)), 8.11 (brs, 1H (min)), 7.51 (dd, J=8.7, 5.3 Hz, 1H (maj)), 7.46 (dd, J=8.7, 5.3 Hz, 1H (min)), 7.14-6.98 (m, 2H), 6.94-6.81 (m, 2H), 6.58 (s, 1H (maj)), 6.55 (s, 1H (min)), 6.41 (s, 1H (min)), 6.40 (s, 1H (maj)), 5.45 (dd, J=8.5, 5.3 Hz, 1H (min)), 4.54 (ddd, J=13.1, 6.4, 1.4 Hz, 1H (maj)), 4.43 (dd, J=7.0, 7.0 Hz, 1H (maj)), 3.84 (s, 3H (maj)), 3.84 (s, 3H (min)), 3.77 (s, 3H (maj)), 3.76-3.68 (m, 4H (min)), 3.62 (ddd, J=13.4, 11.9, 4.5 Hz, 1H (min)), 3.12 (ddd, J=13.1, 11.8, 4.7 Hz, 1H (maj)), 2.98-2.63 (m, 4H), 2.30-2.15 (m, 2H). ESI-MS m/z 383.2 [M+H]$^+$.

Example (S)-C6: Synthesis of Compound (S)-C6

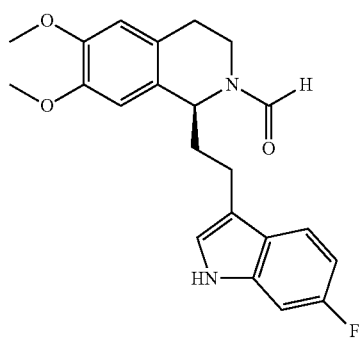 [SMILES: COc1cc2c(cc1OC)[C@H](CCc1c[nH]c3cc(F)ccc13)N(C=O)CC2]

The compound (S)-C6 was obtained according to the synthesis of the compound (S)-A1, while 23-1 in example C1 was replaced with compound 29-1. ESI-MS m/z 383.2 [M+H]$^+$.

Example (R)-C6: Synthesis of Compound (R)-C6

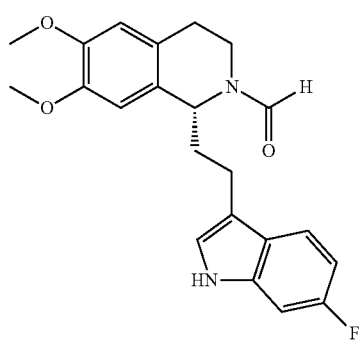 [SMILES: COc1cc2c(cc1OC)[C@@H](CCc1c[nH]c3cc(F)ccc13)N(C=O)CC2]

The compound (R)-C6 was obtained according to the synthesis of the compound (R)-A1, while 23-1 in example C1 was replaced with compound 29-1. ESI-MS m/z 383.2 [M+H]$^+$.

Example C7: Synthesis of Compound C7

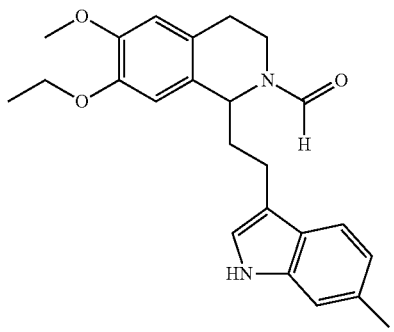 [SMILES: CCOc1cc2c(cc1OC)CCN(C=O)C2CCc1c[nH]c2cc(C)ccc12]

The compound C7 was obtained according to the synthesis of the compound A4, while 23-1 in example C1 was replaced with compound 25-1. $^1$H NMR (400 MHz, Chloroform) δ 8.02 (s, 1H), 7.60 (s, 1H), 7.53 (s, 1H), 7.25-7.16 (m, 3H), 6.97 (s, 1H), 6.88 (s, 1H), 4.70 (s, 1H), 4.13 (s, 2H), 3.92 (s, 1H), 3.75 (s, 3H), 3.33 (s, 1H), 2.91 (d, J=15.0 Hz, 2H), 2.76 (s, 1H), 2.44 (s, 3H), 2.26 (s, 2H), 1.42 (s, 3H). ESI-MS m/z 393.2 [M+H]$^+$.

Example (S)-C7: Synthesis of Compound (S)-C7

ZN 43

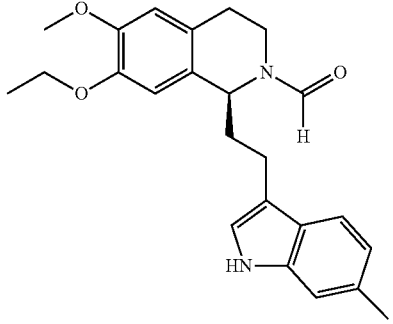

The compound (S)-C7 was obtained according to the synthesis of the compound (S)-A4, while 23-1 in example C1 was replaced with compound 25-1. ESI-MS m/z 393.2 [M+H]$^+$.

Example (R)-C7: Synthesis of Compound (R)-C7

ZN 43

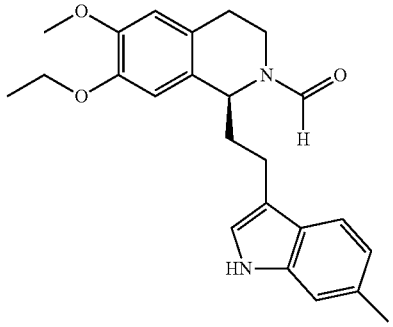

The compound (R)-C7 was obtained according to the synthesis of the compound (R)-A4, while 23-1 in example C1 was replaced with compound 25-1. ESI-MS m/z 393.2 [M+H]⁺.

Example C8: Synthesis of Compound C8

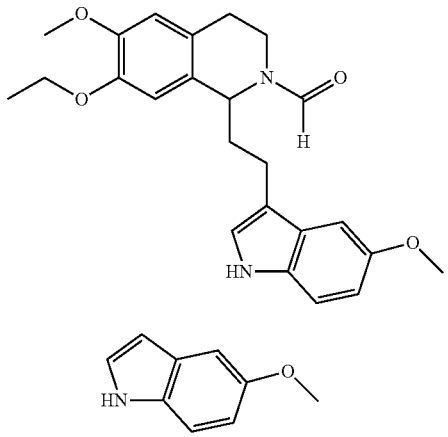

31-1

The compound C8 was obtained according to the synthesis of the compound A4, while 23-1 in example C1 was replaced with compound 31-1. ¹H NMR (400 MHz, CDCl₃) δ 8.28 (s, 1H (min)), 8.21 (s, 1H (maj)), 8.03 (brs. 1H (maj)), 7.96 (brs, 1H (min)), 7.28 (d, J=8.8 Hz, 1H (maj)), 7.25 (d, J=8.8 Hz, 1H (min)), 7.11 (s, 1H (min)), 7.03 (d, J=2.3 Hz, 1H (maj)), 7.00 (d, J=2.0 Hz, 1H (min) 1H (maj)), 6.88 (dd, J=8.8, 2.4 Hz, 1H (maj)), 6.84 (dd, J=8.8, 2.4 Hz, 1H (min)), 6.57 (s, 1H (maj)), 6.55 (s, 1H (min)), 6.42 (s, 1H (maj)). 6.42 (s, 1H (min)), 5.45 (dd, J=8.3, 5.5 Hz, 1H (min)), 4.53 (ddd, J=13.0, 6.3, 1.7 Hz, 1H (maj)), 4.43 (dd, J=7.9, 5.2 Hz, 1H (maj)), 3.98-3.84 (m, 5H), 3.83 (s, 3H (maj)), 3.82 (s, 3H (min)), 3.73 (dd, J=12.9, 6.1 Hz, 1H (min)), 3.66-3.57 (m, 1H (min)), 3.12 (ddd, J=13.1, 11.8, 4.8 Hz, 1H (maj)), 2.96-2.64 (m, 4H), 2.28-2.16 (m, 2H), 1.43-1.34 (m, 3H). ESI-MS m/z 409.2 [M+H]⁺.

Example (S)-C8: Synthesis of Compound (S)-C8

ZN 42

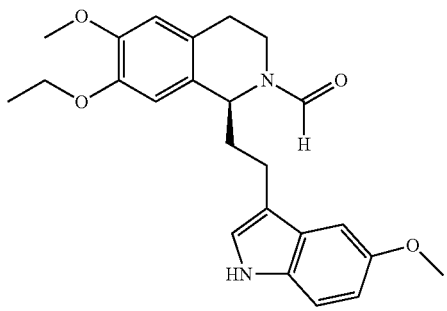 [SMILES: CCOc1cc2c(cc1OC)CCN(C=O)[C@@H]2CCc1c[nH]c2ccc(OC)cc12]

The compound (S)-C8 was obtained according to the synthesis of the compound (S)-A4, while 23-1 in example C1 was replaced with compound 31-1. ESI-MS m/z 409.2 [M+H]⁺.

Example (R)-C8: Synthesis of Compound (R)-C8

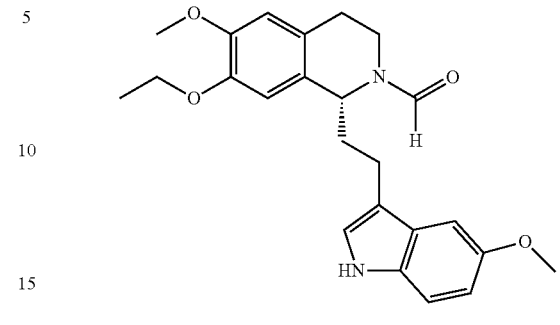

The compound (R)-C8 was obtained according to the synthesis of the compound (R)-A4, while 23-1 in example C was replaced with compound 31-1. ESI-MS m/z 409.2 [M+H]⁺.

Example C9: Synthesis of Compound C9

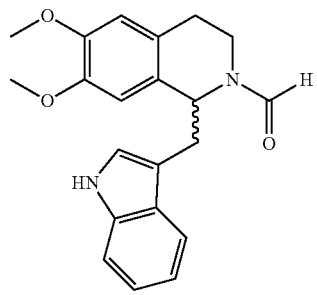 [SMILES: COc1cc2c(cc1OC)C(Cc1c[nH]c3ccccc13)N(C=O)CC2]

The compound C9 was

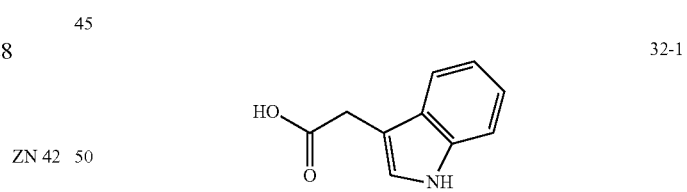

32-1 obtained according to the synthesis of the compound A1, while 1-1 in example A1 was replaced with compound 32-1. ¹H NMR (400 MHz, CDCl₃) δ 8.32 (brs, 1H (maj)), 8.18 (s, 1H (min)), 8.16 (brs, 1H (min)), 7.65 (d, J=7.7 Hz, 1H (maj)), 7.60 (m, 1H (min) 1H (maj)), 7.41 (d, J=7.9 Hz, 1H (maj)), 7.36 (d, J=8.1 Hz, 1H (min)), 7.28-7.07 (m, 2H), 6.95 (s, 1H (maj)), 6.93 (s, 1H (min)), 6.70 (s, 1H (maj)), 6.67 (s, 1H (maj)), 6.57 (s, 1H (min)), 6.34 (s, 1H (min)), 5.69 (dd, J=6.5 Hz, 1H (min)), 4.74 (dd, J=9.8, 3.8 Hz, 1H (maj)), 4.53 (dd, J=13.0, 4.4 Hz, 1H (maj)), 3.91 (s, 3H (maj)), 3.88 (s, 3H (maj)), 3.87 (s, 3H (min)), 3.64-3.54 (m, 4H (min)), 3.48-3.13 (m, 3H), 3.00-2.81 (m, 1H), 2.77 (dd, J=16.0, 2.5 Hz, 1H (maj)), 2.69 (dd, J=16.2, 2.3 Hz, 1H (min)). ESI-MS m/z 351.2 [M+H]⁺.

Example (S)-C9: Synthesis of Compound (S)-C9

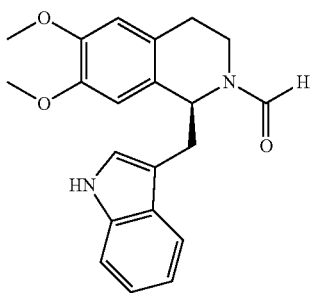

The compound (S)-C9 was obtained according to the synthesis of the compound (S)-A1, while 1-2 in example A1 was replaced with compound 32-1. ESI-MS m/z 351.2 [M+H]$^+$.

Example (R)-C9: Synthesis of Compound (R)-C9

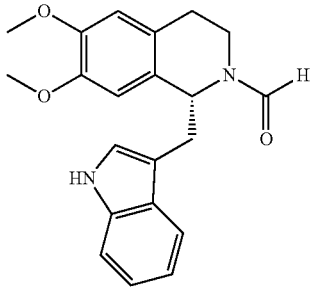 [SMILES: COc1cc2c(cc1OC)[C@@H](Cc1c[nH]c3ccccc13)N(C=O)CC2]

The compound (R)-C9 was obtained according to the synthesis of the compound (R)-A1, while 1-2 in example A1 was replaced with compound 32-1. ESI-MS m/z 351.2 [M+H]$^+$.

Example C10: Synthesis of Compound C10

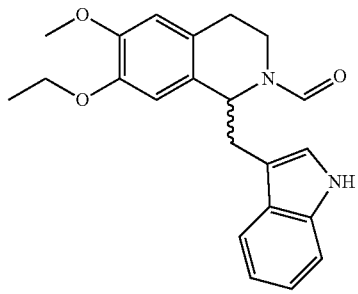 [SMILES: CCOc1cc2c(cc1OC)CCN(C=O)[C@@H]2Cc1c[nH]c2ccccc12]

ZN 27

The compound C10 was obtained according to the synthesis of the compound A4, while 1-2 in example A1 was replaced with compound 32-1. $^1$H NMR (400 MHz, CDCl$_3$) δ 8.27 (brs, 1H (maj)), 8.15 (s, 1H (min)), 8.11 (brs, 1H (min)), 7.62 (d, J=7.5 Hz, 1H (maj)), 7.59-7.53 (m, 1H (min), 1H (maj)), 7.38 (d, J=8.0 Hz, 1H (maj)), 7.33 (d, J=8.1 Hz, 1H (min)), 7.25-7.04 (m, 2H), 6.93 (s, 1H (maj)), 6.93 (s, 1H (min)), 6.71 (s, 1H (maj)), 6.64 (s, 1H (maj)), 6.55 (s, 1H (min)), 6.37 (s, 1H (min)), 5.66 (t, J=6.5 Hz, 1H (min)), 4.69 (dd, J=9.8, 3.8 Hz, 1H (maj)), 4.49 (ddd, J=13.1, 6.2, 2.1 Hz, 1H (maj)), 4.07 (qd, J=7.0, 1.9 Hz, 2H (maj)), 3.87 (s, 3H (maj)), 3.83 (s, 3H (min)), 3.81-3.65 (m, 2H (min)), 3.54 (ddd, J=13.0, 6.0, 1.7 Hz, 1H (min)), 3.43-3.07 (m, 3H), 2.97-2.58 (m, 2H), 1.47 (t, J=7.0 Hz, 3H (maj)), 1.32 (t, J=7.0 Hz, 3H (min)). ESI-MS m/z 365.2 [M+H]$^+$.

Example (s)-C10: Synthesis of Compound (S)-C10

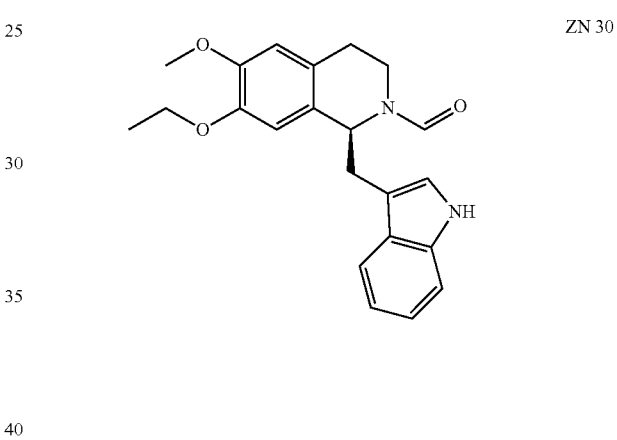

ZN 30

The compound (S)-C10 was obtained according to the synthesis of the compound (S)-A1, while 1-2 in example A1 was replaced with compound 32-1. ESI-MS m/z 365.2 [M+H]$^+$.

Example (R)-C10: Synthesis of Compound (R)-C10

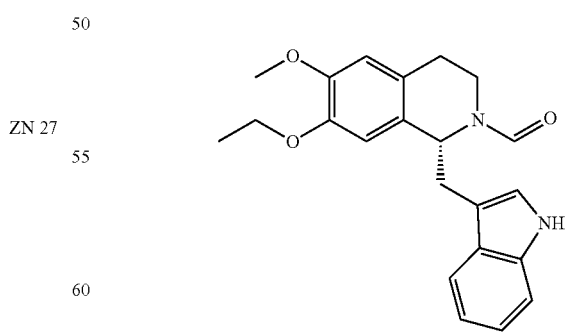

The compound (R)-C10 was obtained according to the synthesis of the compound (R)-A1, while 1-2 in example A1 was replaced with compound 32-1. ESI-MS m/z 365.2 [M+H]$^+$.

Example C11: Synthesis of Compound C11

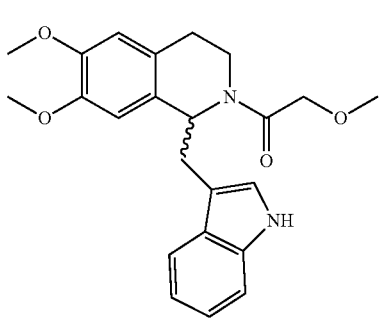

ZN 31

The compound C11 was obtained according to the synthesis of the compound B1, while 1-2 in example A1 was replaced with compound 32-1. $^1$H NMR (400 MHz, CDCl$_3$) δ 8.32 (brs. 1H (min)), 8.08 (brs, 1H (maj)), 7.67 (m, 1H), 7.40 (d, J=7.4 Hz, 1H (min)), 7.33 (d, J=8.1 Hz, 1H (maj)), 7.24-7.05 (m, 2H), 6.93 (s, 1H (min)), 6.88 (s, 1H (maj)), 6.64 (s, 1H (min)), 6.58 (s, 1H (maj)), 6.54 (s, 1H (min)), 6.20 (s, 1H (maj)), 5.79 (dd, J=7.1, 6.0 Hz, 1H (maj)), 4.92 (dd, J=8.6, 5.7 Hz, 1H (min)), 4.80 (dd, J=12.6, 5.7 Hz, 1H (min)), 4.14 (s, 1H (maj)), 3.87 (s, 3H (min)), 3.84 (s, 3H (maj)), 3.78 (s, 3H (min)), 3.69 (m, 1H), 3.49 (s, 3H (maj)), 3.48-3.41 (m, 1H (min)), 3.39 (s, 3H (maj)), 3.37-3.15 (m, 3H), 2.98 (s, 3H (min)), 2.96-2.79 (m, 1H), 2.77-2.63 (m, 1H). ESI-MS m/z 395.2 [M+H]$^+$.

Example (R)-C11: Synthesis of Compound (R)-C11

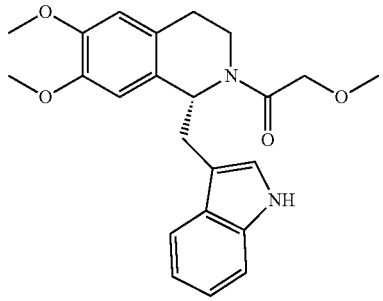

The compound (R)-C11 was obtained according to the synthesis of the compound (R)-B1, while 1-2 in example A was replaced with compound 32-1. ESI-MS m/z 395.2 [M+H]$^+$.

Example C12: Synthesis of Compound C12

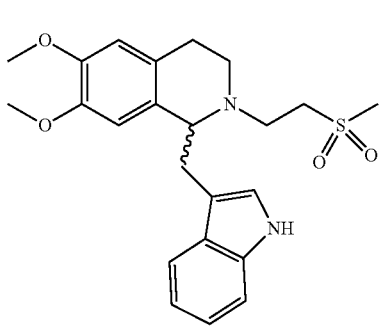

ZN 32

The compound C12 was obtained according to the synthesis of the compound B8, while 1-2 in example A1 was replaced with compound 32-1. $^1$H NMR (400 MHz, CDCl$_3$) δ 7.83 (brs, 1H), 7.57 (dd, J=14.9, 3.0 Hz, 1H), 7.33 (dd, J=15.0, 3.1 Hz, 1H), 7.24-7.13 (m, 2H), 7.05-6.93 (m, 2H), 6.88 (s, 1H), 3.96 (t, J=14.0 Hz, 1H), 3.84 (dd, J=16.4, 15.4 Hz, 1H), 3.77-3.68 (m, 6H), 3.55-3.23 (m, 4H), 3.15-2.96 (m, 2H), 2.84-2.66 (m, 5H), 2.58 (m, 1H). ESI-MS m/z 429.2 [M+H]$^+$.

Example C12: Synthesis of Compound (S)-C12

Example (S)-C11: Synthesis of Compound (S)-C11

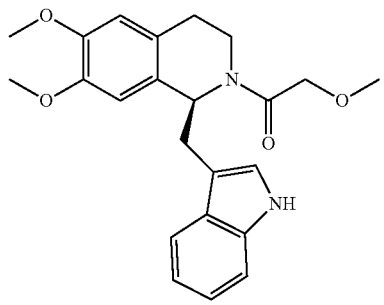

The compound (S)-B11 was obtained according to the synthesis of the compound (S)-B1, while 1-2 in example A1 was replaced with compound 32-1. ESI-MS m/z 395.2 [M+H]$^+$.

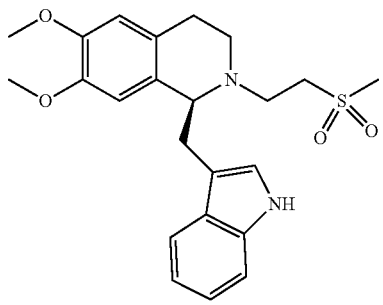

The compound (S)-C12 was obtained according to the synthesis of the compound (S)-B8, while 1-2 in example A1 was replaced with compound 32-1. ESI-MS m/z 429.2 [M+H]⁺.

Example (R)-C12: Synthesis of Compound (R)-C12

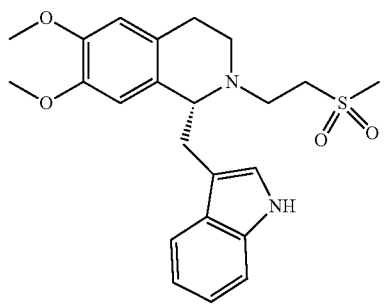

The compound (R)-C12 was obtained according to the synthesis of the compound (R)-B8, while 1-2 in example A was replaced with compound 32-1. ESI-MS m/z 429.2 [M+H]⁺.

Example C13: Synthesis of Compound C13

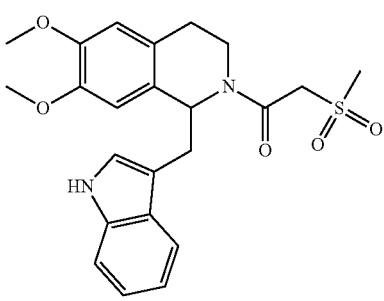 [SMILES: COc1cc2c(cc1OC)[C@@H](Cc1c[nH]c3ccccc13)N(C(=O)CS(C)(=O)=O)CC2]

The compound C13 was obtained according to the synthesis of the example B9, while 1-2 in example A1 was replaced with compound 32-1. ¹H NMR (400 MHz, CDCl₃) δ 8.37 (brs, 1H (min)), 8.12 (brs, 1H (maj)), 7.62 (d, J=7.8 Hz, 1H (maj)), 7.57 (d, J=7.6 Hz, 1H (min)), 7.39 (d, J=7.8 Hz, 1H (min)), 7.33 (d, J=8.1 Hz, 1H (maj)), 7.26-7.07 (m, 2H), 7.02 (s, 1H (min)). 6.87 (s, 1H (maj)), 6.68 (s, 1H (min)), 6.64 (s, 1H (min)), 6.58 (s, 1H (maj)), 6.19 (s, 1H (maj)), 5.81 (dd, J=6.8, 6.8 Hz, 1H (maj)), 5.01 (dd, J=9.7, 4.4 Hz, 1H (min)), 4.74 (dd, J=13.3, 3.2 Hz, 1H (min)), 4.09 (q, J=14.4 Hz, 2H (maj)), 3.87 (s, 3H (maj)), 3.86 (s, 3H (min)), 3.84 (s, 3H (maj)), 3.74-3.64 (m, 1H (maj)). 3.50 (s, 2H), 2.99 (s, 3H), 2.78 (s, 2H). ESI-MS m/z 443.2 [M+H]⁺.

Example (S)-C13: Synthesis of Compound (S)-C13

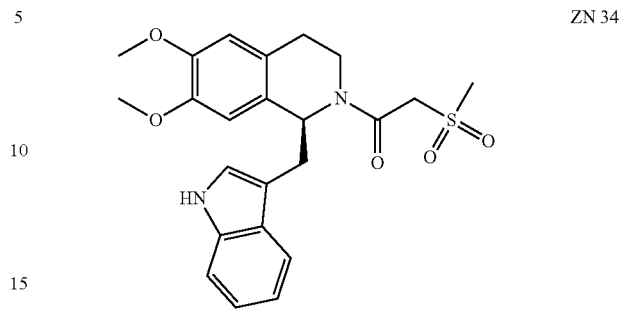

The compound (S)-C13 was obtained according to the synthesis of the example (S)-B9, while 1-2 in example A1 was replaced with compound 32-1. ESI-MS m/z 443.2 [M+H]⁺.

Example (R)-C13: Synthesis of Compound (R)-C13

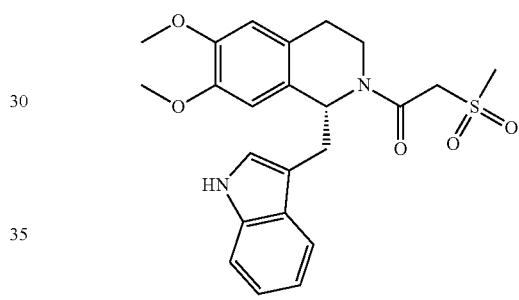

The compound (R)-C13 was obtained according to the synthesis of the example (R)-B9, while 1-2 in example A1 was replaced with compound 32-1. ESI-MS m/z 443.2 [M+H]⁺.

Example C14: Synthesis of Compound C14

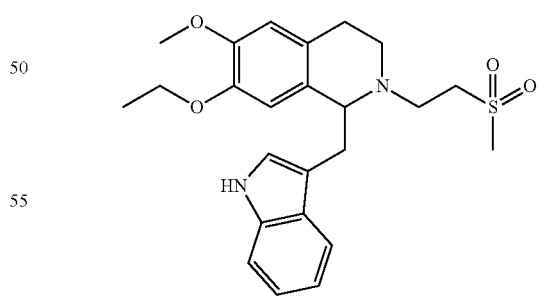

The compound C14 was obtained according to the synthesis of example A4 and example B8, while 1-2 in example A1 was replaced with compound 32-1. ¹H NMR (400 MHz, CDCl₃) δ 8.13 (brs, 1H), 7.58 (d, J=7.8 Hz, 1H), 7.36 (d, J=8.1 Hz, 1H), 7.20 (t, J=7.3 Hz, 1H), 7.13 (t, J=7.3 Hz, 1H), 6.98 (s, 1H), 6.59 (s, 1H), 6.36 (s, 1H), 4.02-3.93 (m, 1H), 3.92-3.74 (m, 5H), 3.51-3.38 (m, 1H), 3.20 (m, 2H), 3.12-

2.83 (m, 6H), 2.55 (d, J=15.6 Hz, 1H), 2.41 (s, 3H), 1.36 (t, J=7.0 Hz, 3H). ESI-MS m/z 443.2 [M+H]⁺.

Example (S)-C14: Synthesis of Compound (S)-C14

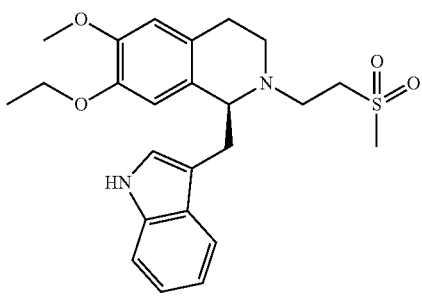 [SMILES: CCOc1cc2c(cc1OC)CCN(CCS(C)(=O)=O)C2Cc1c[nH]c2ccccc12]

The compound (S)-C14 was obtained according to the synthesis of example (S)-A4 and example (S)-B8, while 1-2 in example A1 was replaced with compound 32-1. ESI-MS m/z 443.2 [M+H]⁺.

Example (R)-C14: Synthesis of Compound (R)-C14

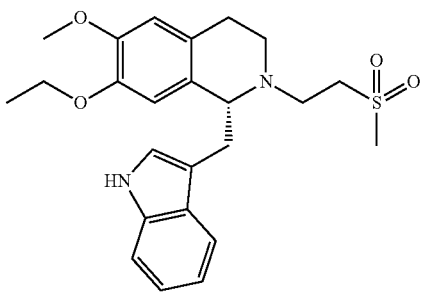 [SMILES: CCOc1cc2c(cc1OC)CCN(CCS(C)(=O)=O)[C@@H]2Cc1c[nH]c2ccccc12]

The compound (R)-C14 was obtained according to the synthesis of example (R)-A4 and example (R)-B8, while 1-2 in example A1 was replaced with compound 32-1. ESI-MS m/z 443.2 [M+H]⁺.

Example C15: Synthesis of Compound C15

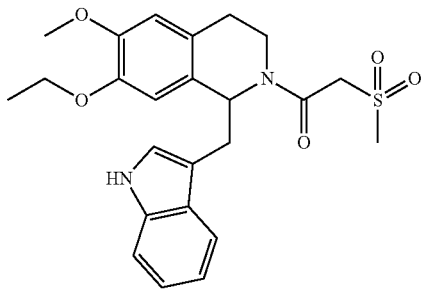 [SMILES: CCOc1cc2c(cc1OC)CCN(C(=O)CS(C)(=O)=O)C2Cc1c[nH]c2ccccc12]

The compound C15 was obtained according to the synthesis of the example A4 and example B9, while 1-2 in example A1 was replaced with compound 32-1. ¹H NMR (400 MHz, CDCl₃) δ 7.71 (brs, 1H), 7.57 (dd, J=7.5, 1.4 Hz, 1H), 7.33 (dd, J=7.5, 1.4 Hz, 1H), 7.23-7.15 (m, 2H), 7.02-6.94 (m, 2H), 6.88 (s, 1H), 5.66 (t, J=7.1 Hz, 1H), 4.35 (s, 2H), 4.17-4.05 (m, 3H), 3.75 (s, 3H), 3.58 (dd, J=12.4, 7.1 Hz, 1H), 3.49 (dt, J=12.4, 5.5 Hz, 1H), 3.32 (dd, J=12.5, 7.0 Hz, 1H), 2.98-2.84 (m, 5H), 1.42 (t, J=5.9 Hz, 3H). ESI-MS m/z 457.2 [M+H]⁺.

Example (S)-C15: Synthesis of Compound (S)-C15

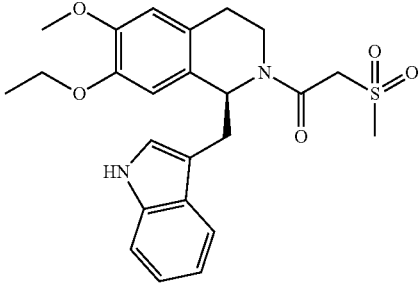

The compound C15 was obtained according to the synthesis of the example (S)-A4 and example (S)-B9, while 1-2 in example A1 was replaced with compound 32-1. ESI-MS m/z 457.2 [M+H]⁺.

Example (R)-C15: Synthesis of Compound (R)-C15

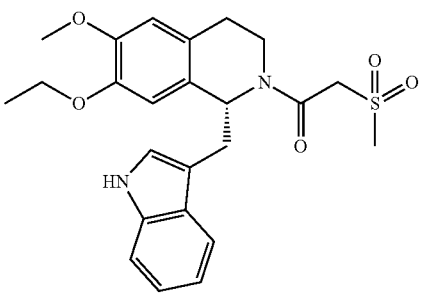 [SMILES: CCOc1cc2c(cc1OC)CCN(C(=O)CS(C)(=O)=O)[C@@H]2Cc1c[nH]c2ccccc12]

The compound (R)-C15 was obtained according to the synthesis of the example (R)-A4 and example (R)-B9, while 1-2 in example A1 was replaced with compound 32-1. ESI-MS m/z 457.2 [M+H]⁺.

Example C16: Synthesis of Compound C16

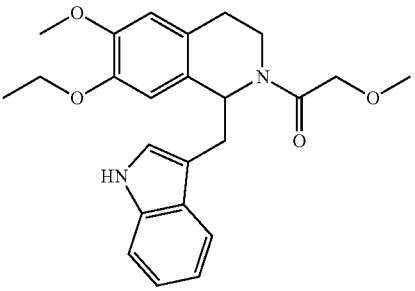 [SMILES: CCOc1cc2c(cc1OC)CCN(C(=O)COC)C2Cc1c[nH]c2ccccc12]

The compound C16 was obtained according to the synthesis of the example A4 and example B4, while 1-2 in example A1 was replaced with compound 32-1. $^1$H NMR (400 MHz, CDCl$_3$) δ 8.42 (brs, 1H (min)), 8.14 (brs, 1H (maj)), 7.66 (d, J=7.1 Hz, 1H (min)), 7.63 (d, J=7.9 Hz, 1H (maj)), 7.39 (d, J=7.2 Hz, 1H (min)), 7.33 (d, J=8.1 Hz, 1H (maj)), 7.25-7.05 (m, 2H), 6.93 (s, 1H (min)), 6.87 (s, 1H (maj)), 6.63 (s, 1H (min)), 6.60 (s, 1H (min)), 6.57 (s, 1H (maj)), 6.26 (s, 1H (maj)), 5.78 (dd, J=6.6, 6.6 Hz, 1H (maj)), 4.88 (dd, J=9.0, 4.8 Hz, 1H (min)), 4.80 (dd, J=12.7, 5.2 Hz, 1H (min)), 4.13 (s, 2H (maj)), 3.99 (dt, J=16.4, 9.4 Hz, 2H (maj)), 3.86 (s, 3H (min)), 3.83 (s, 3H (maj)), 3.78-3.57 (m, 1H (min) 1H (maj)), 3.48-3.13 (m, 3H (maj) 3H (min, maj) 2H (min)), 2.95 (s, 3H (min)), 2.76 (m, 2H), 1.44 (t, J=7.0 Hz, 3H (min)), 1.28 (t, J=7.0 Hz, 3H (maj)). ESI-MS m/z 409.2 [M+H]$^+$.

Example (S)-C16: Synthesis of Compound (S)-C16

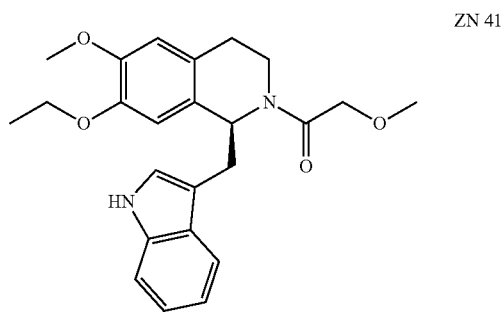 [SMILES: CCOc1cc2c(cc1OC)CCN(C(=O)COC)[C@H]2Cc1c[nH]c2ccccc12]

ZN 41

The compound (S)-C16 was obtained according to the synthesis of the example (S)-A4 and example (S)-B4, while 1-2 in example A1 was replaced with compound 32-1.

Example (R)-C16: Synthesis of Compound (R)-C16

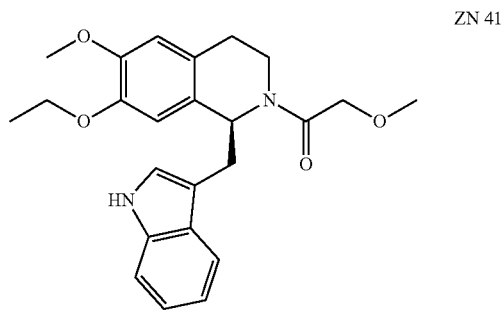 [SMILES: CCOc1cc2c(cc1OC)CCN(C(=O)COC)[C@H]2Cc1c[nH]c2ccccc12]

ZN 41

The compound (R)-C16 was obtained according to the synthesis of the example (R)-A4 and example (R)-B4, while 1-2 in example A1 was replaced with compound 32-1.

Example C17: Synthesis of Compound C17

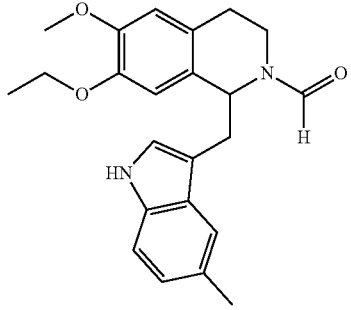

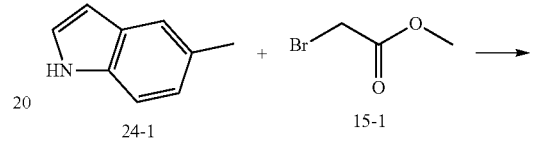

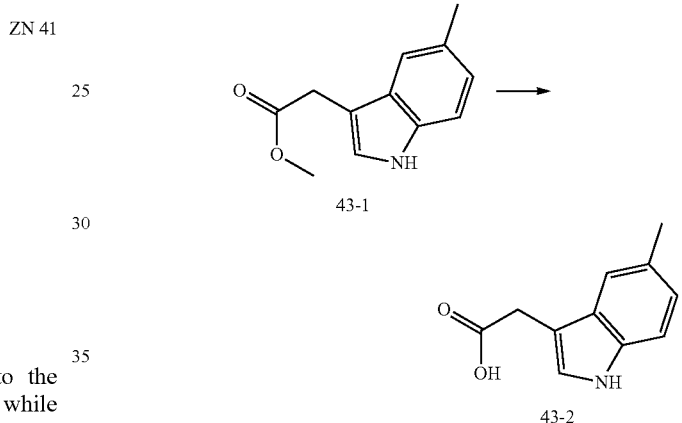

Synthesis of Compound 43-1:

Under the protection of argon, 24-1 was dissolved in anhydrous tetrahydrofuran, and n-butyllithium solution was slowly added dropwise at −78° C. After 30 min, a solution of zinc chloride in tetrahydrofuran was added dropwise, warmed to room temperature, and 15-1 was added and stirred for 24 h. The reaction solution was poured into saturated ammonium chloride solution and extracted three times with ethyl acetate. The organic layer was washed with water, saturated sodium chloride, dried over anhydrous sodium sulfate, and evaporated to dryness. The residue was purified through column chromatograph with petroleum ether/ethyl acetate=10:1 to provide an oil (605 mg, 70%).

Synthesis of Compound 43-2:

43-1 was dissolved in tetrahydrofuran/water=1:1 solvent, lithium hydroxide was added, and stirred at room temperature for 16 h. The mixture was extracted with ethyl acetate, the aqueous layer was collected and adjusted to acidic with 1N diluted hydrochloric acid, then extracted three times with ethyl acetate. The organic layer was collected and dried with anhydrous sodium sulfate, and evaporated to dryness to give a brown solid g, yield 95%.

The white solid compound C17 was obtained according to the synthesis of the example C10, while 1-2 in example A was replaced with compound 43-2. $^1$H NMR (400 MHz, CDCl$_3$) δ 8.19 (brs, 1H (maj)), 8.15 (s, 1H (min)), 8.03 (brs, 1H (min)), 7.57 (s, 1H (maj)), 7.36 (s, 1H (maj)), 7.29 (s, 1H (min)), 7.27 (d, J=7.5 Hz, 1H (maj)), 7.21 (d, J=8.3 Hz, 1H (min)), 7.05 (d, J=8.4 Hz, 1H (maj)), 6.99 (d, J=8.4 Hz, 1H (min)), 6.88 (s, 1H (maj)), 6.84 (s, 1H (min)), 6.72 (s, 1H (maj)), 6.64 (s, 1H (maj)), 6.55 (s, 1H (min)), 6.39 (s, 1H (min)), 5.64 (dd, J=6.3, 6.3 Hz, 1H (min)), 4.69 (dd, J=9.8, 4.0 Hz, 1H (maj)), 4.47 (ddd, J=13.3, 6.3, 2.2 Hz, 1H (maj)), 4.07 (qd, J=6.9, 1.7 Hz, 2H (maj)), 3.87 (s, 3H (maj)). 3.84 (s, 3H (min)), 3.83-3.68 (m, 2H (min)), 3.54 (ddd, J=13.3, 6.3, 2.3 Hz, 1H (min)), 3.42-3.05 (m, 3H), 2.96-2.78 (m, 1H), 2.78-2.59 (m, 1H), 2.49 (s, 3H (maj)), 2.41 (s, 3H (min)), 1.48 (t, J=7.0 Hz, 3H (maj)), 1.33 (t, J=7.0 Hz, 3H (min)). ESI-MS m/z 379.2 [M+H]$^+$.

Example (S)-C17: Synthesis of Compound (S)-C17

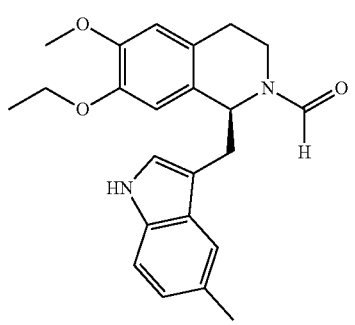

ZN 36

The white solid compound (S)-C17 was obtained according to the synthesis of the example (S)-C10, while 1-2 in example A1 was replaced with compound 43-2.

Example (R)-C17: Synthesis of Compound (R)-C17

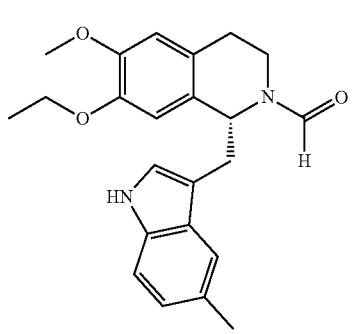 [SMILES: CCOc1cc2c(cc1OC)CCN(C=O)[C@@H]2Cc1c[nH]c2ccc(C)cc12]

The white solid compound (R)-C17 was obtained according to the synthesis of the example (R)-C10, while 1-2 in example A1 was replaced with compound 43-2.

Example C18: Synthesis of Compound C18

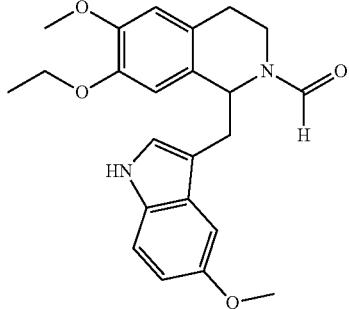 [SMILES: CCOc1cc2c(cc1OC)CCN(C=O)[C@@H]2Cc1c[nH]c2ccc(OC)cc12]

44-1

Compound C18 (white solid) was synthesized according to the synthesis of the compound C17, while 24-1 was replaced with the compound 44-1. $^1$H NMR (400 MHz, CDCl$_3$) δ 8.17 (s, 1H (maj) 1H (min)), 8.00 (brs, 1H (min)), 7.62 (s, 1H (maj)), 7.27 (d, J=8.9 Hz, 1H), 7.21 (d, J=8.8 Hz, 1H (maj)), 7.00 (d, J=2.4 Hz, 1H (min)), 6.98 (d, J=2.4 Hz, 1H (maj)), 6.91 (s, 1H (maj)), 6.88 (dd, J=8.8, 2.4 Hz, 1H (maj)), 6.86 (s, 1H (min)), 6.82 (dd, J=8.7, 2.4 Hz, 1H (min)), 6.69 (s, 1H (maj)), 6.63 (s, 1H (maj)), 6.54 (s, 1H (min)), 6.39 (s, 1H (min)), 5.63 (t, J=6.1 Hz, 1H (min)), 4.68 (dd, J=9.6, 4.4 Hz, 1H (maj)), 4.46 (ddd, J=12.7, 6.2, 2.1 Hz, 1H (maj)), 4.05 (qd, J=6.9, 2.3 Hz, 2H (maj)), 3.87 (s, 3H (maj)), 3.87 (s, 3H (min)), 3.85-3.71 (m, 3H (min, maj) 2H (min)), 3.54 (ddd, J=8.2, 6.1, 2.5 Hz, 1H (min)), 3.37-3.08 (m, 3H), 2.95-2.77 (m, 1H), 2.77-2.56 (m, 1H), 1.46 (t, J=7.0 Hz, 3H (maj)), 1.33 (t, J=7.0 Hz, 3H (min)). ESI-MS m/z 395.2 [M+H]$^+$.

Example (S)-C18: Synthesis of Compound (S)-C18

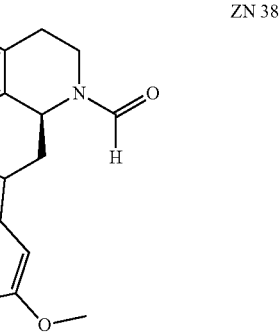

ZN 38

Compound (S)-C18 (white solid) was synthesized according to the synthesis of the compound (S)-C17, while 24-1 in example (S)-C17 was replaced with the compound 44-1.

Example (R)-C18: Synthesis of Compound (R)-C18

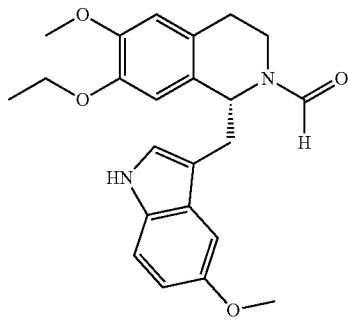

Compound (R)-C18 (white solid) was synthesized according to the synthesis of the compound (R)-C17, while 24-1 in example (R)-C17 was replaced with the compound 44-1.

Example C19: Synthesis of Compound C19

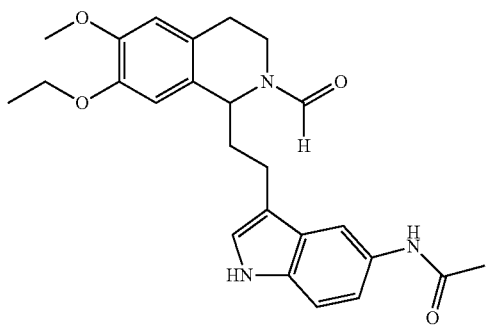 [SMILES: CCOc1cc2c(cc1OC)CCN(C=O)C2CCc1c[nH]c2ccc(NC(C)=O)cc12]

The compound C19 was obtained according to the synthesis of the compound A4, while 23-1 in example C was replaced with the compound 5-acetamido-indole-3 propionic acid.

Example (S)-C19: Synthesis of Compound (S)-C19

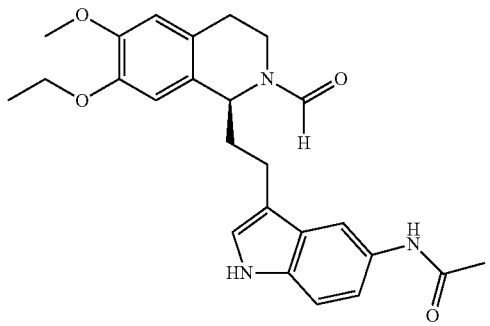 [SMILES: CCOc1cc2c(cc1OC)CCN(C=O)[C@H]2CCc1c[nH]c2ccc(NC(C)=O)cc12]

The compound (S)-C19 was obtained according to the synthesis of the compound (S)-A4, while 23-1 in example C1 was replaced with the compound 5-acetamido-indole-3 propionic acid.

Example (R)-C19: Synthesis of Compound (R)-C19

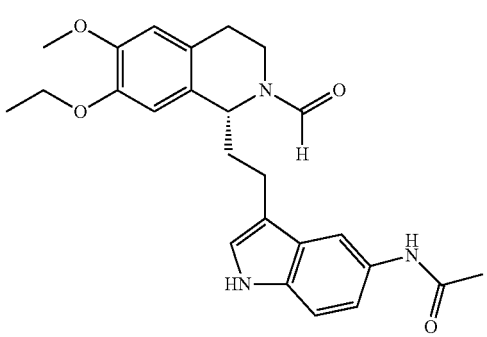 [SMILES: CCOc1cc2c(cc1OC)CCN(C=O)[C@@H]2CCc1c[nH]c2ccc(NC(C)=O)cc12]

The compound (R)-C19 was obtained according to the synthesis of the compound (R)-A4, while 23-1 in example C1 was replaced with the compound 5-acetamido-indole-3 propionic acid.

Example C20: Synthesis of Compound C20

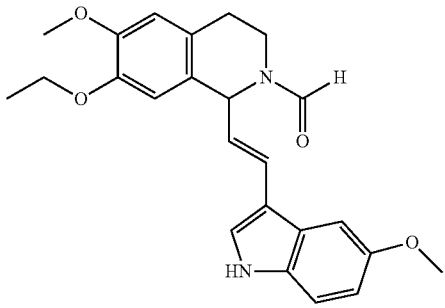

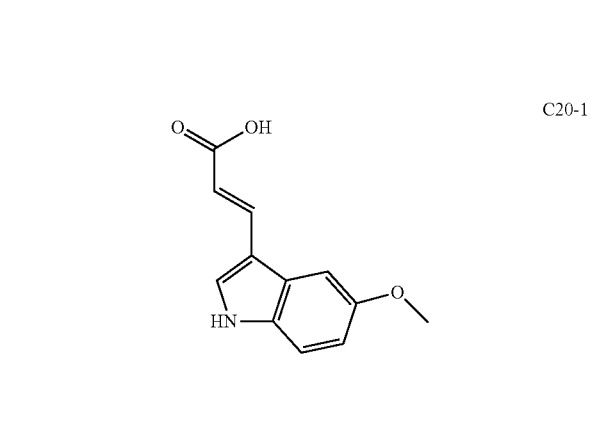

The compound C20 was obtained according to the synthesis of the compound A4, while 1-2 in example A1 was replaced with intermediate C20-1. ESI-MS m/z 407.0 [M+H]$^+$.

Example (S)-C20: Synthesis of Compound (S)-C20

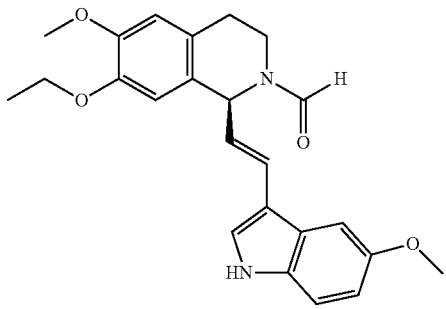 [SMILES: CCOc1cc2c(cc1OC)CCN(C=O)[C@H]2/C=C/c1c[nH]c2ccc(OC)cc12]

The compound (S)-C20 was obtained according to the synthesis of the compound (S)-A4, while 1-2 in example A1 was replaced with intermediate C20-1. $^1$H NMR (500 MHz, Chloroform-d) δ 9.74 (t, J=2.4 Hz, 1H), 8.20 (s, 1H), 7.48 (dd, J=2.5, 0.5 Hz, 1H), 7.34 (dt, J=2.7, 0.6 Hz, 1H), 7.08 (ddd, J=8.4, 2.2, 0.6 Hz, 1H), 6.93 (dd, J=15.4, 0.9 Hz, 1H), 6.84-6.77 (m, 2H), 6.65 (dd, J=15.6, 6.4 Hz, 1H), 6.49 (d, J=1.0 Hz, 1H), 5.22 (dt, J=6.4, 0.9 Hz, 1H), 4.20-4.03 (m, 2H), 3.85 (d, J=13.4 Hz, 5H), 3.73 (ddd, J=11.7, 6.4, 4.3 Hz, 1H), 3.65 (ddd, J=11.5, 6.4, 4.3 Hz, 1H), 2.97 (dddd, J=14.6, 6.4, 4.2, 1.0 Hz, 1H), 2.89 (dddd, J=14.6, 6.4, 4.2, 1.0 Hz, 1H), 1.43 (t, J=6.9 Hz, 3H). ESI-MS m/z 407.2 [M+H]$^+$.

Example (R)-C20: Synthesis of Compound (R)-C20

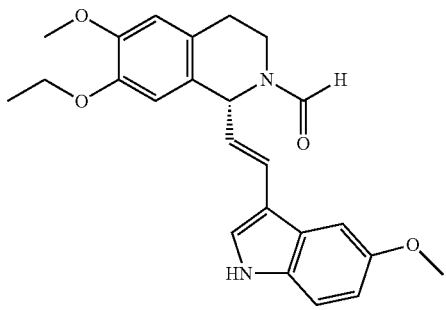 [SMILES: CCOc1cc2c(cc1OC)CCN(C=O)[C@@H]2/C=C/c1c[nH]c2ccc(OC)cc12]

The compound (R)-C20 was obtained according to the synthesis of the compound (R)-A4, while 1-2 in example A1 was replaced with intermediate C20-1. ESI-MS m/z 407.0 [M+H]$^+$.

Example C21: Synthesis of Compound C21

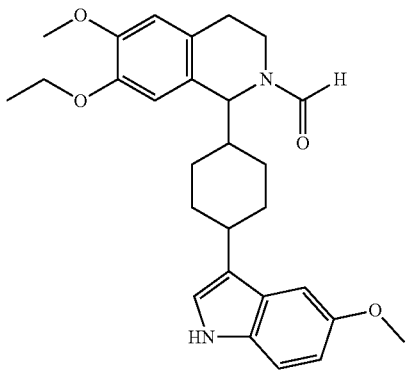

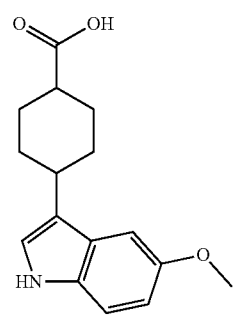

C21-1

The compound C21 was obtained according to the synthesis of the compound A4, while 1-2 in example A1 was replaced with intermediate C21-1. ESI-MS m/z 463.0 [M+H]$^+$.

Example (S)-C21: Synthesis of Compound (S)-C21

The compound (S)-C21 was obtained according to the synthesis of the compound (S)-A4, while 1-2 in example A1 was replaced with intermediate C21-1. $^1$H NMR (500 MHz, Chloroform-d) δ 9.04 (t, J=2.4 Hz, 1H), 8.28 (s, 1H), 7.28-7.22 (m, 1H), 7.11-7.06 (m, 2H), 6.83 (d, J=1.0 Hz, 1H), 6.72 (dd, J=8.4, 2.7 Hz, 1H), 6.63 (t, J=1.0 Hz, 1H), 4.66 (dd, J=6.0, 1.1 Hz, 1H), 4.20-4.02 (m, 2H), 3.84 (d, J=10.1 Hz, 6H), 3.68 (ddd, J=11.7, 6.3, 4.4 Hz, 1H), 3.50 (ddd, J=11.7, 6.3, 4.4 Hz, 1H), 3.42 (p, J=5.9 Hz, 1H), 2.99-2.84 (m, 2H), 2.31 (h, J=6.0 Hz, 1H), 2.07-1.96 (m, 2H), 1.82-1.70 (m, 4H), 1.70-1.60 (m, 2H), 1.42 (t, J=6.9 Hz, 3H). ESI-MS m/z 463.3 [M+H]+.

Example (R)-C21: Synthesis of Compound (R)-C21

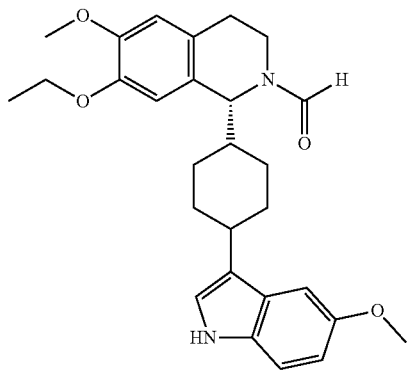 [SMILES: CCOc1cc2c(cc1OC)CCN(C=O)[C@@H]2C1CCC(c2c[nH]c3ccc(OC)cc23)CC1]

The compound (R)-C21 was obtained according to the synthesis of the compound (R)-A4, while 1-2 in example A1 was replaced with intermediate C21-1. ESI-MS m/z 463.3 [M+H]+.

Example C22: Synthesis of Compound C22

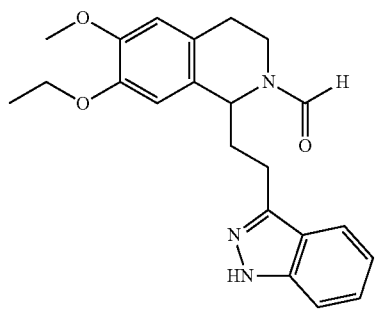

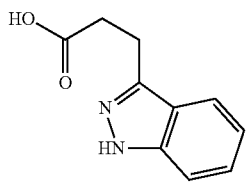

C22-1

The compound C22 was obtained according to the synthesis of the compound A4, while 1-2 in example A was replaced with intermediate C21-1. H NMR (500 MHz, CDCl₃) δ 8.29 (s, 1H), 7.74 (ddd, J=7.9, 1.3, 0.6 Hz, 1H), 7.53-7.47 (m, 1H), 7.37 (td, J=7.7, 1.3 Hz, 1H), 7.21-7.14 (m, 1H), 6.67 (d, J=0.9 Hz, 1H), 6.60 (t, J=1.0 Hz, 1H), 4.98-4.91 (m, 1H), 4.20-4.03 (m, 2H), 3.84 (s, 2H), 3.73 (ddd, J=11.5, 6.2, 4.2 Hz, 1H), 3.56 (ddd, J=11.7, 6.4, 4.3 Hz, 1H), 3.04-2.83 (m, 3H), 2.48-2.29 (m, 3H), 1.42 (t, J=6.9 Hz, 3H). ESI-MS m/z 380.2[M+H]+.

Example (S)-C22: Synthesis of Compound (S)-C22

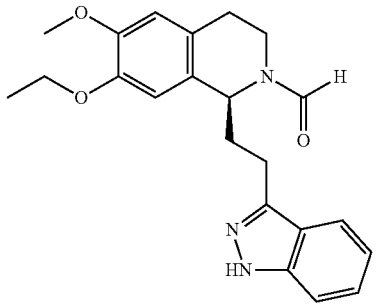 [SMILES: CCOc1cc2c(cc1OC)CCN(C=O)[C@H]2CCc1n[nH]c2ccccc12]

The compound (S)-C22 was obtained according to the synthesis of the compound (S)-A4, while 1-2 in example A1 was replaced with intermediate C22-1. ESI-MS m/z 380.2 [M+H]+.

Example (R)-C22: Synthesis of Compound (R)-C22

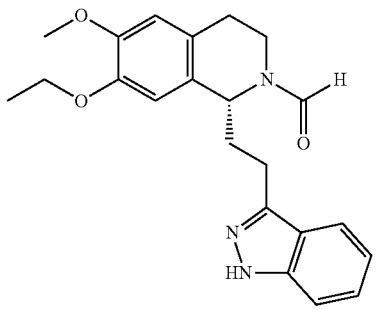 [SMILES: CCOc1cc2c(cc1OC)CCN(C=O)[C@@H]2CCc1n[nH]c2ccccc12]

The compound (R)-C22 was obtained according to the synthesis of the compound (R)-A4, while 1-2 in example A1 was replaced with intermediate C22-1. ESI-MS m/z 380.2 [M+H]+.

Example C23: Synthesis of Compound C23

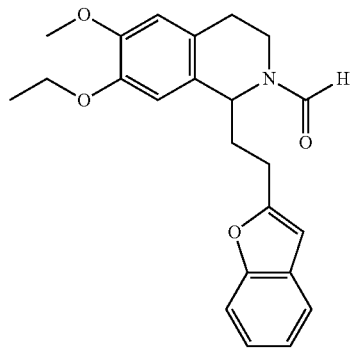

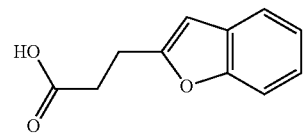

C23-1

The compound C23 was obtained according to the synthesis of the compound A4, while 1-2 in example A1 was replaced with intermediate C23-1. $^1$H NMR (500 MHz, CDCl$_3$) δ 8.28 (s, 1H), 7.55-7.49 (m, 1H), 7.44-7.37 (m, 1H), 7.32-7.25 (m, 1H), 7.18 (ddd, J=7.9, 7.3, 1.1 Hz, 1H), 6.67 (d, J=0.9 Hz, 1H), 6.60 (t, J=1.0 Hz, 1H), 6.47-6.42 (m, 1H), 4.85 (td, J=5.4, 1.0 Hz, 1H), 4.20-4.03 (m, 2H), 3.84 (s, 2H), 3.70 (ddd, J=11.5, 6.2, 4.3 Hz, 1H), 3.54 (ddd, J=11.7, 6.3, 4.4 Hz, 1H), 2.97-2.83 (m, 3H), 2.62 (dt, J=13.7, 7.3 Hz, 1H), 2.30-2.12 (m, 2H), 1.42 (t, J=6.9 Hz, 3H). ESI-MS m/z 380.2[M+H]$^+$.

Example (S)-C23: Synthesis of Compound (S)-C23

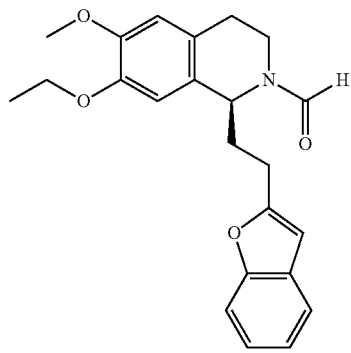 [SMILES: CCOc1cc2c(cc1OC)CCN(C=O)[C@H]2CCc1cc2ccccc2o1]

The compound (S)-C23 was obtained according to the synthesis of the compound (S)-A4, while 1-2 in example A1 was replaced with intermediate C23-1. ESI-MS m/z 380.0 [M+H]$^+$.

Example (R)-C23: Synthesis of Compound (R)-C23

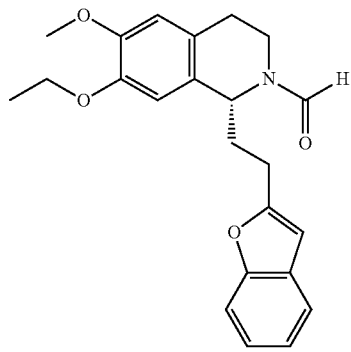 [SMILES: CCOc1cc2c(cc1OC)CCN(C=O)[C@@H]2CCc1cc2ccccc2o1]

The compound (R)-C23 was obtained according to the synthesis of the compound (R)-A4, while 1-2 in example A1 was replaced with intermediate C23-1. ESI-MS m/z 380.0 [M+H]$^+$.

Example C24: Synthesis of Compound C24

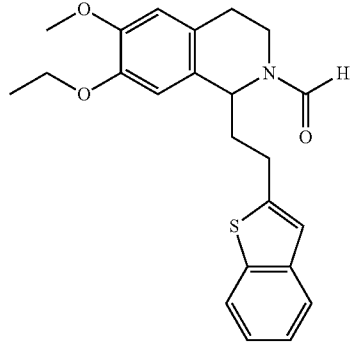

C24-1

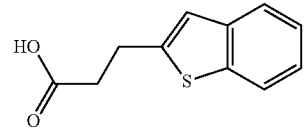

The compound C24 was obtained according to the synthesis of the compound A4, while 1-2 in example A1 was replaced with intermediate C24-1. $^1$H NMR (500 MHz, CDC) δ 8.29 (s, 1H), 7.77-7.67 (m, 2H), 7.39-7.32 (m, 1H), 7.16-7.06 (m, 2H), 6.67 (d, J=0.9 Hz, 1H), 6.61 (t, J=1.0 Hz, 1H), 4.88 (td, J=5.4, 1.0 Hz, 1H), 4.20-4.03 (m, 2H), 3.84 (s, 2H), 3.72 (ddd, J=11.7, 6.2, 4.5 Hz, 1H), 3.55 (ddd, J=11.7, 6.2, 4.5 Hz, 1H), 3.00-2.91 (m, 1H), 2.94-2.84 (m, 2H), 2.76 (dt, J=13.7, 7.3 Hz, 1H), 2.24 (ddtd, J=35.3, 12.5, 7.3, 5.4 Hz, 2H), 1.42 (t, J=7.0 Hz, 3H). ESI-MS m/z 396.2[M+H]$^+$.

Example (S)-C24: Synthesis of Compound (S)-C24

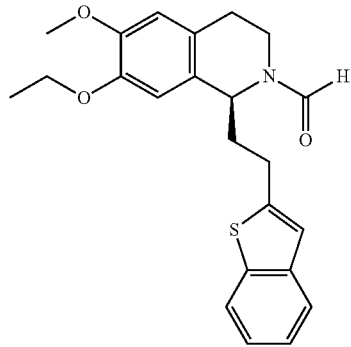 [SMILES: CCOc1cc2c(cc1OC)CCN(C=O)[C@H]2CCc1cc2ccccc2s1]

The compound (S)-C24 was obtained according to the synthesis of the compound (S)-A4, while 1-2 in example A1 was replaced with intermediate C24-1. ESI-MS m/z 396.2 [M+H]$^+$.

Example (R)-C24: Synthesis of Compound (R)-C24

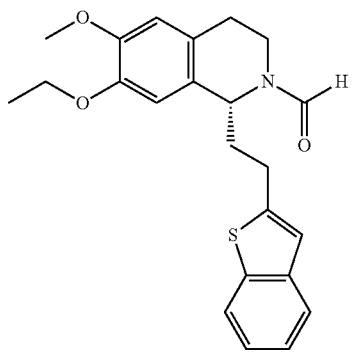 [SMILES: CCOc1cc2c(cc1OC)CCN(C=O)[C@@H]2CCc1cc2ccccc2s1]

The compound (R)-C24 was obtained according to the synthesis of the compound (R)-A4, while 1-2 in example A1 was replaced with intermediate C24-1. ESI-MS m/z 396.2 [M+H]$^+$.

Example C25: Synthesis of Compound C25

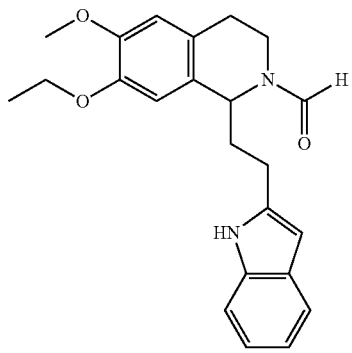

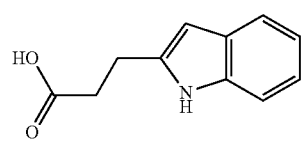
C25-1

The compound C25 was obtained according to the synthesis of the compound A4, while 1-2 in example A1 was replaced with intermediate C25-1. $^1$H NMR (500 MHz, CDCl$_3$) δ 8.30 (s, 1H), 7.38-7.25 (m, 2H), 7.18-7.08 (m, 2H), 6.70 (d, J=1.9 Hz, 1H), 6.65-6.59 (m, 2H), 5.06 (td, J=5.3, 1.0 Hz, 1H), 4.20-4.03 (m, 2H), 3.84 (s, 2H), 3.71 (ddd, J=11.5, 6.2, 4.3 Hz, 1H), 3.55 (ddd, J=11.7, 6.2, 4.4 Hz, 1H), 2.97-2.83 (m, 2H), 2.77 (dt, J=13.5, 7.3 Hz, 1H), 2.60 (dt, J=13.7, 7.4 Hz, 1H), 2.26 (dtd, J=12.6, 7.3, 5.3 Hz, 1H), 2.16 (dtd, J=12.5, 7.2, 5.3 Hz, 1H), 1.42 (t, J=6.9 Hz, 3H). ESI-MS m/z 379.2[M+H]$^+$.

Example (S)-C25: Synthesis of Compound (S)-C25

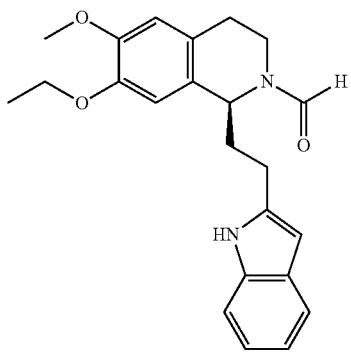 [SMILES: CCOc1cc2c(cc1OC)CCN(C=O)[C@H]2CCc1cc2ccccc2[nH]1]

The compound (S)-C25 was obtained according to the synthesis of the compound (S)-A4, while 1-2 in example A was replaced with intermediate C25-1. ESI-MS m/z 379.2 [M+H]$^+$.

Example (R)-C25: Synthesis of Compound (R)-C25

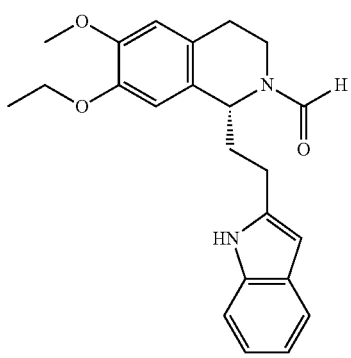

The compound (R)-C25 was obtained according to the synthesis of the compound (R)-A4, while 1-2 in example A1 was replaced with intermediate C25-1. ESI-MS m/z 379.2 [M+H]$^+$.

Example C26: Synthesis of Compound C26

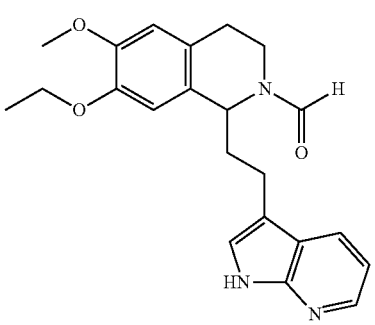

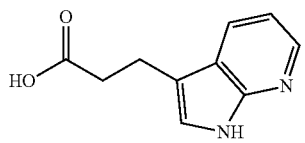

C26-1

The compound C26 was obtained according to the synthesis of the compound A4, while 1-2 in example A1 was replaced with intermediate C26-1. $^1$H NMR (500 MHz, Chloroform-d) δ 8.83-8.76 (m, 2H), 8.30 (s, 1H), 8.03-7.97 (m, 1H), 7.34 (dd, J=7.9, 3.5 Hz, 1H), 6.87-6.82 (m, 1H), 6.65-6.60 (m, 2H), 4.92 (td, J=5.3, 1.0 Hz, 1H), 4.20-4.03 (m, 2H), 3.84 (s, 2H), 3.73 (ddd, J=11.5, 6.2, 4.3 Hz, 1H), 3.56 (ddd, J=11.7, 6.3, 4.4 Hz, 1H), 2.97-2.88 (m, 1H), 2.92-2.84 (m, 1H), 2.88-2.79 (m, 1H), 2.47-2.30 (m, 2H), 2.26 (dtd, J=12.6, 7.2, 5.3 Hz, 1H), 1.42 (t, J=6.9 Hz, 3H). ESI-MS m/z 380.2[M+H]$^+$ Example (S)-C26: Synthesis of Compound (S)-C26

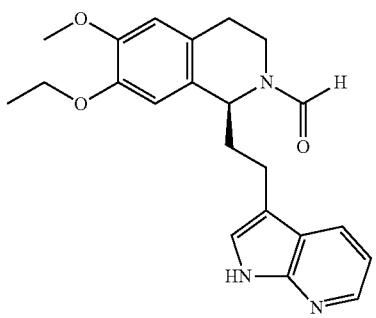 [SMILES: CCOc1cc2c(cc1OC)CCN(C=O)[C@H]2CCc1c[nH]c2ncccc12]

The compound (S)-C26 was obtained according to the synthesis of the compound (S)-A4, while 1-2 in example A1 was replaced with intermediate C26-1. ESI-MS m/z 380.0 [M+H]$^+$.

Example (R)-C26: Synthesis of Compound (R)-C26

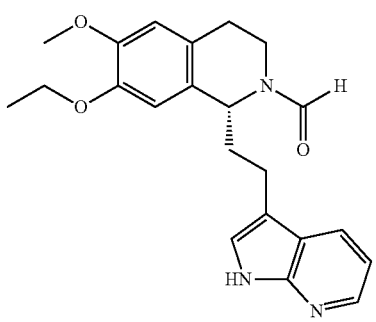 [SMILES: CCOc1cc2c(cc1OC)CCN(C=O)[C@@H]2CCc1c[nH]c2ncccc12]

The compound (R)-C26 was obtained according to the synthesis of the compound (R)-A4, while 1-2 in example A1 was replaced with intermediate C26-1. ESI-MS m/z 380.0 [M+H]$^+$.

Example C27: Synthesis of Compound C27

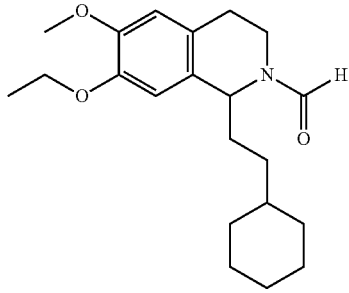

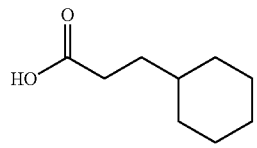

C27-1

The compound C27 was obtained according to the synthesis of the compound A4, while 1-2 in example A1 was replaced with intermediate C27-1. $^1$H NMR (500 MHz, CDCl$_3$) δ 8.24 (s, 1H), 6.86 (d, J=1.1 Hz, 1H), 6.61 (t, J=1.0 Hz, 1H), 4.86 (td, J=5.4, 1.0 Hz, 1H), 4.19-4.02 (m, 2H), 3.84 (s, 2H), 3.69 (ddd, J=11.7, 6.3, 4.4 Hz, 1H), 3.51 (ddd, J=11.7, 6.4, 4.4 Hz, 1H), 2.97-2.82 (m, 2H), 2.01 (dtd, J=12.8, 7.4, 5.3 Hz, 1H), 1.77 (dtd, J=12.8, 7.5, 5.4 Hz, 1H), 1.66-1.38 (m, 11H), 1.35-1.12 (m, 7H). ESI-MS m/z 346.2[M+H]$^+$.

Example (S)-C27: Synthesis of Compound (S)-C27

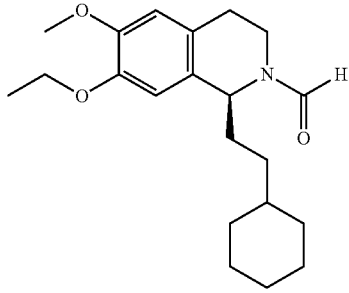 [SMILES: CCOc1cc2c(cc1OC)CCN(C=O)[C@H]2CCC1CCCCC1]

The compound (S)-C27 was obtained according to the synthesis of the compound (S)-A4, while 1-2 in example A1 was replaced with intermediate C27-1. ESI-MS m/z 346.2 [M+H]$^+$.

Example (R)-C27: Synthesis of Compound (R)-C27

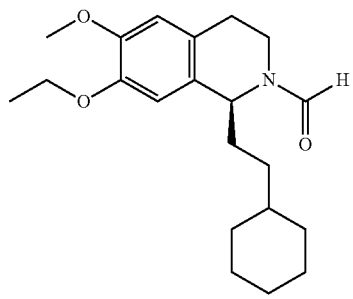 [SMILES: CCOc1cc2c(cc1OC)CCN(C=O)[C@H]2CCC1CCCCC1]

The compound (R)-27 was obtained according to the synthesis of the compound (R)-A4, while 1-2 in example A1 was replaced with intermediate C27-1. ESI-MS m/z 346.2 [M+H]$^+$.

Example C28: Synthesis of Compound C28

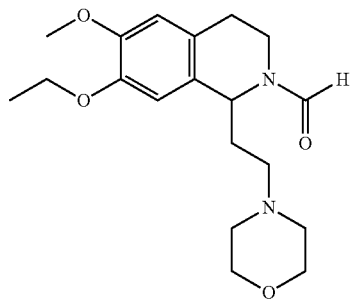

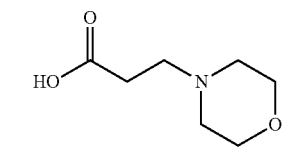

C28-1

The compound C28 was obtained according to the synthesis of the compound A4, while 1-2 in example A1 was replaced with intermediate C28-1. $^1$H NMR (500 MHz, Chloroform-d) δ 8.24 (s, 1H), 6.95 (d, J=0.9 Hz, 1H), 6.62 (t, J=1.0 Hz, 1H), 4.72 (td, J=5.4, 1.0 Hz, 1H), 4.19-4.02 (m, 2H), 3.84 (s, 3H), 3.87-3.79 (m, 1H), 3.76 (t, J=6.0 Hz, 4H), 3.49 (ddd, J=11.7, 6.2, 4.5 Hz, 1H), 2.95-2.83 (m, 2H), 2.72 (dt, J=11.9, 7.2 Hz, 1H), 2.58-2.42 (m, 5H), 2.06 (dtd, J=12.6, 7.3, 5.3 Hz, 1H), 1.92 (dtd, J=12.6, 7.3, 5.5 Hz, 1H), 1.42 (t, J=7.0 Hz, 3H). ESI-MS m/z 349.2[M+H]$^+$.

Example (S)-C28: Synthesis of Compound (S)-C28

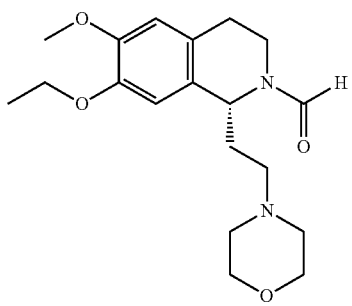

The compound (S)-C28 was obtained according to the synthesis of the compound (S)-A4, while 1-2 in example A1 was replaced with intermediate C28-1. ESI-MS m/z 349.2 [M+H]$^+$.

Example (R)-C28: Synthesis of Compound (R)-C28

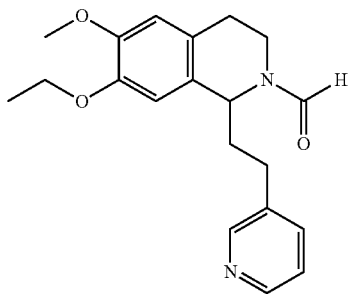

The compound (R)-C28 was obtained according to the synthesis of the compound (R)-A4, while 1-2 in example A1 was replaced with intermediate C28-1. ESI-MS m/z 349.2 [M+H]$^+$.

Example C29: Synthesis of Compound C29

C29-1

The compound C29 was obtained according to the synthesis of the compound A4, while 1-2 in example A1 was replaced with intermediate C29-1. ¹H NMR (500 MHz, CDCl₃) δ 8.48-8.38 (m, 2H), 8.27 (s, 1H), 7.46 (dt, J=7.9, 2.1 Hz, 1H), 7.19 (dd, J=7.8, 3.5 Hz, 1H), 6.63 (t, J=1.0 Hz, 1H), 6.55 (d, J=1.1 Hz, 1H), 4.77 (td, J=5.3, 1.0 Hz, 1H), 4.19-4.02 (m, 2H), 3.84 (s, 2H), 3.76 (ddd, J=11.7, 6.3, 4.4 Hz, 1H), 3.54 (ddd, J=11.7, 6.4, 4.3 Hz, 1H), 2.96-2.80 (m, 3H), 2.66 (dt, J=13.9, 7.3 Hz, 1H), 2.27 (dtd, J=12.6, 7.3, 5.3 Hz, 1H), 2.15 (dtd, J=12.6, 7.2, 5.3 Hz, 1H), 1.42 (t, J=7.0 Hz, 3H). ESI-MS m/z 341.2[M+H]⁺.

Example (S)-C29: Synthesis of Compound (S)-C29

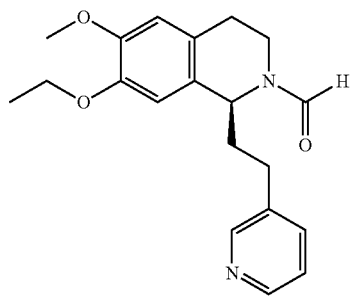 [SMILES: CCOc1cc2c(cc1OC)CCN(C=O)[C@H]2CCc1cccnc1]

The compound (S)-C29 was obtained according to the synthesis of the compound A4, while 1-2 in example A1 was replaced with intermediate C29-1. ESI-MS m/z 341.2 [M+H]⁺.

Example (R)-C29: Synthesis of Compound (R)-C29

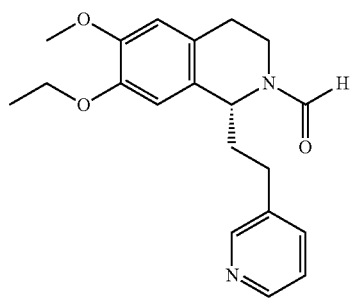 [SMILES: CCOc1cc2c(cc1OC)CCN(C=O)[C@@H]2CCc1cccnc1]

The compound (R)-C29 was obtained according to the synthesis of the compound A4, while 1-2 in example A1 was replaced with intermediate C29-1. ESI-MS m/z 341.2 [M+H]⁺.

Example C30: Synthesis of Compound C30

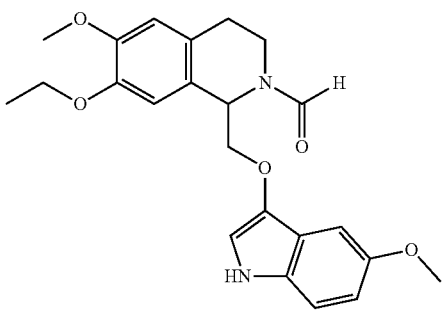

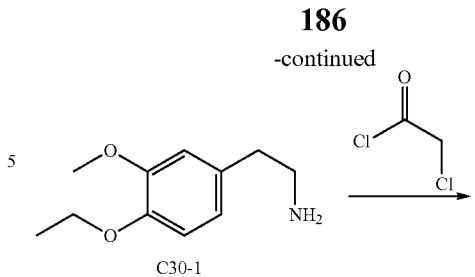

C30-1

-continued

C30-2

C-30-3

C30-4

C30-1 was dissolved in anhydrous dichloromethane, and chloroacetyl chloride and triethylamine were added dropwise under ice bath. The mixture was transferred to room temperature and reacted for 1 h. After quenched with water, the mixture was extracted with DCM, dried and evaporated to dryness, and purified through column chromatography to obtain C30-2. C30-3 was dissolved in acetonitrile, and cesium carbonate was added, stirred at room temperature for 2 h. C30-2 was added under nitrogen protection and stirred for 18 h. The reaction was quenched with saturated ammonium chloride, extracted with ethyl acetate, washed with saturated brine, and dried and evaporated to dryness. The residue was purified through column chromatography to give C30-4. The compound C30 was obtained according to the synthesis of the A4, while 1-3 in example A1 was replaced with intermediate C30-4. ¹H NMR (500 MHz, Chloroform-d) δ 9.86 (dd, J=2.6, 2.1 Hz, 1H), 8.28 (s, 1H), 7.46-7.39 (m, 2H), 7.16 (dd, J=2.5, 0.6 Hz, 1H), 6.81 (dd, J=8.4, 2.7 Hz, 1H), 6.74 (d, J=1.0 Hz, 1H), 6.62 (t, J=1.0 Hz, 1H), 5.23 (td, J=5.4, 1.0 Hz, 1H), 4.70 (dd, J=10.5, 5.4 Hz, 1H), 4.61 (dd, J=10.6, 5.5 Hz, 1H), 4.18-4.02 (m, 2H), 3.84 (d, J=11.7 Hz, 5H), 3.67 (ddd, J=11.7, 6.4, 4.2 Hz, 1H), 3.57 (ddd, J=11.7, 6.5, 4.2 Hz, 1H), 2.97 (dddd, J=14.6, 6.4, 4.2, 1.1 Hz, 1H), 2.87 (dddd, J=14.5, 6.2, 4.1, 1.0 Hz, 1H), 1.42 (t, J=7.0 Hz, 3H). ESI-MS m/z 411.2 [M+H]⁺.

Example (S)-C30: Synthesis of Compound (S)-C30

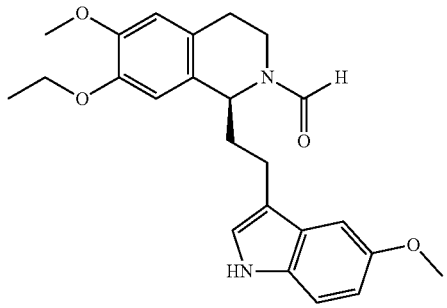

The compound (S)-C30 was obtained according to the synthesis of the (S)-A4, while 1-3 in example A1 was replaced with intermediate C30-4. ESI-MS m/z 411.2 [M+H]⁺.

Example (R)-C30: Synthesis of Compound (R)-C30

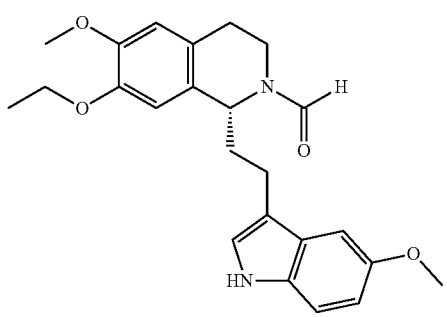

The compound (R)-C30 was obtained according to the synthesis of the (R)-A4, while 1-3 in example A1 was replaced with intermediate C30-4. ESI-MS m/z 411.2 [M+H]⁺.

Example C31: Synthesis of Compound C31

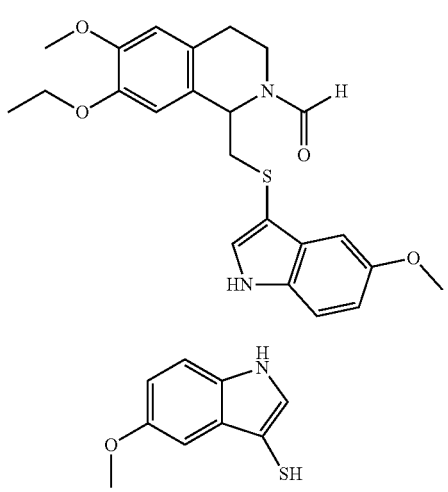

The compound C31 was obtained according to the synthesis of C30, while C30-3 in example C30 was replaced with intermediate C31-1. $^1$H NMR (500 MHz, Chloroform-d) δ 9.99 (dd, J=2.6, 2.0 Hz, 1H), 8.21 (s, 1H), 7.57 (dd, J=2.5, 0.5 Hz, 1H), 7.47 (ddd, J=8.4, 2.2, 0.5 Hz, 1H), 7.35-7.30 (m, 1H), 6.81 (dd, J=8.4, 2.7 Hz, 1H), 6.67 (d, J=1.1 Hz, 1H), 6.61 (t, J=1.0 Hz, 1H), 5.22 (td, J=4.1, 1.0 Hz, 1H), 4.20-4.03 (m, 2H), 3.85 (d, J=17.0 Hz, 5H), 3.75 (dd, J=13.5, 4.1 Hz, 1H), 3.66 (ddd, J=11.7, 6.1, 4.6 Hz, 1H), 3.56 (dd, J=13.5, 4.1 Hz, 1H), 3.42 (ddd, J=11.7, 6.2, 4.4 Hz, 1H), 2.94-2.81 (m, 2H), 1.43 (t, J=6.9 Hz, 3H). ESI-MS m/z 427.2 [M+H]⁺.

Example (S)-C31: Synthesis of Compound (S)-C31

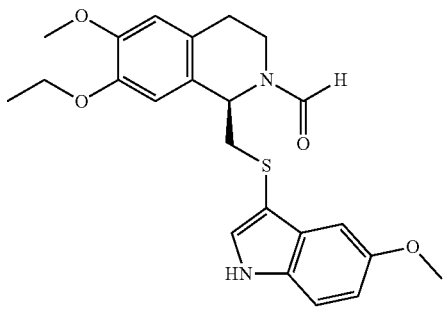 [SMILES: CCOc1cc2c(cc1OC)CCN(C=O)[C@H]2CCc1c[nH]c2ccc(OC)cc12]

The compound (S)-C31 was obtained according to the synthesis of the (S)-C30, while C30-3 in example C30 was replaced with intermediate C31-1. ESI-MS m/z 427.2 [M+H]⁺.

Example (R)-C31: Synthesis of Compound (R)-C31

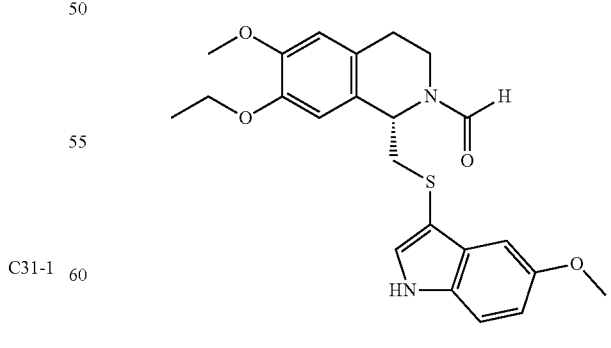

The compound (R)-C31 was obtained according to the synthesis of the (R)-C30, while C30-3 in example C30 was replaced with intermediate C31-1. ESI-MS m/z 427.2 [M+H]⁺.

Example C32: Synthesis of Compound C32

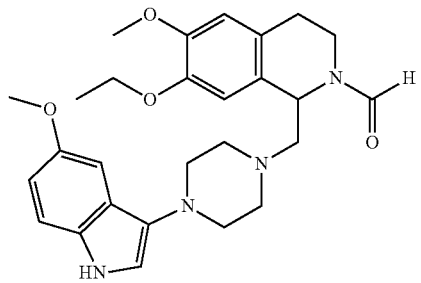

C32-1

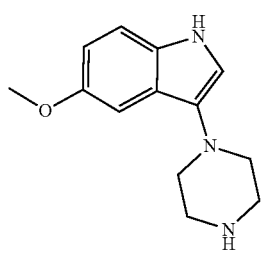

The compound C32 was obtained according to the synthesis of C30, while C30-3 in example C30 was replaced with intermediate C32-1. $^1$H NMR (500 MHz, Chloroform-d) δ 9.43 (t, J=2.4 Hz, 1H), 8.26 (s, 1H), 7.45-7.39 (m, 1H), 7.22 (ddd, J=14.8, 2.6, 0.6 Hz, 2H), 6.80 (dd, J=8.4, 2.7 Hz, 1H), 6.64 (t, J=1.1 Hz, 1H), 6.53 (d, J=1.0 Hz, 1H), 4.64 (td, J=4.7, 1.0 Hz, 1H), 4.10 (q, J=6.9 Hz, 2H), 3.84 (d, J=17.0 Hz, 5H), 3.66 (ddd, J=11.7, 6.4, 4.3 Hz, 1H), 3.60-3.47 (m, 3H), 3.48-3.40 (m, 2H), 2.95 (dddd, J=14.6, 6.4, 4.2, 1.0 Hz, 1H), 2.87 (dddd, J=14.6, 6.4, 4.2, 1.0 Hz, 1H), 2.82 (d, J=4.8 Hz, 2H), 2.75 (t, J=5.3 Hz, 4H), 1.42 (t, J=7.0 Hz, 3H). ESI-MS m/z 479.3[M+H]$^+$.

Example (S)-C32: Synthesis of Compound (S)-C32

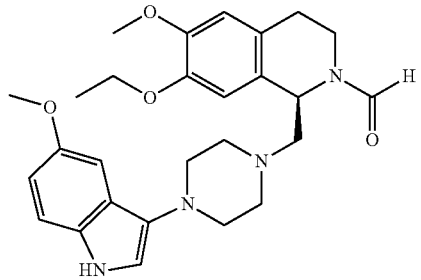 [SMILES: CCOc1cc2c(cc1OC)CCN(C=O)[C@H]2CN1CCN(c2c[nH]c3ccc(OC)cc23)CC1]

The compound (S)-C32 was obtained according to the synthesis of the (S)-C30, while C30-3 in example C30 was replaced with intermediate C32-1. ESI-MS m/z 479.3 [M+H]$^+$.

Example (R)-C32: Synthesis of Compound (R)-C32

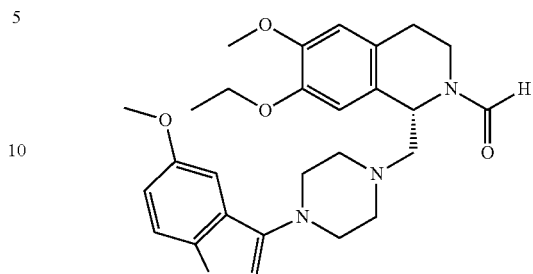

The compound (R)-C32 was obtained according to the synthesis of the (R)-C30, while C30-3 in example C30 was replaced with intermediate C32-1. ESI-MS m/z 479.3 [M+H]$^+$.

Example C33: Synthesis of Compound C33

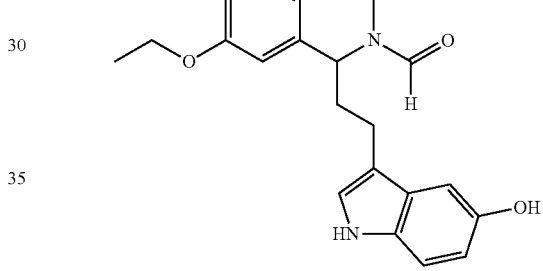

The compound C33 was obtained according to the synthesis of the compound A4, while 1-2 in example A1 was replaced with intermediate 5-hydroxy-indole-3-propionic acid.

Example (S)-C33: Synthesis of Compound (S)-C33

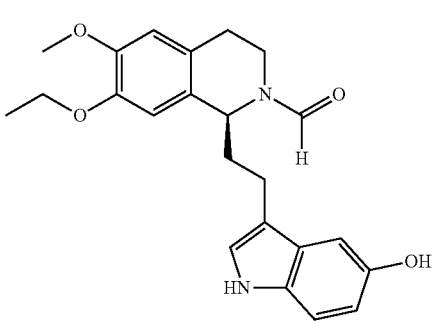

The compound (S)-C33 was obtained according to the synthesis of the compound (S)-A4, while 1-2 in example A1 was replaced with intermediate 5-hydroxy-indole-3-propionic acid.

Example (R)-C33: Synthesis of Compound (R)-C33

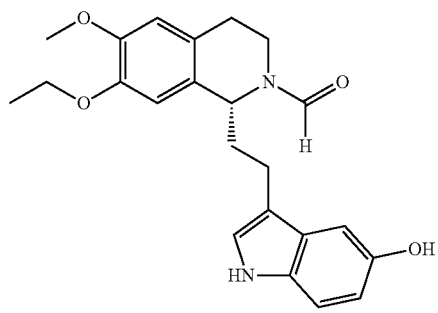 [SMILES: CCOc1cc2c(cc1OC)CCN(C=O)[C@@H]2CCc1c[nH]c2ccc(O)cc12]

The compound (R)-C33 was obtained according to the synthesis of the compound (R)-A4, while 1-2 in example A1 was replaced with intermediate 5-hydroxy-indole-3-propionic acid.

Example C34: Synthesis of Compound C34

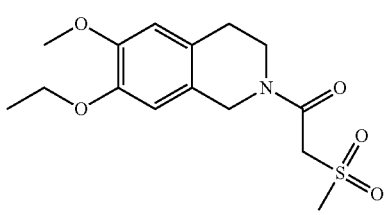 [SMILES: CCOc1cc2c(cc1OC)CCN(C(=O)CS(C)(=O)=O)C2]

The compound C34 was obtained according to the synthesis of the compound B9, while 1-5 in example A1 was replaced with C33-1. $^1$H NMR (500 MHz, Chloroform-d) δ 6.94 (t, J=1.0 Hz, 1H), 6.74 (t, J=1.0 Hz, 1H), 4.54 (d, J=0.9 Hz, 2H), 4.18 (s, 1H), 4.11 (q, J=7.0 Hz, 2H), 3.84 (s, 2H), 3.82-3.68 (m, 2H), 2.95 (s, 2H), 2.89 (td, J=5.3, 1.0 Hz, 2H), 1.42 (t, J=6.9 Hz, 3H). ESI-MS m/z 328.1 [M+H]$^+$.

Example C35: Synthesis of Compound C35

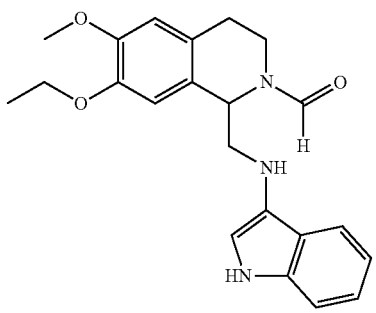 [SMILES: CCOc1cc2c(cc1OC)CCN(C=O)C2CNc1c[nH]c2ccccc12]

The compound C35 was obtained according to the synthesis of C30, while C30-3 in example C30 was replaced with 3-aminoindole.

Example (S)-C35: Synthesis of Compound (S)-C35

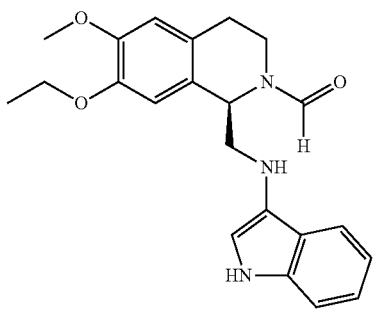 [SMILES: CCOc1cc2c(cc1OC)CCN(C=O)[C@H]2CNc1c[nH]c2ccccc12]

The compound (S)-C35 was obtained according to the synthesis of the (S)-C30, while C30-3 in example C30 was replaced with 3-aminoindole.

Example (R)-C35: Synthesis of Compound (R)-C35

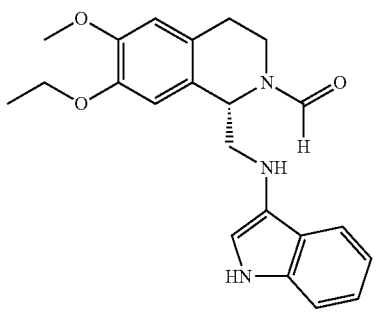

The compound (R)-C35 was obtained according to the synthesis of the (R)-C30, while C30-3 in example C30 was replaced with 3-aminoindole.

Example C36: Synthesis of Compound C36

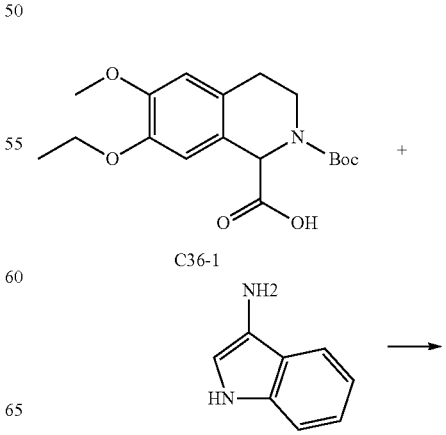

-continued

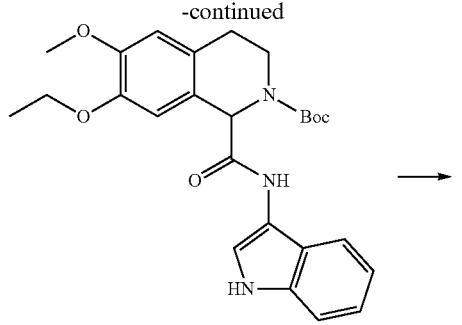

C36-2

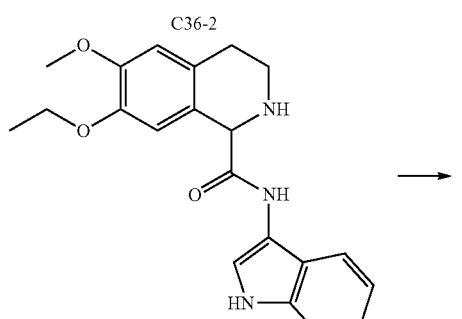

C36-3

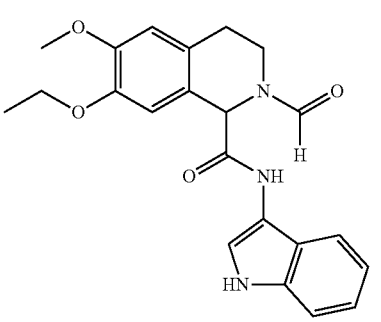

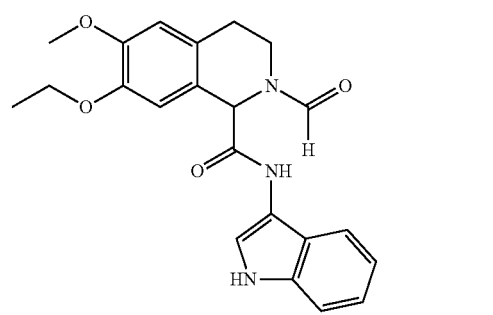

Intermediate C36-1, 3-indole propionic acid were reacted with EDCI, HOBT, TEA in dichloromethane at room temperature overnight to obtain C36-2. C36-2 was reacted with HCl in dioxane for two hours to obtain C36-3. C36-3 was refluxed in ethyl formate overnight and purified through column chromatography with petroleum ether and ethyl acetate to obtain C36.

Example (S)-C36: Synthesis of Compound (S)-C36

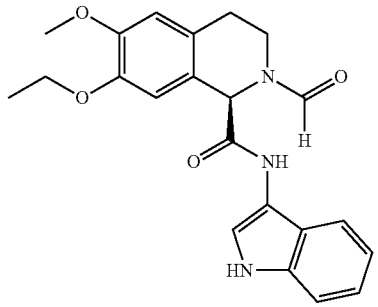 [SMILES: CCOc1cc2c(cc1OC)CCN(C=O)[C@H]2C(=O)Nc1c[nH]c2ccccc12]

(S)-C36 was obtained according to the synthesis of C36, while intermediate C36-1 was replaced with (S)-C36-1.

Example (R)-C36: Synthesis of Compound (R)-C36

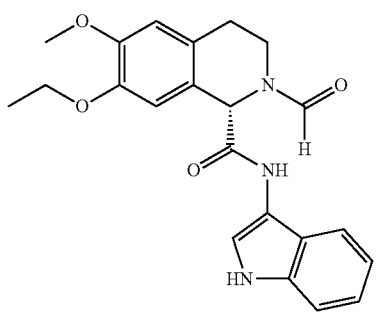 [SMILES: CCOc1cc2c(cc1OC)CCN(C=O)[C@@H]2C(=O)Nc1c[nH]c2ccccc12]

(R)-C36 was obtained according to the synthesis of C36, while intermediate C36-1 was replaced with (R)-C36-1.

Example C37: Synthesis of Compound C37

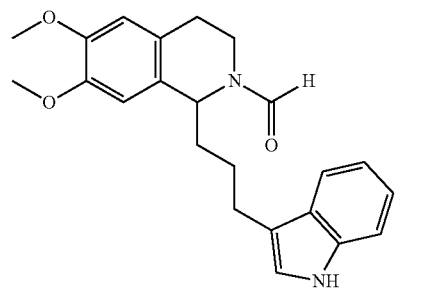

C37-1

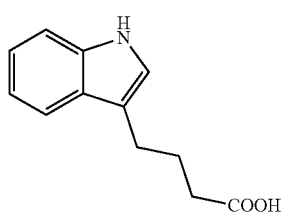

the compound C37 was obtained according to the synthesis of compound A1, while 2-1 in example A1 was replaced with compound C37-1. $^1$H NMR (400 MHz, DMSO): δ 10.86, 10.74 (2×s, 1H), 8.18, 8.15 (2×s, 1H), 7.42-7.22 (m, 2H), 7.08-6.90 (m, 2H), 6.81-6.73 (m, 1H), 6.65-6.52 (m, 2H), 5.55-5.46, 5.06-4.96 (2×m, 1H), 3.71-3.63, 3.41-3.25 (2×m, 1H), 3.65 (s, 3H), 3.58, 3.54 (2×s, 3H), 3.21-3.10, 3.06-2.94 (2×m, 1H), 2.80-2.57 (m, 4H), 2.08-1.68 (m, 4H). ESI-MS m/z 379.2 [M+H]$^+$ HR-MS: (ESI, m/z) calcd for $C_{23}H_{26}N_2O_3$+[M+H]$^+$379.2016, found: 379.2027.

Example (S)-C37: Synthesis of Compound (S)-C37

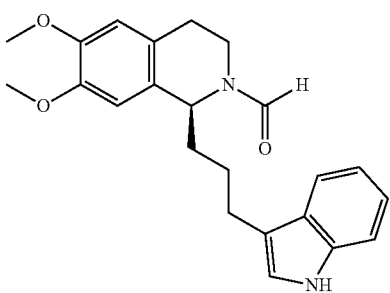 [SMILES: COc1cc2c(cc1OC)[C@H](CCCc1c[nH]c3ccccc13)N(C=O)CC2]

The compound (S)-C37 was obtained according to the synthesis of the compound (S)-A1, while 2-1 in example A1 was replaced with compound C37-1. $^1$H NMR (400 MHz, DMSO): δ 10.87, 10.74 (2×s, 1H), 8.18, 8.15 (2×s, 1H), 7.43-7.23 (m, 2H), 7.08-6.90 (m, 2H), 6.82-6.72 (m, 1H), 6.64-6.52 (m, 2H), 5.55-5.46, 5.06-4.95 (2×m, 1H), 3.73-3.63, 3.41-3.24 (2×m, 1H), 3.65 (s, 3H), 3.58, 3.54 (2×s, 3H), 3.22-3.10, 3.09-2.94 (2×m, 1H), 2.81-2.57 (m, 4H), 2.08-1.71 (m, 4H). ESI-MS m/z 379.2 [M+H]$^+$ HR-MS: (ESI, m/z) calcd for $C_{23}H_{26}N_2O_3$+[M+H]$^+$379.2016, found: 379.2027.

Example (R)-C37: Synthesis of Compound (R)-C37

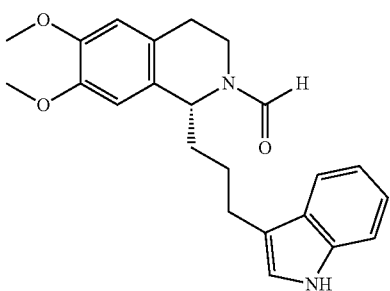 [SMILES: COc1cc2c(cc1OC)[C@@H](CCCc1c[nH]c3ccccc13)N(C=O)CC2]

The compound (R)-C37 was obtained according to the synthesis of the compound (R)-A1, while 2-1 in example A1 was replaced with compound C37-1. $^1$H NMR (400 MHz, DMSO): δ 10.86, 10.74 (2×s, 1H), 8.18, 8.15 (2×s, 1H), 7.44-7.24 (m, 2H), 7.08-6.90 (m, 2H), 6.82-6.73 (m, 1H), 6.65-6.52 (m, 2H), 5.55-5.46, 5.06-4.96 (2×m, 1H), 3.71-3.63, 3.41-3.25 (2×m, 1H), 3.65 (s, 3H), 3.58, 3.54 (2×s, 3H), 3.21-3.10, 3.06-2.94 (2×m, 1H), 2.80-2.57 (m, 4H), 2.08-1.68 (m, 4H). ESI-MS m/z 379.2 [M+H]$^+$ $C_{23}H_{26}N_2O_3^+$ [M+H]$^+$: 379.1943, found: 379.2008.

Example C38: Synthesis of Compound C38

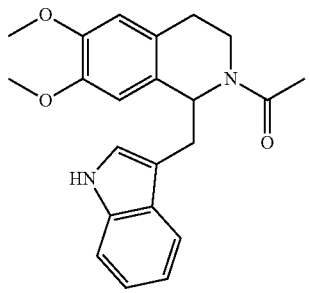 [SMILES: COc1cc2c(cc1OC)C(Cc1c[nH]c3ccccc13)N(C(C)=O)CC2]

The compound C38 was obtained according to the synthesis of the compound B14, while 1-2 in example A1 was replaced with compound 32-1, and B14-1 in example B14 was replaced with acetylchloride. $^1$H NMR (500 MHz, CDCl$_3$) δ 8.89, 8.59 (2×s, 1H), 7.63, 7.58 (2×d, J=31.9, 7.8 Hz, 1H), 7.34 (2×d, J=37.5, 7.9 Hz, 1H), 7.22-7.03 (m, 2H), 6.87, 6.83 (2×s, 1H), 6.64, 6.58 (2×s, 1H), 6.20 (s, 1H), 5.85-5.23 (m, 1H), 4.92, 4.81 (2×dd, J=5.52, 6.32, 5.92, 6.32 Hz, 1H), 3.86, 3.83 (2×s, 3H), 3.80 (s, 1H), 3.68-3.48 (m, 1H), 3.46 (s, 2H), 3.36-3.26 (m, 1H), 3.25-3.16 (m, 2H), 2.96-2.77 (m, 1H), 2.75-2.64 (m, 1H), 2.15, 1.54 (2×s, 3H). ESI-MS m/z 365.1 [M+H]$^+$. HR-MS: (ESI, m/z) calcd for $C_{22}H_{23}N_2O_3^+$[M+H]$^+$ 365.1787, found 365.1863.

Example (S)-C38: Synthesis of Compound (S)-C38

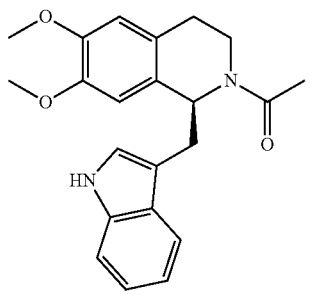 [SMILES: COc1cc2c(cc1OC)[C@H](Cc1c[nH]c3ccccc13)N(C(C)=O)CC2]

The compound (S)-C38 was obtained according to the synthesis of the compound (S)-B14, while 1-2 in example A1 was replaced with compound 32-1, and B14-1 in example B14 was replaced with acetylchloride. $^1$H NMR (500 MHz, CDCl$_3$) δ 8.88, 8.57 (2×s, 1H), 7.64, 7.58 (2×d, J=31.9, 7.8 Hz, 1H), 7.34 (2×d, J=37.5, 7.9 Hz, 1H), 7.22-7.03 (m, 2H), 6.87, 6.83 (2×s, 1H), 6.64, 6.57 (2×s, 1H), 6.20 (s, 1H), 5.85-5.23 (m, 1H), 4.92, 4.81 (2×dd, J=5.52, 6.32, 5.92, 6.32 Hz, 1H), 3.86, 3.83 (2×s, 3H), 3.80 (s, 1H), 3.68-3.48 (m, 1H), 3.46 (s, 2H), 3.36-3.26 (m, 1H), 3.25-3.16 (m, 2H), 2.96-2.77 (m, 1H), 2.74-2.64 (m, 1H), 2.14, 1.52 (2×s, 3H). ESI-MS m/z 365.1 [M+H]$^+$. HR-MS: (ESI, m/z) calcd for $C_{22}H_{23}N_2O_3^+$ [M+H]$^+$365.1787, found 365.1867.

Example C39: Synthesis of Compound C39

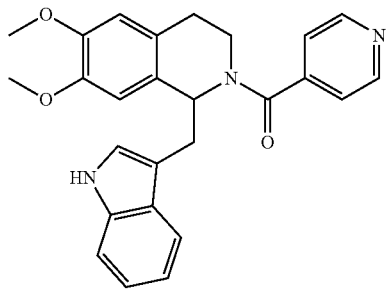 [SMILES: COc1cc2c(cc1OC)C(Cc1c[nH]c3ccccc13)N(C(=O)c1ccncc1)CC2]

The compound C39 was obtained according to the synthesis of the compound B1, while 1-2 in example A1 was replaced with compound 32-1. $^1$H NMR (400 MHz, CDCl$_3$) δ 8.63, 8.50 (2×s, 1H), 8.35, 8.18 (2×s, 1H), 7.70, 7.63 (2×s, 1H), 7.39 (dd, J=8.1, 3.9 Hz, 1H), 7.22 (td, J=7.2, 3.5 Hz, 1H), 7.09-6.96 (m, 1H), 6.89 (d, J=1.9 Hz, 1H), 6.71, 6.60 (2×s, 1H), 6.42 (dd, J=16.8, 11.8 Hz, 1H), 6.00 (t, J=6.8 Hz, 1H), 4.93, 4.82 (2×dd, J=5.83, 6.97, 5.83, 5.51 Hz, 1H), 4.14 (q, J=7.1 Hz, 1H), 3.90 (d, J=13.8 Hz, 3H), 3.77 (s, 1H), 3.64 (d, J=9.5 Hz, 1H), 3.56-3.35 (m, 2H), 3.27-3.06 (m, 2H), 2.92-2.73 (m, 1H), 2.07 (s, 1H). ESI-MS m/z 428.1 [M+H]$^+$. HR-MS: (ESI, m/z) calcd for C$_{20}$H$_{25}$N$_3$O$_3{}^+$ [M+H]$^+$ 428.1896, found 428.1971.

Example C40: Synthesis of Compound C40

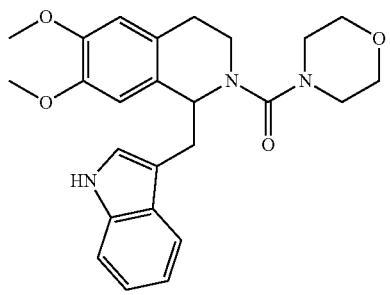 [SMILES: COc1cc2c(cc1OC)C(Cc1c[nH]c3ccccc13)N(C(=O)N1CCOCC1)CC2]

The compound C40 was obtained according to the synthesis of the compound B14, while 1-2 in example A1 was replaced with compound 32-1. $^1$H NMR (500 MHz, CDCl$_3$) δ 8.26 (s, 1H), 7.67 (d, J=7.6 Hz, 1H), 7.36 (d, J=7.9 Hz, 1H), 7.17 (dt, J=21.1, 7.1 Hz, 2H), 6.95 (s, 1H), 6.61 (s, 1H), 6.41 (s, 1H), 5.20-5.11 (m, 1H), 3.85 (s, 3H), 3.67 (s, 3H), 3.52-3.38 (m, 3H), 3.30 (dd, J=14.5, 8.6 Hz, 1H), 3.19 (ddd, J=20.5, 10.7, 5.0 Hz, 3H), 3.06-2.97 (m, 2H), 2.96-2.88 (m, 1H), 2.71 (ddd, J=27.6, 13.4, 3.5 Hz, 3H). ESI-MS m/z 436.1 [M+H]$^+$. HR-MS: (ESI, m/z) calcd for C$_{25}$H$_{29}$N$_3$O$_4{}^+$ [M+H]$^+$ 436.2158, found 436.2241.

Example (S)-C40: Synthesis of Compound (S)-C40

The compound (S)-C40 was obtained according to the synthesis of the compound (S)-B14, while 1-2 in example A1 was replaced with compound 32-1. $^1$H NMR (500 MHz, CDCl$_3$) δ 8.26 (s, 1H), 7.67 (d, J=7.6 Hz, 1H), 7.36 (d, J=7.9 Hz, 1H), 7.17 (dt, J=21.1, 7.1 Hz, 2H), 6.95 (s, 1H), 6.61 (s, 1H), 6.41 (s, 1H), 5.20-5.11 (m, 1H), 3.85 (s, 3H), 3.67 (s, 3H), 3.52-3.38 (m, 3H), 3.30 (dd, J=14.5, 8.6 Hz, 1H), 3.19 (ddd, J=20.5, 10.7, 5.0 Hz, 3H), 3.06-2.97 (m, 2H), 2.96-2.88 (m, 1H), 2.71 (ddd, J=27.6, 13.4, 3.5 Hz, 3H). ESI-MS m/z 436.1 [M+H]$^+$. HR-MS: (ESI, m/z) calcd for C$_{25}$H$_{29}$N$_3$O$_4{}^+$ [M+H]$^+$ 436.2158, found 436.2236.

Example C41: Synthesis of Compound C41

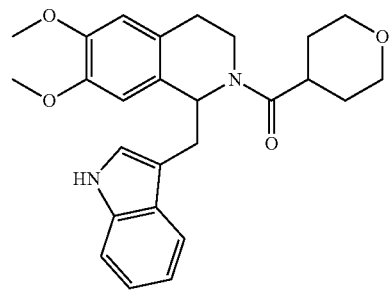 [SMILES: COc1cc2c(cc1OC)C(Cc1c[nH]c3ccccc13)N(C(=O)C1CCOCC1)CC2]

The compound C41 was obtained according to the synthesis of the compound B1, while 1-2 in example A1 was replaced with compound 32-1, and 11-1 in example B1 was replaced with compound 13-1. $^1$H NMR (500 MHz, CDCl$_3$) δ 8.35, 8.13 (2×s, 1H), 7.81-7.58 (m, 1H), 7.43-7.29 (m, 1H), 7.33 (d, J=8.1 Hz, 6H), 7.25 (d, J=3.1 Hz, 1H), 7.15, 7.07 (dt, J=15.1, 15.1 Hz, 1H), 6.94, 6.87 (2×s, 1H), 6.77, 6.65 (2×s, 1H), 6.57-5.83 (m, 1H), 5.07, 4.83 (2×dd. J=10.5, 3.0, 12.9, 5.1, Hz, 1H), 4.04-3.96 (m, 1H), 3.94 (s, 2H), 3.88 (s, 2H), 3.84 (s, 1H), 3.81-3.67 (m, 1H), 3.50-3.43 (m, 2H), 3.41-3.12 (m, 3H), 3.02-2.65 (m, 3H). ESI-MS m/z 436.1 [M+H]$^+$. HR-MS: (ESI, m/z) calcd for C$_{25}$H$_{30}$N$_3$O$_4{}^+$ [M+H]$^+$ 435.2206, found 435.2290.

Example (S)-C41: Synthesis of Compound (S)-C41

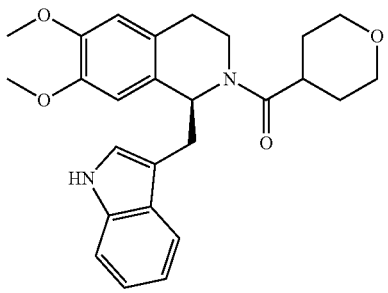 [SMILES: COc1cc2c(cc1OC)[C@H](Cc1c[nH]c3ccccc13)N(C(=O)C1CCOCC1)CC2]

The compound (S)-C41 was obtained according to the synthesis of the compound (S)-B1, while 1-2 in example A1 was replaced with compound 32-1, and 11-1 in example B1 was replaced with compound 13-1. $^1$H NMR (500 MHz, CDCl$_3$) δ 9.12, 8.63 (2×d, J=32.9, 30.9 Hz, 1H), 7.76, 7.57 (2×d, J=5.12, 8.47 Hz, 1H), 7.39, 7.30 (2×d, J=7.13, 9.13 Hz, 1H), 7.25-7.20 (m, 1H), 7.13, 7.04 (2×t, J=13.8, 14.4 Hz, 1H), 6.92, 6.86 (2×s, 1H), 6.80, 6.66 (2×s, 1H), 6.58, 6.22, 5.85 (2×s, t, J=6.5 Hz, 1H), 5.09, 4.85 (2×d, J=10.0, 7.7 Hz, 1H), 4.02-3.78 (m, 6H), 3.72-3.52 (m, 1H), 3.46-3.27 (m, 3H), 2.96-2.70 (m, 3H), 2.09-1.87 (m, 2H), 1.76-1.40 (m, 3H), 1.36-1.12 (m, 2H). ESI-MS m/z 435.1 [M+H]$^+$. HR-MS: (ESI, m/z) calcd for C$_{25}$H$_{30}$N$_3$O$_4^+$ [M+H]$^+$ 435.2206, found 435.2279.

Example C42: Synthesis of Compound C42

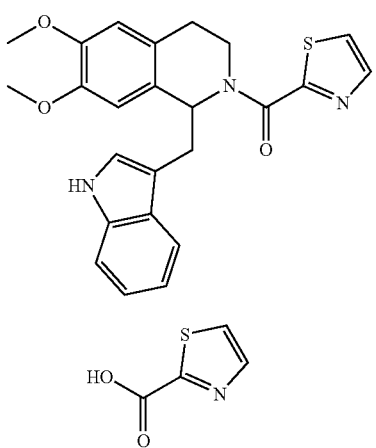

C42-1

The compound C42 was obtained according to the synthesis of the compound B1, while 1-2 in example A1 was replaced with compound 32-1, and 11-1 in example B1 was replaced with compound C42-1. $^1$H NMR (400 MHz, CDCl$_3$) δ 8.09, 7.90 (2×d, J=12.4.2.5 Hz, 1H). 7.90 (2×d, J=7.7, 3.1 Hz, 1H), 7.57-7.52 (m, 1H), 7.34-7.25 (m 1H), 7.23-7.15 (m, 1H), 7.12-7.08 (m, 1H), 7.05-6.95 (m, 1H), 6.84-6.78 (m, 1H), 6.62 (d, J=16.6 Hz, 1H), 6.34, 6.08 (2×s, 1H), 5.93, 4.77 (2×dd, J=8.3, 5.4, 13.4, 3.7 Hz, 1H), 3.85 (d, J=7.1 Hz, 3H), 3.83-3.76 (m, 1H), 3.56 (s, 1H), 3.54-3.44 (m, 1H), 3.44-3.37 (m, 2H), 3.28 (dd, J=14.2, 6.7 Hz, 1H), 3.10-3.00 (m, 1H), 2.89-2.73 (m, 1H), 1.66 (s, 2H). ESI-MS m/z 434.9 [M+H]$^+$. HR-MS: (ESI, m/z) calcd for C$_{24}$H$_{24}$N$_3$O$_3$S$^+$ [M+H]$^+$ 434.1460. found 434.1546.

Example (S)-C42: Synthesis of Compound (S)-C42

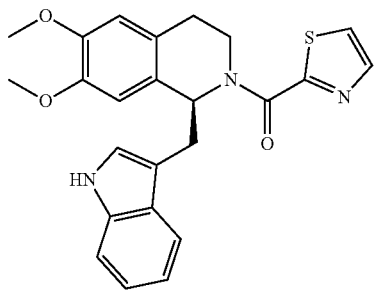 [SMILES: COc1cc2c(cc1OC)[C@H](Cc1c[nH]c3ccccc13)N(C(=O)c1nccs1)CC2]

The compound (S)-C42 was obtained according to the synthesis of the compound B1, while 1-2 in example A1 was replaced with compound 32-1, and 11-1 in example B1 was replaced with compound C42-1. $^1$H NMR (500 MHz, CDCl$_3$) δ 8.07 (d, J=20.6 Hz, 1H), 7.73, 7.67 (3×d, J=3.2, 7.9, 6.1 Hz, 1H), 7.54 (t, J=6.1 Hz, 2H), 7.38-7.21 (m, 1H), 7.17-7.07 (m, 1H), 7.03-6.90 (m, 1H), 6.81 (dd, J=11.8, 4.5 Hz, 1H), 6.65, 6.60 (2×s, 1H), 6.34, 6.09 (2×s, 1H), 5.30-4.73 (m, 1H), 3.95-3.77 (m, 3H), 3.56 (s, 2H), 3.52-3.41 (m, 1H), 3.42-3.37 (m, 2H), 3.34-3.25 (m, 1H), 3.12-2.99 (m, 1H), 2.89-2.73 (m, 1H), 2.62 (s, 1H). ESI-MS m/z 434.1 [M+H]$^+$. HR-MS: (ESI, n/z) calcd for C$_{24}$H$_{24}$N$_3$O$_3$S$^+$ [M+H]$^+$ 434.1460, found 434.1542.

Example C43: Synthesis of Compound C43

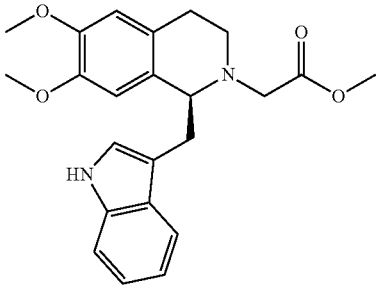

The compound C43 was obtained according to the synthesis of the compound B2, while 1-2 in example A1 was replaced with compound 32-1, and 12-1 in example B2 was replaced with compound 15-1. $^1$H NMR (400 MHz, CDCl$_3$) δ 8.06 (s, 1H), 7.59 (d, J=7.7 Hz, 1H), 7.35 (d, J=8.0 Hz, 1H), 7.14 (ddd, J=14.9, 14.0, 7.0 Hz, 2H), 6.94 (d, J=2.0 Hz, 1H), 6.56 (s, 1H), 5.96 (s, 1H), 4.14-4.05 (m, 1H), 3.83 (s, 3H), 3.67 (s, 3H), 3.54 (q, J=16.7 Hz, 2H), 3.38 (s, 3H), 3.05 (dd, J=14.4, 7.9 Hz, 2H), 2.87 (ddd, J=16.4, 10.4, 6.0 Hz, 1H), 2.61 (dd, J=12.3, 3.8 Hz, 1H), 1.40 (t, J=7.3 Hz, 1H). ESI-MS m/z 395.2 [M+H]$^+$. HR-MS: (ESI, m/z) calcd for C$_{23}$H$_{27}$N$_2$O$_3^+$ [M+H]$^+$ 395.1893, found 395.1971.

Example C44: Synthesis of Compound C44

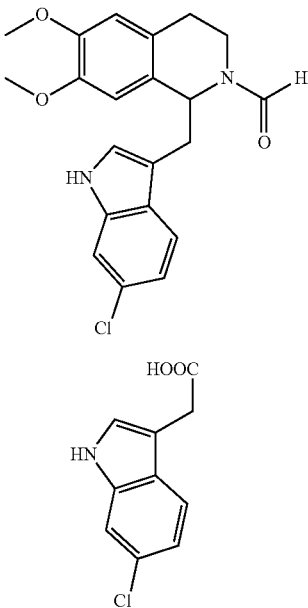

C44-1

The compound C44 was obtained according to the synthesis of the compound A1, while 1-2 in example A1 was replaced with compound C44-1. ¹H NMR (400 MHz, CDCl₃) δ 9.05, 8.80 (2×s, 1H), 8.13, 7.52 (2×s, 1H), 7.48, 7.43 (2×d, J=8.7, 8.3 Hz, 1H), 7.33, 7.29 (2×d, J=1.3, 1.4 Hz, 1H), 7.10, 7.01 (2×dd, J=8.4, 1.7, 8.5, 1.7 Hz, 1H), 6.89, 6.84 (2×d, J=1.6, 1.7 Hz, 1H), 6.67, 6.64 (2×s, 1H), 6.30, 6.61 (s, t, J=6.5 Hz 1H), 4.67, 4.48 (2×dd, J=9.9, 3.8, 12.1, 5.5 Hz, 1H), 3.87 (d, J=2.2 Hz, 3H), 3.84 (s, 1H), 3.57, 3.46 (2×s, 3H), 3.39-3.00 (m, 2H), 2.96-2.60 (m, 2H), 1.35 (t, J=7.3 Hz, 1H). ESI-MS m/z 385.1 [M+H]⁺. HR-MS: (ESI, m/z) calcd for $C_{21}H_{22}ClN_2O_3^+$ [M+H]⁺385.1241, found 385.2241.

Example (S)-C44: Synthesis of Compound (S)-C44

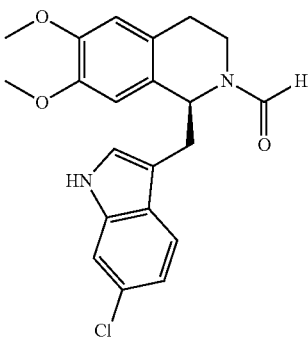 [SMILES: COc1cc2c(cc1OC)[C@H](Cc1c[nH]c3cc(Cl)ccc13)N(C=O)CC2]

The compound (S)-C44 was obtained according to the synthesis of the compound (S)-A1, while 1-2 in example A1 was replaced with compound C44-1. ¹H NMR (500 MHz, CDCl₃) δ 8.48, 8.27 (2×s, 1H), 8.15, 7.57 (2×s, 1H), 7.47 (dd, J=18.5, 8.4 Hz, 1H), 7.34 (dd, J=19.3, 1.6 Hz, 1H), 7.09 (2×dd, J=1.8, 1.8, 1.9, 1.7 Hz, 1H), 6.92, 6.87 (2×s, 1H), 6.65 (d, J=9.2 Hz, 1H), 6.56, 6.32 (2×s, 1H), 4.68-4.46 (m, 1H), 3.94-3.83 (m, 4H), 3.59 (s, 1H), 3.58-f3.34 (m, 1H), 3.26 (dd, J=11.3, 5.2 Hz, 1H), 3.23-3.10 (m, 1H), 2.96-2.77 (m, 1H), 2.79-2.61 (m, 1H), 2.06 (d, J=16.5 Hz, 1H), 1.80 (s, 1H). ESI-MS m/385.1 [M+H]⁺. HR-MS: (ESI, m/z) calcd for $C_{21}H_{22}ClN_2O_3^+$[M+H]⁺385.1241, found 385.1323.

Example C45: Synthesis of Compound C45

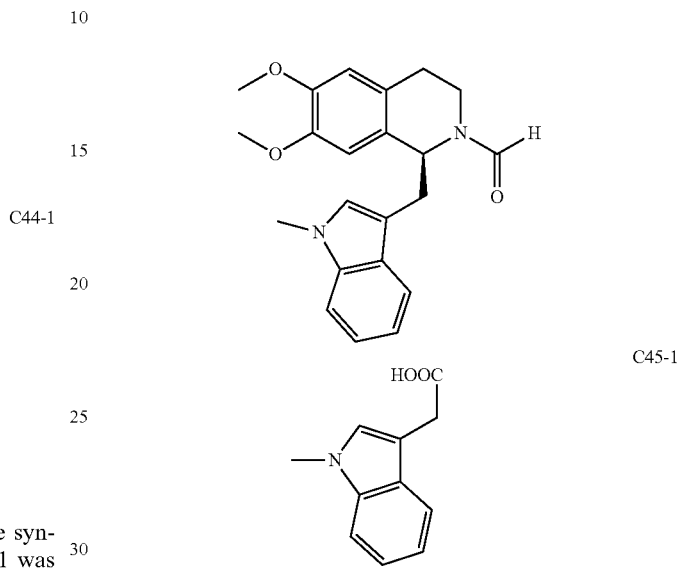

C45-1

The compound C45 was obtained according to the synthesis of the compound A1, while 1-2 in example A1 was replaced with compound C45-1. ¹H NMR (400 MHz, CDCl₃) δ 8.16 (s, 1H), 7.64-7.53 (m, 2H), 7.33 (d, J=8.2 Hz, 1H), 7.18 (dt, J=14.8, 7.0 Hz, 1H), 7.08, 6.80 (m, 1H), 6.65 (2×s, 1H), 6.55, 6.26, 5.64 (2×s, t, J=6.4 Hz, 1H), 4.72-4.47 (m, 1H), 3.88 (s, 1H), 3.85 (d, J=2.1 Hz, 3H), 3.75 (s, 1H), 3.71 (s, 1H), 3.60-3.53 (m, 1H), 3.52 (s, 1H), 3.38-3.07 (m, 3H), 2.96-2.79 (m, 1H), 2.79-2.63 (m, 1H), 1.72 (s, 2H). ESI-MS m/z 365.1 [M+H]⁺. HR-MS: (ESI, m/z) calcd for $C_{22}H_{25}N_2O_3^+$ [M+H]⁺365.1787, found 365.1868.

Example C46: Synthesis of Compound C46

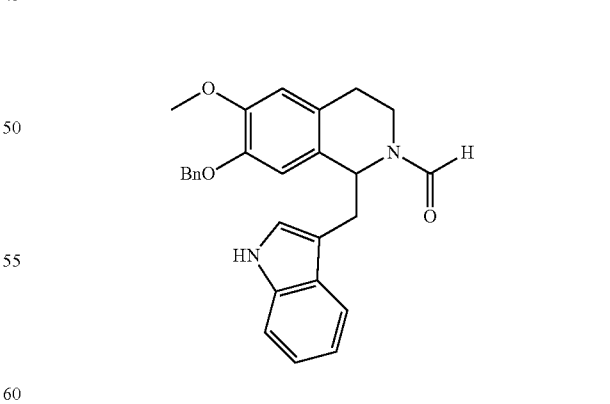

The compound C46 was obtained according to the synthesis of the compound A2, while 1-2 in example A1 was replaced with compound 32-1, and 4-2 in example A2 was replaced with compound benzyl bromide. ¹H NMR (400 MHz, CDCl₃) δ 8.36, 8.17 (2×s, 1H), 7.55 (dd, J=17.0, 8.6 Hz, 2H), 7.47 (d, J=7.3 Hz, 1H), 7.38 (dd, J=12.8, 3.9 Hz, 1H), 7.31 (d, J=7.4 Hz, 1H), 7.26 (t, J=7.2 Hz, 2H), 7.17 (m, 1H), 6.87, 6.73 (2×s, 1H), 6.69 (d, J=4.5 Hz, 1H), 6.58, 6.32 (2×s, 1H), 5.58 (t, 3H), 5.15 (s, 1H), 4.79 (dd, J=39.4, 12.5 Hz, 1H), 4.56 (m, 1H), 4.15 (q, J=7.1 Hz, 1H), 3.92, 3.87 (2×s, 3H), 3.61-3.29 (m, 1H), 3.27-3.02 (m, 2H), 2.98-2.79 (m, 1H), 2.79-2.61 (m, 1H), 2.07 (s, 1H). ESI-MS m/z 427.1 [M+H]$^+$. HR-MS: (ESI, m/z) calcd for $C_{27}H_{27}N_2O_3^+$ [M+H]$^+$ 427.1943, found 427.2025.

Example (S)-C47: Synthesis of Compound (S)-C47

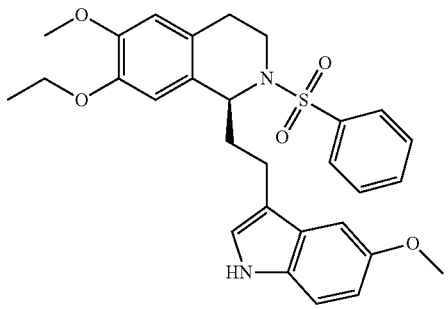 [SMILES: CCOc1cc2c(cc1OC)CCN(S(=O)(=O)c1ccccc1)[C@H]2CCc1c[nH]c2ccc(OC)cc12]

Compound (S)-C47 was obtained according to the synthesis of (S)-C8 and B13, while the methanesulfonyl chloride in example B13 was replaced with benzenesulfonyl chloride. $^1$H NMR (500 MHz, Chloroform-d) δ 7.96 (s, 1H), 7.72 (d, J=7.8 Hz, 2H), 7.41 (t, J=7.4 Hz, 1H), 7.30 (t, J=7.7 Hz, 2H), 7.27-7.23 (m, 1H), 7.12 (d, J=2.2 Hz, 1H), 7.01 (d, J=2.4 Hz, 1H), 6.85 (dd, J=8.8, 2.4 Hz, 1H), 6.29 (d, J=2.3 Hz, 2H), 5.01 (dd, J=9.4, 4.2 Hz, 1H), 3.95 (dt, J=14.3, 4.5 Hz, 1H), 3.85 (s, 3H), 3.85-3.80 (m, 2H), 3.73 (s, 3H), 3.56-3.46 (m, 1H), 2.98-2.86 (m, 2H), 2.40 (dt, J=6.2, 3.8 Hz, 2H), 2.23 (dtd, J=14.6, 8.6, 5.9 Hz, 1H), 2.13 (qd, J=9.0, 8.4, 3.8 Hz, 1H), 1.36 (t, J=7.0 Hz, 3H).

Example (S)-C48: Synthesis of Compound (S)-C48

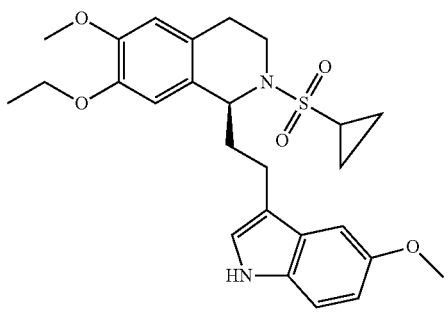 [SMILES: CCOc1cc2c(cc1OC)CCN(S(=O)(=O)C1CC1)[C@H]2CCc1c[nH]c2ccc(OC)cc12]

Compound (S)-C48 was obtained according to the synthesis of (S)-C47, while the benzenesulfonyl chloride in example (S)-C47 was replaced with cyclopropylsulfonyl chloride. $^1$H NMR (500 MHz, Chloroform-d) δ 7.84 (s, 1H), 7.25 (s, 1H), 7.12 (d, J=2.0 Hz, 1H), 7.03 (d, J=2.4 Hz, 1H), 6.85 (dd, J=8.8, 2.4 Hz, 1H), 6.56 (s, 1H), 6.30 (s, 1H), 4.78 (dd, J=9.9, 3.8 Hz, 1H), 4.02 (dd, J=14.8, 6.8 Hz, 1H), 3.85 (s, 3H), 3.85 (q, J=7.0 Hz, 2H), 3.82 (s, 3H), 3.54 (ddd, J=14.8, 12.0, 5.1 Hz, 1H), 3.11-3.00 (m, 1H), 3.00-2.90 (m, 2H), 2.68 (dd, J=16.7, 5.0 Hz, 1H), 2.24 (ddt, J=14.2, 8.3, 4.3 Hz, 1H), 2.15-2.03 (m, 2H), 1.36 (t, J=7.0 Hz, 3H), 1.22-1.16 (m, 1H), 1.07 (ddt, J=10.2, 6.8, 4.9 Hz, 1H), 0.82 (qd, J=7.9, 4.8 Hz, 1H), 0.72 (dt, J=9.6, 6.0 Hz, 1H).

Example (S)-C49: Synthesis of Compound (S)-C49

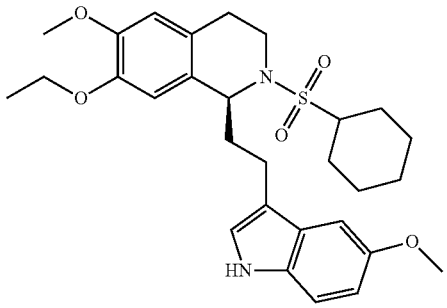 [SMILES: CCOc1cc2c(cc1OC)CCN(S(=O)(=O)C1CCCCC1)[C@H]2CCc1c[nH]c2ccc(OC)cc12]

Compound (S)-C49 was obtained according to the synthesis of (S)-C47, while the benzenesulfonyl chloride in example (S)-C47 was replaced with cyclohexylsulfonyl chloride. $^1$H NMR (500 MHz, Chloroform-d) δ 7.67 (s, 1H), 7.22 (d, J=7.5 Hz, 1H), 7.13 (s, 1H), 7.04 (s, 1H), 6.96 (s, 1H), 6.70 (d, J=7.5 Hz, 1H), 6.26 (s, 1H), 4.61 (dq, J=12.3, 7.9 Hz, 1H), 4.19 (s, 1H), 4.06 (dq, J=12.5, 8.1 Hz, 1H), 3.89 (d, J=15.0 Hz, 6H), 3.62-3.50 (m, 2H), 3.42 (dt, J=16.9, 7.1 Hz, 1H), 3.26 (dt, J=12.5, 7.0 Hz, 1H), 2.88-2.72 (m, 2H), 2.50-2.39 (m, 3H), 2.02-1.85 (m, 6H), 1.78-1.66 (m, 1H), 1.61-1.31 (m, 6H).

Example (S)-C50: Synthesis of Compound (S)-C50

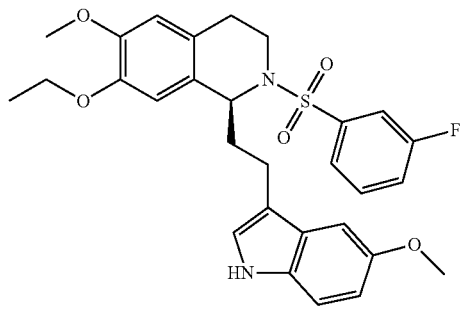 [SMILES: CCOc1cc2c(cc1OC)CCN(S(=O)(=O)c1cccc(F)c1)[C@H]2CCc1c[nH]c2ccc(OC)cc12]

Compound (S)-C50 was obtained according to the synthesis of (S)-C47, while the benzenesulfonyl chloride in example (S)-C47 was replaced with 3-fluorobenzenesulfonyl chloride. $^1$H NMR (500 MHz, Chloroform-d) δ 7.98-7.94 (m, 1H), 7.47 (td, J=7.9, 1.7 Hz, 2H), 7.30-7.23 (m, 2H), 7.13-7.08 (m, 2H), 7.01 (d, J=2.4 Hz, 1H), 6.86 (dd, J=8.8, 2.4 Hz, 1H), 6.33 (s, 1H), 6.29 (s, 1H), 4.97 (dd, J=9.3, 4.3 Hz, 1H), 3.98-3.93 (m, 1H), 3.86 (s, 3H), 3.83 (t, J=7.0 Hz, 2H), 3.75 (s, 3H), 3.58-3.51 (m, 1H), 2.98-2.86 (m, 2H), 2.49-2.43 (m, 2H), 2.24 (dtd, J=14.6, 8.2, 6.0 Hz, 1H), 2.17-2.08 (m, 1H), 1.36 (t, J=7.0 Hz, 3H).

Example (S)-C51: Synthesis of Compound (S)-C51

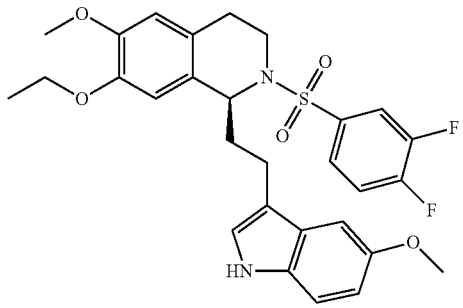 [SMILES: CCOc1cc2c(cc1OC)CCN(S(=O)(=O)c1ccc(F)c(F)c1)[C@H]2CCc1c[nH]c2ccc(OC)cc12]

Compound (S)-C51 was obtained according to the synthesis of (S)-C47, while the benzenesulfonyl chloride in example (S)-C47 was replaced with 3,4-difluorobenzenesulfonyl chloride. $^1$H NMR (500 MHz, Chloroform-d) δ 7.95 (s, 1H), 7.56 (ddd, J=9.5, 7.2, 2.2 Hz, 1H), 7.44 (ddd, J=8.7, 3.8, 1.8 Hz, 1H), 7.26 (d, J=2.5 Hz, 1H), 7.12 (d, J=2.1 Hz, 1H), 7.06 (td, J=9.3, 7.5 Hz, 1H), 7.01 (d, J=2.4 Hz, 1H), 6.86 (dd, J=8.8, 2.4 Hz, 1H), 6.34 (s, 1H), 6.29 (s, 1H), 4.95 (dd, J=9.3, 4.3 Hz, 1H), 3.97-3.90 (m, 1H), 3.86 (s, 3H), 3.83 (q, J=7.0 Hz, 2H), 3.76 (s, 3H), 3.55 (ddd, J=14.5, 11.0, 5.7 Hz, 1H), 2.98-2.87 (m, 2H), 2.51-2.39 (m, 2H), 2.24 (dtd, J=14.5, 8.4, 6.0 Hz, 1H), 2.18-2.10 (m, 1H), 1.37 (t, J=7.0 Hz, 3H).

Example (S)-C52: Synthesis of Compound (S)-C52

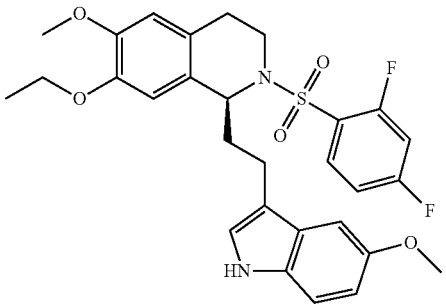 [SMILES: CCOc1cc2c(cc1OC)CCN(S(=O)(=O)c1ccc(F)cc1F)[C@H]2CCc1c[nH]c2ccc(OC)cc12]

Compound (S)-C52 was obtained according to the synthesis of (S)-C47, while the benzenesulfonyl chloride in example (S)-C47 was replaced with 2,4-difluorobenzenesulfonyl chloride. $^1$H NMR (500 MHz, Chloroform-d) δ 7.97 (s, 1H), 7.95-7.88 (m, 1H), 7.24 (d, J=8.7 Hz, 1H), 7.07 (d, J=2.2 Hz, 1H), 6.98 (d, J=2.4 Hz, 1H), 6.91-6.87 (m, 1H), 6.85 (dd, J=8.8, 2.5 Hz, 1H), 6.69 (ddd, J=10.6, 8.5, 2.4 Hz, 1H), 6.39 (s, 1H), 6.32 (s, 1H), 5.04 (dd, J=9.3, 4.4 Hz, 1H), 4.05-3.97 (m, 1H), 3.85 (d, J=2.7 Hz, 4H), 3.83 (q, J=7.0 Hz, 2H), 3.77 (s, 3H), 3.57 (ddd, J=14.3, 9.5, 7.0 Hz, 1H), 2.95-2.81 (m, 2H), 2.55-2.48 (m, 2H), 2.24 (dtd, J=14.6, 8.9, 5.7 Hz, 1H), 2.17-2.08 (m, 1H), 1.36 (t, J=7.0 Hz, 3H).

Example (S)-C53: Synthesis of Compound (S)-C53

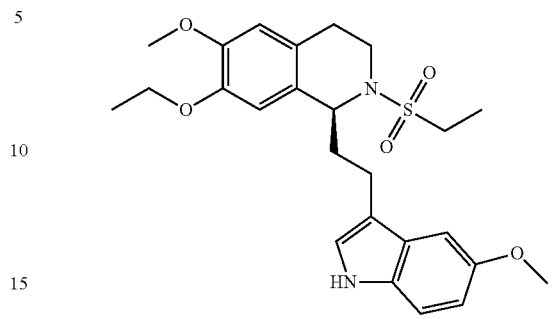

Compound (S)-C53 was obtained according to the synthesis of (S)-C47, while the benzenesulfonyl chloride in example (S)-C47 was replaced with ethylsulfonyl chloride. $^1$H NMR (500 MHz, Chloroform-d) δ 8.01 (s, 1H), 7.24 (d, J=8.7 Hz, 1H), 7.10 (d, J=2.3 Hz, 1H), 7.02 (d, J=2.4 Hz, 1H), 6.84 (dd, J=8.8, 2.4 Hz, 1H), 6.57 (s, 1H), 6.32 (s, 1H), 4.77 (dd, J=9.4, 4.2 Hz, 1H), 4.03-3.95 (m, 1H), 3.84 (s, 3H), 3.83 (q, J=7.0 Hz, 2H), 3.82 (s, 3H), 3.54 (ddd, J=14.6, 11.8, 5.0 Hz, 1H), 3.01-2.78 (m, 5H), 2.68 (ddd, J=16.8, 5.0, 1.9 Hz, 1H), 2.25 (dtd, J=14.6, 8.7, 5.8 Hz, 1H), 2.11 (dtd, J=14.3, 8.1, 4.2 Hz, 1H), 1.36 (t, J=7.0 Hz, 3H), 1.26 (t, J=7.4 Hz, 3H).

Example (S)-C54: Synthesis of Compound (S)-C54

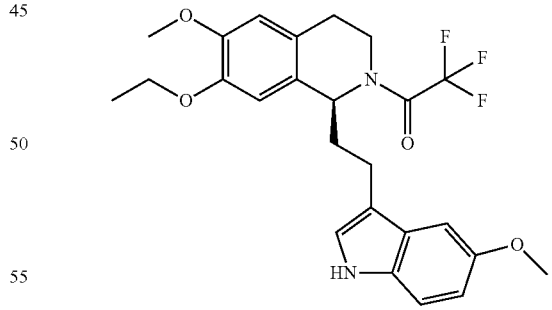

Compound (S)-C54 was obtained according to the synthesis of (S)-C47, while the benzenesulfonyl chloride in example (S)-C47 was replaced with trifluoroacetyl chloride. $^1$H NMR (500 MHz, Chloroform-d) δ 8.32 (d, J=9.0 Hz, 1H), 7.31 (d, J=2.4 Hz, 1H), 7.03-6.93 (m, 2H), 6.61 (s, 1H), 6.52 (s, 1H), 5.59 (dd, J=9.6, 4.5 Hz, 1H), 4.09-3.97 (m, 2H), 3.93-3.80 (m, 8H), 3.67 (tdd, J=11.3, 9.2, 5.0 Hz, 1H), 2.99 (ddd, J=16.7, 11.3, 5.6 Hz, 1H), 2.89-2.67 (m, 3H), 2.38-2.16 (m, 2H), 1.41 (t, J=7.0 Hz, 3H).

Example (S)-C55: Synthesis of Compound (S)-C55

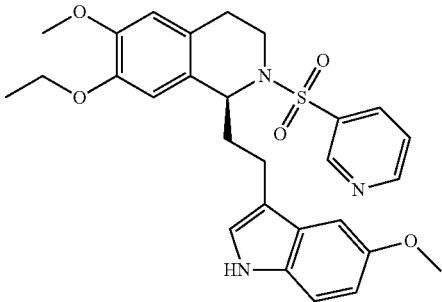 [SMILES: CCOc1cc2c(cc1OC)CCN(S(=O)(=O)c1cccnc1)[C@H]2CCc1c[nH]c2ccc(OC)cc12]

Compound (S)-C55 was obtained according to the synthesis of (S)-C47, while the benzenesulfonyl chloride in example (S)-C47 was replaced with pyridine-3-sulfonyl chloride. $^1$H NMR (500 MHz, Chloroform-d) δ 8.99 (d, J=2.2 Hz, 1H), 8.64-8.57 (m, 1H), 8.03 (s, 1H), 7.92 (dt, J=8.1, 2.0 Hz, 1H), 7.26 (s, 1H), 7.20 (dd, J=8.1, 4.9 Hz, 1H), 7.14 (d, J=2.0 Hz, 1H), 7.01 (d, J=2.3 Hz, 1H), 6.87 (dd, J=8.8, 2.4 Hz, 1H), 6.30 (s, 1H), 6.26 (s, 1H), 4.97 (dd, J=9.4, 4.2 Hz, 1H), 4.01 (ddd, J=14.7, 7.0, 2.4 Hz, H), 3.86 (s, 3H), 3.82 (q, J=7.0 Hz, 2H), 3.74 (s, 3H), 3.57 (ddd, J=14.6, 11.0, 5.8 Hz, 1H), 2.94 (q. J=7.1, 6.3 Hz, 2H), 2.53-2.40 (m, 2H), 2.25 (dddd, J=14.8, 13.2, 9.6, 5.7 Hz, 1H), 2.15 (dtd, J=14.3, 7.9, 4.4 Hz, 1H), 1.36 (t, J=6.9 Hz, 3H).

Example (S)-C56: Synthesis of Compound (S)-C56

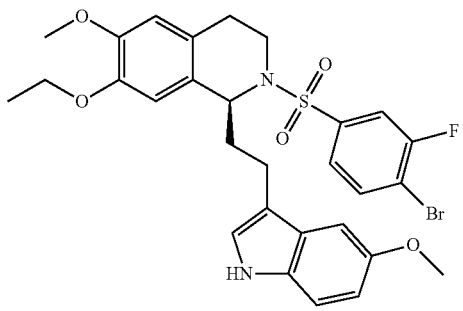 [SMILES: CCOc1cc2c(cc1OC)CCN(S(=O)(=O)c1ccc(Br)c(F)c1)[C@H]2CCc1c[nH]c2ccc(OC)cc12]

Compound (S)-C56 was obtained according to the synthesis of (S)-C47, while the benzenesulfonyl chloride in example (S)-C47 was replaced with 3-fluoro-4-bromosulfonyl chloride. $^1$H NMR (500 MHz, Chloroform-d) δ 7.98 (s, 1H), 7.51-7.43 (m, 2H), 7.31 (dd, J=8.3, 2.0 Hz, 1H), 7.11 (d, J=2.3 Hz, 1H), 7.01 (d, J=2.4 Hz, 1H), 6.86 (dd, J=8.8, 2.4 Hz, 1H), 6.33 (s, 1H), 6.29 (s, 1H), 4.96 (dd, J=9.3, 4.4 Hz, 1H), 3.93 (ddd, J=14.7, 6.4, 2.9 Hz, 1H), 3.86 (s, 3H), 3.83 (q, J=6.9 Hz, 2H), 3.76 (s, 3H), 3.55 (ddd, J=14.5, 10.6, 6.0 Hz, 1H), 2.92 (td, J=7.9, 4.7 Hz, 2H), 2.46 (dq, J=11.4, 6.3, 4.8 Hz, 2H), 2.24 (dtd, J=14.5, 8.3, 6.0 Hz, 1H), 2.14 (dtd. J=14.4, 7.8, 4.3 Hz, 1H), 1.37 (t, J=7.0 Hz, 3H).

Example (S)-C57: Synthesis of Compound (S)-C57

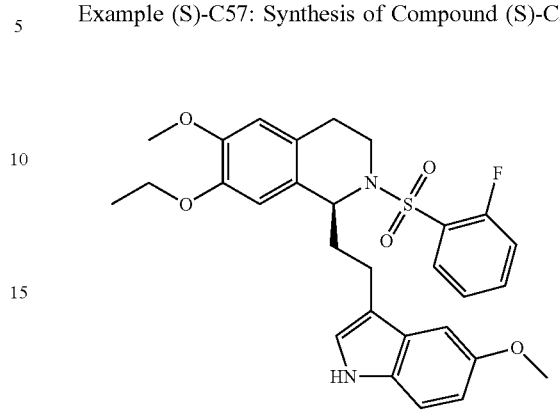

Compound (S)-C57 was obtained according to the synthesis of (S)-C47, while the benzenesulfonyl chloride in example (S)-C47 was replaced with 2-fluorosulfonyl chloride. $^1$H NMR (500 MHz, Chloroform-d) δ 7.99-7.94 (m, 1H), 7.94-7.90 (m, 1H), 7.45-7.39 (m, 1H), 7.17 (td, J=7.7, 1.1 Hz, 1H), 7.07 (d, J=2.3 Hz, 1H), 7.00-6.93 (m, 2H), 6.84 (dd, J=8.8, 2.4 Hz, 1H), 6.36 (s, 1H), 6.31 (s, 1H), 5.07 (dd, J=9.4, 4.3 Hz, 1H), 4.04 (ddd, J=14.5, 6.2, 2.7 Hz, 1H), 3.85 (s, 3H), 3.83 (q, J=7.0 Hz, 2H), 3.75 (s, 3H), 3.56 (ddd, J=14.3, 10.9, 5.6 Hz, 1H), 2.93-2.81 (m, 2H), 2.57-2.46 (m, 2H), 2.24 (dtd, J=14.6, 9.1, 5.5 Hz, 1H), 2.12 (dddd, J=13.9, 8.9, 7.1, 4.4 Hz, 1H), 1.36 (t, J=7.0 Hz, 3H).

Example (S)-C58: Synthesis of Compound (S)-C58

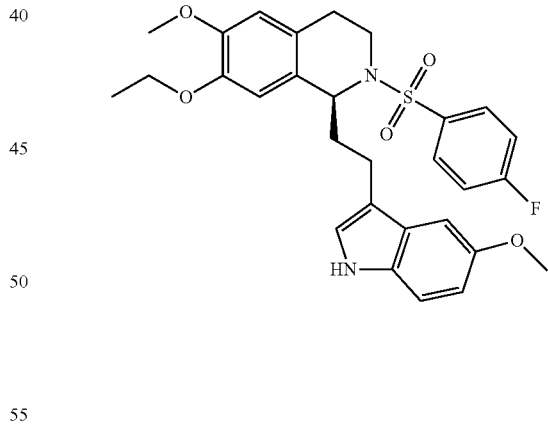

Compound (S)-C58 was obtained according to the synthesis of (S)-C47, while the benzenesulfonyl chloride in example (S)-C47 was replaced with 4-fluorosulfonyl chloride. $^1$H NMR (500 MHz, Chloroform-d) δ 7.98 (s, 1H), 7.73-7.67 (m, 2H), 7.12 (d, J=2.3 Hz, 1H), 7.01 (d, J=2.4 Hz, 1H), 6.96 (t, J=8.6 Hz, 2H), 6.86 (dd, J=8.7, 2.4 Hz, 1H), 6.30 (s, 1H), 6.28 (s, 1H), 4.98 (dd, J=9.5, 4.1 Hz, 1H), 3.94 (ddd, J=14.4, 7.0, 2.2 Hz, 1H), 3.85 (s, 3H), 3.83 (q, J=6.9 Hz, 2H), 3.74 (s, 3H), 3.52 (ddd, J=14.5, 11.3, 5.5 Hz, 1H), 2.99-2.88 (m, 2H), 2.46-2.32 (m, 2H), 2.23 (dtd, J=14.5, 8.7, 5.7 Hz, 1H), 2.16-2.09 (m, 1H), 1.37 (t, J=7.0 Hz, 3H).

Example (S)-C59: Synthesis of Compound (S)-C59

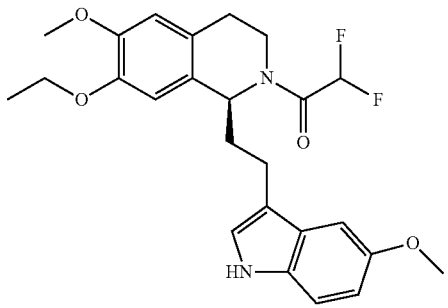 [SMILES: CCOc1cc2c(cc1OC)CCN(C(=O)C(F)F)[C@H]2CCc1c[nH]c2ccc(OC)cc12]

Compound (S)-C59 was obtained according to the synthesis of (S)-C47, while the benzenesulfonyl chloride in example (S)-C47 was replaced with difluoroacetyl chloride. ¹H NMR (500 MHz, Chloroform-d) δ 7.61 (s, 1H), 7.22 (d, J=7.5 Hz, 1H), 7.14 (d, J=1.0 Hz, 1H), 7.04 (s, 1H), 6.79 (d, J=1.6 Hz, 1H), 6.70 (dd, J=7.5, 1.5 Hz, 1H), 6.23-6.16 (m, 1H), 4.95 (s, 1H), 4.57 (dq, J=12.3, 7.9 Hz, 1H), 4.40-4.26 (m, 1H), 3.89 (m, 8H), 3.56 (dt, J=12.5, 7.1 Hz, 1H), 3.38 (dtd, J=14.1, 7.0, 1.0 Hz, 1H), 2.95-2.76 (m, 2H), 2.54 (ddd, J=12.5, 9.9, 6.5 Hz, 1H), 2.16-2.06 (m, 2H), 1.46 (t, J=8.0 Hz, 3H).

Example (S)-C60: Synthesis of Compound (S)-C60

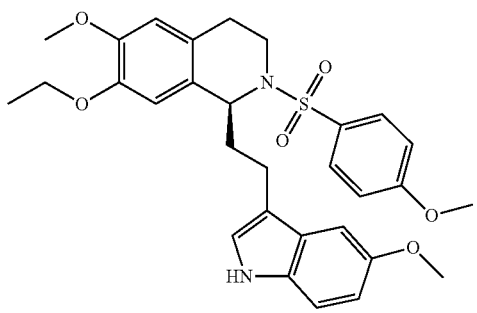 [SMILES: CCOc1cc2c(cc1OC)CCN(S(=O)(=O)c1ccc(OC)cc1)[C@H]2CCc1c[nH]c2ccc(OC)cc12]

Compound (S)-C60 was obtained according to the synthesis of (S)-C47, while the benzenesulfonyl chloride in example (S)-C47 was replaced with 4-methoxysulfonyl chloride. ¹H NMR (500 MHz, Chloroform-d) δ 7.92 (s, 1H), 7.63 (d, J=8.8 Hz, 2H), 7.12 (d, J=1.8 Hz, 1H), 7.01 (d, J=2.4 Hz, 1H), 6.85 (dd, J=8.7, 2.4 Hz, 1H), 6.79-6.74 (m, 2H), 6.31 (d, J=11.7 Hz, 2H), 4.98 (dd, J=9.3, 4.3 Hz, 1H), 3.94-3.88 (m, 1H), 3.85 (s, 3H), 3.83 (q, J=7.0 Hz, 2H), 3.77 (s, 3H), 3.75 (s, 3H), 3.50 (dt, J=14.4, 8.8 Hz, 1H), 2.92 (q, J=7.7, 7.0 Hz, 2H), 2.45-2.39 (m, 2H), 2.21 (ddd, J=14.7, 10.1, 5.9 Hz, 1H), 2.16-2.08 (m, 1H), 1.36 (t, J=7.0 Hz, 3H).

Example (S)-C61: Synthesis of Compound (S)-C61

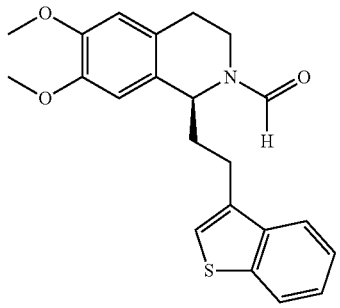

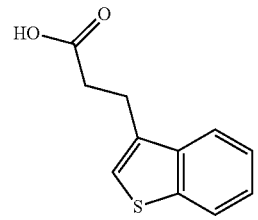

61-1

Compound (S)-C61 was obtained according to the synthesis of (S)-A1, while the 1-2 in example (S)-A1 was replaced with 61-1. ¹H NMR (500 MHz, Chloroform-d) δ 8.28 (2×s, 1H), 7.86-7.83 (2×m, 1H), 7.71 (2×dd, J=6.7, 2.0 Hz, 1H), 7.45-7.37 (2×m, 2H), 7.22 (2×s, 1H), 6.60 (2×s, 1H), 6.47 (2×s, 1H), 4.51 (2×dd, J=9.4, 4.7 Hz, 1H), 3.84 (2×s, 3H), 3.74 (2×s, 3H), 3.60 (2×m, 1H), 3.04 (2×dd, J=15.4, 7.9 Hz, 1H), 2.94-2.90 (2×m, 3H), 2.71 (2×ddd, J=16.2, 4.8, 2.1 Hz, 1H), 2.26 (2×m, 2H).

Example (S)-C62: Synthesis of Compound (S)-C62

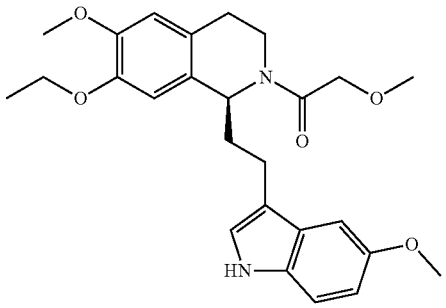 [SMILES: CCOc1cc2c(cc1OC)CCN(C(=O)COC)[C@H]2CCc1c[nH]c2ccc(OC)cc12]

Compound (S)-C62 was obtained according to the synthesis of (S)-C47, while the benzenesulfonyl chloride in example (S)-C47 was replaced with methoxyacetyl chloride. ¹H NMR (500 MHz, Chloroform-d) δ 7.82 (2×s, 1H), 7.39 (2×d, J=2.3 Hz, 1H), 7.22 (2×d, J=7.5 Hz, 1H), 7.16 (2×d, J=0.9 Hz, 1H), 7.10 (2×d, J=1.7 Hz, 1H), 6.70 (2×dd, J=7.5, 1.5 Hz, 1H), 5.02 (2×dd, J=7.6, 6.6 Hz, 1H), 4.93 (2×d, J=12.5 Hz, 1H), 4.66 (2×d, J=12.3 Hz, 1H), 4.35 (2×dq, J=12.3, 7.9 Hz, 1H), 4.04-3.85 (2×m, 8H), 3.64 (2×dt, J=12.5, 7.1 Hz, 1H), 3.36-3.26 (2×m, 1H), 3.25 (2×s, 3H), 3.01 (2×dt, J=12.5, 7.9 Hz, 1H), 2.89-2.71 (2×m, 2H), 2.15-2.07 (2×m, 2H), 1.46 (2×t, J=8.0 Hz, 3H).

Example (S)-C63: Synthesis of Compound (S)-C63

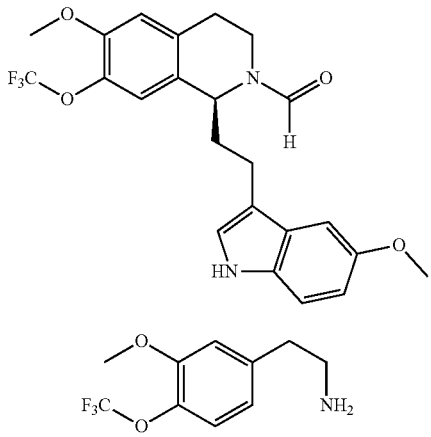

63-1

Compound (S)-C63 was obtained according to the synthesis of (S)-A1 and (S)-C8, while the 1-1 in example (S)-A1 was replaced with 63-1. ESI-MS m/z 449.2.

Example (S)-C64: Synthesis of Compound (S)-C64

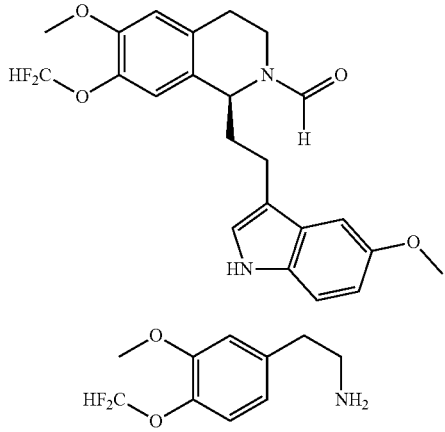

64-1

The compound (S)-C64 was obtained according to the synthesis of the compound (S)-C63, while 63-1 in example (S)-C63 was replaced with 64-1. ESI-MS m/z 431.2.

Example (S)-C65: Synthesis of Compound (S)-C65

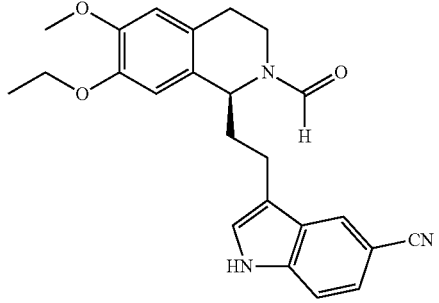

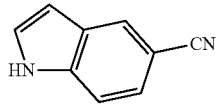

65-1

The compound (S)-C65 was obtained according to the synthesis of the compound (S)-C8, while 31-1 in example (S)-C8 was replaced with 65-1. ESI-MS m/z 404.2.

Example (S)-C66: Synthesis of Compound (S)-C66

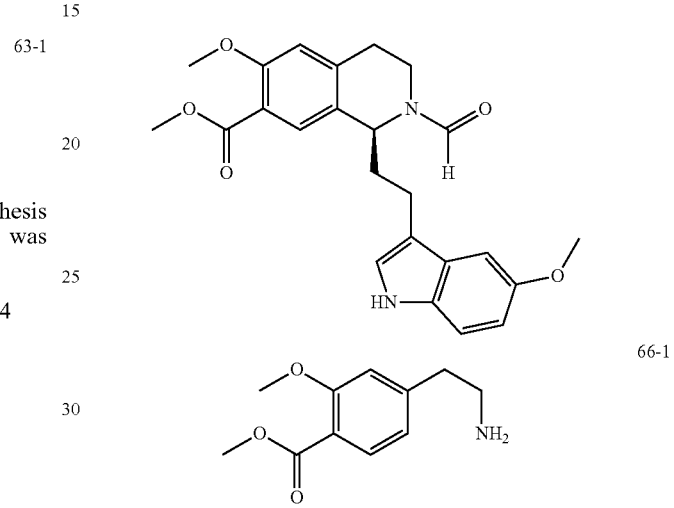

66-1

The compound (S)-C66 was obtained according to the synthesis of the compound (S)-C63, while 63-1 in example (S)-C63 was replaced with 66-1. ESI-MS m/z 423.1.

Example (S)-C67: Synthesis of Compound (S)-C67

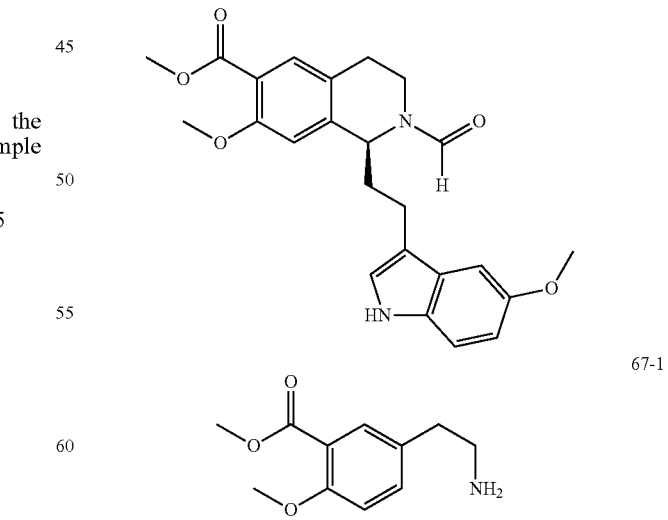

67-1

The compound (S)-C67 was obtained according to the synthesis of the compound (S)-C63, while 63-1 in example (S)-C63 was replaced with 67-1. ESI-MS m/z 423.1.

Example (S)-C68: Synthesis of Compound (S)-C68

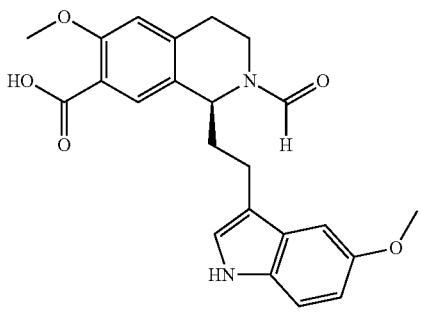

Compound (S)-C66 was dissolved in methanol, and 1M NaOH was added and stirred at room temperature for 2 hours. The mixture was neutralized with 1M hydrochloric acid solution, extracted with ethyl acetate, and separated through column chromatography to obtain compound (S)-C68. ESI-MS m/z 409.2.

Example (S)-C69: Synthesis of Compound (S)-C69

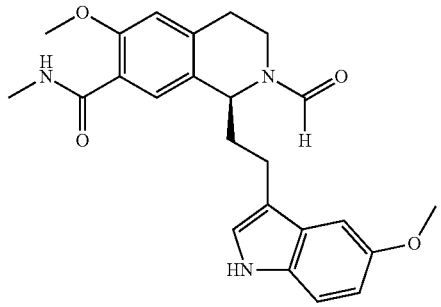

Compound (S)-C68 was dissolved in dichloromethane, and 2 equivalents of methylamine solution in tetrahydrofuran, 1.5 equivalents of HATU and 2 equivalents of triethylamine were added and stirred at room temperature overnight. Dichloromethane was added and washed with water, and the organic phase was dried and purified through column chromatography to provide compound (S)-C69. ESI-MS m/z 422.2.

Example (S)-C70: Synthesis of Compound (S)-C70

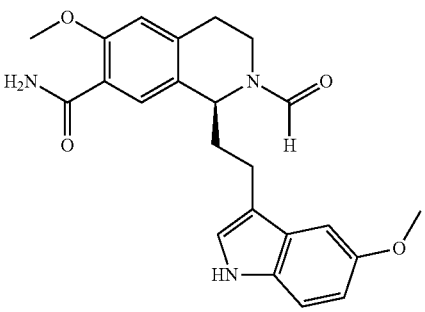

Compound (S)-C68 was dissolved in dioxane, 2 equivalents of ammonium bicarbonate, 2 equivalents of BOC anhydride, 5 equivalents of pyridine were added and stirred at room temperature overnight. Dichloromethane was added and washed with water, while the dried organic phase was purified through column chromatography to provide compound (S)-C70. ESI-MS m/z 408.2.

Example (S)-C71: Synthesis of Compound (S)-C71

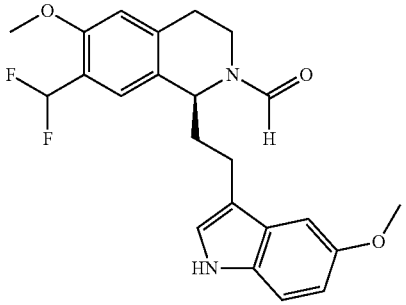

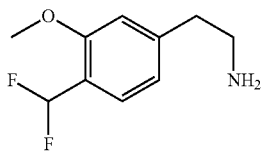

71-1

The compound (S)-C71 was obtained according to the synthesis of the compound (S)-C63, while 63-1 in example (S)-C63 was replaced with 71-1. ESI-MS m/z 415.2.

Example (S)-C72: Synthesis of Compound (S)-C72

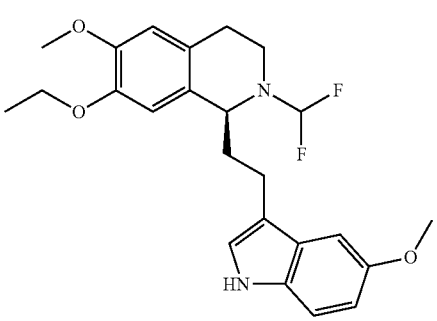 [SMILES: CCOc1cc2c(cc1OC)CCN(C(F)F)[C@H]2CCc1c[nH]c2ccc(OC)cc12]

The compound (S)-C72 was obtained according to the synthesis of the compound (S)-B2, while 12-1 in example (S)-B2 was replaced with difluoromethyl iodide. ESI-MS m/z 431.2.

Example (S)-C73: Synthesis of Compound (S)-C73

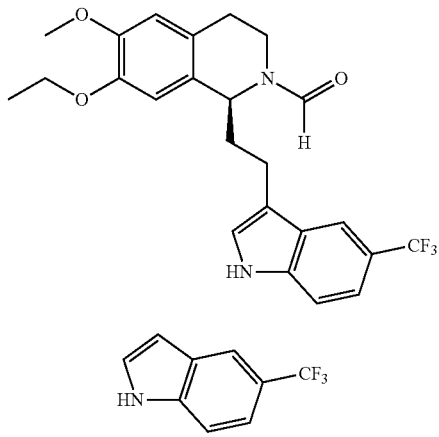

73-1

The compound (S)-C73 was obtained according to the synthesis of the compound (S)-C65, while 65-1 in example (S)-C65 was replaced with 73-1. ESI-MS m/z 447.2.

Example (S)-C74: Synthesis of Compound (S)-C74

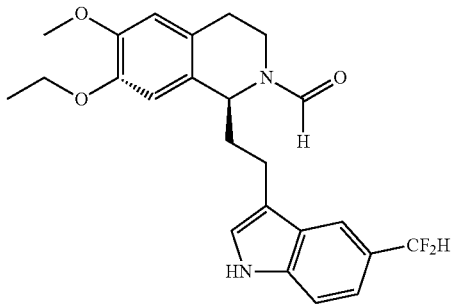

The compound (S)-C74 was obtained according to the synthesis of the compound (S)-C65, while 65-1 in example (S)-C65 was replaced with 5-difluoromethyl indole. ESI-MS m/z 429.2.

Example (S)-C75: Synthesis of Compound (S)-C75

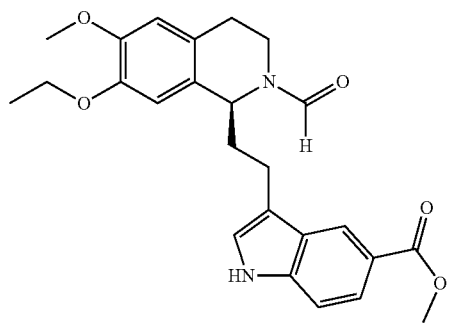 [SMILES: CCOc1cc2c(cc1OC)CCN(C=O)[C@H]2CCc1c[nH]c2ccc(C(=O)OC)cc12]

The compound (S)-C75 was obtained according to the synthesis of the compound (S)-C65, while 65-1 in example (S)-C65 was replaced with methyl indole-5-carboxylate. ESI-MS m/z 437.2.

Example (S)-C76: Synthesis of Compound (S)-C76

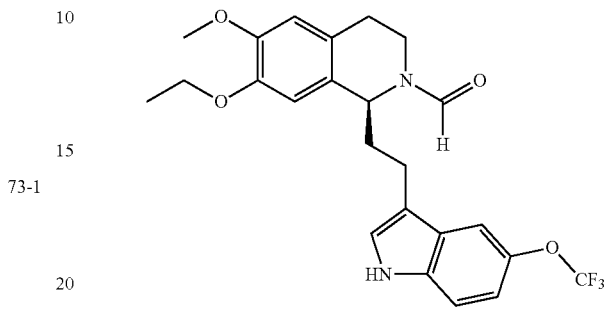

The compound (S)-C76 was obtained according to the synthesis of the compound (S)-C65, while 65-1 in example (S)-C65 was replaced with 5-trifluoromethoxyindole. ESI-MS m/z 463.2.

Example (S)-C77: Synthesis of Compound (S)-C77

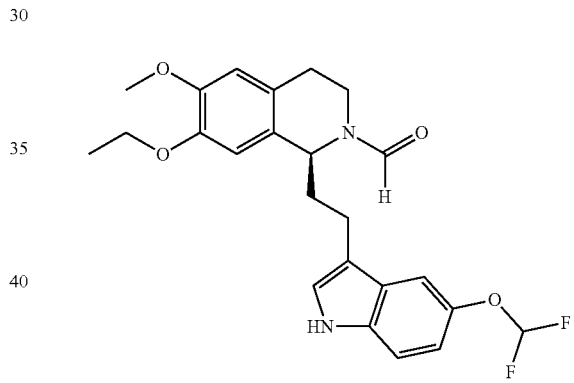

The compound (S)-C77 was obtained according to the synthesis of the compound (S)-C65, while 65-1 in example (S)-C65 was replaced with 5-difluoromethoxyindole. ESI-MS m/z 445.2.

Example (S)-C78: Synthesis of Compound (S)-C78

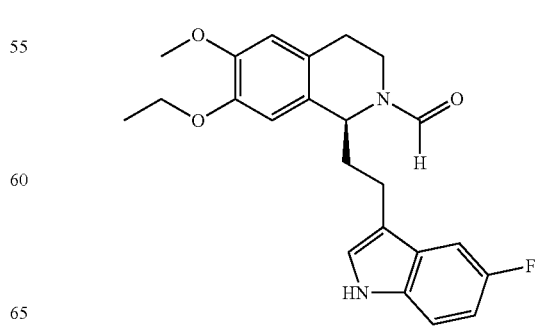

The compound (S)-C78 was obtained according to the synthesis of the compound (S)-C65, while 65-1 in example (S)-C65 was replaced with 5-fluoroindole. ESI-MS m/z 397.2.

Example (S)-C79: Synthesis of Compound (S)-C79

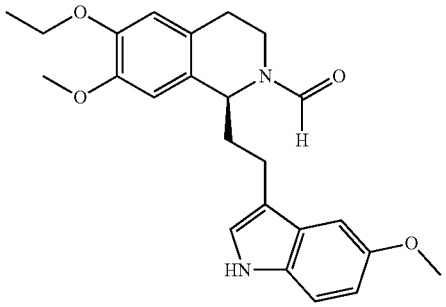

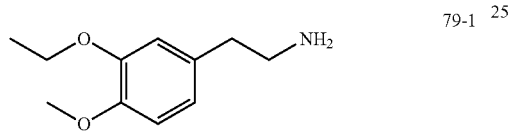

79-1

The compound (S)-C79 was obtained according to the synthesis of the compound (S)-C63, while 63-1 in example (S)-C63 was replaced with 79-1. ESI-MS m/z 409.20.

Example (S)-C80: Synthesis of Compound (S)-C80

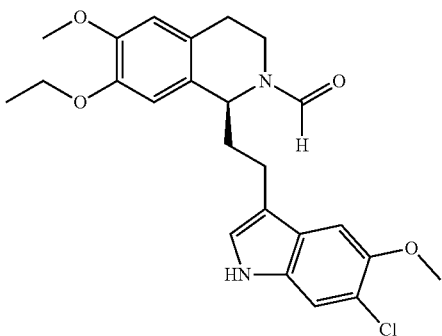 [SMILES: CCOc1cc2c(cc1OC)CCN(C=O)[C@H]2CCc1c[nH]c2cc(Cl)c(OC)cc12]

The compound (S)-C80 was obtained according to the synthesis of the compound (S)-C65, while 65-1 in example (S)-C65 was replaced with 6-chloro-5-methoxyindole. ESI-MS m/z 443.2.

Example (S)-C81: Synthesis of Compound (S)-C81

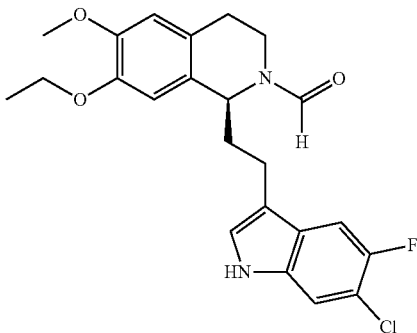 [SMILES: CCOc1cc2c(cc1OC)CCN(C=O)[C@H]2CCc1c[nH]c2cc(Cl)c(F)cc12]

The compound (S)-C81 was obtained according to the synthesis of the compound (S)-C65, while 65-1 in example (S)-C65 was replaced with 5-fluoro-6-chloroindole. ESI-MS m/z 431.1.

Example (S)-C82: Synthesis of Compound (S)-C82

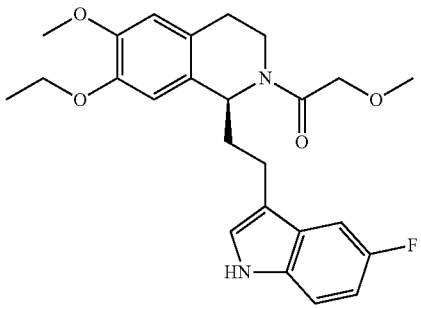 [SMILES: CCOc1cc2c(cc1OC)CCN(C(=O)COC)[C@H]2CCc1c[nH]c2ccc(F)cc12]

The compound (S)-C82 was obtained according to the synthesis of the compound (S)-C62, while 5-methoxyindole in example (S)-C62 was replaced with 5-fluoroindole. ESI-MS m/z 441.2.

Example (S)-C83: Synthesis of Compound (S)-C83

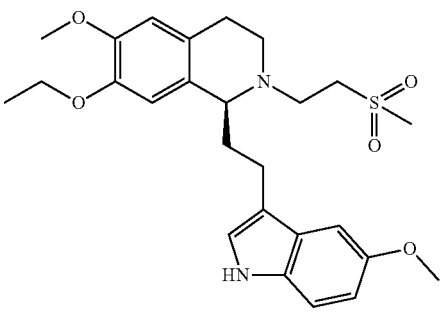 [SMILES: CCOc1cc2c(cc1OC)CCN(CCS(C)(=O)=O)[C@H]2CCc1c[nH]c2ccc(OC)cc12]

Compound (S)-C83 was obtained according to the synthesis of (S)-C72, while the difluoroiodomethane in example (S)-C72 was replaced with 1-chloro-2-(methylsulfonyl)ethane. ESI-MS m/z 487.2.

BIOLOGICAL ACTIVITY EXPERIMENT SECTION

Experimental Example B1. Determination of Molecular Enzyme Activity Inhibition of the Compound on PDE4

The scintillation Proximity Assay (SPA) method was used to determine the inhibitory effect of compounds on the activity of PDE4D catalytic domain. Human PDE4D catalytic domain protein was obtained by expression and purification in E. coli. The positive compound Apremilast was purchased from Topscience Biochemical, Microplate Scintillation Counter (MicroBeta2, Perkin Elmer), constant temperature water bath (DK420, Shanghai Medical Device Factory), Micro-vibrator (XW-80A, Shanghai Jingke Industrial Co., Ltd.) are a public instrument in the radioactive laboratory, and the step-by-step pipette (Multipette Plus, Eppendorf) and supporting tips were purchased from Ebende Biotechnology Company, 3.5. [$^3$H]-cAMP, scintillation beads (RPNQO150, Perkin Elmer), and 96-well scintillation microplates (Isoplate-96, Perkin Elmer) were purchased from Perkin Elmer Company. 10× SPA buffer was prepared in the laboratory (500 mM Tris pH7.5, 83 mM MgCl2, 17 mM EGTA).

In the experiment, 60 μl water and 10 μl reaction solution were added into 100 μl total volume reaction to achieve the final concentration of each component being 50 mM Tris-HCl, pH7.5, 8.3 mM MgCl$_2$, 1.7 mM EGTA, 10 μl compound and 10 μl enzyme (0.1 ng/ul). Finally, 10 μl [$^3$H]-cAMP (0.005 μCi/μl) was added and incubated for 30 min at 30° C. in a water bath. 50 μl SPA beads was added to quench the reaction, shaked appropriately, and stood for 20 minutes. A microplate scintillation counter was used.

Table B1 shows the compound's inhibition rate to PDE4D enzyme activity and IC$_{50}$ value

TABLE B1

| Compound | PDE4D enzyme activity inhibition rate % (Compound concentration: 1 μM) | IC$_{50}$ (mM) | Compound | PDE4D enzyme activity inhibition rate % (Compound concentration: 1 μM) |
|---|---|---|---|---|
| Apremilast | | 0.074[a] | C37 | 29.3 |
| (S)-A1 [b] | 78 | 0.38 | (S)-C37 | 39.7 |
| (R)-A1 [b] | 6.4 | | (R)-C37 | 10.6 |
| A2 | 19.2 | 2.99 | C38 | 56.3 |
| A3 | 19.9 | | (S)-C38 | 71.7 |
| A5 | 10.8 | | C39 | 26.6 |
| C1 | 26.4 | 1.5 | C40 | 47.5 |
| C2 | 21.5 | | (S)-C40 | 67.4 |
| C3 | 6.4 | | C41 | 36.8 |
| (R)-A1 | 17.6 | | (S)-C41 | 59.2 |
| (S)-A1 | 77.4 | 0.27 | C42 | 39.7 |
| C9 | 76.9 | 0.21 | (S)-C42 | 50.8 |
| (S)-A3 | 29.1 | 1.8 | C43 | 46.4 |
| (S)-C9 | 80.2 | 0.12 | C44 | 41.7 |
| (R)-C9 | 26.9 | | (S)-C44 | 83.2 |
| (S)-C3 | 24.1 | | C45 | 42.0 |
| (S)-C4 | 62 | 0.24 | C46 | 50.1 |
| (S)-C5 | 92.5 | 0.24 | (S)-C47 | 49.4 |
| B1 | 30.7 | | (S)-C48 | 62.0 |
| B2 | 19.2 | | (S)-C49 | 70.8 |
| B3 | 16.4 | | (S)-C50 | 49.4 |
| B4 | 82.6 | 0.3 | (S)-C51 | 37.9 |
| (S)-C6 | 92.4 | 0.25 | (S)-C52 | 36.8 |
| B5 | 39.1 | | (S)-C53 | 56.3 |
| B6 | 19.5 | | (S)-C54 | 46.0 |
| B7 | 6.7 | | (S)-C55 | 20.5 |
| A4 | 83.7 | 0.23 | (S)-C56 | 66.4 |
| C10 | 87.3 | 0.08 | (S)-C57 | 66.5 |
| (S)-A4 | 90.8 | 0.13 | (S)-C58 | 49.7 |
| (S)-B11 | 82.9 | 0.19 | (S)-C59 | 42.4 |
| (S)-C10 | 90.5 | 0.05 | (S)-C60 | 42.0 |
| C11 | 34.7 | | (S)-C61 | 70.8 |
| C12 | 42.7 | | (S)-C62 | 79.4 |
| (S)-B12 | 92.2 | 0.25 | (S)-C63 | 75.3 |
| (S)-C13 | 19.4 | | (S)-C64 | 76.5 |
| (S)-B10 | 29.5 | | (S)-C65 | 68.7 |
| (S)-C17 | 50.9 | 1.1 | (S)-C66 | 88.4 |
| B8 | 68.5 | 0.57 | (S)-C67 | 85.9 |
| (S)-C18 | 42.8 | | (S)-C68 | 83.1 |
| (S)-C14 | 22.9 | | (S)-C69 | 80.5 |
| (S)-C15 | 5 | | (S)-C70 | 83.8 |
| (S)-C16 | 20.3 | | (S)-C71 | 81.8 |
| (S)-C8 | 95 | 0.08 | (S)-C76 | 92.3 |
| (S)-C7 | 82.8 | 0.33 | (S)-C77 | 93.5 |

[a] Man H W, et al. J. Med. Chem. 2009, 52: 1522-1524
[b] obtained by seperation Conclusion: After measuring the inhibitory rate of PDE4 at 1 μM concentration, the IC$_{50}$ value of PDE4 inhibitory activity of compounds with high inhibitory efficiency was measured. Among them, 14 compounds had IC$_{50}$ values of 100 nmol level, and 3 compounds (C10, (S)-C10 and (S)-C8) had IC$_{50}$ values lower than 100 nmol, which was comparable to IC$_{50}$ value of positive control compound Apremilast.

Experimental Example 2. Determination of the Inhibitory Activity of the Compound on TNF-α Secretion in PBMC Among the many functions of PDE4, the most studied is the anti-inflammatory effect. Monocytes and macrophages in the immune system are important producers of TNF-α. PDE4 is the main enzyme in these cells. The anti-inflammatory effects of existing inhibitors targeting PDE4 are closely related to the expression of TNF-α in the immune system. According to the difference in cell density in human blood, PBMC (peripheral blood mononuclear cell, PBMC) was directly separated and purified by gradient centrifugation using lymphocyte separation fluid. The cell type was mononuclear cells in blood, mainly including lymphocytes (T/B), monocytes, macrophages, dendritic cells and other minor cell types, of which lymphocytes account for a large part, which can directly in vitro simulate the blood immune environment. Lipopolysaccharide (LPS) is a component of the gram-negative bacterial cell wall, which can significantly stimulate the expression of inflammatory factor TNF-α through various signaling pathways such as MAPK, thereby evaluating the cellular activity of some PDE4 inhibitors and simulating in vitro inflammation effect. The inhibitory effect of some PDE4 inhibitors on the expression of TNF-α in human PBMC cells mainly referred to the work of George W. Muller et al.

During the experiment, the positive compound Apremilast was purchased from Topscience Biochemical Technology Co., Ltd. Whole blood of healthy people was provided by Shanghai Blood Center; fetal bovine serum (FBS) was purchased from Hyclone (South Logan, UT, USA); RPMI- 1640 medium and human-derived TNF-α ELISA test kit were purchased from Invitrogen (San Diego, CA, USA); bacterial lipopolysaccharide LPS was purchased from Sigma (L9764, St. Louis, MO, USA).

PBMC cells isolated from human blood were implanted into 96-well plates at $2*10^5$/ml; compounds in gradients were added, with at least three replicates for each gradient; After the PBMCs were incubated at 37° C., 5% $CO_2$ for 1 hour, LPS was added (the final concentration was 10 ug/ml) to stimulate PBMC to express TNF-α, and incubated for another 18-20 h at 37° C., 5% C02. The 96-well plate was collected. The background control with no stimulant and stimulation control wells were also set, with a total volume of 200 μl. The culture supernatant was collected by centrifugation, and the expression level of TNF-α in the culture supernatant was detected by ELISA.

Table 2 shows the experimental results of the compounds inhibiting the secretion of inflammatory factor TNF-α in PBMC

TABLE 2

| Compound | Inhibition rate % | | $IC_{50}$ |
| --- | --- | --- | --- |
|  | 10 μM | 1 μM | (μM) |
| Apremilast |  |  | 0.074[a] |
| (S)-A1[b] | 93.17 | 68.63 | 0.63 |
| (R)-A1[b] | 7.45 |  |  |
| A2 | 43.03 |  |  |
| A3 | 65.70 | 0.84 | 5.69 |
| A5 | 23.83 |  |  |
| C1 | 72.41 | 27.11 |  |
| C2 | 52.40 | 15.80 |  |
| C3 | 36.39 |  |  |
| (R)-A1 | 5.27 |  |  |
| (S)-A1 | 84.15 | 23.99 | 2.73 |
| C9 | 53.60 | 13.81 | 2.16 |
| (S)-A3 | 76.58 | 31.24 | 2.65 |
| (S)-C9 | 59.66 | 8.99 | 2.75 |
| (R)-C9 | 32.05 |  |  |
| (S)-C3 | 79.17 | 12.05 |  |
| (S)-C4 | 76.87 | 31.96 | 2.12 |
| (S)-C5 | 87.84 | 43.83 | 1.21 |
| B1 | 58.50 | 39.84 |  |
| B2 | 25.69 |  |  |
| B3 | 60.24 | 33.28 |  |
| B4 | 89.10 | 44.06 | 8.02 |
| (S)-C6 | 85.22 | 32.90 | 5.37 |
| B5 | 55.23 | 21.72 |  |
| B6 | −23.23 |  |  |
| B7 | 36.65 |  |  |
| A4 | 68.76 | 20.11 | 3.72 |
| C10 | 60.14 | 25.44 | 10 |
| (S)-A4 | 80.88 | 32.57 | 2.56 |
| (S)-B11 | 90.73 | 60.13 | 0.24 |
| (S)-C10 | 81.98 | 38.60 | 5.38 |
| C11 | 50.01 | 39.91 |  |
| C12 | 52.71 | 45.44 |  |
| (S)-B12 | 80.69 | 44.16 |  |
| (S)-C13 | 29.85 |  |  |
| (S)-B10 | 59.62 | 19.93 |  |
| (S)-C17 | 18.79 |  |  |
| B8 | 77.81 | 31.55 |  |
| (S)-C18 | 39.37 |  |  |
| (S)-C14 | 54.45 | 17.02 |  |
| (S)-C15 | −23.85 |  |  |
| (S)-C16 | 1.89 |  |  |
| (S)-C8 | 86.76 | 79.74 | 0.026 |
| (S)-C7 | 65.53 | 36.54 |  |

[a]Man H W, et al. J. Med. Chem. 2009, 52: 1522-1524
[b]obtained by seperation

Conclusion: Compounds with better inhibitory efficiency on enzyme activity at molecular level have better inhibitory effects on TNF-α secretion in PBMC, of which $IC_{50}$ value was around a level of single-digit mmol, while the $IC_{50}$ value of most active compound (S)-C8 reached up to 26 nmol, which is better than the positive control compound Apremilast.

Experimental Example B3. Determination of the Inhibitory Activity of the Compound on Secretion of Tumor Necrosis Factor-α in RAW 264.7 Cells Tumor necrosis factor-α, as an important inflammatory mediator in the development of diseases, such as inflammation, autoimmune diseases, is mainly produced by activated monocytes/macrophages, which can mediate the occurrence of various inflammatory reactions and accelerate the deterioration process of the disease. The mouse mononuclear/macrophage leukemia cell line RAW 264.7 cell is one of the commonly used inflammatory cell models. After the activation by bacterial lipopolysaccharide (LPS), various inflammatory mediators such as tumor necrosis factor-α will be released; Phosphodiesterase PDE4 is also expressed in macrophages, and the inhibitory activity of the compound on phosphodiesterase PDE4 can be reflected by detecting the secretion of tumor necrosis factor-α.

(1) Test of cytotoxicity of a compound on RAW 264.7: The cytotoxicity of the test compound on RAW 264.7 cells was tested by the CCK-8 method. Mouse RAW 264.7 cells were purchased from American Type Culture Collection (Manassas, VA, USA), and cultivated in DMEM culture medium (Hyclone, South Logan, UT, USA) containing 10% fetal bovine serum (Hyclone, South Logan, UT, USA). Cells were collected and counted before use, and inoculated in a 96-well plate (Corning, NY, USA) at $1\times10^5$/well. After the cells were incubated for 24 h, compounds of different concentrations were added, and the corresponding vehicle control and culture medium background control were also set, of which the total volume was 200 μl, And incubated at 37° C. and 5% $CO_2$ incubator for 4 h. 20 μl of CCK-8 solution (Dojindo, Kumamoto, Japan) was added at 30 min before the end of the culture. After the cultivation was ended, the absorbance OD value was measured at 450 nm (reference 650 nm) on amicroplate reader (Molecular Devices, Sunnyvale, CA, USA). The toxicity of the compound on RAW 264.7 cells was calculated by dividing the OD value of the test sample by the OD value of the cell control well, which was labeled as the cell survival rate M %.

(2) Inhibitory activity of compounds on secretion of tumor necrosis factor-α of RAW 264.7 cell: RAW 264.7 cells ($1\times10^5$/well) were seeded in a 96-well plate, and after incubated for 24 h, compounds of different concentrations were added and incubated for 30 min. Under the stimulation of 1 μg/ml LPS (L5886, Sigma, St. Louis, MO, USA), the cells were cultured in a 37° C., 5% $CO_2$ incubator for 4 h. The background control with no stimulant and stimulation control wells were also set, with a total volume of 200 μl. The culture supernatant was collected by centrifugation, and the secretion level of tumor necrosis factor-α in the culture supernatant was detected by enzyme-linked immunosorbent assay. The tumor necrosis factor-α detection kit was purchased from BD Pharmingen (San Diego, CA, USA).

Table B3 shows the experimental results of the compounds inhibiting the secretion of inflammatory factor tumor necrosis factor-α in RAW 264.7 cells

TABLE B3

| Compound | Cell survival rate/% | | | Tumor necrosis factor-α inhibition rate/% | | |
|---|---|---|---|---|---|---|
| | 50 μM | 5 μM | 0.5 μM | 50 μM | 5 μM | 0.5 μM |
| (S)-A1[b] | 102 | 100.2 | 103 | 61.9 | 3.8 | 9.7 |
| (R)-A1[b] | 122.5 | 110.1 | 135.9 | 37.3 | 19.9 | 17.9 |
| A2 | 55.1 | 113 | 111.6 | 99.4 | −4.4 | 9.7 |
| A3 | 94 | 108.2 | 96.9 | 27.3 | −15.5 | −0.5 |
| A5 | 111.3 | 120.8 | 118.7 | 79.3 | −8.1 | −0.2 |
| C1 | 110.5 | 125.1 | 100.9 | 33.7 | −5.2 | 2.8 |
| C2 | 62.7 | 106.3 | 112.4 | 97.2 | −24.5 | −18.2 |
| C3 | 112.6 | 120.5 | 115.1 | 59.7 | 5.9 | −0.9 |
| (R)-A1[c] | 89.3 | 106.2 | 102.7 | 43 | 1.8 | 1.8 |
| (S)-A1[c] | 88.8 | 126.4 | 112.3 | 74.7 | −2.1 | 14.4 |
| C9 | 112.6 | 88.4 | 92.5 | 1.7 | −11.3 | −7.4 |
| (S)-A3 | 77.3 | 86.5 | 110.9 | 54.6 | −3.5 | −2.9 |
| (S)-C9 | 77.9 | 77.8 | 80.9 | 29.2 | 21.6 | −11.3 |
| (R)-C9 | 83.9 | 98.4 | 112.8 | −7 | 2.5 | 3.5 |
| (S)-C3 | 89.2 | 100 | 88.2 | 95.1 | 6 | 6.3 |
| (S)-C4 | 77.3 | 71.8 | 97.6 | 54.5 | −25.6 | −30.1 |
| (S)-C5 | 93.4 | 109.4 | 98 | 75.5 | −17.1 | −14 |
| B1 | 78.8 | 74.9 | 78 | 67.9 | −17.8 | −2.4 |
| B2 | 71.4 | 83.5 | 88.3 | 83.9 | 18.8 | 6.2 |
| B3 | 79.6 | 113.9 | 97.7 | 62.5 | 10.8 | 4.4 |
| B4 | 71.5 | 82.7 | 116.6 | 54.5 | −11 | −9.2 |
| (S)-C6 | 93.7 | 118.4 | 108.6 | 77.2 | −0.7 | −20.7 |
| B5 | 103.8 | 88.2 | 86 | 47.9 | 20 | −2.1 |
| B6 | 95.3 | 87 | 117.3 | 67.5 | −7.1 | 8.2 |
| B7 | 122.6 | 114.1 | 98.1 | 82.2 | 2.3 | 4.3 |
| A4 | 95.3 | 113.4 | 100.6 | 47.4 | −15.3 | −13.9 |
| C10 | 94 | 111.4 | 119.5 | −4.2 | −14.1 | −31 |
| (S)-A4 | 98.1 | 100.8 | 103 | 53.4 | −7.3 | −7.7 |
| (S)-B11 | 102.2 | 111.2 | 110.9 | 51.3 | 1.1 | −7.8 |
| (S)-C10 | 104.1 | 84.6 | 89.1 | 23.4 | 2.7 | −2.1 |
| C11 | 87.3 | 91.2 | 97.9 | 20.1 | −11.9 | −12.7 |
| C12 | 103.8 | 115.7 | 93.6 | 25.5 | −7.9 | −15.1 |
| (S)-B12 | 75.2 | 95.3 | 83.8 | 52.4 | 6.8 | −12.7 |
| (S)-C13 | 101.7 | 91.4 | 111.2 | −37.3 | −13.7 | −3 |
| (S)-B10 | 93.8 | 84.9 | 89.2 | 33.7 | −27.9 | −3 |
| (S)-C17 | 103.9 | 87.3 | 101.7 | −13.4 | −33.7 | −32.2 |
| B8 | 100.5 | 100.7 | 113.4 | 31.8 | 36.1 | 33.6 |
| (S)-C18 | 112.9 | 111.5 | 118 | 38.8 | 14.5 | 15.8 |
| (S)-C14 | 97.3 | 98.8 | 128.3 | 13.6 | −2.2 | 2.4 |
| (S)-C15 | 101.2 | 110.5 | 107.3 | −37.7 | −4.5 | 18 |
| (S)-C16 | 113.1 | 133.1 | 123.2 | 10.4 | 12.7 | 2.6 |
| (S)-C8 | 93.8 | 96.1 | 89.2 | 58.1 | 60.4 | −6 |
| (S)-C7 | 96.1 | 93.4 | 71.3 | 79.7 | 24.5 | 8.1 |

Table B4 is the experimental results of cytotoxicity on the of RAW 264.7 (CC50) and inhibition to secretion of tumor necrosis factor-α (IC50) of some compounds.

TABLE B4

| Compound | $CC_{50}$ (μM) [a] | Tumor necrosis factor-α $IC_{50}$ (μM) [b] | SI[c] |
|---|---|---|---|
| Apremilast | >10 | 4.2 | >2.4 |
| (S)-A1 | >50 | 23.1 | >2.2 |
| (S)-C5 | >50 | 5.4 | >9.3 |
| (S)-C6 | >50 | 11.8 | >4.2 |
| (S)-C8 | >50 | 1.9 | >26.3 |
| (S)-C7 | >50 | 9.1 | >5.5 |

[a] $CC_{50}$ is the drug concentration required to cause median cytotoxicity;
[b] $IC_{50}$ is the drug concentration that effectively inhibits 50% tumor necrosis factor-α;
[c] SI is $CC_{50}/IC_{50}$.

Conclusion: By detecting the inhibitory activity of the tested compounds on the secretion of tumor necrosis factor-α in RAW 264.7 cells, some compounds with better inhibitory activity were found. Based on the inhibitory activity of the compound on the catalytic domain of PDE4D in combination with the biological activity results of PBMCs, Compounds (S)-A1, (S)-C5, (S)-C6, (S)-C8, (S)-C7 were selected for testing cytotoxicity on RAW 264.7 cell and inhibitory activity on tumor necrosis factor-α, of which the experimental results are shown in Table B3 and Table B4. Compared with the positive compound Apremilast, compounds (S)-C5 and (S)-C8 have comparable or stronger inhibitory activity on tumor necrosis factor-α.

Experimental Example B4. Therapeutic Effects of Compound (S)-C5, (S)-C8 on Acute Inflammation Model of Mouse Back Air Sac As a classic model for evaluating the in vivo anti-inflammatory activity of candidate compounds, the acute inflammation model of mouse back air sac has high feasibility and good repeatability. On the first day of the experiment, mice were subcutaneously injected with 3 ml of air on the back, and subcutaneously injected with 1.5 ml of air on the back on day 3, and subcutaneously injected with 1 ml of 2% carrageenan (Sigma-Aldrich, St. Louis, MO, USA) on the back on day 6 for sensitization. 4 hours after sensitization, secretion in the air sac was lavaged with phosphate buffer solution. The lavage fluid was used for white blood cell count and inflammatory factor detection. Among them, the positive drug Apremilast, the test drugs (8)-C5, (S)-C8 were dispersed in 0.5% sodium carboxymethyl cellulose (Sigma-Aldrich, St. Louis, MO, USA)+0.25% Tween −80 (purchased from Sinopharm Group). The drug was orally administered (5 mg/kg) by gavage 24 h and 1 h before sensitization. Tumor necrosis factor-α and interleukin-6 detection kits were purchased from BD Pharmingen (San Diego, CA, USA).

Conclusion: As shown in FIG. 1, oral administration of the test compounds (S)-C5, (S)-C8 by gavage can significantly reduce the inflammatory response and reduce the number of leukocyte infiltration, and the secretion level of tumor necrosis factor-α and interleukin-6 in lavage of the acute inflammation mouse model.

Experimental Example 5: Rat Pharmacokinetic Test

1. Experimental Steps:
   Six male healthy rats weighing 150-200 g were randomly divided into 2 groups (n=3). Compounds 14, 16, 17, 18, 22 and 29 of the present invention were administered by gavage and intravenous injection, respectively, at a administration volume of 10 mL/kg. The drug was formulated with DMSO/Tween 80/saline solution (5:5:90, v/v/v). The rats were fasted for 12 h before testing, water ad lib, and uniformly feeded 2 h after administration.
2. Time Points for Blood Sampling and Sample Process:
   gavage administration: 0.25, 0.5, 1.0, 2.0, 4.0, 6.0, 8.0 and 24 h after administration:
   intravenous administration: 5 min, 0.25, 0.5, 1.0, 2.0, 4.0, 6.0, 8.0 and 24 h after administration;
   0.3 mL of venous blood was collected at the above time points via the rat eye vein venous plexus, placed in heparinized test tube, centrifuged at 11000 rpm for 5 min. Plasma was separated and frozed in a −20° C. refrigerator.
3. Sample Testing and Data Analysis
   The concentration of compounds in rat plasma was determined by LC/MS/MS. The pharmacokinetic parameters after administration were calculated by a non-compartmental model of DAS 3.0 software.
4. Experimental Results:
   Table B5 is the pharmacokinetic experiment results of compound (S)-C7 and (S)-C8 in rats

TABLE B5

| Compound | Administration pattern | $T_{max}$ (h) | $C_{max}$ (ng/mL) | $AUC_{0-t}$ (ng·h/mL) | $AUC_{0-\infty}$ (ng·h/mL) | MRT (h) | $t_{1/2}$ (h) | $V_{ss}$ (L/kg) | F (%) |
|---|---|---|---|---|---|---|---|---|---|
| (S)-C7 | Intravenous injection | \ | \ | 6761.8 | 6761.8 | 0.9 | 0.2 | 0.53 | \ |
|  | gavage | 1 | 2383.6 | 9232.3 | 9232.3 | 2.6 | 1.0 | \ | 68.3 |
| (S)-C8 | Intravenous injection | \ | \ | 2640 | 2643 | 0.544 | 0.707 | 2.1 |  |
|  | gavage | 1.33 | 219 | 491 | 508 | 2.00 | 1.03 | \ | 9.30 |

Compound (S)-C7: After administration of 20 mg/kg Compound (S)-C7 to rats by gavage, the plasma concentration peak time Tmax was 1 h, and the peak concentration Cmax was 2383.6 ng/ml; The area under the curve $AUC_{0-t}$ was 9232.3 ng·h/ml; the terminal elimination half-life $t_{1/2}$ was 1 h. After intravenous administration of 10 mg/kg compound (S)-C7, $AUC_{0-t}$ was 6761.8 ng·h/ml; after administration of 20 mg/kg compound (S)-C7 to rats by gavage, the absolute bioavailability was 68.3% based on dosage standardization.

Compound (S)-C8: After administration of 20 mg/kg Compound (S)-C8 to rats by gavage, the plasma concentration peak time Tmax was 1.33 h, and the peak concentration Cmax was 491 ng/ml; The area under the curve $AUC_{0-t}$ was 508 ng h/ml; the terminal elimination half-life $t_{1/2}$ was 1.03 h. After intravenous administration of 10 mg/kg Compound (S)-C8, $AUC_{0-t}$ was 2640 ng-h/ml; after administration of 20 mg/kg compound (S)-C8 to rats by gavage, the absolute bioavailability was 9.30% based on dosage standardization.

Experimental conclusion: From the above experimental results, it can be seen that in the rat pharmacokinetic experiments, the compound (S)-C7 showed a relatively good absolute bioavailability, which achieved up to 68.3%.

Experimental Example 6: Beagle Dog Pharmacokinetic Test

1. Experimental Steps:

Six male healthy beagle dogs weighing 9-11 kg were randomly divided into 2 groups (n=3). The compound (S)-C8 of the present invention was administered by gavage administration and intravenous injection, respectively, and the administration volume was 5 mL/kg and 1 mL/kg, respectively. The gavage administration was formulated with 0.5% CMC-Na+0.25% Tween 80, and intravenous administration was formulated with 5% DMSO/40% PEG400/55% saline.

2. Time Points for Blood Sampling and Sample Process:
    gavage administration: 0.25, 0.5, 1.0, 2.0, 4.0, 6.0, 8.0 and 24 h after administration;
    intravenous administration: 5 min, 0.25, 0.5, 1.0, 2.0, 4.0, 6.0, 8.0 and 24 h after administration;
    1 ml of venous blood was taken at the above time points from the veins of the extremities, placed in an EDTA-2K anticoagulation tube, and centrifuged at 3500 rpm for 10 minutes. Plasma was separated, and frozen in a −20° C. refrigerator.

3. Sample Testing and Data Analysis

The concentration of compound (S)-C8 in Beagle dog plasma was determined by LC/MS/MS.

The pharmacokinetic parameters after administration were calculated by a non-compartmental model of Phoenix 1.3 software (Pharsight, USA).

4. Experimental Results:

Table B6 shows the pharmacokinetic test results of compound (S)-C8 in Beagle dogs

TABLE B6

| Compound | Administration pattern | $T_{max}$ (h) | $C_{max}$ (ng/mL) | $AUC_{0-t}$ (ng·h/mL) | $AUC_{0-\infty}$ (ng·h/mL) | MRT (h) | $t_{1/2}$ (h) | $V_{ss}$ (L/kg) | F (%) |
|---|---|---|---|---|---|---|---|---|---|
| (S)-C8 | Intravenous injection | \ | \ | 9610 | 9803 | 2.37 | 1.96 | 0.96 |  |
|  | gavage | 0.5 | 4685 | 16601 | \ | 3.61 | 2.92 | \ | 52.3 |

After administration of 10 mg/kg of compound (S)-C8 to Beagle dogs by gavage, the plasma concentration peak time $T_{max}$ was 0.5 h, and the peak concentration $C_{max}$ was 4685 ng/ml; The area under the drug time curve $AUC_{0-t}$, was 16601 ng·h/ml; the terminal elimination half-life $t_{1/2}$ was 2.92 h. After intravenous administration of 3 mg/kg Compound (S)-C8, $AUC_{0-t}$ was 9610 ngh/ml; after administration of 10 mg/kg Compound (S)-C8 to Beagle dogs by gavage, the absolute bioavailability was 52.3% based on dosage standardization.

Experimental conclusion: From the above experimental results, it can be seen that in the Beagle dog pharmacokinetic experiment, the compound (S)-C8 showed good absolute bioavailability.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A tetrahydroisoquinoline compound represented by general formula (I), or a pharmaceutically acceptable salt, enantiomer, diastereomer or racemate thereof:

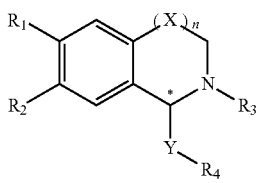

(I)

wherein,
the chiral carbon atom C* is independently of S type or R type;
n=1;
X is —CH₂—;
Y is a linking group selected from a C1-C6 linear or branched alkylene, —CH₂O—, —CH₂NH—,

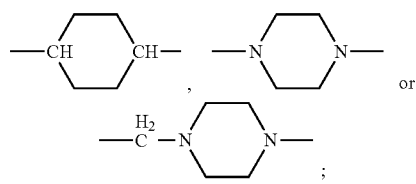

;

R¹ is selected from the group consisting of substituted or unsubstituted C1-C6 linear or branched alkoxy, COOR₅ or CONR₅R₆;
R² is selected from the group consisting of substituted or unsubstituted C1-C6 linear or branched alkoxy, substituted or unsubstituted C3-C7 cycloalkoxy, substituted or unsubstituted C3-C7 cycloalkylmethoxy, benzyloxy, C1-C6 acyloxy, carboxy substituted C2-C8 linear alkoxy, N, N-dimethylamino substituted C2-C8 linear alkoxy, COOR₅ or CONR₅R₆; the substitutent is selected from deuterium or halogen;
R³ is selected from the following groups that are unsubstituted or substituted with 1-3 substituents: —C(O)—(5 to 7-membered heteroaryl), —C(O)—(4 to 7-membered heterocyclic group), —C1-C4 acyl, —CHO, R₇SO₂—, R₇SO₂(CH₂)ₘ—, R₇O(CH₂)ₘCO—, R₇OCO(CH₂)ₘ—, difluoromethyl, trifluoromethyl; wherein each of the heterocyclic groups or heteroaryl groups contains 1 to 3 heteroatoms selected from oxygen, sulfur or nitrogen; and the substituents are each independently selected from a deuterium, halogen, C1-C6 linear or branched alkoxy, C1-C4 sulfonyl;
R₅, R₆ and R₇ are each independently selected from a hydrogen, substituted or unsubstituted C1-C4 linear or branched alkyl, substituted or unsubstituted C3-C8 cycloalkyl, substituted or unsubstituted C6-C10 aryl; wherein the substituent is selected from deuterium or halogen;
m is selected from 0, 1, 2, 3 or 4;
R₄ is an unsubstituted or substituted heteroaryl group selected from the group consisting of indole, imidazopyridine, benzothiophene, quinoxaline, benzofuran, indazole, benzimidazole, and quinoline, wherein the substitution means substitution with 1-3 groups independently selected from a deuterium, halogen, C1-C6 linear or branched alkyl, C1-C6 linear or branched alkoxy, C1-C6 linear or branched alkylcarbonyloxy, cyano, nitro, hydroxy, amino, hydroxymethyl, trifluoromethyl, trifluoromethoxy, difluoromethyl, difluoromethoxy, or COOR₅.

2. The tetrahydroisoquinoline compound of claim 1, or a pharmaceutically acceptable salt, enantiomer, diastereomer or racemate thereof, wherein in the general formula (I):

R₁ is selected from the group consisting of substituted or unsubstituted C1-C6 linear or branched alkoxy, COOR₅ or CONR₅R₆;

R₂ is selected from the group consisting of a substituted or unsubstituted C1-C6 linear or branched alkoxy, substituted or unsubstituted C3-C7 cycloalkoxy, substituted or unsubstituted C3-C7 cycloalkyl-methoxy, C1-C6 acyloxy, carboxy substituted C2-C8 linear alkoxy, N, N-dimethylamino substituted C2-C8 linear alkoxy, COOR₅ or CONR₅R₆; and the substituent is selected from a deuterium or halogen.

3. The tetrahydroisoquinoline compound of claim 2, or a pharmaceutically acceptable salt, an enantiomer, a diastereomer or a racemate thereof, wherein in the general formula (I):

Y is selected from the group consisting of —CH₂—, —CH₂—CH₂—,

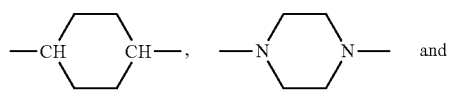 and

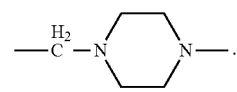.

4. The tetrahydroisoquinoline compound of claim 3, or a pharmaceutically acceptable salt, enantiomer, diastereomer or racemate thereof, wherein in the general formula (I):

R₃ is a group which is unsubstituted or substituted with 1-3 substituents and selected from a C1-C4 acyl, R₇SO₂—, R₇O(CH₂)ₘCO—; the substituents are each independently selected from a deuterium, halogen, C1-C6 linear or branched alkoxy, C1-C4 sulfonyl;

R₇ is selected from a hydrogen, C1-C4 linear or branched alkyl;

m is selected from 0, 1, or 2.

5. The tetrahydroisoquinoline compound of claim 1, or a pharmaceutically acceptable salt, enantiomer, diastereomer or racemate thereof, wherein in the general formula (I), the chiral carbon atom C* is of S type.

6. A tetrahydroisoquinoline compound, or a pharmaceutically acceptable salt, enantiomer, diastereomer or racemate thereof, wherein the tetrahydroisoquinoline compound is selected from the following compounds:

| No. | Name | Structure |
|---|---|---|
| A1 | 1-(2-(1H-indol-3-yl)ethyl)-6,7-dimethoxy-3,4-dihydroisoquinoline-2(1H)-formaldehyde | 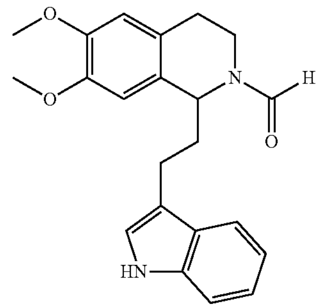 [SMILES: COc1cc2c(cc1OC)C(CCc1c[nH]c3ccccc13)N(C=O)CC2] |
| (S)-A1 | (S)-1-(2-(1H-indol-3-yl)ethyl)-6,7-dimethoxy-3,4-dihydroisoquinoline-2(1H)-formaldehyde | 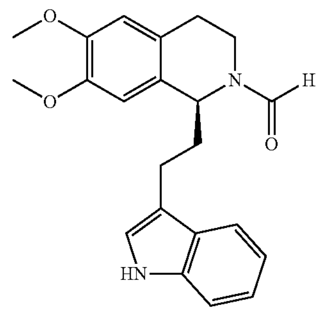 [SMILES: COc1cc2c(cc1OC)[C@H](CCc1c[nH]c3ccccc13)N(C=O)CC2] |
| (R)-A1 | (R)-1-(2-(1H-indol-3-yl)ethyl)-6,7-dimethoxy-3,4-dihydroisoquinoline-2(1H)-formaldehyde | 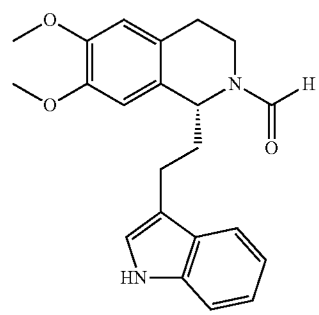 [SMILES: COc1cc2c(cc1OC)[C@@H](CCc1c[nH]c3ccccc13)N(C=O)CC2] |
| A2 | 1-(2-(1H-indol-3-yl)ethyl)-7-(cyclopentyloxy)-6-methoxy-3,4-dihydroisoquinoline-2(1H)-formaldehyde | 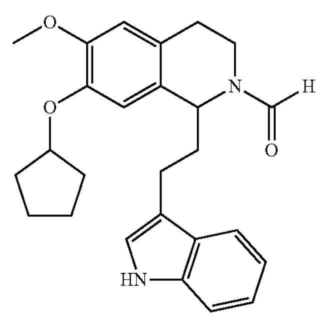 [SMILES: COc1cc2c(cc1OC1CCCC1)C(CCc1c[nH]c3ccccc13)N(C=O)CC2] |
| (S)-A2 | (S)-1-(2-(1H-indol-3-yl)ethyl)-7-(cyclopentyloxy)-6-methoxy-3,4-dihydroisoquinoline-2(1H)-formaldehyde | 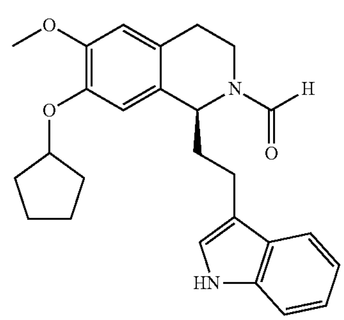 [SMILES: COc1cc2c(cc1OC1CCCC1)[C@H](CCc1c[nH]c3ccccc13)N(C=O)CC2] |

| No. | Name | Structure |
|---|---|---|
| (R)-A2 | (R)-1-(2-(1H-indol-3-yl)ethyl)-7-(cyclopentyloxy)-6-methoxy-3,4-dihydroisoquinoline-2(1H)-formaldehyde | 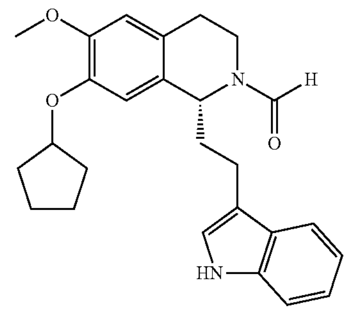 [SMILES: COc1cc2c(cc1OC1CCCC1)[C@@H](CCc1c[nH]c3ccccc13)N(C=O)CC2] |
| A3 | 1-(2-(1H-indol-3-yl)ethyl)-7-(cyclopropylmethoxy)-6-methoxy-3,4-dihydroisoquinoline-2(1H)-formaldehyde | 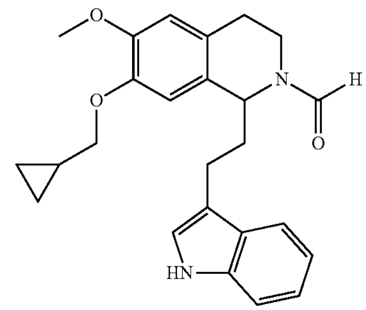 [SMILES: COc1cc2c(cc1OCC1CC1)C(CCc1c[nH]c3ccccc13)N(C=O)CC2] |
| (S)-A3 | (S)-1-(2-(1H-indol-3-yl)ethyl)-7-(cyclopropylmethoxy)-6-methoxy-3,4-dihydroisoquinoline-2(1H)-formaldehyde | 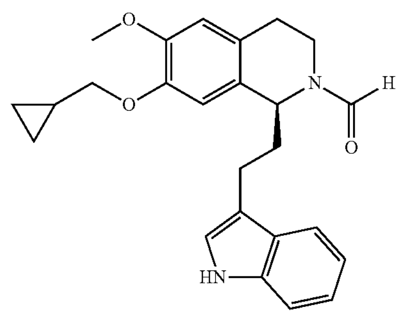 [SMILES: COc1cc2c(cc1OCC1CC1)[C@H](CCc1c[nH]c3ccccc13)N(C=O)CC2] |
| (R)-A3 | (R)-1-(2-(1H-indol-3-yl)ethyl)-7-(cyclopropylmethoxy)-6-methoxy-3,4-dihydroisoquinoline-2H)-formaldehyde | 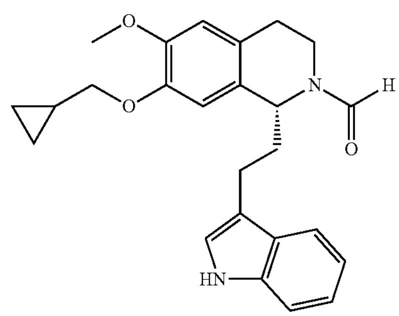 [SMILES: COc1cc2c(cc1OCC1CC1)[C@@H](CCc1c[nH]c3ccccc13)N(C=O)CC2] |
| A4 | 1-(2-(1H-indol-3-yl)ethyl)-7-ethoxy-6-methoxy-3,4-dihydroisoquinoline-2(1H)-formaldehyde | 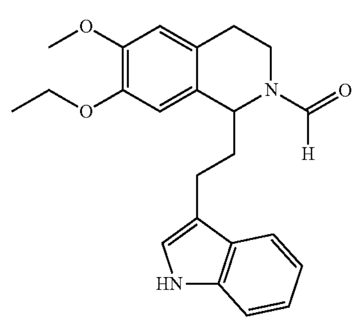 |

| No. | Name | Structure |
|---|---|---|
| (S)-A4 | (S)-1-(2-(1H-indol-3-yl)ethyl)-7-ethoxy-6-methoxy-3,4-dihydroisoquinoline-2(1H)-formaldehyde | 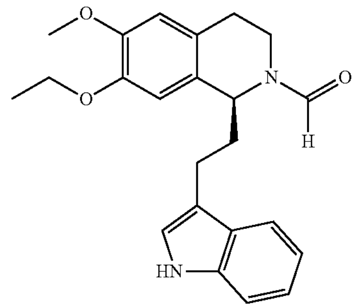 [SMILES: CCOc1cc2c(cc1OC)CCN(C=O)[C@H]2CCc1c[nH]c2ccccc12] |
| (R)-A4 | (R)-1-(2-(1H-indol-3-yl)ethyl)-7-ethoxy-6-methoxy-3,4-dihydroisoquinoline-2(1H)-formaldehyde | 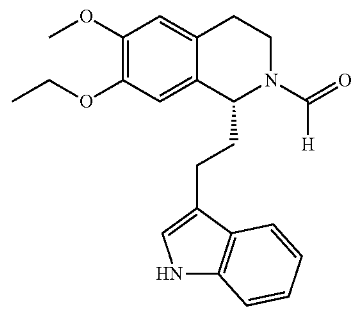 |
| A5 | 1-(2-(1H-indol-3-yl)ethyl)-7-(benzyloxy)-6-methoxy-3,4-dihydroisoquinoline-2(1H)-formaldehyde | 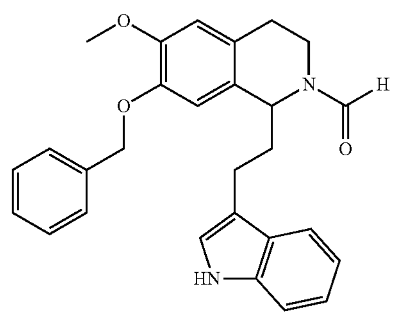 [SMILES: COc1cc2c(cc1OCc1ccccc1)C(CCc1c[nH]c3ccccc13)N(C=O)CC2] |
| (S)-A5 | (S)-1-(2-(1H-indol-3-yl)ethyl)-7-(benzyloxy)-6-methoxy-3,4-dihydroisoquine-2(1H)-formaldehyde | 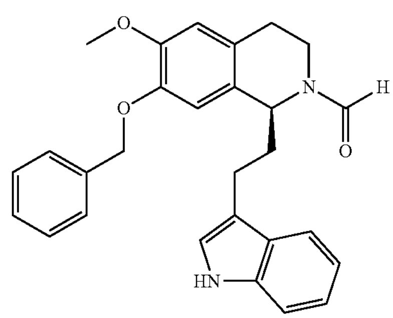 [SMILES: COc1cc2c(cc1OCc1ccccc1)[C@H](CCc1c[nH]c3ccccc13)N(C=O)CC2] |
| (R)-A5 | (R)-1-(2-(1H-indol-3-yl)ethyl)-7-(benzyloxy)-6-methoxy-3,4-dihydroisoquine-2(1H)-formaldehyde | 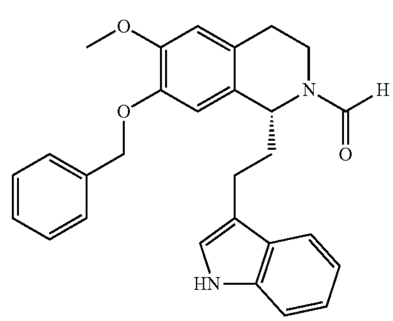 [SMILES: COc1cc2c(cc1OCc1ccccc1)[C@@H](CCc1c[nH]c3ccccc13)N(C=O)CC2] |

-continued

| No. | Name | Structure |
|---|---|---|
| A6 | 1-(2-(1H-indol-3-yl)ethyl)-7-(2-(dimethylamino)ethoxy)-6-methoxy-3,4-dihydroisoquinoline-2(1H)-formaldehyde | 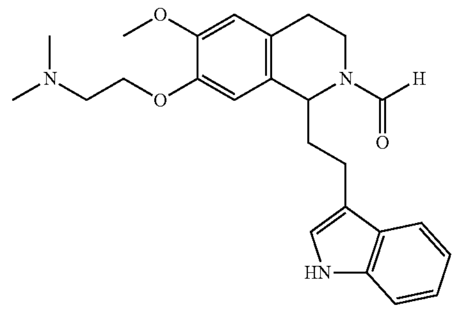 [SMILES: COc1cc2c(cc1OCCN(C)C)C(CCc1c[nH]c3ccccc13)N(C=O)CC2] |
| (S)-A6 | (S)-1-(2-(1H-indol-3-yl)ethyl)-7-(2-(dimethylamino)ethoxy)-6-methoxy-3,4-dihydroisoquinoline-2(1H)-formaldehyde | 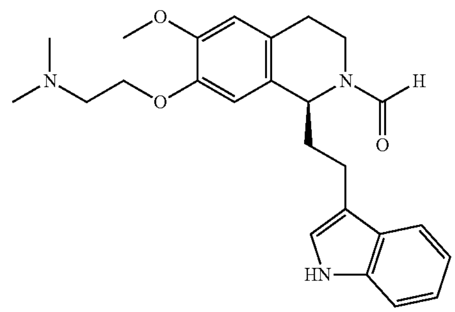 [SMILES: COc1cc2c(cc1OCCN(C)C)[C@H](CCc1c[nH]c3ccccc13)N(C=O)CC2] |
| (R)-A6 | (S)-1-(2-(1H-indol-3-yl)ethyl)-7-(2-(dimethylamino)ethoxy)-6-methoxy-3,4-dihydroisoquinoline-2(1H)-formaldehyde | 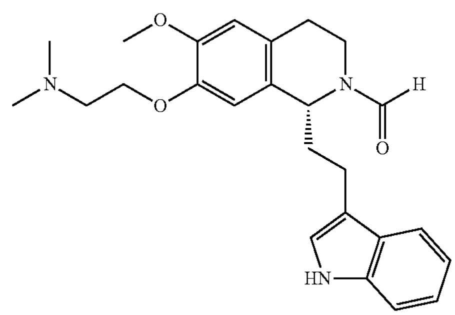 |
| A7 | 3-((1-(2-(1H-indol-3-yl)ethyl)-2-formyl-6-methoxy-1,2,3,4-tetrahydroisoquinoline-7-yl)oxy)propionic acid | 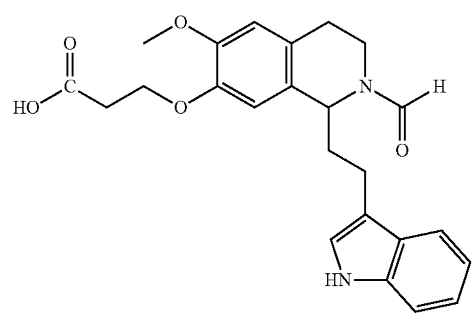 [SMILES: COc1cc2c(cc1OCCC(=O)O)C(CCc1c[nH]c3ccccc13)N(C=O)CC2] |
| (S)-A7 | (S)-3-((1-(2-(1H-indol-3-yl)ethyl)-2-formyl-6-methoxy-1,2,3,4-tetrahydroisoquinolin-7-yl)oxo)propionic acid | 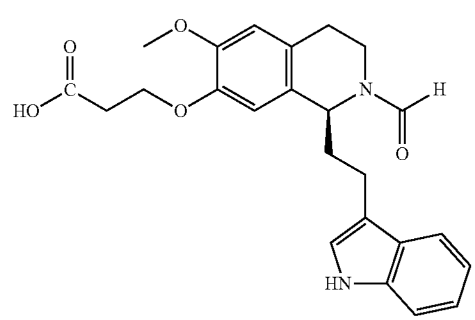 [SMILES: COc1cc2c(cc1OCCC(=O)O)[C@H](CCc1c[nH]c3ccccc13)N(C=O)CC2] |

| No. | Name | Structure |
|---|---|---|
| (R)-A7 | (R)-3-((1-(2-(1H-indol-3-yl)ethyl)-2-formyl-6-methoxy-1,2,3,4-tetrahydroisoquinolin-7-yl)oxo)propionic acid | 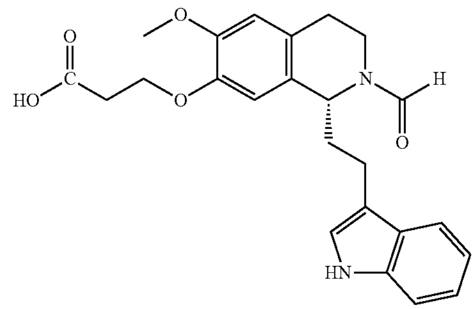 [SMILES: COc1cc2c(cc1OCCC(=O)O)[C@@H](CCc1c[nH]c3ccccc13)N(C=O)CC2] |
| A8 | 1-(2-(1H-indol-3-yl)ethyl)-7-ethoxy-6-(methoxy-d₃)-3,4-dihydroisoquinoline-2(1H)-formaldehyde | 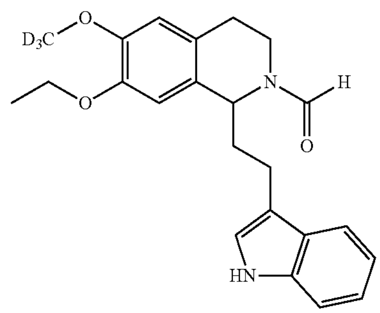 [SMILES: [2H]C([2H])([2H])Oc1cc2c(cc1OCC)C(CCc1c[nH]c3ccccc13)N(C=O)CC2] |
| (S)-A8 | (S)-1-(2-(1H-indol-3-yl)ethyl)-7-ethoxy-6-(methoxy-d₃)-3,4-dihydroisoquinoline-2(1H)-formaldehyde | 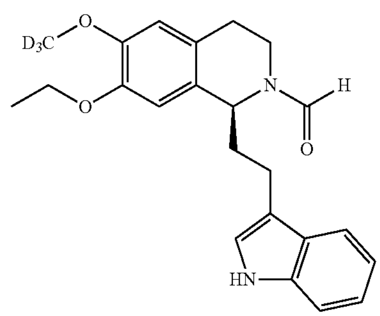 [SMILES: [2H]C([2H])([2H])Oc1cc2c(cc1OCC)[C@H](CCc1c[nH]c3ccccc13)N(C=O)CC2] |
| (R)-A8 | (R)-1-(2-(1H-indol-3-yl)ethyl)-7-ethoxy-6-(methoxy-d₃)-3,4-dihydroisoquinoline-2(1H)-formaldehyde | 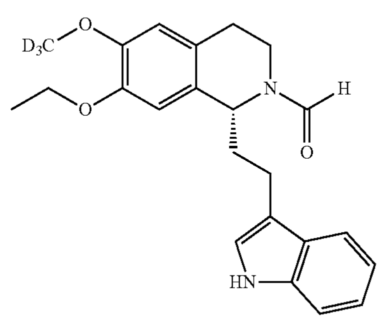 [SMILES: [2H]C([2H])([2H])Oc1cc2c(cc1OCC)[C@@H](CCc1c[nH]c3ccccc13)N(C=O)CC2] |
| B1 | (1-(2-(1H-indol-3-yl)ethyl)-6,7-dimethoxy-3,4-dihydroisoquinoline-2(1H)-yl)(pyridin-4-yl)methanone | 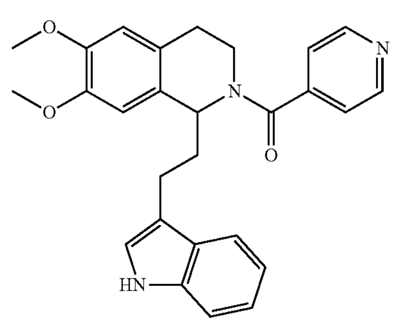 [SMILES: COc1cc2c(cc1OC)C(CCc1c[nH]c3ccccc13)N(C(=O)c1ccncc1)CC2] |

| No. | Name | Structure |
|---|---|---|
| (S)-B1 | (S)-(1-(2-(1H-indol-3-yl)ethyl)-6,7-dimethoxy-3,4-dihydroisoquinoline-2(1H)-yl)(pyridin4-yl)methanone | 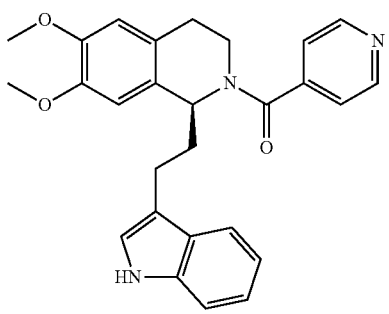 [SMILES: COc1cc2c(cc1OC)[C@H](CCc1c[nH]c3ccccc13)N(C(=O)c1ccncc1)CC2] |
| (R)-B1 | (R)-(1-(2-(1H-indol-3-yl)ethyl)-6,7-dimethoxy-3,4-dihydroisoquinoline-2(1H)-yl)(pyridin-4-yl)methanone | 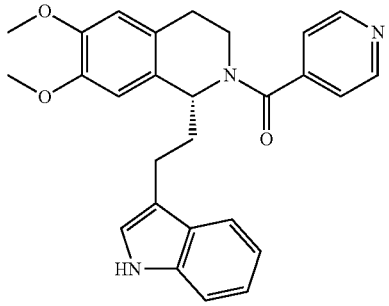 |
| B2 | 1-(2-(1H-indol-3-yl)ethyl)-6,7-dimethoxy-2-(2-methoxyethyl)-1,2,3,4-tetrahydroisoquinoline | 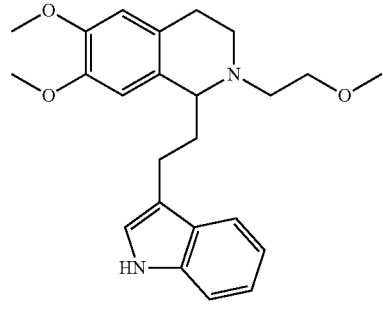 |
| (S)-B2 | (S)-1-(2-(1H-indol-3-yl)ethyl)-6,7-dimethoxy-2-(2-methoxyethyl)-1,2,3,4-tetrahydroisoquinoline | 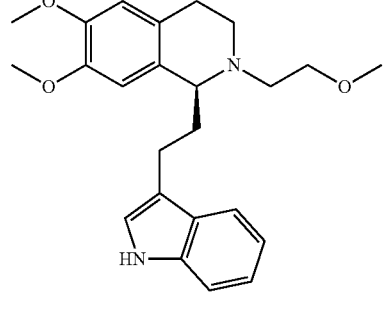 |
| (R)-B2 | (R)-1-(2-(1H-indol-3-yl)ethyl)-6,7-dimethoxy-2-(2-methoxyethyl)-1,2,3,4-tetrahydroisoquinoline | 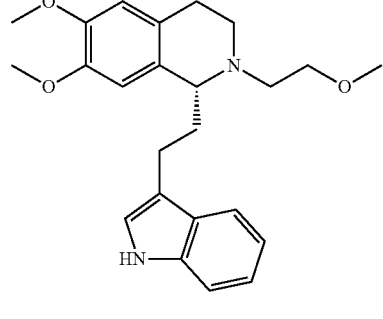 |

-continued

| No. | Name | Structure |
|---|---|---|
| B3 | (1-(2-(1H-indol-3-yl)ethoxy)-6,7-dimethoxy-3,4-dihydro-isoquinoline-2(1H)-yl)(tetrahydro-2H-pyran-4-yl)ketone | 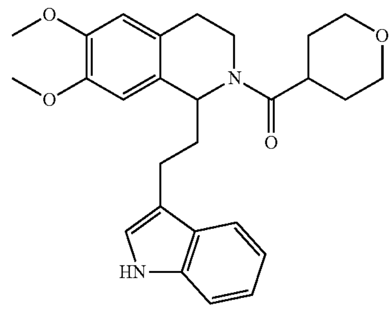 [SMILES: COc1cc2c(cc1OC)C(CCc1c[nH]c3ccccc13)N(C(=O)C1CCOCC1)CC2] |
| (S)-B3 | (S)-(1-(2-(1H-indol-3-yl)ethyl)-6,7-dimethoxy-3,4-dihydroisoquinoline-2(1H)-yl)(tetrahydro-2H-pyran-4-yl)methanone | 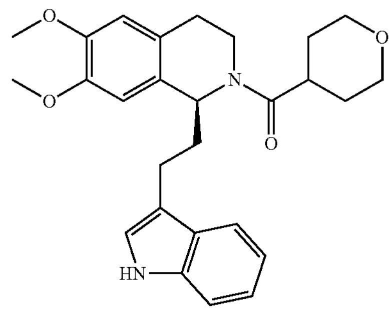 [SMILES: COc1cc2c(cc1OC)[C@H](CCc1c[nH]c3ccccc13)N(C(=O)C1CCOCC1)CC2] |
| (R)-B3 | (R)-(1-(2-(1H-indol-3-yl)ethyl)-6,7-dimethoxy-3,4-dihydroisoquinoline-2(1H)-yl)(tetrahydro-2H-pyran-4-yl)methanone | 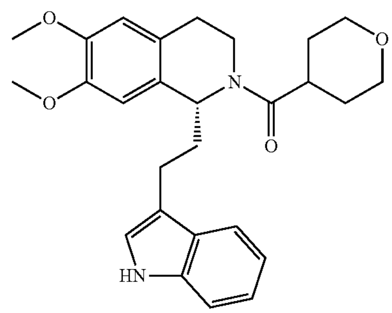 [SMILES: COc1cc2c(cc1OC)[C@@H](CCc1c[nH]c3ccccc13)N(C(=O)C1CCOCC1)CC2] |
| B4 | 1-(1-(2-(1H-indol-3-yl)ethyl)-6,7-dimethoxy-3,4-dihydroisoquinoline-2(1H)-yl)-2-methoxyethane-1-one | 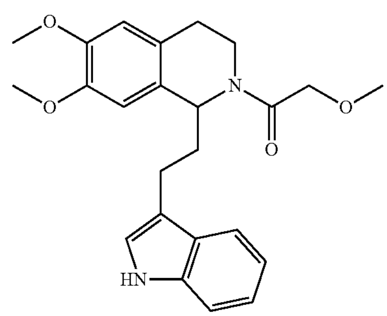 |
| (S)-B4 | (S)-1-(1-(2-(1H-indol-3-yl)ethyl)-6,7-dimethoxy-3,4-dihydroisoquinoline-2(1H)-yl)-2-methoxyethane-1-one | 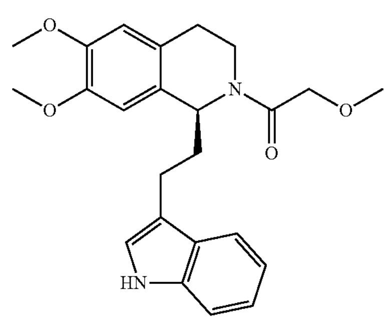 |

-continued

| No. | Name | Structure |
|---|---|---|
| (R)-B4 | (R)-1-(1-(2-(1H-indol-3-yl)ethyl)-6,7-dimethoxy-3,4-dihydroisoquinoline-2(1H)-yl)-2-methoxyethane-1-one | 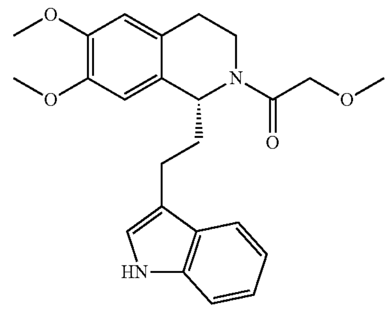 |
| B5 | methyl-2-(1-(2-(1H-indol-3-yl)ethyl)-6,7-dimethoxy-3,4-dihydroisoquinoline-2(1H)-yl)acetate | 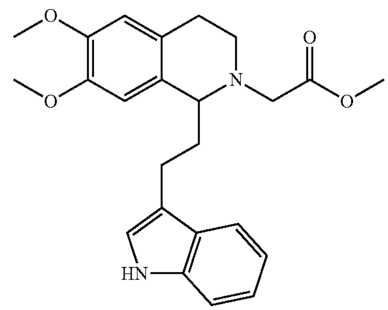 |
| (S)-B5 | (S)-methyl-2-(1-(2-(1H-indol-3-yl)ethyl)-6,7-dimethoxy-3,4-dihydroisoquinoline-2(1H)-yl)acetate | 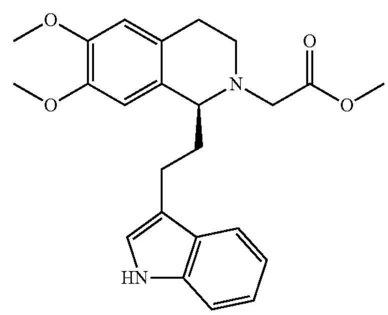 |
| (R)-B5 | (R)-methyl-2-(1-(2-(1H-indol-3-yl)ethyl)-6,7-dimethoxy-3,4-dihydroisoquinoline-2(1H)-yl)acetate | 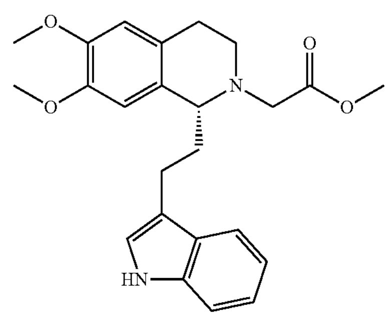 |
| B6 | 1-(2-(1H-indol-3-yl)ethyl)-6,7-dimethoxy-2-(2,2,2-trifluoroethyl)-1,2,3,4-tetrahydroisoquinoline | 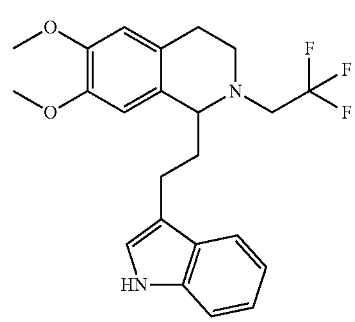 [SMILES: COc1cc2c(cc1OC)C(CCc1c[nH]c3ccccc13)N(CC(F)(F)F)CC2] |

| No. | Name | Structure |
|---|---|---|
| (S)-B6 | (S)-1-(2-(1H-indol-3-yl)ethyl)-6,7-dimethoxy-2-(2,2,2-trifluoroethyl)-1,2,3,4-tetrahydroisoquinoline | 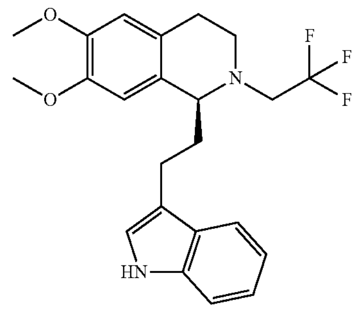 [SMILES: COc1cc2c(cc1OC)[C@H](CCc1c[nH]c3ccccc13)N(CC(F)(F)F)CC2] |
| (R)-B6 | (R)-1-(2-(1H-indol-3-yl)ethyl)-6,7-dimethoxy-2-(2,2,2-trifluoroethyl)-1,2,3,4-tetrahydroisoquinoline | 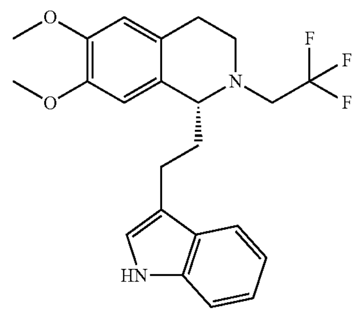 |
| B7 | 1-(2-(1H-indol-3-yl)ethyl)-6,7-dimethoxy-2-((tetrahydro-2H-pyran-4-yl)methyl)-1,2,3,4-tetrahydroisoquinoline | 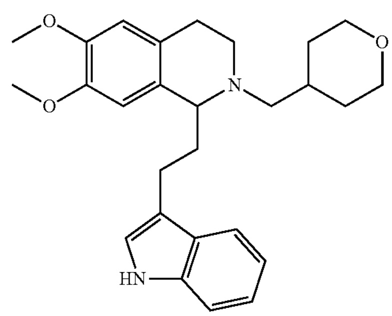 |
| (S)-B7 | (S)-1-(2-(1H-indol-3-yl)ethyl)-6,7-dimethoxy-2-((tetrahydro-2H-pyran-4-yl)methyl)-1,2,3,4-tetrahydroisoquinoline | 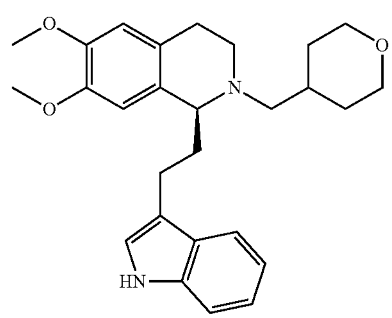 [SMILES: COc1cc2c(cc1OC)[C@H](CCc1c[nH]c3ccccc13)N(CC1CCOCC1)CC2] |
| (R)-B7 | (R)-1-(2-(1H-indol-3-yl)ethyl)-6,7-dimethoxy-2-((tetrahydro-2H-pyran-4-yl)methyl)-1,2,3,4-tetrahydroisoquinoline | 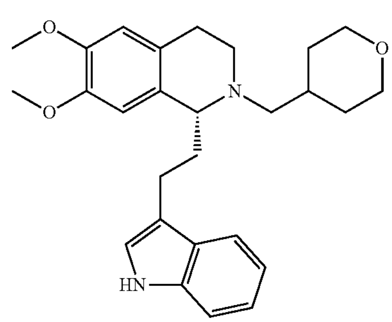 [SMILES: COc1cc2c(cc1OC)[C@@H](CCc1c[nH]c3ccccc13)N(CC1CCOCC1)CC2] |

-continued

| No. | Name | Structure |
|---|---|---|
| B8 | 1-(2-(1H-indol-3-yl)ethyl)-6,7-dimethoxy-2-(2-(methylsulfonyl)ethyl)-1,2,3,4-tetrahydroisoquinoline | 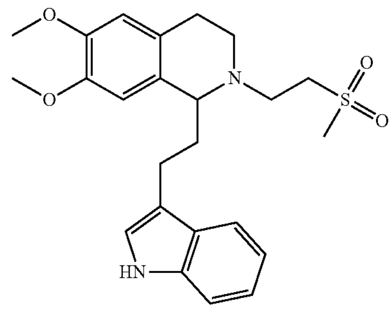 [SMILES: COc1cc2c(cc1OC)C(CCc1c[nH]c3ccccc13)N(CCS(C)(=O)=O)CC2] |
| (S)-B8 | (S)-1-(2-(1H-indol-3-yl)ethyl)-6,7-dimethoxy-2-(2-(methylsulfonyl)ethyl)-1,2,3,4-tetrahydroisoquinoline | 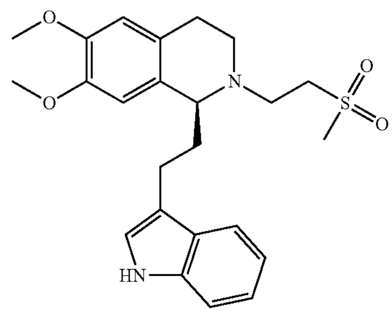 [SMILES: COc1cc2c(cc1OC)[C@H](CCc1c[nH]c3ccccc13)N(CCS(C)(=O)=O)CC2] |
| (R)-B8 | (R) 1-(2-(1H-indol-3-yl)ethyl)-6,7-dimethoxy-2-(2-(methylsulfonyl)ethyl)-1,2,3,4-tetrahydroisoquinoline | 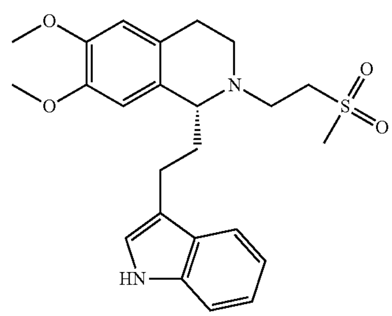 |
| B9 | 1-(2-(1H-indol-3-yl)ethyl)-6,7-dimethoxy-3,4-dihydroisoquinolin-2(1H)-yl)-2-(methanesulfonyl)ethane-1-one | 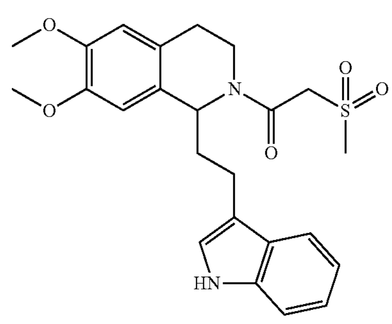 [SMILES: COc1cc2c(cc1OC)C(CCc1c[nH]c3ccccc13)N(C(=O)CS(C)(=O)=O)CC2] |
| (S)-B9 | (S)-1-(2-(1H-indol-3-yl)ethyl)-6,7-dimethoxy-3,4-dihydroisoquinoline-2(1H)-yl)-2-(methanesulfonyl)ethane-1-one | 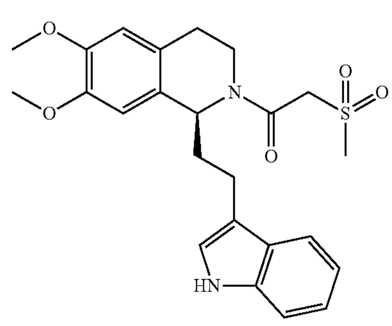 [SMILES: COc1cc2c(cc1OC)[C@H](CCc1c[nH]c3ccccc13)N(C(=O)CS(C)(=O)=O)CC2] |

| No. | Name | Structure |
|---|---|---|
| (R)-B9 | (R)-1-(2-(1H-indol-3-yl)ethyl)-6,7-dimethoxy-3,4-dihydroisoquinoline-2(1H)-yl)-2-(methanesulfonyl)ethane-1-one | 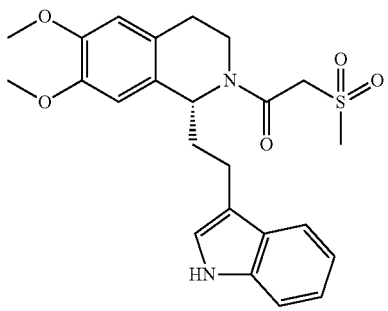 [SMILES: COc1cc2c(cc1OC)[C@@H](CCc1c[nH]c3ccccc13)N(C(=O)CS(C)(=O)=O)CC2] |
| B10 | 1-(1-(2-(1H-indol-3-yl)ethyl)-6,7-dimethoxy-3,4-dihydroisoquinoline-2(1H)-yl)-2,2,2-trifluoroethane-1-one | 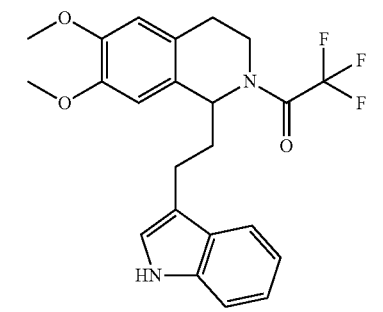 [SMILES: COc1cc2c(cc1OC)C(CCc1c[nH]c3ccccc13)N(C(=O)C(F)(F)F)CC2] |
| (S)-B10 | (S)-1-(1-(2-(1H-indol-3-yl)ethyl)-6,7-dimethoxy-3,4-dihydroisoquinoline-2(1H)-yl)-2,2,2-trifluoroethane-1-one | 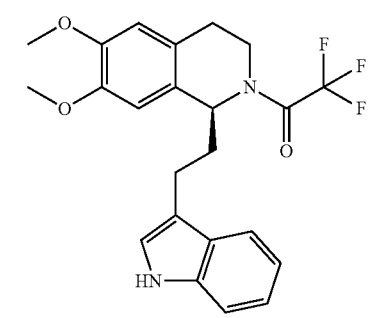 [SMILES: COc1cc2c(cc1OC)[C@H](CCc1c[nH]c3ccccc13)N(C(=O)C(F)(F)F)CC2] |
| (R)-B10 | (R) 1-(1-(2-(1H-indol-3-yl)ethyl)-6,7-dimethoxy-3,4-dihydroisoquinoline-2(1H)-yl)-2,2,2-trifluoroethane-1-one | 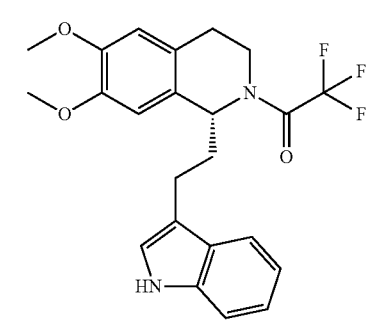 |
| B11 | 1-(1-(2-(1H-indol-3-yl)ethyl)-6,7-dimethoxy-3,4-dihydroisoquinoline-2(1H)-yl)-2-methoxyethane-1-one | 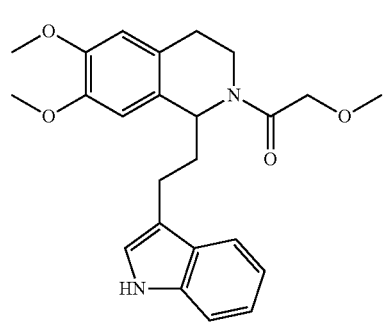 |

-continued

| No. | Name | Structure |
|---|---|---|
| (S)-B11 | (S)-1-(1-(2-(1H-indol-3-yl)ethyl)-6,7-dimethoxy-3,4-dihydroisoquinoline-2(1H)-yl)-2-methoxyethane-1-one | 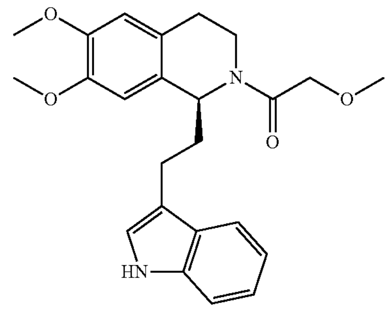 |
| (R)-B11 | (R)-1-(1-(2-(1H-indol-3-yl)ethyl)-6,7-dimethoxy-3,4-dihydroisoquinoline-2(1H)-yl)-2-methoxyethane-1-one | 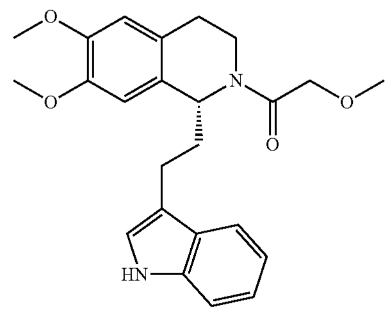 |
| B12 | 1-(1-(2-(1H-indol-3-yl)ethyl)-7-ethoxy-6-methoxy-3,4-dihydroisoquinoline-2(1H)-yl)-2-methoxyethane-1-one | 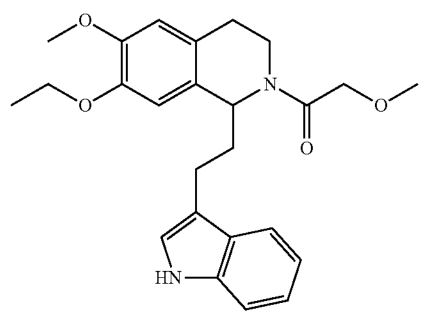 [SMILES: CCOc1cc2c(cc1OC)CCN(C(=O)COC)C2CCc1c[nH]c2ccccc12] |
| (S)-B12 | (S)-1-(1-(2-(1H-indol-3-yl)ethyl)-7-ethoxy-6-methoxy-3,4-dihydroisoquinoline-2(1H)-yl)-2-methoxyethane-1-one | 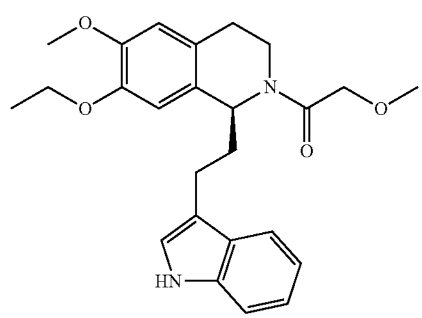 [SMILES: CCOc1cc2c(cc1OC)CCN(C(=O)COC)[C@H]2CCc1c[nH]c2ccccc12] |
| (R)-B12 | (R) 1-(1-(2-(1H-indol-3-yl)ethyl)-7-ethoxy-6-methoxy-3,4-dihydroisoquinoline-2(1H)-yl)-2-methoxyethane-1-one | 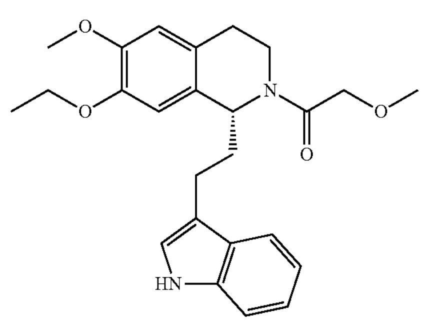 [SMILES: CCOc1cc2c(cc1OC)CCN(C(=O)COC)[C@@H]2CCc1c[nH]c2ccccc12] |

| No. | Name | Structure |
| --- | --- | --- |
| B13 | 1-(2-(1H-indol-3-yl)ethyl)-6,7-dimethoxy-2-(methylsulfonyl)-1,2,3,4-tetrahydroisoquinoline | 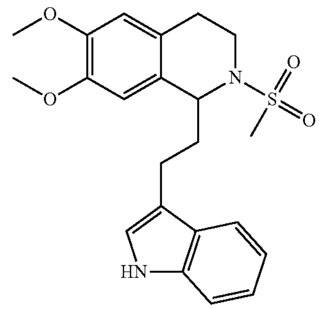 [SMILES: COc1cc2c(cc1OC)C(CCc1c[nH]c3ccccc13)N(S(C)(=O)=O)CC2] |
| (S)-B13 | (S)-1-(2-(1H-indol-3-yl)ethyl)-6,7-dimethoxy-2-(methylsulfonyl)-1,2,3,4-tetrahydroisoquinoline | 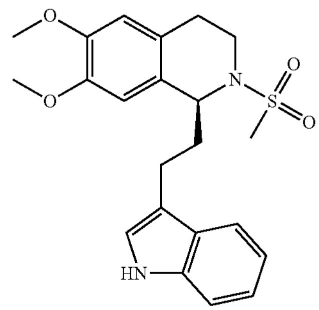 [SMILES: COc1cc2c(cc1OC)[C@H](CCc1c[nH]c3ccccc13)N(S(C)(=O)=O)CC2] |
| (R)-B13 | (R)-1-(2-(1H-indol-3-yl)ethyl)-6,7-dimethoxy-2-(methylsulfonyl)ethyl)-1,2,3,4-tetrahydroisoquinoline | 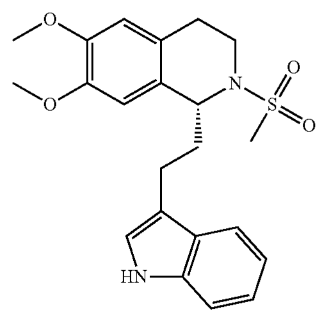 [SMILES: COc1cc2c(cc1OC)[C@@H](CCc1c[nH]c3ccccc13)N(S(C)(=O)=O)CC2] |
| B14 | (1-(2-(1H-indol-3-yl)ethyl)-6,7-dimethoxy-3,4-dihydroisoquinoline-2(1H)-yl)(morpholino)ketone | 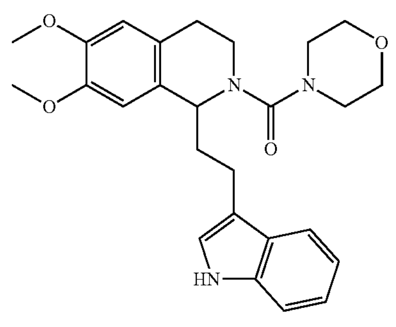 [SMILES: COc1cc2c(cc1OC)C(CCc1c[nH]c3ccccc13)N(C(=O)N1CCOCC1)CC2] |
| (S)-B14 | (S)-(1-(2-(1H-indol-3-yl)ethyl)-6,7-dimethoxy-3,4-dihydroisoquinoline-2(1H)-yl)(morpholino)ketone | 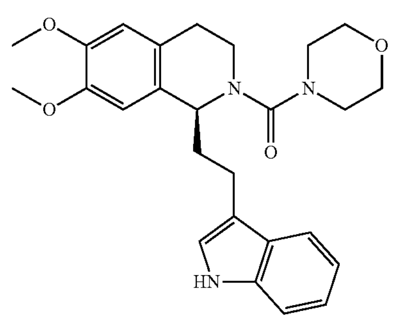 [SMILES: COc1cc2c(cc1OC)[C@H](CCc1c[nH]c3ccccc13)N(C(=O)N1CCOCC1)CC2] |

| No. | Name | Structure |
| --- | --- | --- |
| (R)-B14 | (R)-(1-(2-(1H-indol-3-yl)ethyl)-6,7-dimethoxy-3,4-dihydroisoquinoline-2(1H)-yl)(morpholino)ketone | 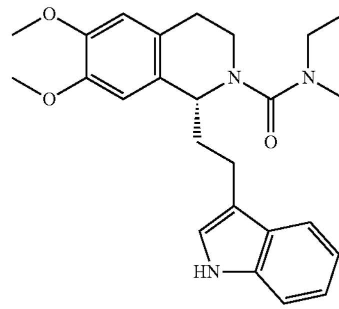 |
| B15 | methyl-1-(2-(1H-indol-3-yl)ethyl)-6,7-dimethoxy-3,4-dihydroisoquinoline-2(1H)-carboxylate | 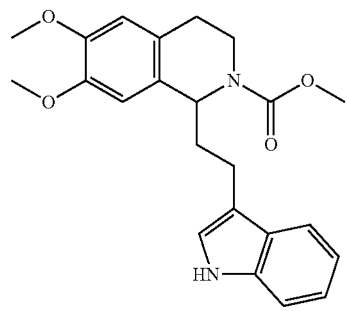 |
| (S)-B15 | (S)-methyl-1-(2-(1H-indol-3-yl)ethyl)-6,7-dimethoxy-3,4-dihydroisoquinoline-2(1H)-carboxylate | 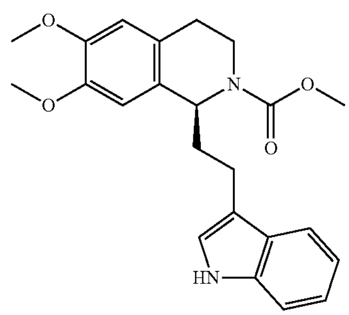 |
| (R)-B15 | (R)-methyl-1-(2-(1H-indol-3-yl)ethyl)-6,7-dimethoxy-3,4-dihydroisoquinoline-2(1H)-carboxylate | 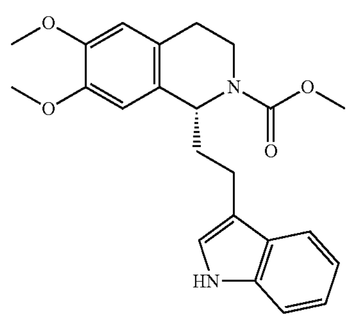 |
| B16 | 2-(1-(2-(1H-indol-3-yl)ethyl)-7-ethoxy-6-methoxy-3,4-dihydroisoquinoline-2(1H)-yl)acetamide | 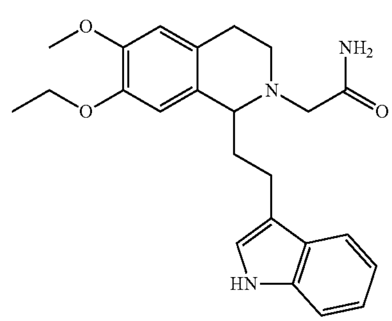 [SMILES: CCOc1cc2c(cc1OC)CCN(CC(N)=O)C2CCc1c[nH]c2ccccc12] |

-continued

| No. | Name | Structure |
|---|---|---|
| (S)-B16 | (S)-2-(1-(2-(1H-indol-3-yl)ethyl)-7-ethoxy-6-methoxy-3,4-dihydroisoquinoline-2(1H)-yl)acetamide | 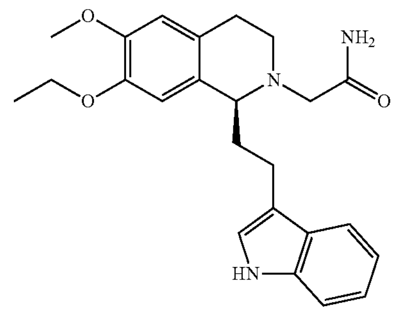 [SMILES: CCOc1cc2c(cc1OC)CCN(CC(N)=O)[C@H]2CCc1c[nH]c2ccccc12] |
| (R)-B16 | (R)-2-(1-(2-(1H-indol-3-yl)ethyl)-7-ethoxy-6-methoxy-3,4-dihydroisoquinoline-2(1H)-yl)acetamide | 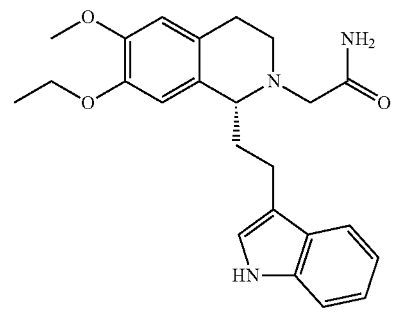 [SMILES: CCOc1cc2c(cc1OC)CCN(CC(N)=O)[C@@H]2CCc1c[nH]c2ccccc12] |
| C1 | 1-(2-(5-bromo-1H-indol-3-yl)ethyl)-7-(cyclopentyloxy)-6-methoxy-3,4-dihydroisoquinoline-2(1H)-formaldehyde | 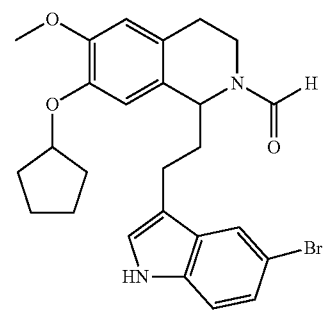 |
| (S)-C1 | (S)-1-(2-(5-bromo-1H-indol-3-yl)ethyl)-7-(cyclopentyloxy)-6-methoxy-3,4-dihydroisoquinoline-2(1H)-formaldehyde | 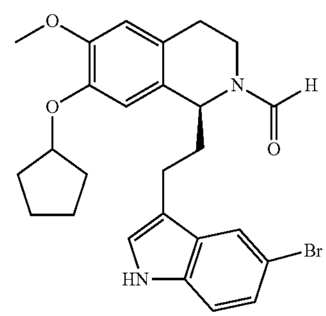 [SMILES: COc1cc2c(cc1OC1CCCC1)[C@H](CCc1c[nH]c3ccc(Br)cc13)N(C=O)CC2] |
| (R)-C1 | (R)-1-(2-(5-bromo-1H-indol-3-yl)ethyl)-7-(cyclopentyloxy)-6-methoxy-3,4-dihydroisoquinoline-2(1H)-formaldehyde | 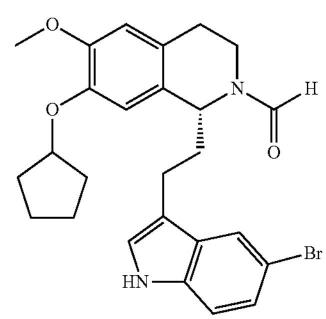 |

-continued

| No. | Name | Structure |
|---|---|---|
| C2 | 7-(cyclopentyloxy)-6-methoxy-1-(2-(5-methyl-1H-indol-3-yl)ethyl)-3,4-dihydroisoquinoline-2(1H)-formaldehyde | 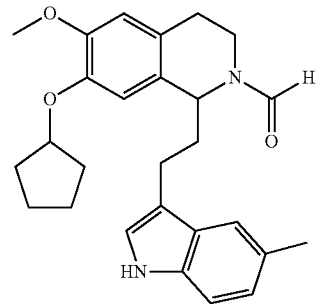 |
| (S)-C2 | (S)-7-(cyclopentyloxy)-6-methoxy-1-(2-(5-methyl-1H-indol-3-yl)ethyl)-3,4-dihydroisoquinoline-2(1H)-formaldehyde | 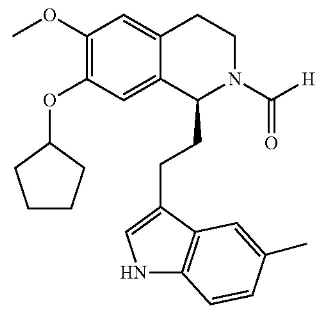 [SMILES: COc1cc2c(cc1OC1CCCC1)[C@H](CCc1c[nH]c3ccc(C)cc13)N(C=O)CC2] |
| (R)-C2 | (R)-7-(cyclopentyloxy)-6-methoxy-1-(2-(5-methyl-1H-indol-3-yl)ethyl)-3,4-dihydroisoquinoline-2(1H)-formaldehyde | 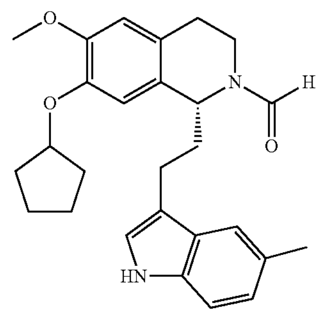 |
| C3 | 7-(cyclopentyloxy)-6-methoxy-1-(2-(6-methyl-1H-indol-3-yl)ethyl)-3,4-dihydroisoquinoline-2(1H)-formaldehyde | 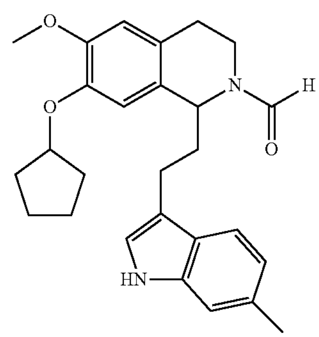 |
| (S)-C3 | (S)-7-(cyclopentyloxy)-6-methoxy-1-(2-(6-methyl-1H-indol-3-yl)ethyl)-3,4-dihydroisoquinoline-2(1H)-formaldehyde | 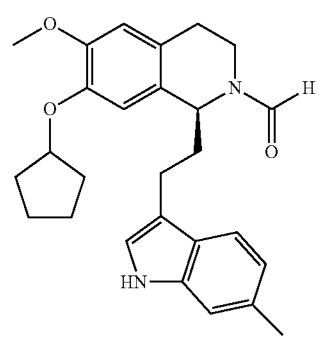 [SMILES: COc1cc2c(cc1OC1CCCC1)[C@H](CCc1c[nH]c3cc(C)ccc13)N(C=O)CC2] |

| No. | Name | Structure |
|---|---|---|
| (R)-C3 | (R)-7-(cyclopentyloxy)-6-methoxy-1-(2-(6-methyl-1H-indol-3-yl)ethyl)-3,4-dihydroisoquinolin-2(1H)-formaldehyde | 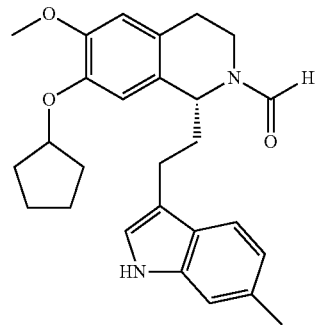 |
| C4 | 7-(cyclopropylmethoxy)-6-methoxy-1-(2-(6-methyl-1H-indol-3-yl)ethyl)-3,4-dihydroisoquinoline-2(1H)-formaldehyde | 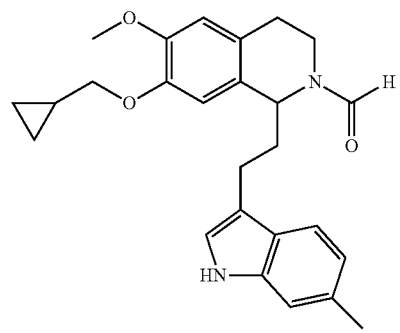 [SMILES: COc1cc2c(cc1OCC1CC1)C(CCc1c[nH]c3cc(C)ccc13)N(C=O)CC2] |
| (S)-C4 | (S)-7-(cyclopropylmethoxy)-6-methoxy-1-(2-(6-methyl-1H-indol-3-yl)ethyl)-3,4-dihydroisoquinoline-2(1H)-formaldehyde | 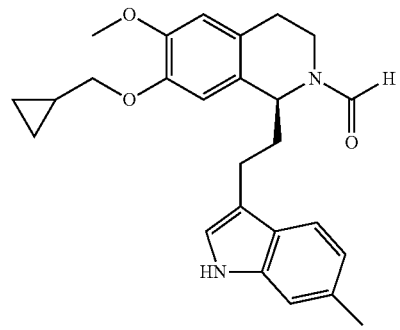 [SMILES: COc1cc2c(cc1OCC1CC1)[C@H](CCc1c[nH]c3cc(C)ccc13)N(C=O)CC2] |
| (R)-C4 | (R)-7-(cyclopropylmethoxy)-6-methoxy-1-(2-(6-methyl-1H-indol-3-yl)ethyl)-3,4-dihydroisoquinoline-2(1H)-formaldehyde | 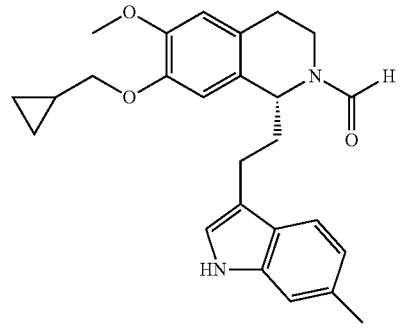 [SMILES: COc1cc2c(cc1OCC1CC1)[C@@H](CCc1c[nH]c3cc(C)ccc13)N(C=O)CC2] |

| No. | Name | Structure |
|---|---|---|
| C5 | 6,7-dimethoxy-1-(2-(6-methyl-1H-indol-3-yl)ethyl)-3,4-dihydroisoquinoline-2(1H)-formaldehyde | 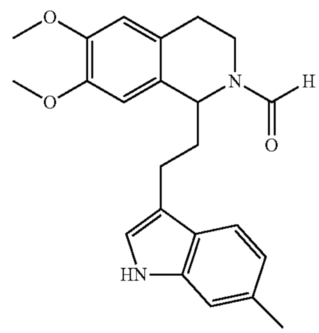 [SMILES: COc1cc2c(cc1OC)C(CCc1c[nH]c3cc(C)ccc13)N(C=O)CC2] |
| (S)-C5 | (S)-6,7-dimethoxy-1-(2-(6-methyl-1H-indol-3-yl)ethyl)-3,4-dihydroisoquinoline-2(1H)-formaldehyde | 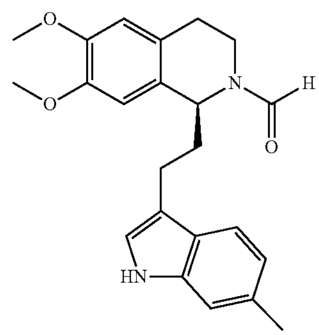 [SMILES: COc1cc2c(cc1OC)[C@H](CCc1c[nH]c3cc(C)ccc13)N(C=O)CC2] |
| (R)-C5 | (R)-6,7-dimethoxy-1-(2-(6-methyl-1H-indol-3-yl)ethyl)-3,4-dihydroisoquinoline-2(1H)-formaldehyde | 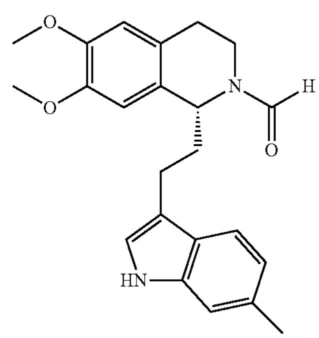 [SMILES: COc1cc2c(cc1OC)[C@@H](CCc1c[nH]c3cc(C)ccc13)N(C=O)CC2] |
| C6 | 1-(2-(6-fluoro-1H-indol-3-yl)ethyl)-6,7-dimethoxy-3,4-dihydroisoquinoline-2(1H)-formaldehyde | 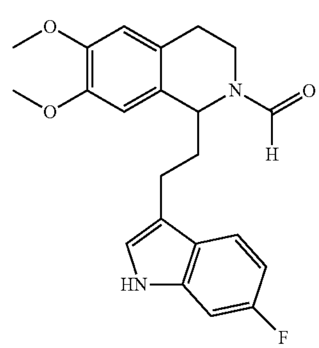 [SMILES: COc1cc2c(cc1OC)C(CCc1c[nH]c3cc(F)ccc13)N(C=O)CC2] |

| No. | Name | Structure |
|---|---|---|
| (S)-C6 | (S)-1-(2-(6-fluoro-1H-indol-3-yl)ethyl)-6,7-dimethoxy-3,4-dihydroisoquinoline-2(1H)-formaldehyde | 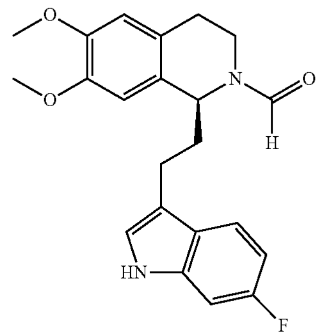 [SMILES: COc1cc2c(cc1OC)[C@H](CCc1c[nH]c3cc(F)ccc13)N(C=O)CC2] |
| (R)-C6 | (R)-1-(2-(6-fluoro-1H-indol-3-yl)ethyl)-6,7-dimethoxy-3,4-dihydroisoquinoline-2(1H)-formaldehyde | 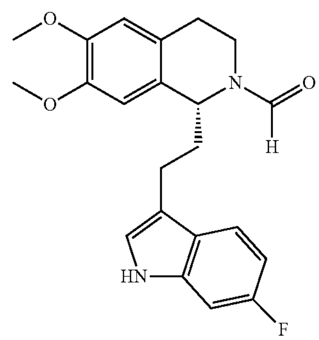 |
| C7 | 7-ethoxy-6-methoxy-1-(2-(6-methyl-1H-indol-3-yl)ethyl)-3,4-dihydroisoquinoline-2(1H)-formaldehyde | 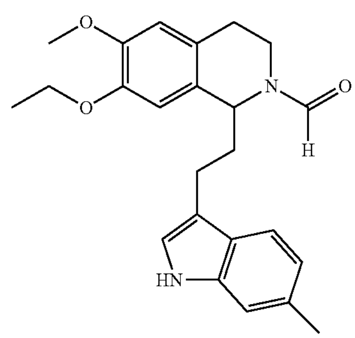 [SMILES: CCOc1cc2c(cc1OC)CCN(C=O)C2CCc1c[nH]c2cc(C)ccc12] |
| (S)-C7 | (S)-7-ethoxy-6-methoxy-1-(2-(6-methyl-1H-indol-3-yl)ethyl)-3,4-dihydroisoquinoline-2(1H)-formaldehyde | 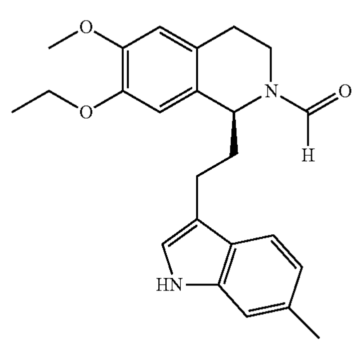 [SMILES: CCOc1cc2c(cc1OC)CCN(C=O)[C@H]2CCc1c[nH]c2cc(C)ccc12] |

-continued

| No. | Name | Structure |
|---|---|---|
| (R)-C7 | (R)-7-ethoxy-6-methoxy-1-(2-(6-methyl-1H-indol-3-yl)ethyl)-3,4-dihydroisoquinoline-2(1H)-formaldehyde | 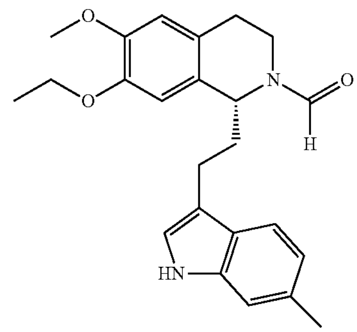 |
| C8 | 7-ethoxy-6-methoxy-1-(2-(5-methoxy-1H-indol-3-yl)ethyl)-3,4-dihydroisoquinoline-2(1H)-formaldehyde | 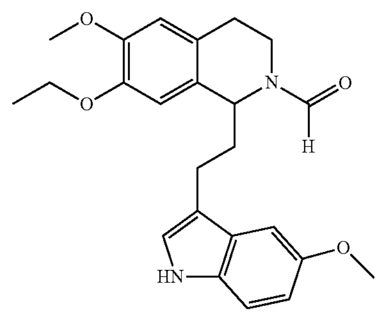 [SMILES: CCOc1cc2c(cc1OC)CCN(C=O)C2CCc1c[nH]c2ccc(OC)cc12] |
| (S)-C8 | (S)-7-ethoxy-6-methoxy-1-(2-(5-methoxy-1H-indol-3-yl)ethyl)-3,4-dihydroisoquinoline-2(1H)-formaldehyde | 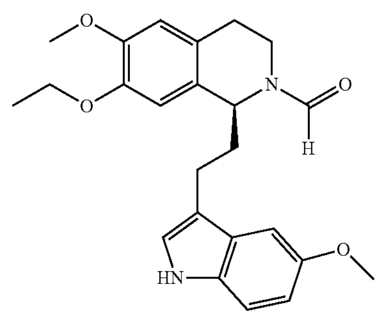 [SMILES: CCOc1cc2c(cc1OC)CCN(C=O)[C@H]2CCc1c[nH]c2ccc(OC)cc12] |
| (R)-C8 | (R)-7-ethoxy-6-methoxy-1-(2-(5-methoxy-1H-indol-3-yl)ethyl)-3,4-dihydroisoquinoline-2(1H)-formaldehyde | 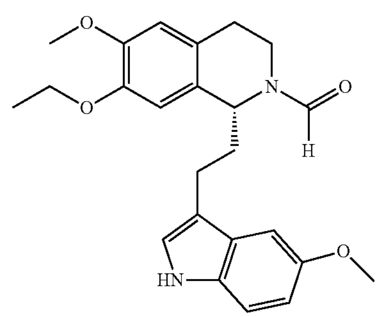 [SMILES: CCOc1cc2c(cc1OC)CCN(C=O)[C@@H]2CCc1c[nH]c2ccc(OC)cc12] |
| C9 | 1-((1H-indol-3-yl)methyl)-6,7-dimethoxy-3,4-dihydroisoquinoline-2(1H)-formaldehyde | 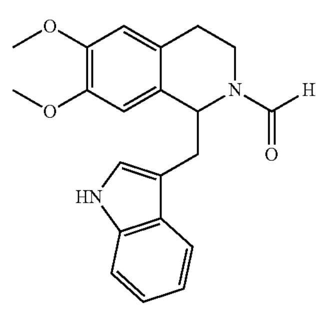 [SMILES: COc1cc2c(cc1OC)C(Cc1c[nH]c3ccccc13)N(C=O)CC2] |

-continued

| No. | Name | Structure |
|---|---|---|
| (S)-C9 | (S)-1-((1H-indol-3-yl)methyl)-6,7-dimethoxy-3,4-dihydroisoquinoline-2(1H)-formaldehyde | 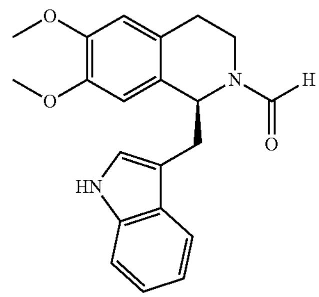 [SMILES: COc1cc2c(cc1OC)[C@H](Cc1c[nH]c3ccccc13)N(C=O)CC2] |
| (R)-C9 | (R)-1-((1H-indol-3-yl)methyl)-6,7-dimethoxy-3,4-dihydroisoquinoline-2(1H)-formaldehyde | 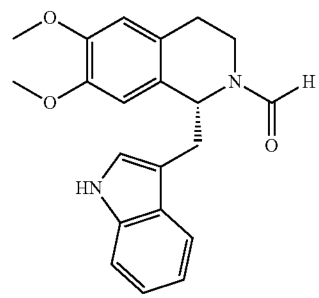 [SMILES: COc1cc2c(cc1OC)[C@@H](Cc1c[nH]c3ccccc13)N(C=O)CC2] |
| C10 | 1-((1H-indol-3-yl)methyl)-7-ethoxy-6-methoxy-3,4-dihydroisoquinoline-2(1H)-formaldehyde | 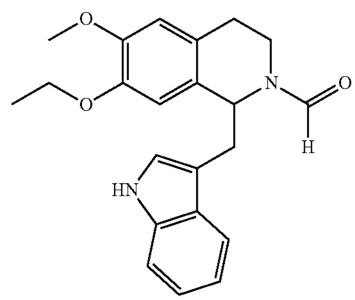 [SMILES: CCOc1cc2c(cc1OC)CCN(C=O)C2Cc1c[nH]c2ccccc12] |
| (S)-C10 | (S)-1-((1H-indol-3-yl)methyl)-7-ethoxy-6-methoxy-3,4-dihydroisoquinoline-2(1H)-formaldehyde | 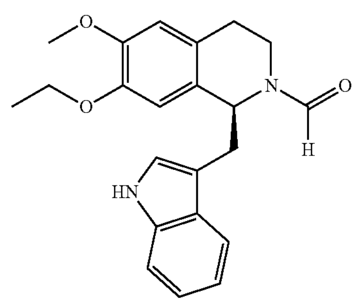 [SMILES: CCOc1cc2c(cc1OC)CCN(C=O)[C@H]2Cc1c[nH]c2ccccc12] |
| (R)-C10 | (R)-1-((1H-indol-3-yl)methyl)-7-ethoxy-6-methoxy-3,4-dihydroisoquinoline-2(1H)-formaldehyde | 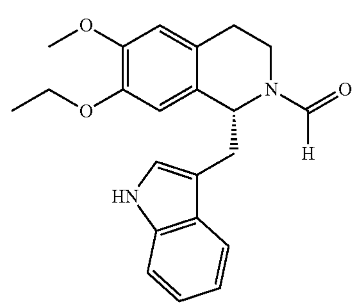 |

| No. | Name | Structure |
| --- | --- | --- |
| C11 | 1-(1-((1H-indol-3-yl)methyl)-6,7-dimethoxy-3,4-dihydroisoquinoline-2(1H)-yl)-2-methoxyethane-1-one | 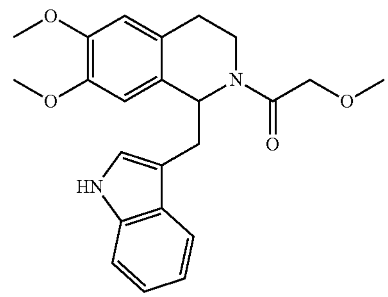 |
| (S)-C11 | (S)-1-(1-((1H-indol-3-yl)methyl)-6,7-dimethoxy-3,4-dihydroisoquinoline-2(1H)-yl)-2-methoxyethane-1-one | 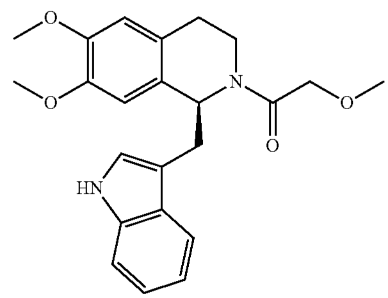 |
| (R)-C11 | (R)-1-(1-((1H-indol-3-yl)methyl)-6,7-dimethoxy-3,4-dihydroisoquinoline-2(1H)-yl)-2-methoxyethane-1-one | 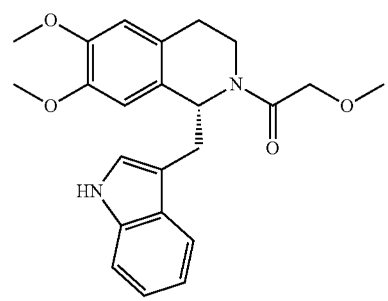 |
| C12 | 1-((1H-indol-3-yl)methyl)-6,7-dimethoxy-2-(2-(methylsulfonyl)ethyl)-1,2,3,4-tetrahydroisoquinoline | 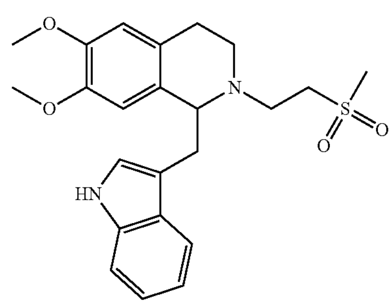 [SMILES: COc1cc2c(cc1OC)C(Cc1c[nH]c3ccccc13)N(CCS(C)(=O)=O)CC2] |
| (S)-C12 | (S)-1-((1H-indol-3-yl)methyl)-6,7-dimethoxy-2-(2-(methylsulfonyl)ethyl)-1,2,3,4-tetrahydroisoquinoline | 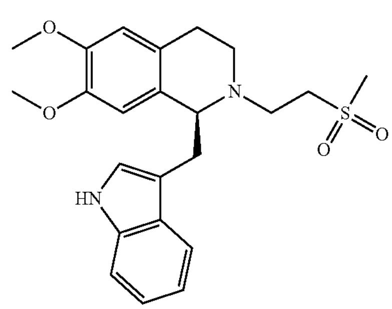 [SMILES: COc1cc2c(cc1OC)[C@H](Cc1c[nH]c3ccccc13)N(CCS(C)(=O)=O)CC2] |

| No. | Name | Structure |
| --- | --- | --- |
| (R)-C12 | (R)-1-((1H-indol-3-yl)methyl)-6,7-dimethoxy-2-(2-(methylsulfonyl)ethyl)-1,2,3,4-tetrahydroisoquinoline | 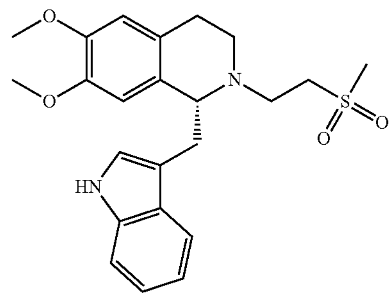 [SMILES: COc1cc2c(cc1OC)[C@@H](Cc1c[nH]c3ccccc13)N(CCS(C)(=O)=O)CC2] |
| C13 | 1-(1-((1H-indol-3-yl)methyl)-6,7-dimethoxy-3,4-dihydroisoquinoline-2(1H)-yl)-2-(methanesulfonyl)ethane-1-one | 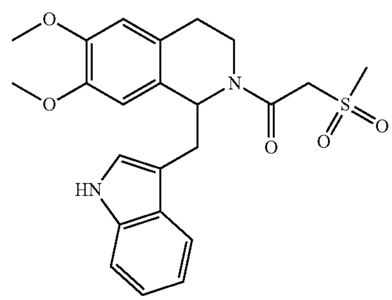 [SMILES: COc1cc2c(cc1OC)C(Cc1c[nH]c3ccccc13)N(C(=O)CS(C)(=O)=O)CC2] |
| (S)-C13 | (S)-1-(1-((1H-indol-3-yl)methyl)-6,7-dimethoxy-3,4-dihydroisoquinoline-2(1H)-yl)-2-(methanesulfonyl)ethane-1-one | 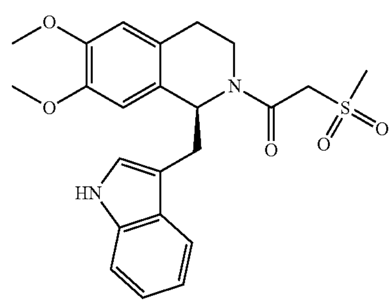 [SMILES: COc1cc2c(cc1OC)[C@H](Cc1c[nH]c3ccccc13)N(C(=O)CS(C)(=O)=O)CC2] |
| (R)-C13 | (R)-1-(1-((1H-indol-3-yl)methyl)-6,7-dimethoxy-3,4-dihydroisoquinoline-2(1H)-yl)-2-(methanesulfonyl)ethane-1-one | 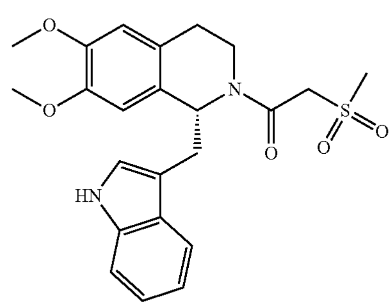 [SMILES: COc1cc2c(cc1OC)[C@@H](Cc1c[nH]c3ccccc13)N(C(=O)CS(C)(=O)=O)CC2] |
| C14 | 1-((1H-indol-3-yl)methyl)-7-ethoxy-6-methoxy-2-(2-(methylsulfonyl)ethyl)-1,2,3,4-tetrahydroisoquinoline | 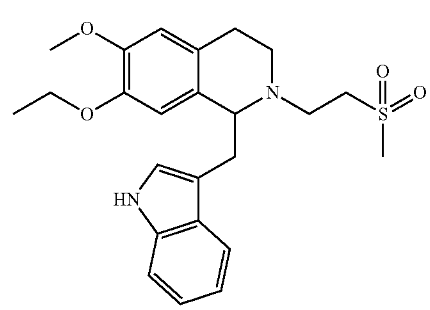 [SMILES: CCOc1cc2c(cc1OC)CCN(CCS(C)(=O)=O)C2Cc1c[nH]c2ccccc12] |

-continued

| No. | Name | Structure |
|---|---|---|
| (S)-C14 | (S)-1-((1H-indol-3-yl)methyl)-7-ethoxy-6-methoxy-2-(2-(methylsulfonyl)ethyl)-1,2,3,4-tetrahydroisoquinoline | 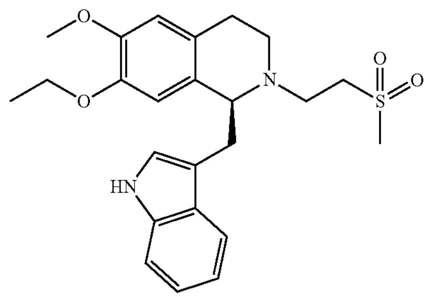 [SMILES: CCOc1cc2c(cc1OC)CCN(CCS(C)(=O)=O)[C@H]2Cc1c[nH]c2ccccc12] |
| (R)-C14 | (R)-1-((1H-indol-3-yl)methyl)-7-ethoxy-6-methoxy-2-(2-(methylsulfonyl)ethyl)-1,2,3,4-tetrahydroisoquinoline | 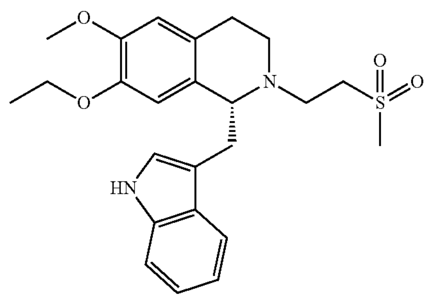 [SMILES: CCOc1cc2c(cc1OC)CCN(CCS(C)(=O)=O)[C@@H]2Cc1c[nH]c2ccccc12] |
| C15 | 1-(1-((1H-indol-3-yl)methyl)-7-ethoxy-6-methoxy-3,4-dihydroisoquinoline-2(1H)-yl)-2-(methanesulfonyl)ethane-1-one | 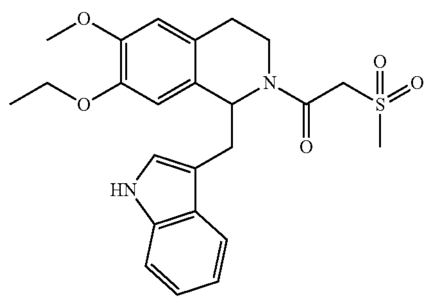 [SMILES: CCOc1cc2c(cc1OC)CCN(C(=O)CS(C)(=O)=O)C2Cc1c[nH]c2ccccc12] |
| (S)-C15 | (S)-1-(1-((1H-indol-3-yl)methyl)-7-ethoxy-6-methoxy-3,4-dihydroisoquinoline-2(1H)-yl)-2-(methanesulfonyl)ethane-1-one | 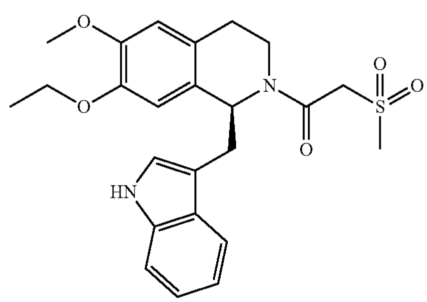 [SMILES: CCOc1cc2c(cc1OC)CCN(C(=O)CS(C)(=O)=O)[C@H]2Cc1c[nH]c2ccccc12] |
| (R)-C15 | (R)-1-(1-((1H-indol-3-yl)methyl)-7-ethoxy-6-methoxy-3,4-dihydroisoquinoline-2(1H)-yl)-2-(methanesulfonyl)ethane-1-one | 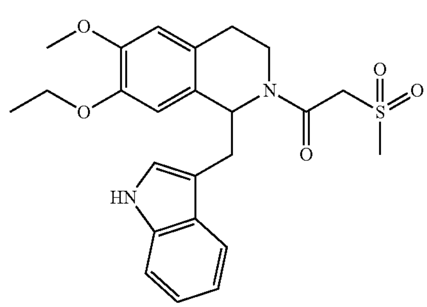 [SMILES: CCOc1cc2c(cc1OC)CCN(C(=O)CS(C)(=O)=O)C2Cc1c[nH]c2ccccc12] |

| No. | Name |
|---|---|
| C16 | 1-(1-((1H-indol-3-yl)methyl)-7-ethoxy-6-methoxy-3,4-dihydroisoquinoline-2(1H)-yl)-2-methoxyethane-1-one |
| (S)-C16 | (S)-1-(1-((1H-indol-3-yl)methyl)-7-ethoxy-6-methoxy-3,4-dihydroisoquinoline-2(1H)-yl)-2-methoxyethane-1-one |
| (R)-C16 | (R)-1-(1-((1H-indol-3-yl)methyl)-7-ethoxy-6-methoxy-3,4-dihydroisoquinoline-2(1H)-yl)-2-methoxyethane-1-one |
| C17 | 7-ethoxy-6-methoxy-1-((5-methyl-1H-indol-3-yl)methyl)-3,4-dihydroisoquinoline-2(1H)-formaldehyde |
| (S)-C17 | (S)-7-ethoxy-6-methoxy-1-((5-methyl-1H-indol-3-yl)methyl)-3,4-dihydroisoquinoline-2(1H)-formaldehyde |

-continued

| No. | Name | Structure |
|---|---|---|
| (R)-C17 | (R)-7-ethoxy-6-methoxy-1-((5-methyl-1H-indol-3-yl)methyl)-3,4-dihydroisoquinoline-2(1H)-formaldehyde | 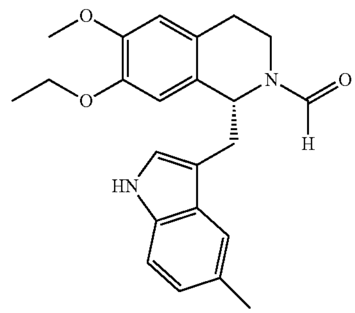 [SMILES: CCOc1cc2c(cc1OC)CCN(C=O)[C@@H]2Cc1c[nH]c2ccc(C)cc12] |
| C18 | 7-ethoxy-6-methoxy-1-((5-methoxy-1H-indol-3-yl)methyl)-3,4-dihydroisoquinoline-2(1H)-formaldehyde | 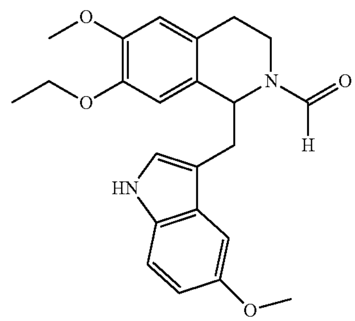 [SMILES: CCOc1cc2c(cc1OC)CCN(C=O)C2Cc1c[nH]c2ccc(OC)cc12] |
| (S)-C18 | (S)-7-ethoxy-6-methoxy-1-((5-methoxy-1H-indol-3-yl)methyl)-3,4-dihydroisoquinoline-2(1H)-formaldehyde | 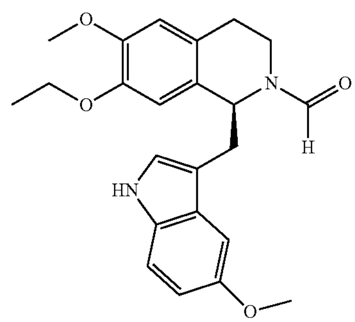 [SMILES: CCOc1cc2c(cc1OC)CCN(C=O)[C@H]2Cc1c[nH]c2ccc(OC)cc12] |
| (R)-C18 | (R)-7-ethoxy-6-methoxy-1-((5-methoxy-1H-indol-3-yl)methyl)-3,4-dihydroisoquinoline-2(1H)-formaldehyde | 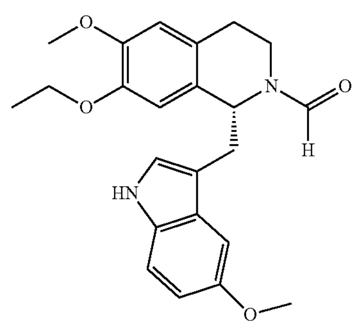 [SMILES: CCOc1cc2c(cc1OC)CCN(C=O)[C@@H]2Cc1c[nH]c2ccc(OC)cc12] |
| C19 | N-(3-(2-(7-ethoxy-2-formyl-6-methoxy-1,2,3,4-tetrahydroisoquinolin-1-yl)ethyl)-1H-indol-5-yl)acetamide | 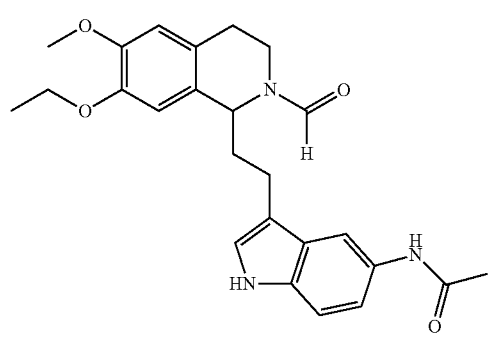 [SMILES: CCOc1cc2c(cc1OC)CCN(C=O)C2CCc1c[nH]c2ccc(NC(C)=O)cc12] |

-continued
| No. | Name | Structure |
|---|---|---|
| (S)-C19 | (S)-N-(3-(2-(7-ethoxy-2-formyl-6-methoxy-1,2,3,4-tetrahydroisoquinolin-1-yl)ethyl)-1H-indol-5-yl)acetamide | 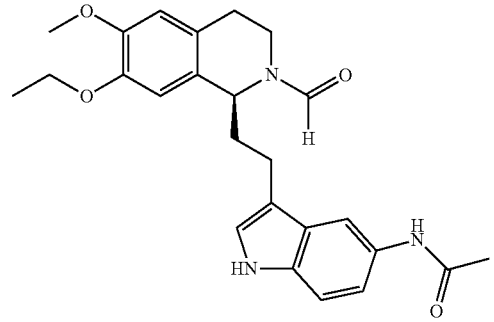 [SMILES: CCOc1cc2c(cc1OC)CCN(C=O)[C@H]2CCc1c[nH]c2ccc(NC(C)=O)cc12] |
| (R)-C19 | (R)-N-(3-(2-(7-ethoxy-2-formyl-6-methoxy-1,2,3,4-tetrahydroisoquinolin-1-yl)ethyl)-1H-indol-5-yl)acetamide | 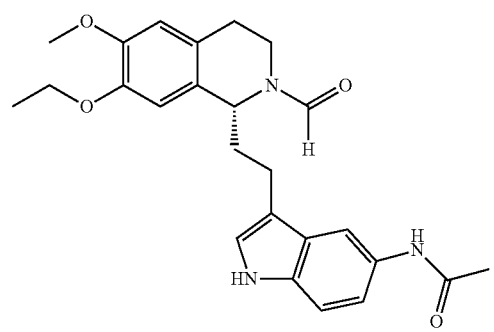 [SMILES: CCOc1cc2c(cc1OC)CCN(C=O)[C@@H]2CCc1c[nH]c2ccc(NC(C)=O)cc12] |
| C20 | (E)-7-ethoxy-6-methoxy-1-(2-(5-methoxy-1H-indol-3-yl)vinyl)-3,4-dihydroisoquinolin-2(1H)-formaldehyde | 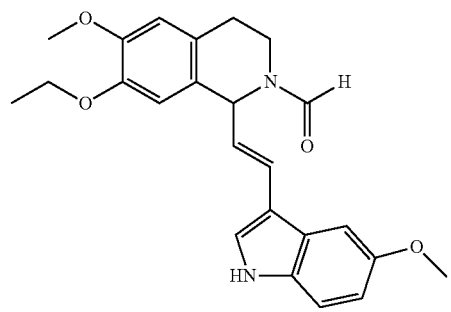 [SMILES: CCOc1cc2c(cc1OC)CCN(C=O)C2/C=C/c1c[nH]c2ccc(OC)cc12] |
| (S)-C20 | (S,E)-7-ethoxy-6-methoxy-1-(2-(5-methoxy-1H-indol-3-yl)vinyl)-3,4-dihydroisoquinolin-2(1H)-formaldehyde | 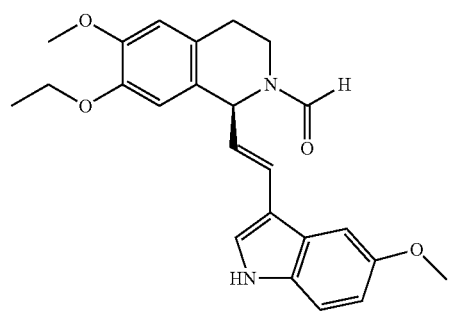 [SMILES: CCOc1cc2c(cc1OC)CCN(C=O)[C@H]2/C=C/c1c[nH]c2ccc(OC)cc12] |

| No. | Name | Structure |
|---|---|---|
| (R)-C20 | (R,E)-7-ethoxy-6-methoxy-1-(2-(5-methoxy-1H-indol-3-yl)vinyl-3,4-dihydroisoquinoline-2(1H)-formaldehyde | 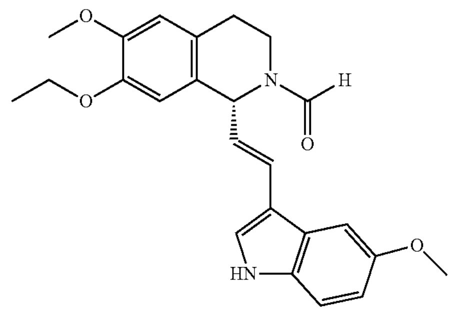 [SMILES: CCOc1cc2c(cc1OC)CCN(C=O)[C@@H]2/C=C/c1c[nH]c2ccc(OC)cc12] |
| C21 | 7-ethoxy-6-methoxy-1-(4-(5-methoxy-1H-indol-3-yl)cyclohexyl)-3,4-dihydroisoquinoline-2(1H)-formaldehyde | 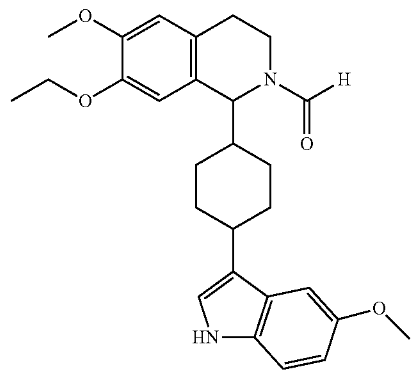 [SMILES: CCOc1cc2c(cc1OC)CCN(C=O)C2C1CCC(c2c[nH]c3ccc(OC)cc23)CC1] |
| (S)-C21 | (1S)-7-ethoxy-6-methoxy-1-(4-(5-methoxy-1H-indol-3-yl)cyclohexyl)-3,4-dihydroisoquinoline-2(1H)-formaldehyde | 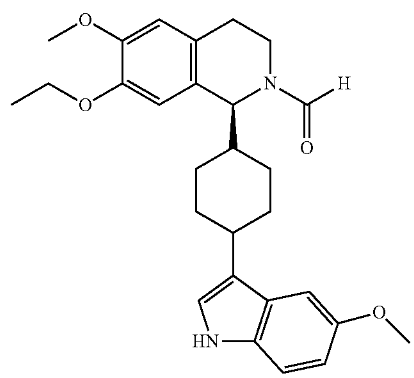 [SMILES: CCOc1cc2c(cc1OC)CCN(C=O)[C@H]2C1CCC(c2c[nH]c3ccc(OC)cc23)CC1] |
| (R)-C21 | (1R)-7-ethoxy-6-methoxy-1-(4-(5-methoxy-1H-indol-3-yl)cyclohexyl)-3,4-dihydroisoquinoline-2(1H)-formaldehyde | 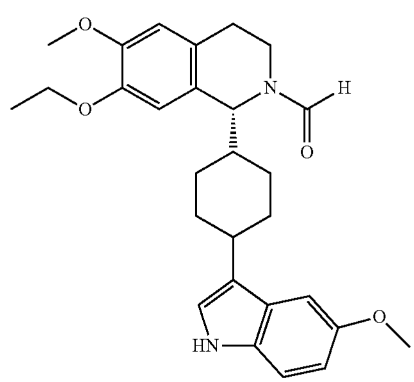 [SMILES: CCOc1cc2c(cc1OC)CCN(C=O)[C@@H]2C1CCC(c2c[nH]c3ccc(OC)cc23)CC1] |

| No. | Name | Structure |
| --- | --- | --- |
| C22 | 1-(2-(1H-indazol-3-yl)ethyl)-7-ethoxy-6-methoxy-3,4-dihydroisoquinolin-2(1H)-formaldehyde | 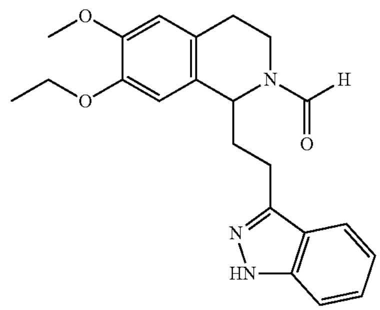 [SMILES: CCOc1cc2c(cc1OC)CCN(C=O)C2CCc1n[nH]c2ccccc12] |
| (S)-C22 | (S)-1-(2-(1H-indazol-3-yl)ethyl)-7-ethoxy-6-methoxy-3,4-dihydroisoquinolin-2(1H)-formaldehyde | 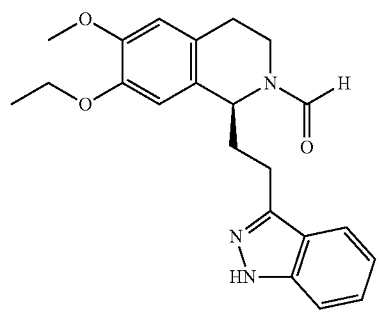 [SMILES: CCOc1cc2c(cc1OC)CCN(C=O)[C@H]2CCc1n[nH]c2ccccc12] |
| (R)-C22 | (R)-1-(2-(1H-indazol-3-yl)ethyl)-7-ethoxy-6-methoxy-3,4-dihydroisoquinolin-2(1H)-formaldehyde | 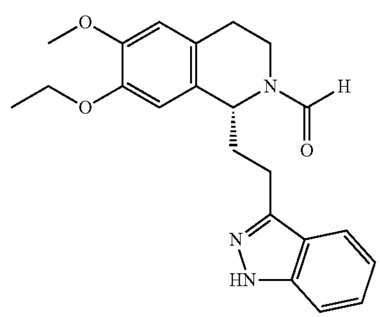 |
| C23 | 1-(2-(benzofuran-2-yl)ethyl)-7-ethoxy-6-methoxy-3,4-dihydroisoquinoline-2(1H)-formaldehyde | 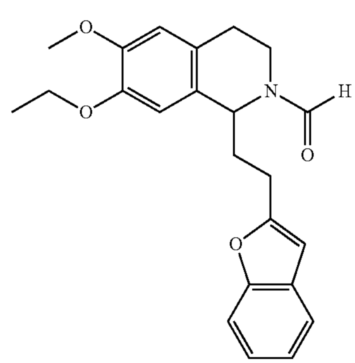 |

| No. | Name | Structure |
|---|---|---|
| (S)-C23 | (S)-1-(2-(benzofuran-2-yl)ethyl)-7-ethoxy-6-methoxy-3,4-dihydroisoquinoline-2(1H)-formaldehyde | 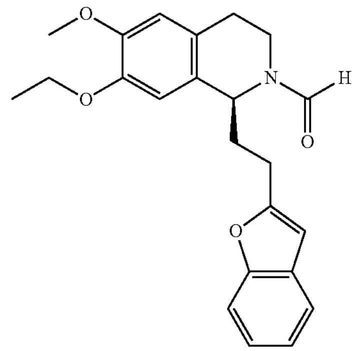 |
| (R)-C23 | (R)-1-(2-(benzofuran-2-yl)ethyl)-7-ethoxy-6-methoxy-3,4-dihydroisoquinolin-2(1H)-formaldehyde | 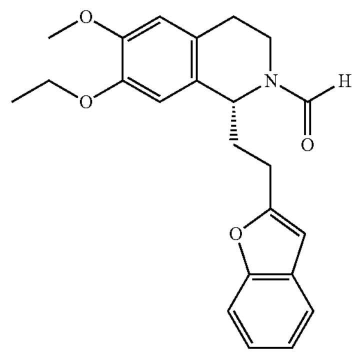 |
| C24 | 1-(2-(benzo[b]thiophen-2-yl)ethyl)-7-ethoxy-6-methoxy-3,4-dihydroisoquinolin-2(1H)-formaldehyde | 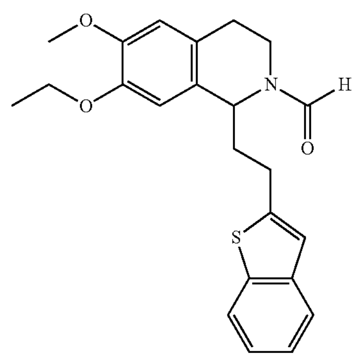 |
| (S)-C24 | (S)-1-(2-(benzo[b]thiophen-2-yl)ethyl)-7-ethoxy-6-methoxy-3,4-dihydroisoquinoline-2(1H)-formaldehyde | 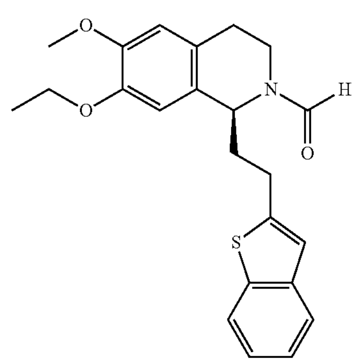 |

| No. | Name | Structure |
| --- | --- | --- |
| (R)-C24 | (R)-1-(2-(benzo[b]thiophen-2-yl)ethyl)-7-ethoxy-6-methoxy-3,4-dihydroisoquinoline-2(1H)-formaldehyde | 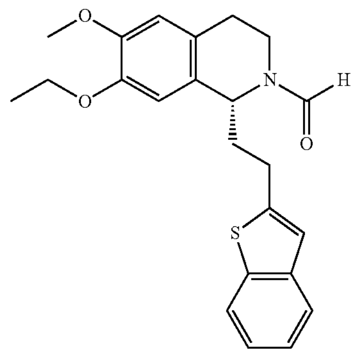 |
| C25 | 1-(2-(1H-indol-2-yl)ethyl)-7-ethoxy-6-methoxy-3,4-dihydroisoquinoline-2(1H)-formaldehyde | 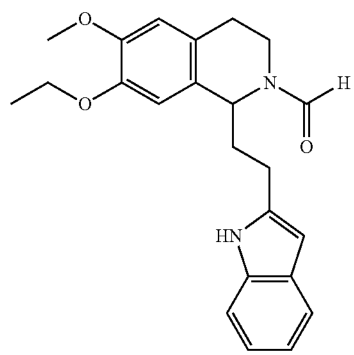 |
| (S)-C25 | (S)-1-(2-(1H-indol-2-yl)ethyl)-7-ethoxy-6-methoxy-3,4-dihydroisoquinoline-2(1H)-formaldehyde | 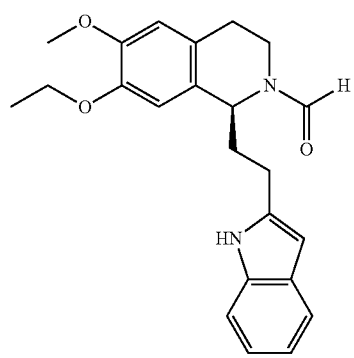 |
| (R)-C25 | (R)-1-(2-(1H-indol-2-yl)ethyl)-7-ethoxy-6-methoxy-3,4-dihydroisoquinoline-2(1H)-formaldehyde | 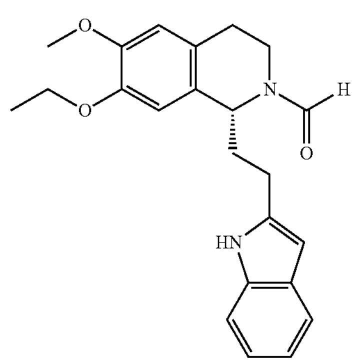 |

| No. | Name | Structure |
|---|---|---|
| C26 | 1-(2-(1H-pyrrolo[2,3-b]pyridin-3-yl)ethyl)-7-ethoxy-6-methoxy-3,4-dihydroisoquinolin-2(1H)-form-aldehyde | 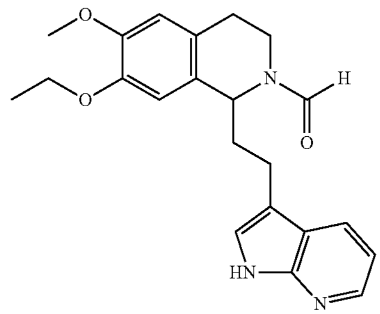 [SMILES: CCOc1cc2c(cc1OC)CCN(C=O)C2CCc1c[nH]c2ncccc12] |
| (S)-C26 | (S)-1-(2-(1H-pyrrolo[2,3-b]pyridin-3-yl)ethyl)-7-ethoxy-6-methoxy-3,4-dihydroisoquinoline-2(1H)-formaldehyde | 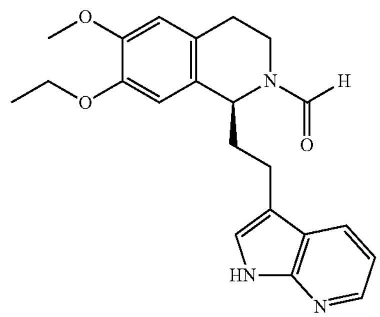 [SMILES: CCOc1cc2c(cc1OC)CCN(C=O)[C@H]2CCc1c[nH]c2ncccc12] |
| (R)-C26 | (R)-1-(2-(1H-pyrrolo[2,3-b]pyridin-3-yl)ethyl)-7-ethoxy-6-methoxy-3,4-dihydroisoquinoline-2(1H)-formaldehyde | 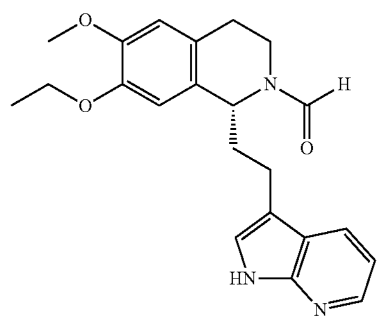 |
| C27 | 1-(2-cyclohexylethyl)-7-ethoxy-6-methoxy-3,4-dihydroisoquinoline-2(1H)-formaldehyde | 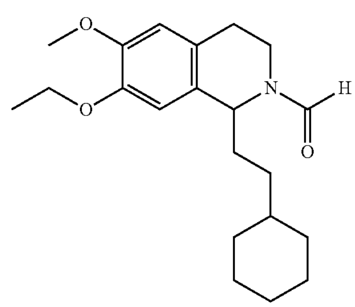 |
| (S)-C27 | (S)-1-(2-cyclohexylethyl)-7-ethoxy-6-methoxy-3,4-dihydroisoquinoline-2(1H)-formaldehyde | 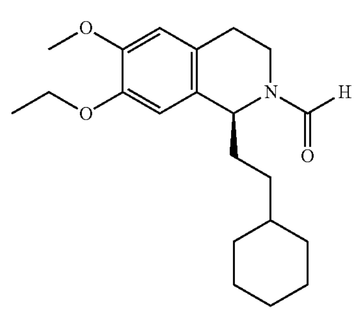 [SMILES: CCOc1cc2c(cc1OC)CCN(C=O)[C@H]2CCC1CCCCC1] |

-continued

| No. | Name | Structure |
|---|---|---|
| (R)-C27 | (R)-1-(2-cyclohexylethyl)-7-ethoxy-6-methoxy-3,4-dihydroisoquinoline-2(1H)-formaldehyde | 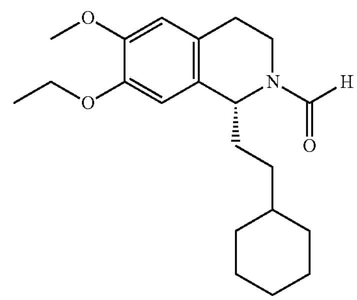 |
| C28 | 7-ethoxy-6-methoxy-1-(2-morpholinoethyl)-3,4-dihydroisoquinoline-2(1H)-formaldehyde | 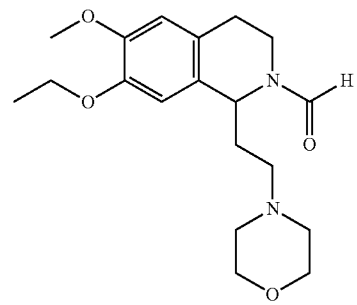 |
| (S)-C28 | (S)-7-ethoxy-6-methoxy-1-(2-morpholinoethyl)-3,4-dihydroisoquinolin-2(1H)-formaldehyde | 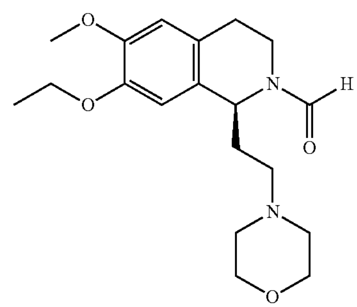 [SMILES: CCOc1cc2c(cc1OC)CCN(C=O)[C@H]2CCN1CCOCC1] |
| (R)-C28 | (R)-7-ethoxy-6-methoxy-1-(2-morpholinoethyl)-3,4-dihydroisoquinolin-2(1H)-formaldehyde | 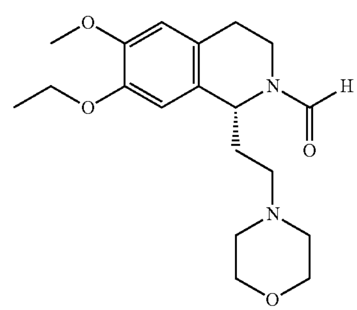 |
| C29 | 7-ethoxy-6-methoxy-1-(2-(pyridin-3-yl)ethyl)-3,4-dihydroisoquinolin-2(1H)-formaldehyde | 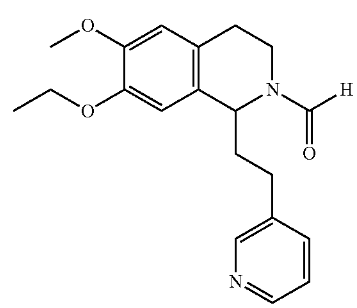 |

-continued

| No. | Name | Structure |
|---|---|---|
| (S)-C29 | (S)-7-ethoxy-6-methoxy-1-(2-(pyridin-3-yl)ethyl)-3,4-dihydroisoquinoline-2(1H)-formaldehyde | 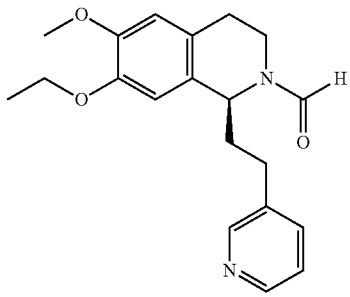 [SMILES: CCOc1cc2c(cc1OC)CCN(C=O)[C@H]2CCc1cccnc1] |
| (R)-C29 | (R)-7-ethoxy-6-methoxy-1-(2-(pyridin-3-yl)ethyl)-3,4-dihydroisoquinolin-2(1H)-formaldehyde | 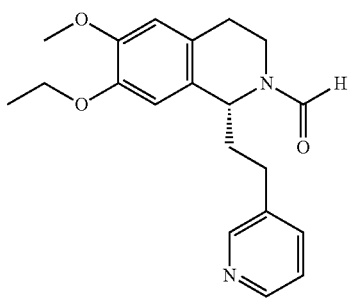 [SMILES: CCOc1cc2c(cc1OC)CCN(C=O)[C@@H]2CCc1cccnc1] |
| C30 | 7-ethoxy-6-methoxy-1-(((5-methoxy-1H-indol-3-yl)oxo)methyl)-3,4-dihydroisoquinoline-2(1H)-formaldehyde | 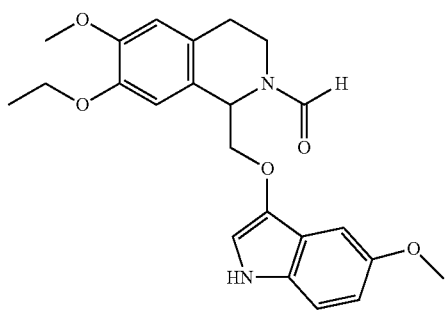 [SMILES: CCOc1cc2c(cc1OC)CCN(C=O)C2COc1c[nH]c2ccc(OC)cc12] |
| (S)-C30 | (R)-7-ethoxy-6-methoxy-1-(((5-methoxy-1H-indol-3-yl)oxo)methyl)-3,4-dihydroisoquinoline-2(1H)-formaldehyde | 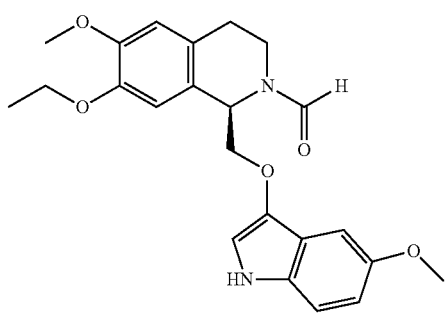 |
| (R)-C30 | (S)-7-ethoxy-6-methoxy-1-(((5-methoxy-1H-indol-3-yl)oxo)methyl)-3,4-dihydroisoquinoline-2(1H)-formaldehyde | 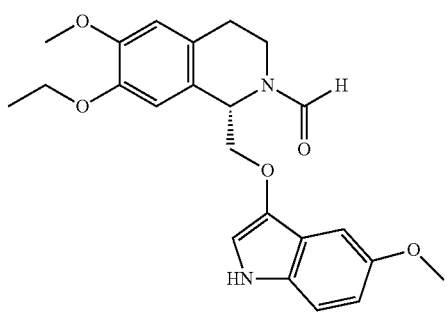 |

-continued

| No. | Name | Structure |
|---|---|---|
| C31 | 7-ethoxy-6-methoxy-1-(((5-methoxy-1H-indol-3-yl)thio)methyl)-3,4-dihydroisoquinoline-2(1H)-formaldehyde | 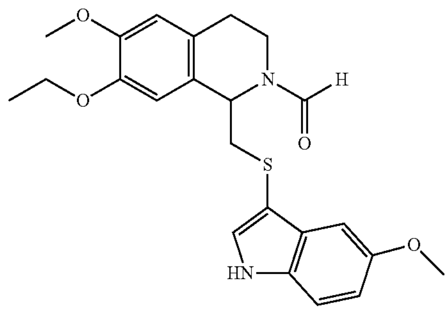 [SMILES: CCOc1cc2c(cc1OC)CCN(C=O)C2CSc1c[nH]c2ccc(OC)cc12] |
| (S)-C31 | (R)-7-ethoxy-6-methoxy-1-(((5-methoxy-1H-indol-3-yl)thio)methyl)-3,4-dihydroisoquinoline-2(1H)-formaldehyde | 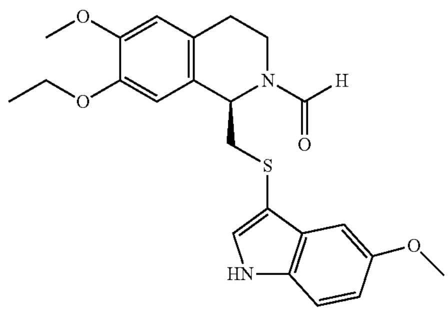 |
| (R)-C31 | (S)-7-ethoxy-6-methoxy-1-(((5-methoxy-1H-indol-3-yl)thio)methyl)-3,4-dihydroisoquinoline-2(1H)-formaldehyde | 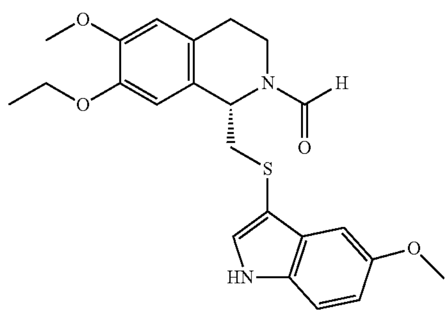 [SMILES: CCOc1cc2c(cc1OC)CCN(C=O)[C@@H]2CSc1c[nH]c2ccc(OC)cc12] |
| C32 | 7-ethoxy-6-methoxy-1-((4-(5-methoxy-1H-indol-3-yl)piperazin-1-yl)methyl)-3,4-dihydroisoquinoline-2(1H)-formaldehyde | 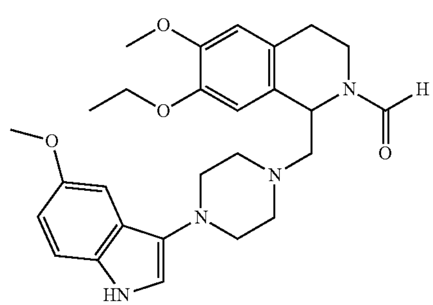 [SMILES: CCOc1cc2c(cc1OC)CCN(C=O)C2CN1CCN(c2c[nH]c3ccc(OC)cc23)CC1] |
| (S)-C32 | (R)-7-ethoxy-6-methoxy-1-((4-(5-methoxy-1H-indol-3-yl)piperazin-1-yl)methyl)-3,4-dihydroisoquinoline-2(1H)-formaldehyde | 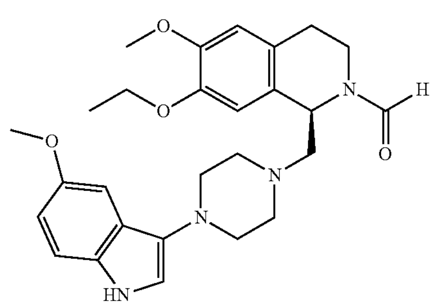 [SMILES: CCOc1cc2c(cc1OC)CCN(C=O)[C@H]2CN1CCN(c2c[nH]c3ccc(OC)cc23)CC1] |

-continued

| No. | Name | Structure |
|---|---|---|
| (R)-C32 | (S)-7-ethoxy-6-methoxy-1-((4-(5-methoxy-1H-indol-3-yl)piperazin-1-yl)methyl)-3,4-dihydroiso-quinoline-2(1H)-formaldehyde | 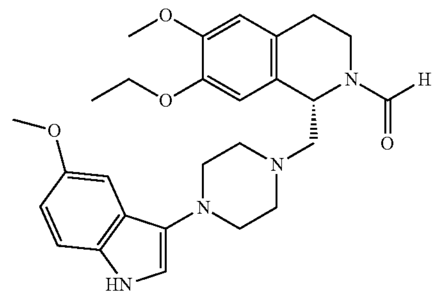 [SMILES: CCOc1cc2c(cc1OC)CCN(C=O)[C@@H]2CN1CCN(c2c[nH]c3ccc(OC)cc23)CC1] |
| C33 | 7-ethoxy-1-(2-(5-hydroxy-1H-indol-3-yl)ethyl)-6-methoxy-3,4-dihydroisoquinoline-2(1H)-formaldehyde | 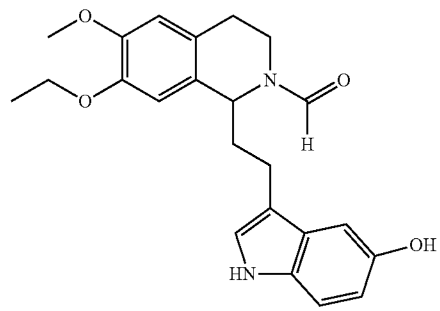 [SMILES: CCOc1cc2c(cc1OC)CCN(C=O)C2CCc1c[nH]c2ccc(O)cc12] |
| (S)-C33 | (S)-7-ethoxy-1-(2-(5-hydroxy-1H-indol-3-yl)ethyl)-6-methoxy-3,4-dihydroisoquinoline-2(1H)-formaldehyde | 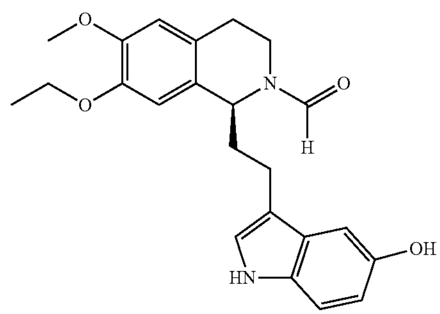 |
| (R)-C33 | (R)-7-ethoxy-1-(2-(5-hydroxy-1H-indol-3-yl)ethyl)-6-methoxy-3,4-dihydroisoquinoline-2(1H)-formaldehyde | 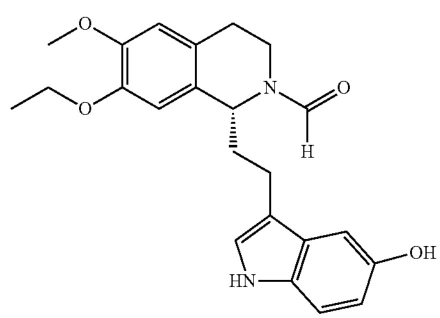 [SMILES: CCOc1cc2c(cc1OC)CCN(C=O)[C@@H]2CCc1c[nH]c2ccc(O)cc12] |
| C35 | 1-(((1H-indol-3-yl)amino)methyl)-7-ethoxy-6-methoxy-3,4-dihydroisoquinoline-2(1H)-formaldehyde | 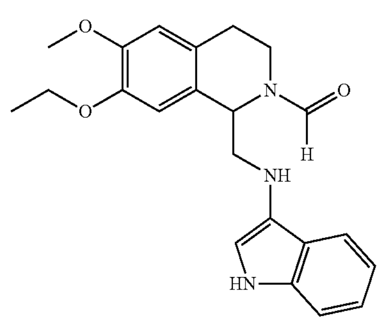 [SMILES: CCOc1cc2c(cc1OC)CCN(C=O)C2CNc1c[nH]c2ccccc12] |

| No. | Name | Structure |
|---|---|---|
| (S)-C35 | (S)-1-(((1H-indol-3-yl)amino)methyl)-7-ethoxy-6-methoxy-3,4-dihydroisoquinoline-2(1H)-formaldehyde | 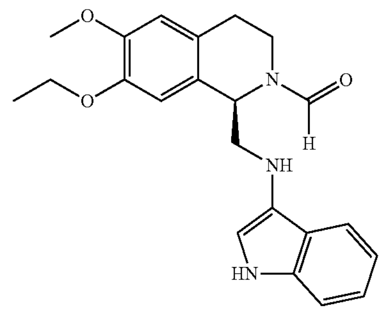 [SMILES: CCOc1cc2c(cc1OC)CCN(C=O)[C@H]2CNc1c[nH]c2ccccc12] |
| (R)-C35 | (R)-1-(((1H-indol-3-yl)amino)methyl)-7-ethoxy-6-methoxy-3,4-dihydroisoquinoline-2(1H)-formaldehyde | 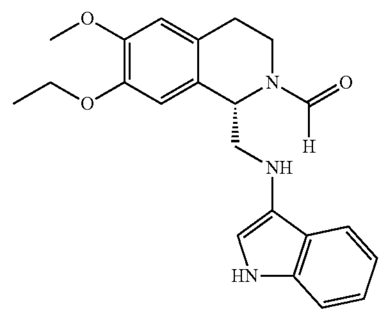 [SMILES: CCOc1cc2c(cc1OC)CCN(C=O)[C@@H]2CNc1c[nH]c2ccccc12] |
| C36 | 7-ethoxy-2-formyl-N-(1H-indol-3-yl)-6-methoxy-1,2,3,4-tetrahydroisoquinoline-1-formamide | 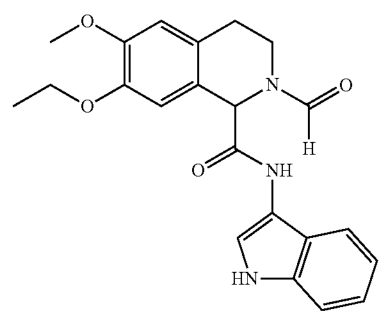 [SMILES: CCOc1cc2c(cc1OC)CCN(C=O)C2C(=O)Nc1c[nH]c2ccccc12] |
| (S)-C36 | (S)-7-ethoxy-2-formyl-N-(1H-indol-3-yl)-6-methoxy-1,2,3,4-tetrahydroisoquinoline-1-formamide | 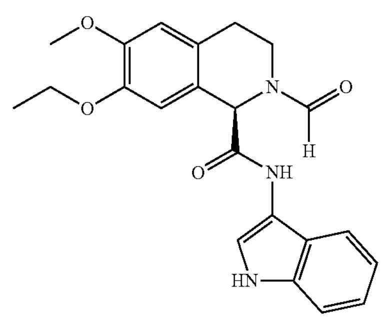 [SMILES: CCOc1cc2c(cc1OC)CCN(C=O)[C@H]2C(=O)Nc1c[nH]c2ccccc12] |
| (R)-C36 | (R)-7-ethoxy-2-formyl-N-(1H-indol-3-yl)-6-methoxy-1,2,3,4-tetrahydroisoquinoline-1-formamide | 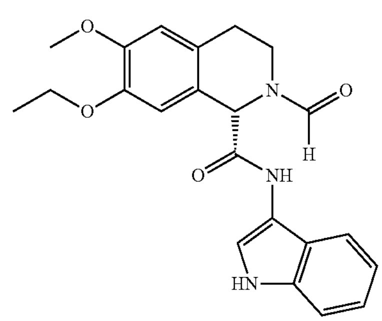 |

-continued

| No. | Name | Structure |
|---|---|---|
| C37 | 1-(2-(1H-indol-3-y)propyl)-6,7-dimethoxy-3,4-dihydroisoquinoline-2(1H)-formaldehyde | 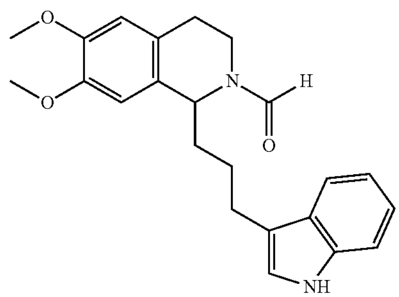 [SMILES: COc1cc2c(cc1OC)C(CCCc1c[nH]c3ccccc13)N(C=O)CC2] |
| (S)-C37 | (S)-1-(2-(1H-indol-3-yl)propyl)-6,7-dimethoxy-3,4-dihydroisoquinoline-2(1H)-formaldehyde | 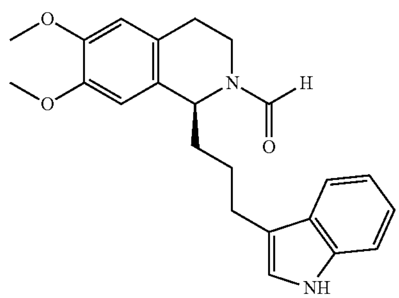 [SMILES: COc1cc2c(cc1OC)[C@H](CCCc1c[nH]c3ccccc13)N(C=O)CC2] |
| (R)-C37 | (R)-1-(2-(1H-indol-3-yl)propyl)-6,7-dimethoxy-3,4-dihydroisoquinoline-2(1H)-formaldehyde | 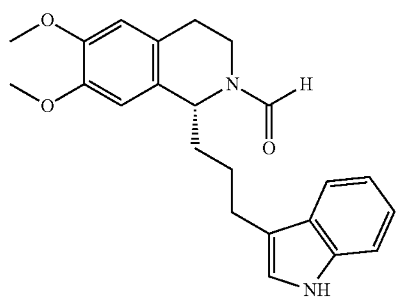 [SMILES: COc1cc2c(cc1OC)[C@@H](CCCc1c[nH]c3ccccc13)N(C=O)CC2] |
| C38 | 1-((1H-indol-3-yl)methyl)-6,7-dimethoxy-3,4-dihydroisoquinoline-2(1H)-ethyl-1-one | 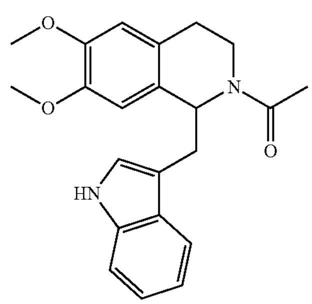 [SMILES: COc1cc2c(cc1OC)C(Cc1c[nH]c3ccccc13)N(C(C)=O)CC2] |
| (S)-C38 | (S)-1-((1H-indol-3-yl)methyl)-6,7-dimethoxy-3,4-dihydroisoquinoline-2(1H)-ethyl-1-one | 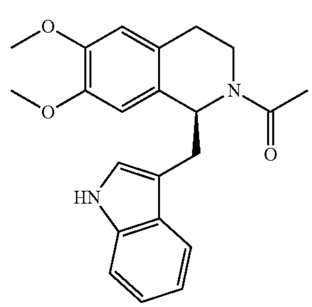 [SMILES: COc1cc2c(cc1OC)[C@H](Cc1c[nH]c3ccccc13)N(C(C)=O)CC2] |

-continued

| No. | Name | Structure |
|---|---|---|
| C39 | (1-((1H-indol-3-yl)methyl)-6,7-dimethoxy-3,4-dihydro-isoquinolin-2(1H)-yl)(pyridin-4-yl)-methanone | 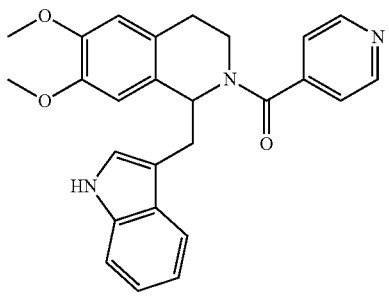 [SMILES: COc1cc2c(cc1OC)C(Cc1c[nH]c3ccccc13)N(C(=O)c1ccncc1)CC2] |
| C40 | (1-((1H-indol-3-yl)methyl)-6,7-dimethoxy-3,4-dihydro-isoquinolin-2(1H)-yl)(morpholine)-methanone | 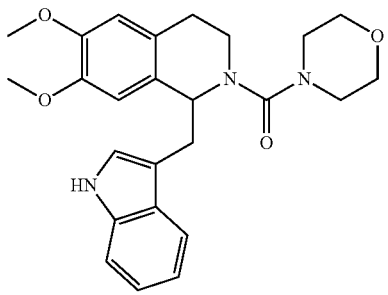 [SMILES: COc1cc2c(cc1OC)C(Cc1c[nH]c3ccccc13)N(C(=O)N1CCOCC1)CC2] |
| (S)-C40 | (S)-(1-((1H-indol-3-yl)methyl)-6,7-dimethoxy-3,4-dihydroisoquinoline-2(1H)-yl(morpholine)-methanone | 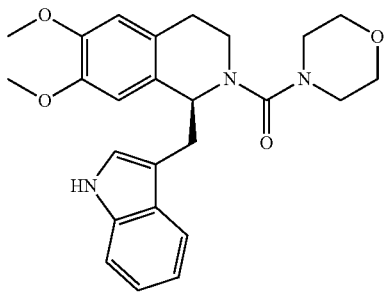 |
| C41 | (1-((1H-indol-3-yl)methyl)-6,7-dimethoxy-3,4-dihydro-isoquinolin-2(1H)-yl)(tetrahydro-2H-pyran-4-yl)-methanone | 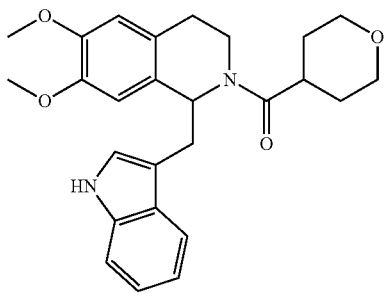 [SMILES: COc1cc2c(cc1OC)C(Cc1c[nH]c3ccccc13)N(C(=O)C1CCOCC1)CC2] |
| (S)-C41 | (S)-(1-((1H-indol-3-yl)methyl)-6,7-dimethoxy-3,4-dihydroisoquinoline-2(1H)-yl)(tetrahydro-2H-pyran-4-yl)-methanone | 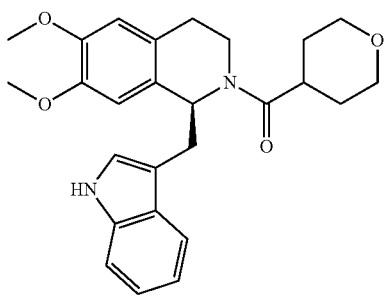 [SMILES: COc1cc2c(cc1OC)[C@H](Cc1c[nH]c3ccccc13)N(C(=O)C1CCOCC1)CC2] |

-continued

| No. | Name | Structure |
|---|---|---|
| C42 | (1-((1H-indol-3-yl)methyl)-6,7-dimethoxy-3,4-di-hydroisoquinolin-2(1H)-yl)(thiazole-2-yl)-methanone | 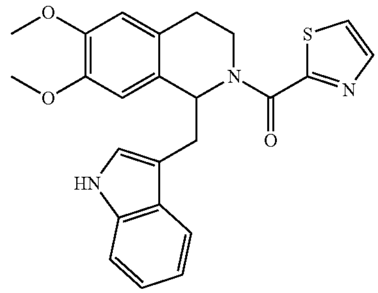 [SMILES: COc1cc2c(cc1OC)C(Cc1c[nH]c3ccccc13)N(C(=O)c1nccs1)CC2] |
| (S)-C42 | (S)-(1-((1H-indol-3-yl)methyl)-6,7-dimethoxy-3,4-dihydroisoquinoline-2(1H)-yl)(thiazol-2-yl)-methanone | 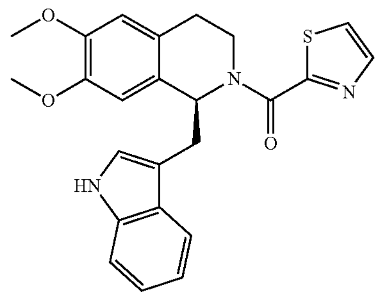 [SMILES: COc1cc2c(cc1OC)[C@H](Cc1c[nH]c3ccccc13)N(C(=O)c1nccs1)CC2] |
| C43 | methyl-2-(1-((1H-indol-3-yl)methyl)-6,7-dimethoxy-3,4-dihydroisoquinoline-2(1H)-yl)acetate | 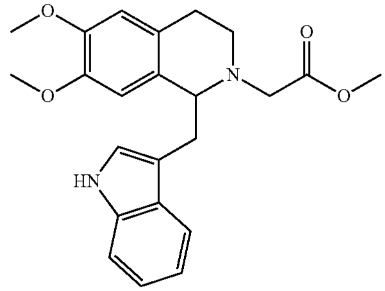 |
| C44 | 1-((6-chloro-1H-indol-3-yl)methyl)-6,7-dimethoxy-3,4-dihydroisoquinoline-2(1H)-formaldehyde | 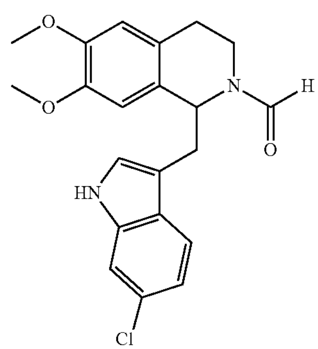 [SMILES: COc1cc2c(cc1OC)C(Cc1c[nH]c3cc(Cl)ccc13)N(C=O)CC2] |
| (S)-C44 | (S)-1-((6-chloro-1H-indol-3-yl)methyl)-6,7-dimethoxy-3,4-dihydroisoquinoline-2(1H)-formaldehyde | 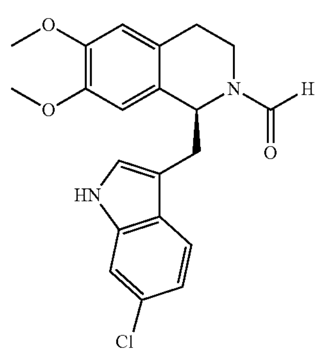 [SMILES: COc1cc2c(cc1OC)[C@H](Cc1c[nH]c3cc(Cl)ccc13)N(C=O)CC2] |

| No. | Name | Structure |
|---|---|---|
| C45 | 6,7-dimethoxy-1-((1-methyl-1H-indol-3-yl)methyl)-3,4-dihydroisoquinoline-2(1H)-formaldehyde | 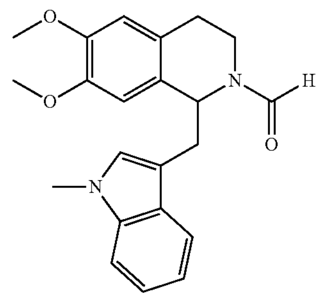 [SMILES: COc1cc2c(cc1OC)C(Cc1cn(C)c3ccccc13)N(C=O)CC2] |
| C46 | 1-((1H-indol-3-yl)methyl)-7-benzyloxy-6-methoxy-3,4-dihydroisoquinoline-2(1H)-formaldehyde | 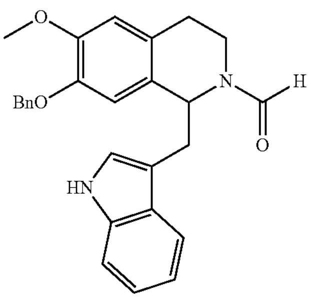 [SMILES: COc1cc2c(cc1OCc1ccccc1)C(Cc1c[nH]c3ccccc13)N(C=O)CC2] |
| (S)-C47 | (S)-7-ethoxy-6-methoxy-1-(2-(5-methoxy-1H-indol-3-yl)ethyl)-2-benzylsulfonyl-1,2,3,4-tetrahydroisoquinoline | 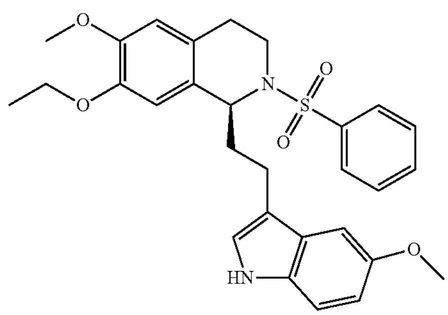 [SMILES: CCOc1cc2c(cc1OC)CCN(S(=O)(=O)c1ccccc1)[C@H]2CCc1c[nH]c2ccc(OC)cc12] |
| (S)-C48 | (S)-7-ethoxy-6-methoxy-1-(2-(5-methoxy-1H-indol-3-yl)ethyl)-2-cyclopropylsulfonyl-1,2,3,4-tetrahydroisoquinoline | 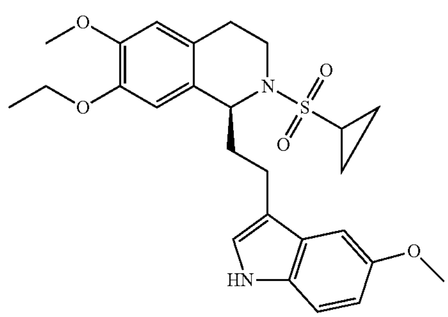 [SMILES: CCOc1cc2c(cc1OC)CCN(S(=O)(=O)C1CC1)[C@H]2CCc1c[nH]c2ccc(OC)cc12] |
| (S)-C49 | (S)-7-ethoxy-6-methoxy-1-(2-(5-methoxy-1H-indol-3-yl)ethyl)-2-cyclohexylsulfonyl-1,2,3,4-tetrahydroisoquinoline | 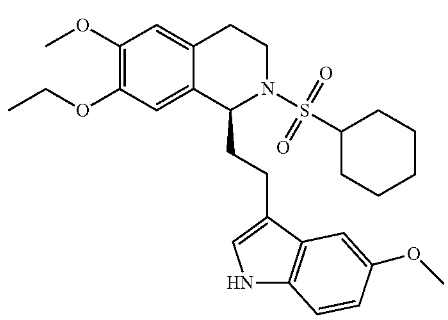 [SMILES: CCOc1cc2c(cc1OC)CCN(S(=O)(=O)C1CCCCC1)[C@H]2CCc1c[nH]c2ccc(OC)cc12] |

-continued

| No. | Name | Structure |
|---|---|---|
| (S)-C50 | (S)-7-ethoxy-6-methoxy-1-(2-(5-methoxy-1H-indol-3-yl)ethyl)-2-(3-fluorophenyl)sulfonyl-1,2,3,4-tetrahydroisoquinoline | 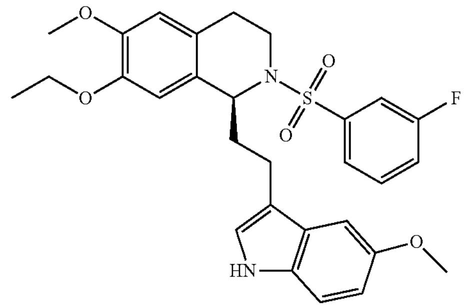 [SMILES: CCOc1cc2c(cc1OC)CCN(S(=O)(=O)c1cccc(F)c1)[C@H]2CCc1c[nH]c2ccc(OC)cc12] |
| (S)-C51 | (S)-7-ethoxy-6-methoxy-1-(2-(5-methoxy-1H-indol-3-yl)ethyl)-2-(3,4-difluorophenyl)sulfonyl-1,2,3,4-tetrahydroisoquinoline | 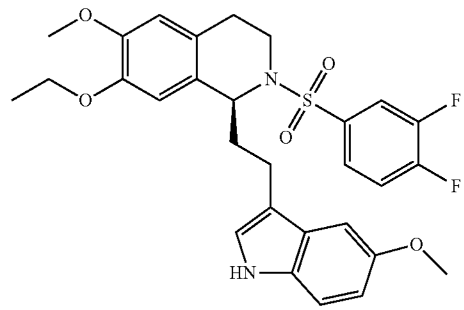 [SMILES: CCOc1cc2c(cc1OC)CCN(S(=O)(=O)c1ccc(F)c(F)c1)[C@H]2CCc1c[nH]c2ccc(OC)cc12] |
| (S)-C52 | (S)-7-ethoxy-6-methoxy-1-(2-(5-methoxy-1H-indol-3-yl)ethyl)-2-(2,4-difluorophenyl)sulfonyl-1,2,3,4-tetrahydroisoquinoline | 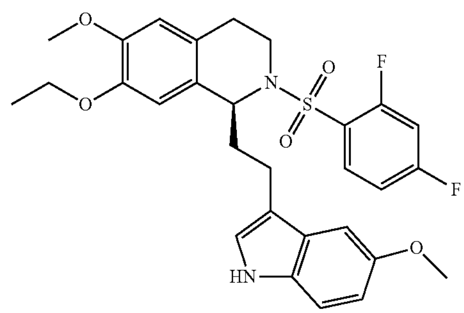 [SMILES: CCOc1cc2c(cc1OC)CCN(S(=O)(=O)c1ccc(F)cc1F)[C@H]2CCc1c[nH]c2ccc(OC)cc12] |
| (S)-C53 | (S)-7-ethoxy-6-methoxy-1-(2-(5-methoxy-1H-indol-3-yl)ethyl)-2-ethylsulfonyl-1,2,3,4-tetrahydroisoquinoline | 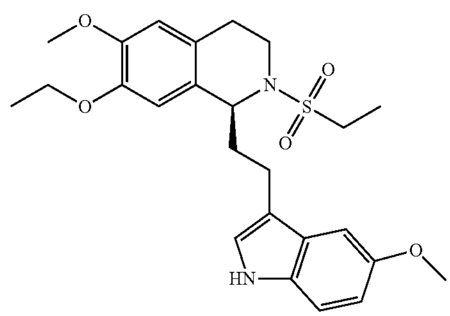 [SMILES: CCOc1cc2c(cc1OC)CCN(S(=O)(=O)CC)[C@H]2CCc1c[nH]c2ccc(OC)cc12] |
| (S)-C54 | (S)-7-ethoxy-1-(2-(5-methoxy-1H-indol-3-yl)ethyl)-6-methoxy-3,4-dihydroisoquinoline-2(1H)-trifluoroethane-1-one | 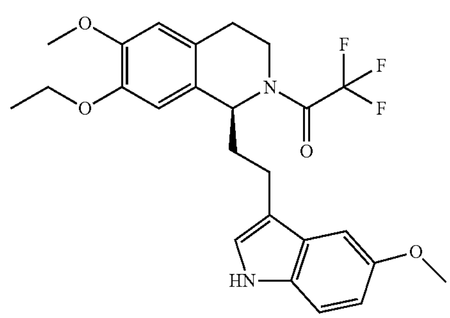 [SMILES: CCOc1cc2c(cc1OC)CCN(C(=O)C(F)(F)F)[C@H]2CCc1c[nH]c2ccc(OC)cc12] |

| No. | Name | Structure |
|---|---|---|
| (S)-C55 | (S)-7-ethoxy-6-methoxy-1-(2-(5-methoxy-1H-indol-3-yl)ethyl)-2-(pyridin-3-yl)sulfonyl-1,2,3,4-tetrahydroisoquinoline | 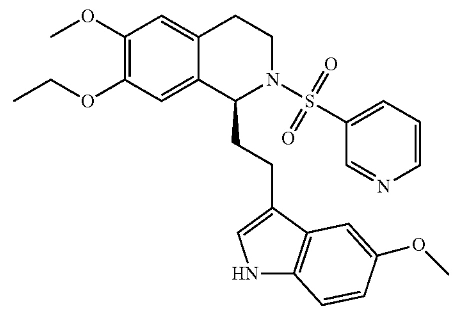 [SMILES: CCOc1cc2c(cc1OC)CCN(S(=O)(=O)c1cccnc1)[C@H]2CCc1c[nH]c2ccc(OC)cc12] |
| (S)-C56 | (S)-7-ethoxy-6-methoxy-1-(2-(5-methoxy-1H-indol-3-yl)ethyl)-2-(3-fluoro-4-bromophenyl)sulfonyl-1,2,3,4-tetrahydroisoquinoline | 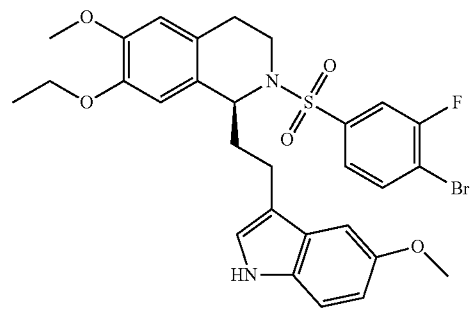 [SMILES: CCOc1cc2c(cc1OC)CCN(S(=O)(=O)c1ccc(Br)c(F)c1)[C@H]2CCc1c[nH]c2ccc(OC)cc12] |
| (S)-C57 | (S)-7-ethoxy-6-methoxy-1-(2-(5-methoxy-1H-indol-3-yl)ethyl)-2-(2-fluorophenyl)sulfonyl-1,2,3,4-tetrahydroisoquinoline | 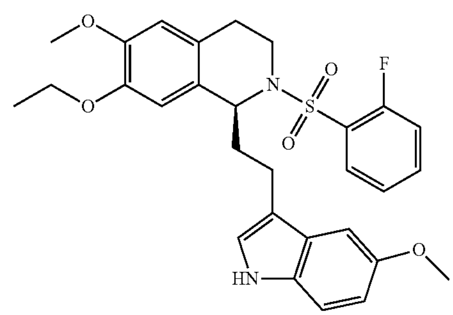 [SMILES: CCOc1cc2c(cc1OC)CCN(S(=O)(=O)c1ccccc1F)[C@H]2CCc1c[nH]c2ccc(OC)cc12] |
| (S)-C58 | (S)-7-ethoxy-6-methoxy-1-(2-(5-methoxy-1H-indol-3-yl)ethyl)-2-(4-fluorophenyl)sulfonyl-1,2,3,4-tetrahydroisoquinoline | 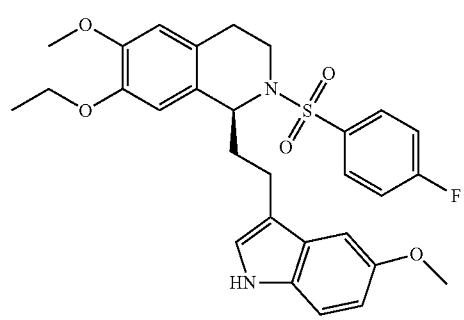 [SMILES: CCOc1cc2c(cc1OC)CCN(S(=O)(=O)c1ccc(F)cc1)[C@H]2CCc1c[nH]c2ccc(OC)cc12] |
| (S)-C59 | (S)-7-ethoxy-1-(2-(5-methoxy-1H-indol-3-yl)ethyl)-6-methoxy-3,4-dihydroisoquinolin-2(1H)-2,2-difluoroethane-1-one | 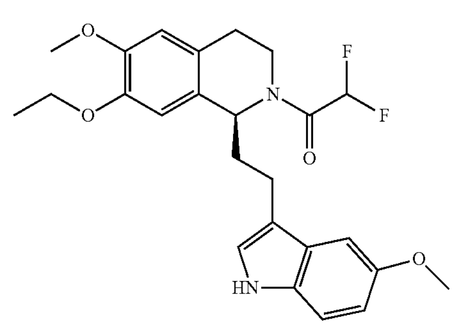 [SMILES: CCOc1cc2c(cc1OC)CCN(C(=O)C(F)F)[C@H]2CCc1c[nH]c2ccc(OC)cc12] |

-continued

| No. | Name | Structure |
|---|---|---|
| (S)-C60 | (S)-7-ethoxy-6-methoxy-1-(2-(5-methoxy-1H-indol-3-yl)ethyl)-2-(4-methoxyphenyl)sulfonyl-1,2,3,4-tetrahydroisoquinoline | 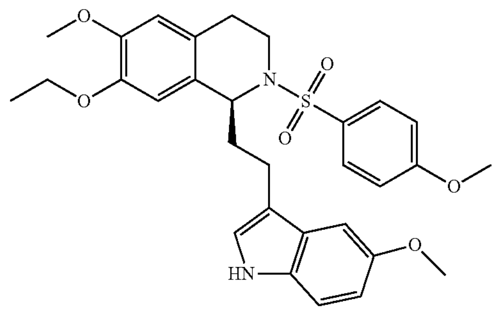 [SMILES: CCOc1cc2c(cc1OC)CCN(S(=O)(=O)c1ccc(OC)cc1)[C@H]2CCc1c[nH]c2ccc(OC)cc12] |
| (S)-C61 | (S)-1-(2-(benzo[b]thiothiophen-3-yl)ethyl)-6,7-dimethoxy-3,4-dihydroisoquinoline-2(1H)-formaldehyde | 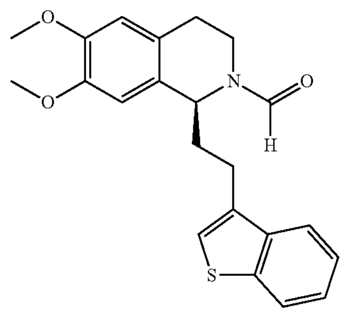 [SMILES: COc1cc2c(cc1OC)[C@H](CCc1csc3ccccc13)N(C=O)CC2] |
| (S)-C62 | (S)-7-ethoxy-1-(2-(5-methoxy-1H-indol-3-yl)ethyl)-6-methoxy-3,4-dihydroisoquinoline-2(1H)-ethoxyethane-1-one | 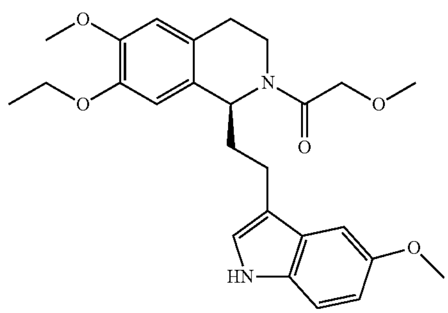 [SMILES: CCOc1cc2c(cc1OC)CCN(C(=O)COC)[C@H]2CCc1c[nH]c2ccc(OC)cc12] |
| (S)-C63 | (S)-7-trifluoromethoxy-1-(2-(5-methoxy-1H-indol-3-yl)ethyl)-6-methoxy-3,4-dihydroisoquinoline-2(1H)-formaldehyde | 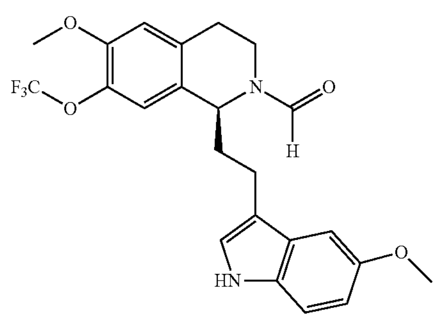 [SMILES: COc1ccc2[nH]cc(CC[C@H]3c4cc(OC(F)(F)F)c(OC)cc4CCN3C=O)c2c1] |
| (S)-C64 | (S)-7-difluoromethoxy-1-(2-(5-methoxy-1H-indol-3-yl)ethyl)-6-methoxy-3,4-dihydroisoquinoline-2(1H)-formaldehyde | 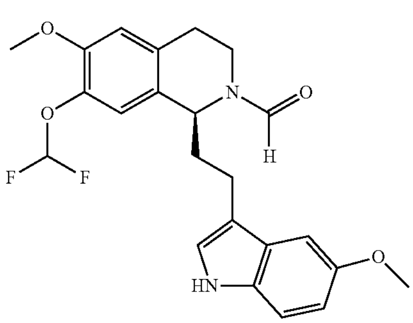 |

-continued

| No. | Name | Structure |
|---|---|---|
| (S)-C65 | (S)-7-ethoxy-6-methoxy-1-(2-(5-cyano-1H-indol-3-yl)ethyl)-3,4-dihydroisoquinoline-2(1H)-formaldehyde | 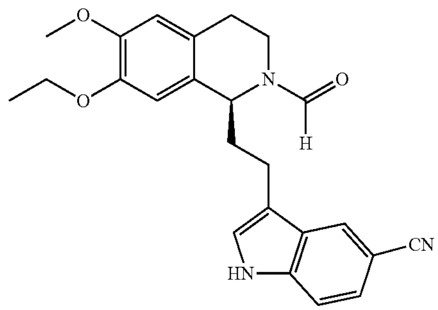 |
| (S)-C66 | methyl-(S)-2-formyl-6-methoxy-1-(2-(5-methoxy-1H-indol-3-yl)ethyl)-1,2,3,4-tetrahydroisoquinoline-7-carboxylate | 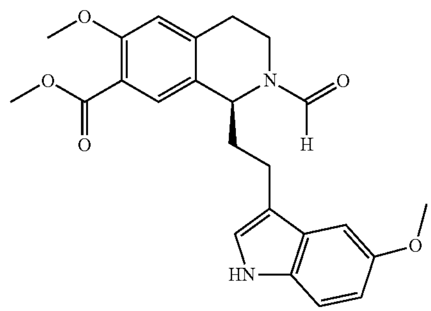 |
| (S)-C67 | methyl-(S)-2-formyl-7-methoxy-1-(2-(5-methoxy-1H-indol-3-yl)ethyl)-1,2,3,4-tetrahydroisoquinoline-6-carboxylate | 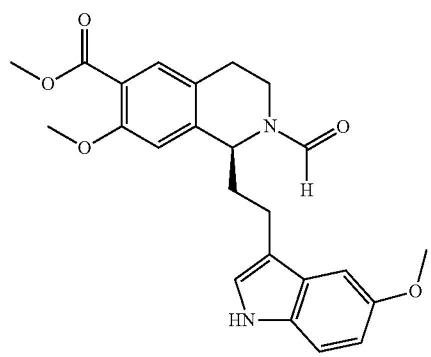 |
| (S)-C68 | (S)-2-formyl-6-methoxy-1-(2-(5-methoxy-1H-indol-3-yl)ethyl)-1,2,3,4-tetrahydroisoquinoline-7-carboxylic acid | 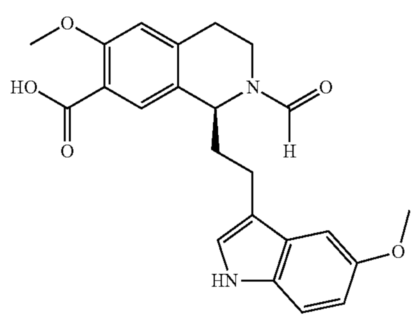 |
| (S)-C69 | (S)-2-formyl-6-methoxy-1-(2-(5-methoxy-1H-indol-3-yl)ethyl)-N-methyl-1,2,3,4-tetrahydroisoquinoline-7-carboxamide | 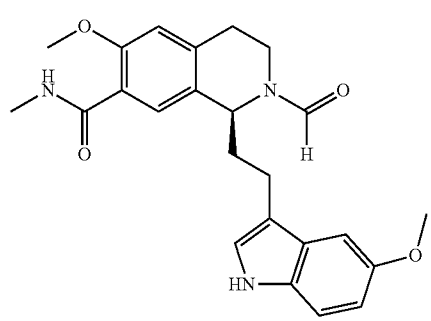 |

| No. | Name | Structure |
|---|---|---|
| (S)-C70 | (S)-2-formyl-6-methoxy-1-(2-(5-methoxy-1H-indol-3-yl)ethyl)-1,2,3,4-tetrahydroisoquinoline-7-carboxamide | 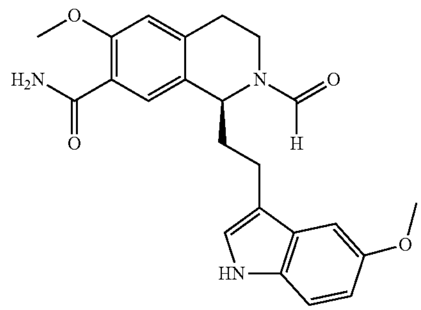 |
| (S)-C71 | (S)-7-difluoromethyl-1-(2-(5-methoxy-1H-indol-3-yl)ethyl)-6-methoxy-3,4-dihydroisoquinoline-2(1H)-formaldehyde | 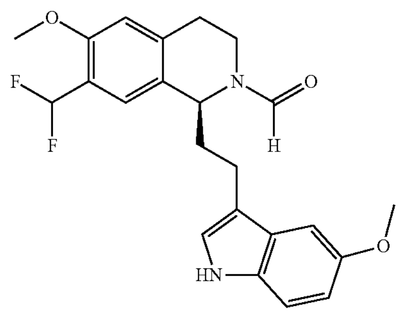 |
| (S)-C72 | (S)-2-difluoromethyl-7-ethoxy-6-methoxy-1-(2-(5-methoxy-1H-indol-3-yl)ethyl)-1,2,3,4-tetrahydro-isoquinoline | 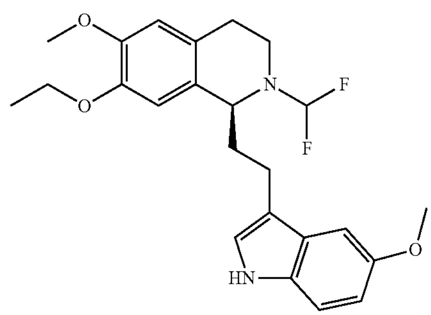 [SMILES: CCOc1cc2c(cc1OC)CCN(C(F)F)[C@H]2CCc1c[nH]c2ccc(OC)cc12] |
| (S)-C73 | (S)-7-ethoxy-6-methoxy-1-(2-(5-trifluoromethyl-1H-indol-3-yl)ethyl)-3,4-dihydroisoquinoline-2(1H)-formaldehyde | 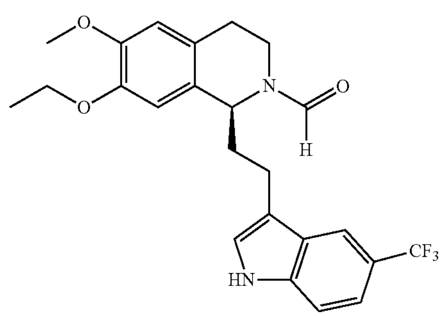 [SMILES: CCOc1cc2c(cc1OC)CCN(C=O)[C@H]2CCc1c[nH]c2ccc(C(F)(F)F)cc12] |
| (S)-C74 | (S)-7-ethoxy-6-methoxy-1-(2-(5-difluoromethyl-1H-indol-3-yl)ethyl)-3,4-dihydroisoquinoline-2(1H)-formaldehyde | 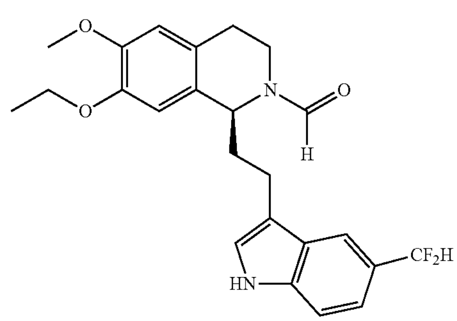 [SMILES: CCOc1cc2c(cc1OC)CCN(C=O)[C@H]2CCc1c[nH]c2ccc(C(F)F)cc12] |

| No. | Name | Structure |
|---|---|---|
| (S)-C75 | methyl-(S)-3-(2-(7-ethoxy-2-formyl-6-methoxy-1,2,3,4-tetrahydroisoquinolin-1-yl)ethyl)-1H-indole-5-carboxylate | 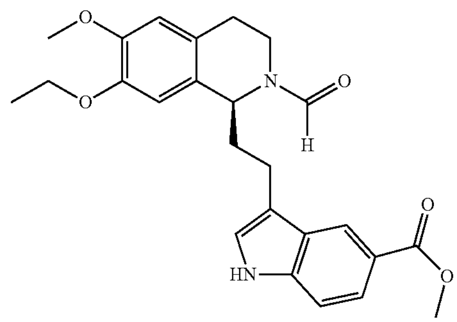 [SMILES: CCOc1cc2c(cc1OC)CCN(C=O)[C@H]2CCc1c[nH]c2ccc(C(=O)OC)cc12] |
| (S)-C76 | (S)-7-ethoxy-6-methoxy-1-(2-(5-trifluoromethoxy-1H-indol-3-yl)ethyl)-3,4-dihydroisoquinoline-2(1H)-formaldehyde | 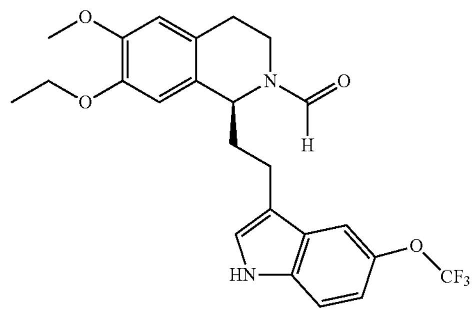 [SMILES: CCOc1cc2c(cc1OC)CCN(C=O)[C@H]2CCc1c[nH]c2ccc(OC(F)(F)F)cc12] |
| (S)-C77 | (S)-7-ethoxy-6-methoxy-1-(2-(5-difluoromethoxy-1H-indol-3-yl)ethyl)-3,4-dihydroisoquinoline-2(1H)-formaldehyde | 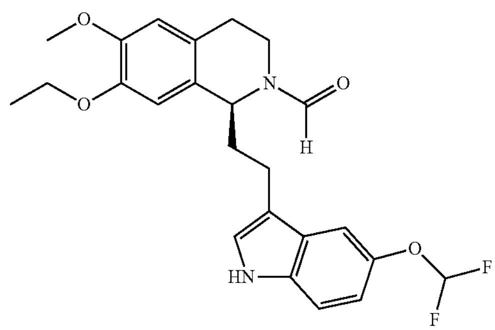 [SMILES: CCOc1cc2c(cc1OC)CCN(C=O)[C@H]2CCc1c[nH]c2ccc(OC(F)F)cc12] |
| (S)-C78 | (S)-7-ethoxy-6-methoxy-1-(2-(5-fluoro-1H-indol-3-yl)ethyl)-3,4-dihydroisoquinoline-2(1H)-formaldehyde | 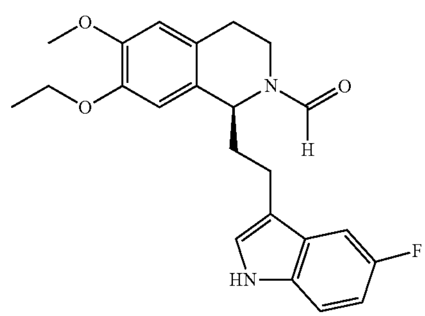 [SMILES: CCOc1cc2c(cc1OC)CCN(C=O)[C@H]2CCc1c[nH]c2ccc(F)cc12] |
| (S)-C79 | (S)-6-ethoxy-7-methoxy-1-(2-(5-methoxy-1H-indol-3-yl)ethyl)-3,4-dihydroisoquinoline-2(1H)-formaldehyde | 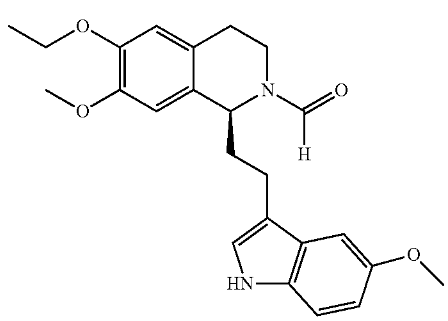 [SMILES: CCOc1cc2c(cc1OC)[C@H](CCc1c[nH]c3ccc(OC)cc13)N(C=O)CC2] |

| No. | Name | Structure |
|---|---|---|
| (S)-C80 | (S)-7-ethoxy-6-methoxy-1-(2-(5-methoxy-6-chloro-1H-indol-3-yl)ethyl)-3,4-dihydroisoquinoline-2(1H)-formaldehyde | 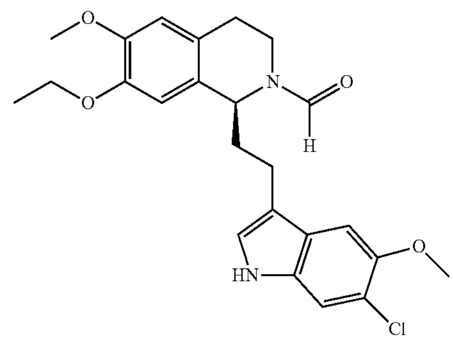 [SMILES: CCOc1cc2c(cc1OC)CCN(C=O)[C@H]2CCc1c[nH]c2cc(Cl)c(OC)cc12] |
| (S)-C81 | (S)-7-ethoxy-6-methoxy-1-(2-(5-fluoro-6-chloro-1H-indol-3-yl)ethyl)-3,4-dihydroisoquinoline-2(1H)-formaldehyde | 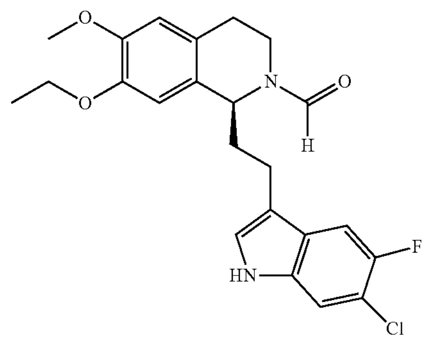 [SMILES: CCOc1cc2c(cc1OC)CCN(C=O)[C@H]2CCc1c[nH]c2cc(Cl)c(F)cc12] |
| (S)-C82 | (S)-7-ethoxy-1-(2-(5-fluoro-1H-indol-3-yl)ethyl)-6-methoxy-3,4-dihydroisoquinoline-2(1H)-ethoxy-ethane-1-one | 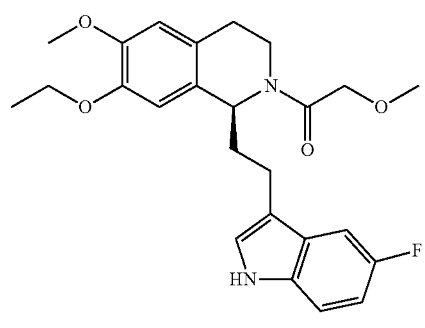 [SMILES: CCOc1cc2c(cc1OC)CCN(C(=O)COC)[C@H]2CCc1c[nH]c2ccc(F)cc12] |
| (S)-C83 | (S)-7-ethoxy-6-methoxy-1-(2-(5-methoxy-1H-indol-3-yl)ethyl)-2-(2-(methylsulfonyl)ethyl)-1,2,3,4-tetrahydroisoquinoline | 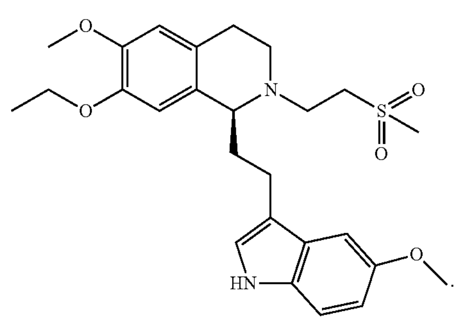 [SMILES: CCOc1cc2c(cc1OC)CCN(CCS(C)(=O)=O)[C@H]2CCc1c[nH]c2ccc(OC)cc12] |

7. A method for preparation of the tetrahydroisoquinoline compound represented by the general formula (I) of claim 1, comprising steps:
(1) in an inert solvent, in presence of a condensing agent, reacting a compound of formula II and a compound of formula Ic to obtain a compound of formula Id;

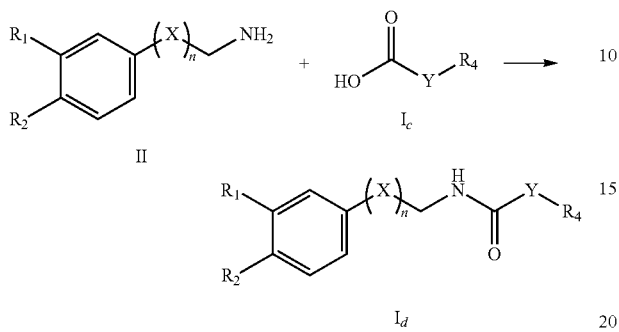

(2) subjecting the compound of formula Id to Bischler-Napieralski ring closure reaction in an inert solvent to obtain a compound of formula Ie;

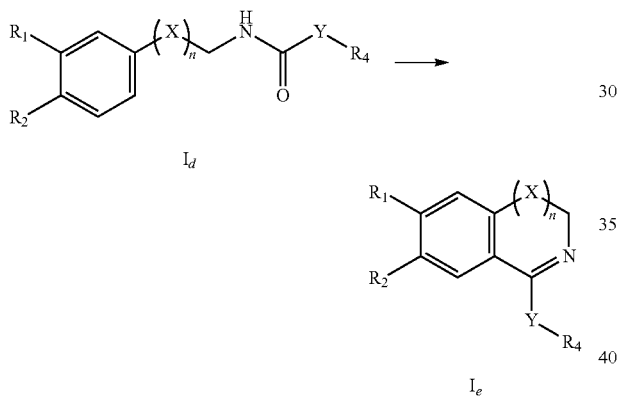

(3) in an inert solvent, subjecting the compound of formula Ie to a reduction reaction to obtain a compound of formula If;

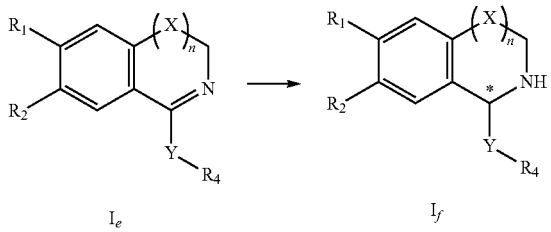

(4) in an inert solvent, subjecting the compound of formula If to a condensation reaction or an N-alkylation reaction or a Buchwald-Hartwig reaction to obtain the compound of formula (I);

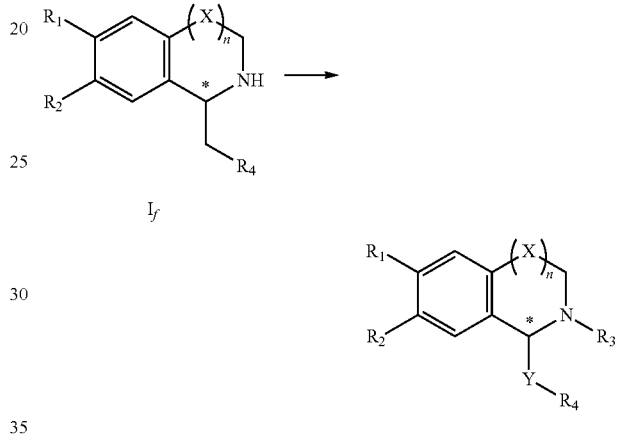

wherein the groups are defined as in claim 1.

8. A pharmaceutical composition, which comprises: a therapeutically effective amount of one or more compounds of the general formula (I) according to claim 1, or a pharmaceutically acceptable salt.

* * * * *